US006117978A

United States Patent [19]
St. George-Hyslop et al.

[11] Patent Number: 6,117,978
[45] Date of Patent: Sep. 12, 2000

[54] PRESENILIN-2 AND MUTATIONS THEREOF

[75] Inventors: Peter H. St. George-Hyslop; Johanna M. Rommens; Paul E. Fraser, all of Toronto, Canada

[73] Assignees: The Governing Council of the University of Toronto; HSC Research and Development Limited Partnership, both of Toronto, Canada

[21] Appl. No.: 09/124,698

[22] Filed: Jul. 29, 1998

Related U.S. Application Data

[62] Division of application No. 08/967,101, Nov. 10, 1997, Pat. No. 5,840,540, which is a division of application No. 08/592,541, Jan. 26, 1996, Pat. No. 5,986,054, which is a continuation-in-part of application No. 08/509,359, Jul. 31, 1995, which is a continuation-in-part of application No. 08/496,841, Jun. 28, 1995, which is a continuation-in-part of application No. 08/431,048, Apr. 28, 1995.

[51] Int. Cl.[7] .................................................. C07K 14/00
[52] U.S. Cl. ............................................................ 530/350
[58] Field of Search .............................................. 530/350

[56] References Cited

U.S. PATENT DOCUMENTS

| | | | |
|---|---|---|---|
| 5,262,332 | 11/1993 | Selkoe | 436/518 |
| 5,297,562 | 3/1994 | Potter | 128/898 |
| 5,449,604 | 9/1995 | Schellenberg et al. | 435/6 |
| 5,545,808 | 8/1996 | Hew et al. | |
| 5,668,006 | 9/1997 | Hadcock et al. | 435/252.3 |

FOREIGN PATENT DOCUMENTS

| | | |
|---|---|---|
| 2054302 | 4/1992 | Canada . |
| 2071105 | 12/1992 | Canada . |
| 2096911 | 11/1993 | Canada . |
| WO 91/19810 | 12/1991 | WIPO . |
| WO 94/00569 | 1/1994 | WIPO . |
| 94/10569 | 5/1994 | WIPO . |
| 94/23049 | 10/1994 | WIPO . |
| WO 97/03086 | 1/1997 | WIPO . |
| WO 97/03192 | 1/1997 | WIPO . |
| WO 97/03999 | 2/1997 | WIPO . |

OTHER PUBLICATIONS

Johansson et al., *J. Biol. Chem.*, 270(35):20615–20620 (1995).
Pawlak et al., EMBL Sequence Data Library, Dec. 20, 1994, Accession No. T18858.
Auffray et al., EMBL Sequence Data Library, Feb. 17, 1995, Accession No. F08730.
Zahraoui et al., EMBL Sequence Data Library, Jul. 22, 1994, Accession No. X56740.
Drivas et al., EMBL Sequence Data Library, Feb. 19, 1991, Accession No. X53143.
Chambon et al., EMBL Sequence Data Library, Feb. 7, 1992, Accession No. M84820.
Fleischhauer et al., EMBL Sequence Data Library, Mar. 31, 1992, Accession No. X63522.
Yu et al., EMBL Sequence Data Library, Dec. 10, 1991, Accession No. M81766.
Sevigny et al., EMBL Sequence Data Library, Jan. 7, 1995, Accession No. U17104.
Walkley et al., EMBL Sequence Data Library, Jan. 1, 1994, Accession No. X74801.
Hillier et al., EMBL Sequence Data Library, Apr. 22, 1995, Accession No. R12984.
Fujiwara et al., EMBL Sequence Data Library, Aug. 25, 1995, Accession No. D55326.
Hillier et al., EMBL Sequence Data Library, Mar. 6, 1995, Accession No. T64843.
Barinaga, "New Alzheimer's Gene Found," *Science*, 268:1845–1846(1995).
Barinaga, "Missing Alzheimer's Gene Found," *Science*, 269:81–92(1995).
Campion et al., "Mutations of the presenilin I gene in families with early–onset Alzheimer's disease," *Human Molecular Genetics*, 4(12):2372–2377 (1995).
Chartier–Harlin et al., "Early onset Alzheimer's disease caused by mutations at codon 717 of the β–amyloid precursor protein gene," *Nature*, 353:844–846 (1991).
Cruts et al., "Molecular genetic analysis of familial early–onset Alzheimer's disease linked to chromosome 14q24.3," *Human Molecular Genetics*, 4(12):2363–2371 (1995).
Foncin et al., "Alzheimer's Presenile dementia transmitted in an extended kindred," *Rev. Neurol. (Paris)*, 141:194–202 (1985).
Goate et al., "Segregation of a missense mutation in the amyloid precursor protein gene with familial Alzheimer's disease," *Nature*, 349:704–706 (1991).
Goudsmit et al., "Familial Alzheimer's Disease in two kindreds of the same geographic and ethnic origin: a clinical and genetic study," *J. Neurol. Sci.*, 49:79–89 (1981).
Gyapay et al., "The 1993–94 Genethon human genetic linkage map," *Nature Genetics*, 7:246–311 (1994).
Karlinsky et al., "Molecular and prospective phenotypic characterization of a pedigree with familial Alzheimer's disease and a missense mutation in codon 717 of the β–amyloid precursor protein (APP) gene," *Neurology*, 42:1445–1453 (1992).
Katzman, "Alzheimer's Disease," *N..Eng.J.Med.*, 314:964–973 (1986).
Levy–Lahad et al., "A Familiar Alzheimer's Disease Locus on Chromosome I," *Science*, 269:970–973 (1995).
Levy–Lahad et al., "Candidate Gene for the Chromosome 1 Familial Alzheimer's Disease Locus," *Science*, 269:973–977 (1995).

(List continued on next page.)

*Primary Examiner*—Karen Cochrane Carlson
*Attorney, Agent, or Firm*—Darby & Darby

[57] ABSTRACT

The present invention describes the identification, isolation and cloning of two human presenilin genes, PS-1 and PS-2, mutations in which lead to Familial Alzheimer's Disease. Also identified are presenilin homologue genes in mice, *C. elegans* and *D. melanogaster*. Transcripts and products of these genes are useful in detecting and diagnosing Alzheimer's disease, developing therapeutics for treatment of Alzheimer's disease, as well as the isolation and manufacture of the protein and the constructions of transgenic animals expressing the mutant genes.

26 Claims, 12 Drawing Sheets

OTHER PUBLICATIONS

Mullan et al., "A pathogenic mutation for probable Alzheimer's disease in the APP gene at the N–terminus of β–amyloid," *Nature Genetics,* 1:345–347 (1992).

Mullan et al., "A locus for familial early–onset Alzheimer's disease on the long arm of chromosome 14, proximal to the α1–antichymotrypsin gene," *Nature Genetics,* 2:340–342 (1992).

Murrell et al., "A mutation in the amyloid precursor protein associated with hereditary Alzheimer's Disease," *Science,* 254:97–99 (1991).

Nee et al., "A family with histologically confirmed Alzheimer's Disease," *Arch. Neurol.,* 40:203–208 (1983).

Pericak–Vance et al., "Genetic linkage studies in Alzheimer's Disease families," *Exp. Neurol,* 102:271–279 (1988).

Rogaev et al., "Analysis of the c–FOS gene on chromosome 14 and the promoter of the amyloid precursor protein gene in familial Alzheimer's disease," *Neurology,* 43:2275–2279 (1993).

Rogeav et al., "Familial Alzheimer's disease in kindreds with missense mutations in a gene on chromosome 1 related to the Alzheimer's disease type 3 gene," *Nature,* 376:775–778 (1995).

Rommens et al., "A transcription map of the region containing the Huntington disease gene," *Hum. Molec. Genet.,* 2:901–907 (1993).

Sherrington et al., "Cloning of a gene bearing missense mutations in early–onset familial Alzheimer's disease," *Nature,* 375:754–760 (1995).

St. George–Hyslop et al., "Genetic linkage studies suggest that Alzheimer's disease is not a single homogeneous disorder," *Nature,* 347:194–197 (1990).

St. George–Hyslop et al., "Genetic evidence for a novel familial Alzheimer's disease locus on chromosome 14," *Nature Genetics,* 2:330–334 (1992).

St. George–Hyslop et al., "Alzheimer's Disease and Possible Gene Interaction," *Science,* 263:537 (1994).

Saunders et al., "Association of apolipoprotein E allele e4 with the late–onset familial and sporadic Alzheimer's disease," *Neurology,* 43:1467–1472 (1993).

Schellenberg et al., "Genetic Linkage Evidence for a Familial Alzheimer's Disease Locus on Chromosome 14," *Science,* 258:668–670 (1992).

Schellenberg et al., "Chromosome 14 and Late–Onset Familial Alzheimer Disease (FAD)," *Am. J. Hum. Genet.,* 53:619–628 (1993).

Strittmatter et al., "Apolipoprotein E: high avidity binding to β–amyloid and increased frequency of type 4 allele in late–onset familial Alzheimer's disease," *Proc. Nat'l. Acad. Sci. USA,* 90:1977–1981 (1993).

Van Broeckhoven et al., "Mapping of a gene predisposing to early–onset Alzheimer's disease to chromosome 14q24.3," *Nature Genetics,* 2:335–339 (1992).

Van Broeckhoven, "Presenilins and Alzheimer disease," *Nature Genetics,* 11:230–232 (1995).

Wong et al., "Mutation of the gene for the human lysosomal serine protease Cathepsin G is not the cause of aberrannt APP processing in familial Alzheimer disease," *Neurosci. Lett,* 152:96–98 (1993).

L'Hernault et al., "Mutation of a Putative Sperm Membrane Protein in *Caenorhabditis elegans* Prevents Sperm Differentiation but Not Its Associated Meiotic Divisions," *J. Cell Biol.,* 119(1):55–68 (1992).

Li et al., "Identification and expression analysis of a potential familial Alzheimer disease gene on chromosome 1 related to AD3," *Proc. Natl. Acad. Sci. USA,* 92:12180–4 (1995).

Murrell et al., "A Mutation in the Amyloid Precursor Protein Associated with Hereditary Alzheimer's Disease," *Science,* 254:97–99 (1991).

Yamada et al., "Complementary DNA for the mouse homolog of the human amyloid beta protein precursor," *Biochem. Biophys. Res. Comm.* 149(2):665–71 (1987).

Taniguchi et al., "Cloning of the cDNA encoding rat Presenilin–1," Gene, 186:1, 73–75 (1997).

Mullins et al., "Transgenesis in Nonmurine Species," Hypertension, vol. 22(4): 630–633 (1993).

Pursel et al., "Genetic Engineering of Livestock," Science, 244: 1281–1288 (1989).

Salter et al., "Transgenic Chickens: Insertion of Retroviral Genes into the Chicken Germ Line." Virology, 157: 236–240 (1987).

Felsenstein et al., "Transgenic Rat and In–Vitro Studies of β–Amyloid Precursor Protein Processing," Alzheimer's and Parkinson's Diseases, pp. 401–409 (Hanin, et al., Plenum Press, NY)(1995).

Selkoe, "In the Beginning . . . ," Nature, 354: 532–433 (1991).

Lannfelt, et al., "Alzheimer's disease: molecular genetics and transgenic animal models," Behav. Brain Res. 57: 207–213 (1993).

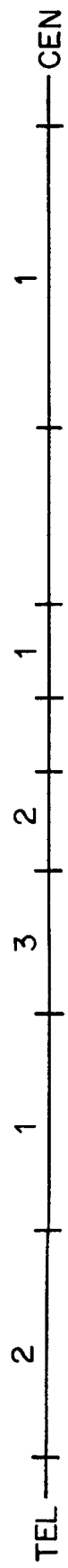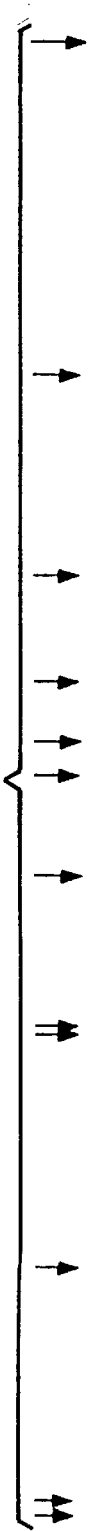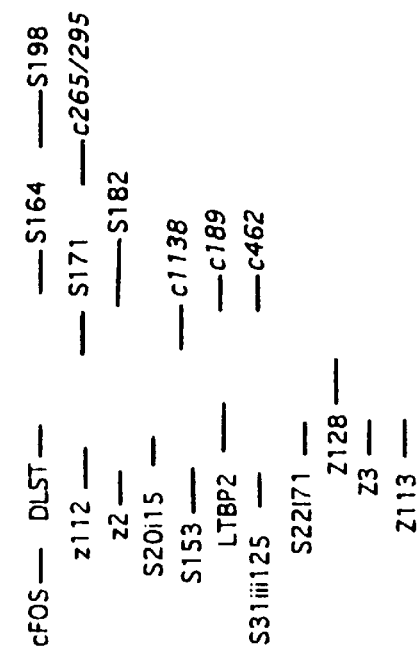
FIG. 1A
FIG. 1B
FIG. 1C
FIG. 1D

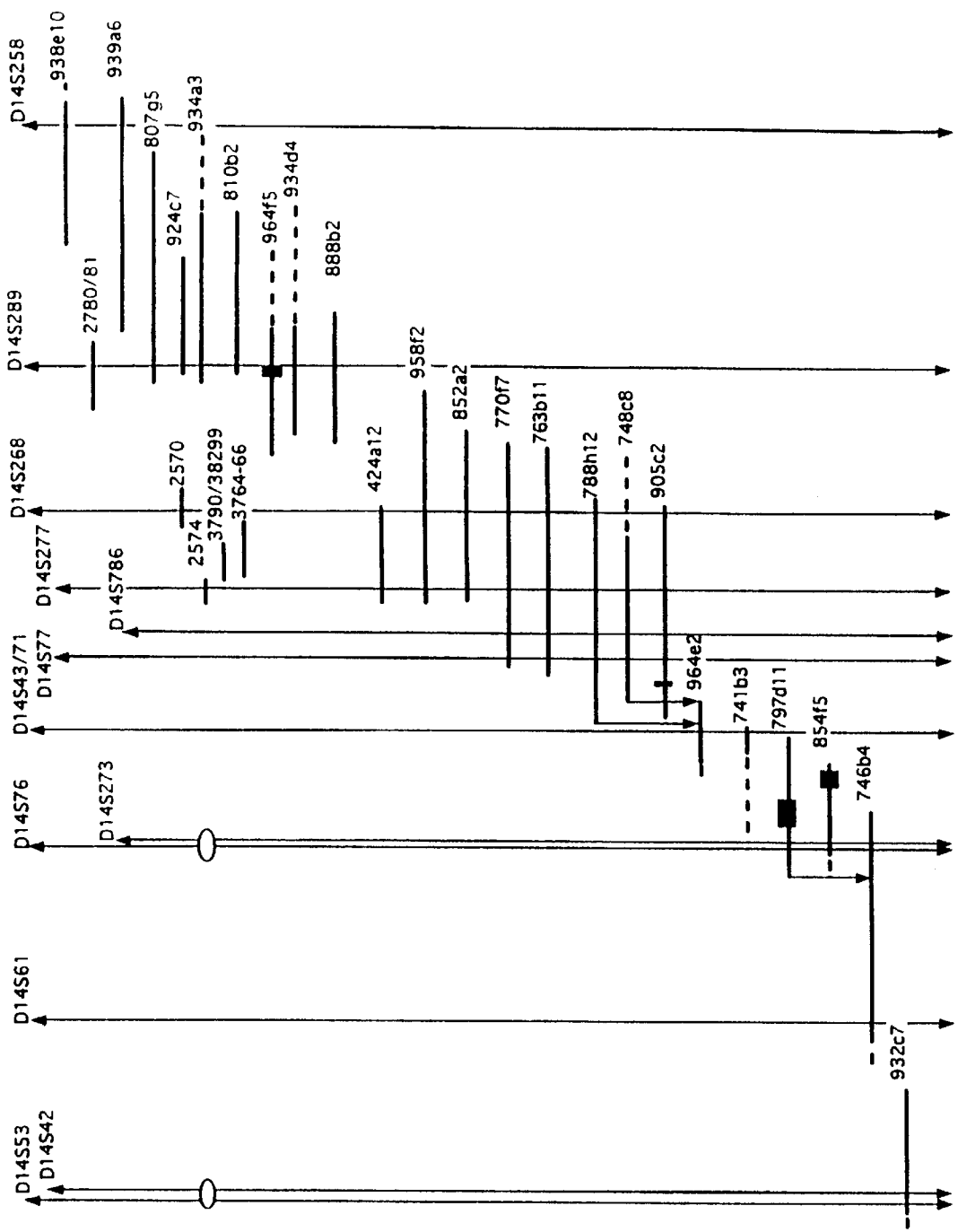
FIG. IB
Approx. Scale: 1 Mb

Met 146 Leu

Ala     246     Glu

Leu 286 Val

Cys 410 Tyr

6,117,978

PRESENILIN-2 AND MUTATIONS THEREOF

CROSS REFERENCE TO RELATED APPLICATIONS

This application is a Divisional of U.S. application Ser. No. 08/967,101, filed Nov. 10, 1997 now U.S. Pat. No. 5,840,540, which is a Divisional of U.S. application Ser. No. 08/592,541, filed Jan. 26, 1996, now U.S. Pat. No. 5,986,054 which is a Continuation-In-Part of U.S. application Ser. No. 08/509,359, filed Jul. 31, 1995, which is a Continuation-In-Part of U.S. application Ser. No. 08/496,841, filed Jun. 28, 1995, which is a Continuation-In-Part of U.S. application Ser. No. 08/431,048, filed Apr. 28, 1995, all of which are incorporated herein by reference.

FIELD OF THE INVENTION

The present invention relates generally to the field of neurological and physiological dysfunctions associated with Alzheimer's Disease. More particularly, the invention is concerned with the identification, isolation and cloning of genes which when mutated are associated with Alzheimer's Disease as well as their transcripts, gene products and associated sequence information and neighbouring genes. The present invention also relates to methods for diagnosing and detecting carriers of the genes, and to Alzheimer's Disease diagnosis and gene therapy using recombinant technologies and therapy using the information derived from the DNA, protein, and the metabolic function of the protein.

BACKGROUND OF THE INVENTION

In order to facilitate reference to various journal articles, a listing of the articles is provided at the end of this specification.

Alzheimer's Disease (AD) is a degenerative disorder of the human central nervous system characterized by progressive memory impairment and cognitive and intellectual decline during mid to late adult life (Katzman, 1986). The disease is accompanied by a constellation of neuropathologic features principal amongst which are the presence of extracellular amyloid or senile plaques and the neurofibrillary degeneration of neurons. The etiology of this disease is complex, although in some families it appears to be inherited as an autosomal dominant trait. However, even amongst these inherited forms of AD, there are at least three different genes which confer inherited susceptibility to this disease (St. George-Hyslop et al., 1990). The ε4 (Cys112Arg) allelic polymorphism of the Apolipoprotein E (ApoE) gene has been associated with AD in a significant proportion of cases with onset late in life (Saunders et al., 1993; Strittmatter et al., 1993). Similarly, a very small proportion of familial cases with onset before age 65 years have been associated with mutations in the β-amyloid precursor protein (APP) gene (Chartier-Harlin et al., 1991; Goate et al., 1991; Murrell et al., 1991; Karlinsky et al., 1992; Mullan et al., 1992). A third locus (AD3) associated with a larger proportion of cases with early onset AD has recently been mapped to chromosome 14q24.3 (Schellenberg et al., 1992; St. George-Hyslop et al., 1992; Van Broeckhoven et al., 1992).

Although chromosome 14q carries several genes which could be regarded as candidate genes for the site of mutations associated with AD3 (e.g. cFOS, alpha-1-antichymotrypsin, and cathepsin G), most of these candidate genes have been excluded on the basis of their physical location outside the AD3 region and/or the absence of mutations in their respective open reading frames (Schellenberg, GD et al., 1992; Van Broeckhoven, C et al., 1992; Rogaev et al., 1993; Wong et al., 1993).

There have been several developments and commercial directions in respect of treatment of Alzheimer's Disease and diagnosis thereof. Published PCT application WO 94 23049 describes transfection of high molecular weight YAC DNA into specific mouse cells. This method is used to analyze large gene complexes, for example the transgenic mice may have increased amyloid precursor protein gene dosage, which mimics the trisomic condition that prevails in Downs Syndrome, and allows the generation of animal models with β-amyloidosis similar to that prevalent in individuals with Alzheimer's Disease. Published international application WO 94 00569 describes transgenic non-human animals harbouring large transgenes such as the transgene comprising a human amyloid precursor protein gene. Such animal models can provide useful models of human genetic diseases such as Alzheimer's Disease.

Canadian Patent application No. 2096911 describes a nucleic acid coding for amyloid precursor protein-cleaving protease, which is associated with Alzheimer's Disease and Down's syndrome. The genetic information may be used to diagnose Alzheimer's Disease. The genetic information was isolated from chromosome 19. Canadian patent application 2071105, describes detection and treatment of inherited or acquired Alzheimer's Disease by the use of YAC nucleotide sequences. The YACs are identified by the numbers 23CB10, 28CA12 and 26FF3.

U.S. Pat. No. 5,297,562, describes detection of Alzheimer's Disease associated with trisomy of chromosome 21. Treatment involves methods for reducing the proliferation of chromosome 21 trisomy. Canadian Patent application No. 2054302 describes monoclonal antibodies which recognize a human brain cell nucleus protein encoded by chromosome 21 and are used to detect changes or expression due to Alzheimer's Disease or Down's Syndrome. The monoclonal antibody is specific to a protein encoded by human chromosome 21 and is found in large pyramidal cells of human brain tissue.

SUMMARY OF THE INVENTION

By extensive effort and a unique approach to investigating the AD3 region of chromosome 14q, the Alzheimer's related membrane protein (ARMP) gene (or presenilin I (PS1) gene has been isolated, cloned and sequenced from within the AD3 region on chromosome 14q24.3. In addition, direct sequencing of RT-PCR products spanning this 3.0 kb cDNA transcript isolated from affected members of at least eight large pedigrees linked to chromosome 14, has led to the discovery of missense mutations in each of these different pedigrees. These mutations are absent in normal chromosomes. It has now been established that the PS1 (or ARMP) gene is causative of familial Alzheimer's Disease type AD3. In realizing this link, it is understood that mutations in this gene can be associated with other cognitive, intellectual, or psychological diseases such as cerebral hemorrhage, schizophrenia, depression, mental retardation and epilepsy. These clinical diagnoses and phenotypes are present in these AD families and these phenotypes have been seen in mutations of the APP protein gene. The Amyloid Precursor Protein (APP) gene is also associated with inherited Alzheimer's Disease. The identification of both normal and mutant forms of the PS1 gene and gene products has allowed for the development of screening and diagnostic tests for PS1 utilizing nucleic acid probes and antibodies to the gene product. Through interaction with the defective gene product and the pathway in which this gene product is involved, gene therapy, therapeutic intervention, manipulation and delivery are not made possible.

A second gene associated with AD has now been identified on human chromosome 1. This gene, the ES-1 or presenilin II (PS2) gene, also has been isolated and cloned. Mutations of this gene have been identified in patients with early onset familial AD. The PS2 (or ES-1) gene and protein have been shown to have high degrees of sequence homology at both the nucleic acid and amino acid sequence levels, and share major structural similarities, including conserved regions, tissue-specific alternative splicing patterns and predicted tertiary structure. Thus, they are believed to be representatives of a new gene family, the presenilins.

Non-human homologues of the PS1 and PS2 genes and proteins have now been identified, isolated and cloned. Amongst those disclosed herein are the murine homologue (PS1) of human PS1, a *C. elegans* member (SEL-12), and a *D. melanogaster* member (DmPS) of the presenilin gene family. Each of these genes and proteins have been identified on the basis of their high degrees of homology to the PS1/PS2 genes.

Various aspects of the invention are summarized as follows. In accordance with a first aspect of the invention, a purified mammalian polynucleotide is provided which codes for Alzheimer's related membrane protein (ARMP) or presenilin I (PS1). The polynucleotide has a sequence which is the functional equivalent of the DNA sequence of ATCC deposit 97124, deposited Apr. 28, 1995. The mammalian polynucleotide may be in the form of DNA, genomic DNA, cDNA, mRNA and various fragments and portions of the gene sequence encoding PS1. The mammalian DNA is conserved in many species, including humans and rodents, for example mice; the DNA is conserved also in all other non-mammalian vertebrates and most invertebrate organisms.

Purified human nucleotide sequences which encode mutant PS1 include those having mutations at nucleotide position (i) 685, A→C (A is replaced by C); (ii) 737, A→G; (iii) 986, C→A, iv) 1105, C→G; (v) 1478, G→A; (vi) 1027, C→T; (vii) 1102, C→T; and (viii) 1422, C→G of SEQ ID NO:1 as well as in the cDNA sequence of a further human clone of a sequence identified by SEQ ID NO:133.

The nucleotide sequences encoding both PS1 and PS2 have an alternative splice form in the gene's open reading frame. The human cDNA sequence which codes for PS1 has SEQ ID NO:1 as well as SEQ ID NO:133 as sequenced in another human clone. The mouse sequence which encodes mPS1 has SEQ ID NO:3, as well as SEQ ID NO:135 derived from a further clone containing the entire coding region. Various DNA and RNA probes and primers may be made from appropriate polynucleotide lengths selected from the sequences. Portions of the sequence also encode antigenic determinants of these presenilins.

Suitable expression vectors comprising the nucleotide sequences are provided along with suitable host cells transfected with such expression vectors.

In accordance with another aspect of the invention, purified mammalian Alzheimer's related membrane protein (ARMP) or presenilin I (PS1) is provided. The purified protein has an amino acid sequence encoded by polynucleotide sequence as identified above which for the human is SEQ ID NO:2 and SEQ ID NO:134 (derived from another clone). The mouse PS1 amino acid sequence is defined by SEQ ID NO:4, the which is translated from another clone containing the entire coding region. The purified protein may have substitution mutations selected from the group consisting of the following positions identified in SEQ ID NO:2 and SEQ ID NO:134: (i) M 146 L; (ii) H 163 R; (iii) A 246 E; (iv) L286 V; (v) C 410 Y; (vi) A 260 V; (vii) A 285 V; and (viii) L 392 V.

In accordance with another aspect of the invention, polyclonal and monoclonal antibodies raised to specific predicted sequences of the presenilin proteins are provided. Polypeptides of at least six amino acid residues are provided. The polypeptides of six or greater amino acid residues may define antigenic epitopes of a presenilin. Monoclonal antibodies having suitably specific binding affinity for the antigenic regions of a presenilin are prepared by use of corresponding hybridoma cell lines. In addition, other polyclonal antibodies may be prepared by inoculation of animals with suitable peptides or holoprotein which add suitable specific binding affinities for antigenic regions of a presenilin.

In accordance with another aspect of the invention, an isolated DNA molecule is provided which codes for E5-1 protein.

In accordance with another aspect of the invention, purified PS2 protein is provided, having amino acid SEQ ID NO:137.

In accordance with another aspect of the invention a bioassay is provided for determining if a subject has a normal or mutant PS1 or PS2, where the bioassay comprises providing a biological sample from the subject, conducting a biological assay on the sample to detect a normal or mutant gene sequence coding for PS1 or PS2, a normal or mutant PS1 or PS2 amino acid sequence, or a normal or defective protein function.

In accordance with another aspect of the invention, a process is provided for producing PS1 or PS2 comprising culturing one of the above described transfected host cells under suitable conditions, to produce the presenilin by expressing the DNA sequence. Alternatively, a PS1 or PS2 protein may be isolated from mammalian cells in which the presenilin is normally expressed.

In accordance with another aspect of the invention, is a therapeutic composition comprising PS1 or PS2 and a pharmaceutically acceptable carrier.

In accordance with another aspect of the invention, a recombinant vector for transforming a mammalian tissue cell to express therapeutically effective amounts of PS1 or PS2 in the cells is provided. The vector is normally delivered to the cells by a suitable vehicle. Suitable vehicles include vaccinia virus, adenovirus, adenoassociated virus, retrovirus, liposome transport, neuraltropic viruses, Herpes simplex virus and other vector systems.

In accordance with another aspect of the invention, a method of treating a patient deficient in normal PS1 or PS2 comprising administering to the patient a therapeutically effective amount of the protein targeted at a variety of patient cells which normally express the presenilin. The extent of administration of normal PS1 or PS2 being sufficient to override any effect the presence of the mutant presenilin may have on the patient. As an alternative to protein, suitable ligands and therapeutic agents such as small molecules and other drug agents may be suitable for drug therapy designed to replace the protein and defective presenilin, displace mutant presenilin, or to suppress its formation.

In accordance with another aspect of the invention, an immunotherapy for treating a patient having Alzheimer's Disease comprises treating the patient with antibodies specific to the mutant presenilin to reduce biological levels or activity of the mutant protein in the patient. To facilitate such amino acid therapy, a vaccine composition may be provided for evoking an immune response in a patient of Alzheimer's Disease where the composition comprises a mutant PS1 and a pharmaceutically acceptable carrier with or without a suitable excipient. The antibodies developed specific to the mutant PS1 could be used to target appropriately encapsulated drugs/molecules, specific cellular/tissue sites. Therapies utilizing specific ligands which bind to normal or wild type PS1 and which augment normal function of PS1 in membranes and/or cells or inhibits the deleterious effect of the mutant protein are also made possible.

In accordance with another aspect of the invention, a transgenic animal model for Alzheimer's Disease which has the mammalian polynucleotide sequence with at least one mutation which when expressed results in mutant PS1 or PS2 in the animal cells and thereby manifests a phenotype. For example, the human Prion gene when over-expressed in rodent peripheral nervous system and muscle cells causes a quite different response in the animal than the human. The animal may be a rodent and is preferably a mouse, but may also be other animals including rat, pig, *D. melanogaster, C. elegans* (nematode), all of which are used for transgenic models. Yeast cells can also be used in which a presenilin sequence is expressed from an artificial vector.

In accordance with another aspect of the invention a transgenic mouse model for Alzheimer's Disease has the mouse gene encoding a human or murine PS1 or PS2 homologue mutated to manifest the symptoms. The transgenic mouse may exhibit symptoms of cognitive memory low or behavioural disturbances. In addition or alternatively, the symptoms may appear as another cellular tissue disorder such as in mouse liver, kidney, spleen, bone marrow or other organs in which the presenilin gene product is normally expressed.

In accordance with another aspect of the invention, the presenilin proteins and nucleic acids may be used in the screening of small molecules which will be candidates for drug therapy of Alzheimer's and related diseases. In one series of embodiments, small molecules may be screened for their ability to bind to a presenilin, especially human PS1 or PS2. In particular, assays are provided which may be used to identify small molecules which will bind selectively or preferentially to either the normal or mutant forms of PS1 or PS2. Such small molecules may be further tested using the animal models disclosed mergon to further evaluate their therapeutic utility. In another series of embodiments, compounds may be tested for their ability to induce or repress expression of the presenilins, especially human PS1 or PS2. Thus, assays are provided in which the ability of a compound to alter the levels of presenilin mRNA transcripts or protein in a cell or cell culture is tested. In preferred embodiments, the 5' regulatory region of a presenilin gene, especially a human PS1 or PS2 gene, are operatively joined to a reporter gene and cells are transformed with this recombinant construct. Such recombinant cells may then be used in high through-put assays for compounds which affect the expression of the presenilins.

In accordance with another aspect of the invention, the proteins of the invention can be used as starting points for rational drug design to provide ligands, therapeutic drugs or other types of small chemical molecules. Alternatively, small molecules or other compounds identified by the above-described screening assays may serve as "lead compounds" in rational drug design.

DETAILED DESCRIPTION OF THE INVENTION

Various aspects of the invention are described hereinafter with respect to the drawings where:

FIG. 1, panel A is a schematic drawing of the genomic physical and transcriptional map of the AD3 region of chromosome 14. Genetic map inter-marker genetic distances averaged for male and female meiosis are indicated in centiMorgans.

FIG. 1, panel B is a schematic drawing of the constructed physical contig map of overlapping genomic DNA fragments cloned into YACs spanning a FAD locus on chromosome 14q.

FIG. 1, panel C is a schematic drawing of regions of interest within the constructed physical contig map.

FIG. 1, panel D is a schematic drawing of a transcriptional map illustrating physical locations of the 19 independent longer cDNA clones.

FIG. 2, panel A is a reproduction of the output of an automated fluorescent chromatogram representing the change in nucleic acids which direct the Met 146 Leu change in the amino acid sequence of the ARMP or PS1 gene.

FIG. 2, panel B is a reproduction of the output of an automated fluorescent chromatogram representing the change in nucleic acids which direct the His 163 Ala change in the amino acid sequence of the gene.

FIG. 2, panel C is a reproduction of the output of an automated fluorescent chromatogram representing the change in nucleic acids which direct the Ala 246 Glu change in the amino acid sequence of the gene.

FIG. 2, panel D is a reproduction of the output of an automated fluorescent chromatogram representing the change in nucleic acids which direct the Leu 286 Val change in the amino acid sequence of the gene.

FIG. 2, panel E is a reproduction of the output of an automated fluorescent chromatogram representing the change in nucleic acids which direct the Cys 410 Tyr change in the amino acid sequence of the gene.

FIG. 3, panel A is a representation of a hydropathy plot of the putative PS1 protein.

FIG. 3, panel B is a schematic drawing of a model for the structural organization of the putative PS1 protein. Roman numerals depict the transmembrane domains. Putative glycosylation sites are indicated as asterisks and most of the phosphorylation sites are located on the same membrane face as the two acidic hydrophilic loops. The MAP kinase site is present at residue 115 and the PKC site at residue 114. FAD mutation sites are indicated by horizontal arrows.

DESCRIPTION OF THE PREFERRED EMBODIMENTS

Figure 2A:
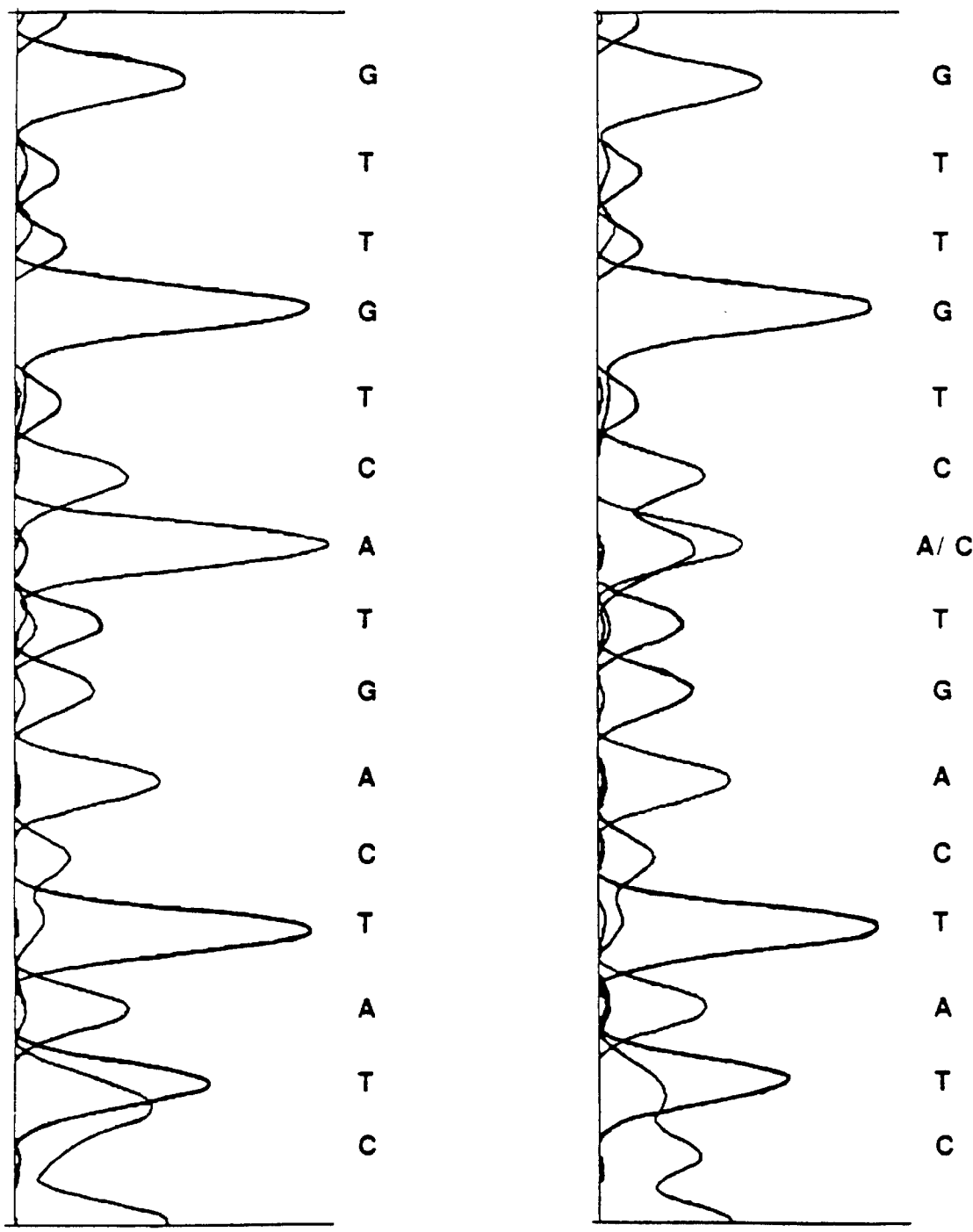
Figure 2B:
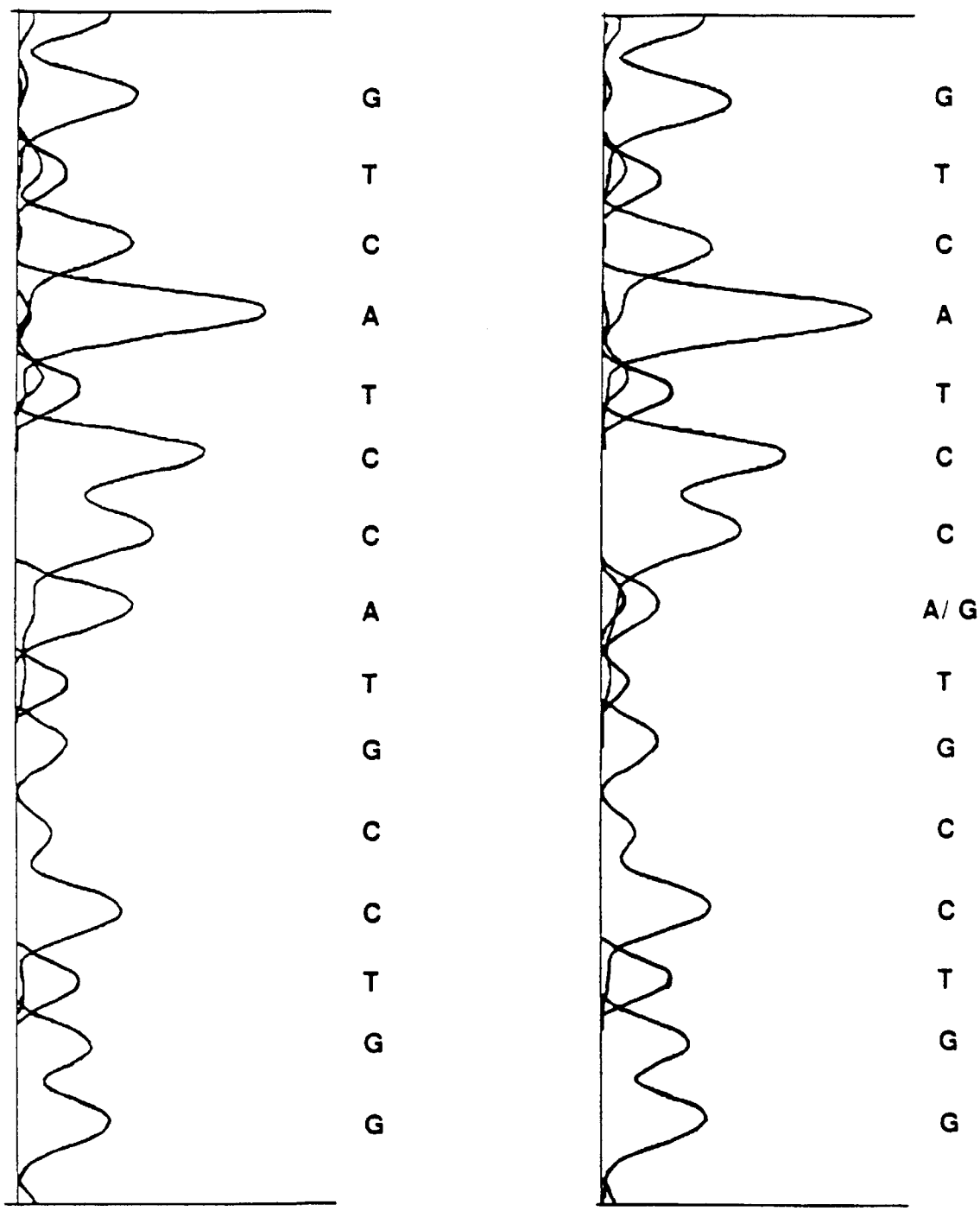
Figure 2C:
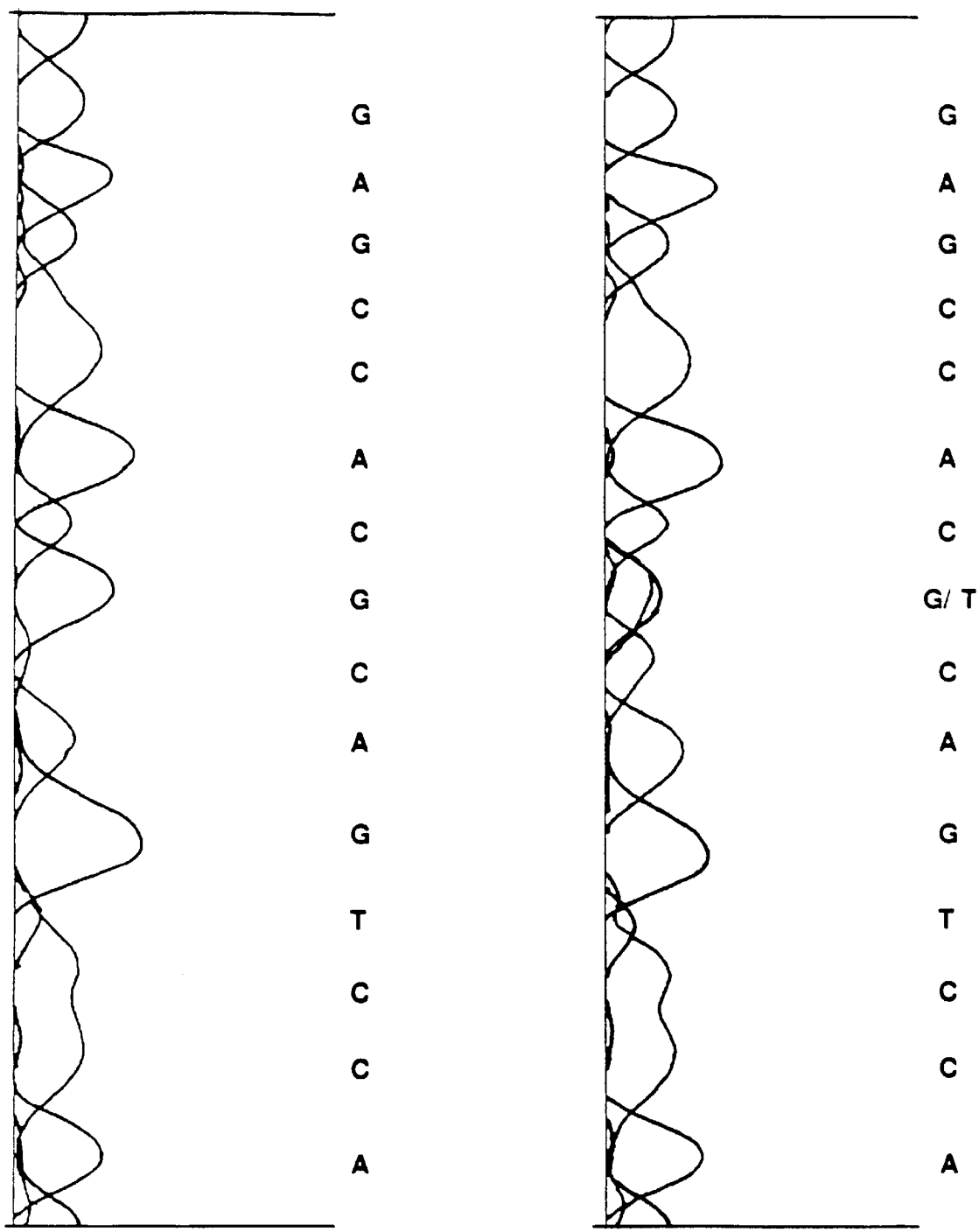
Figure 2D:
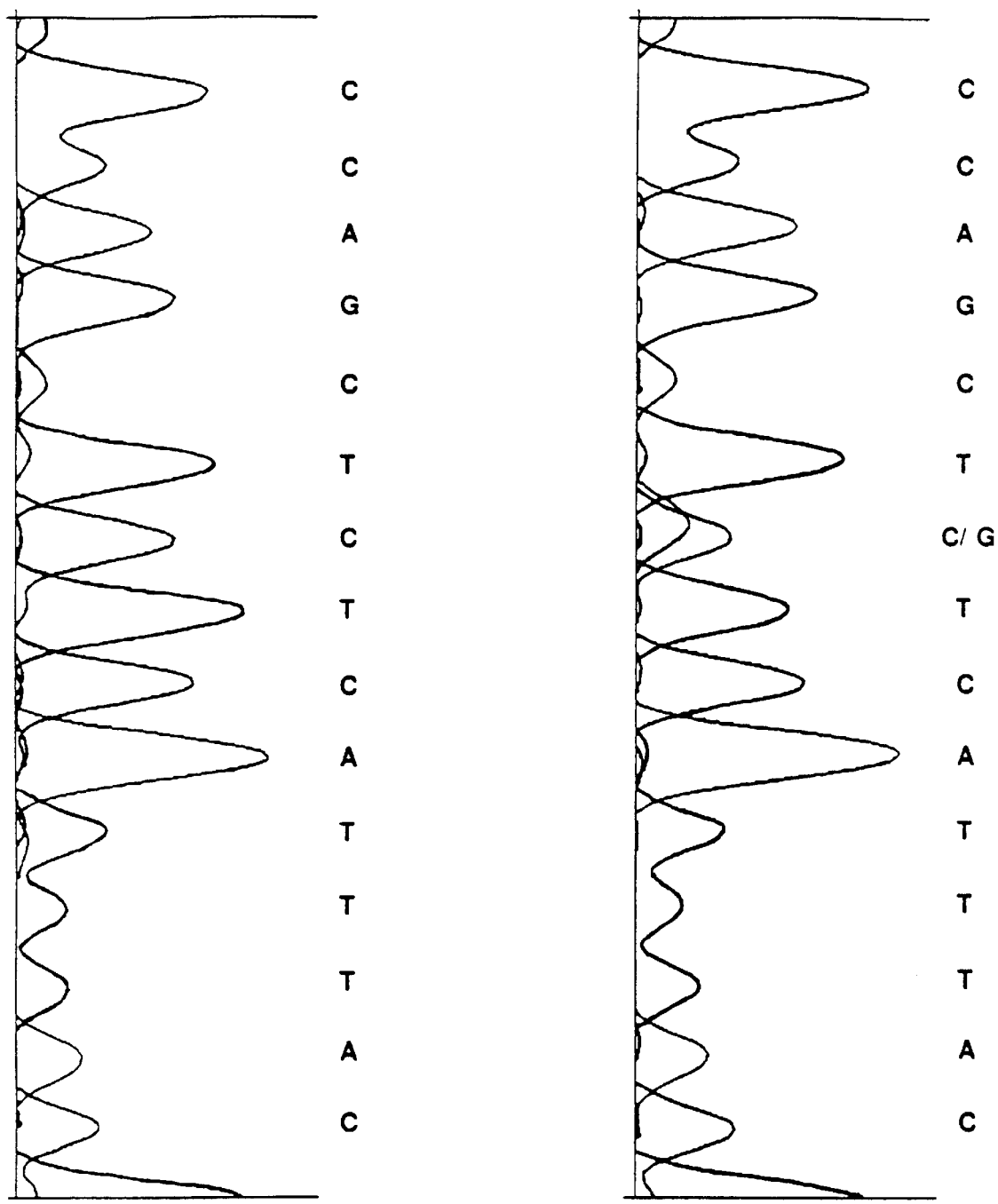
Figure 2E:
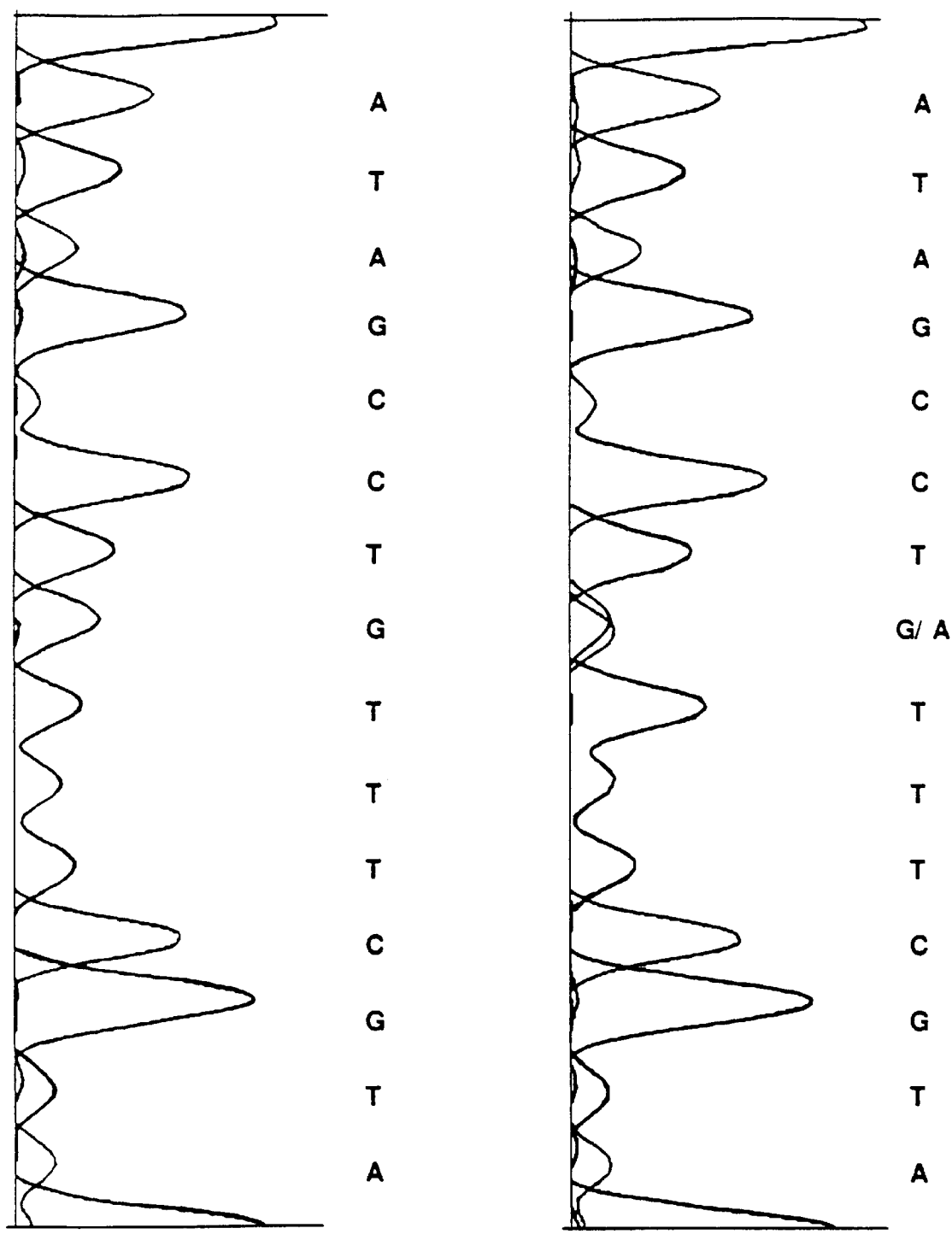

In order to facilitate review of the various embodiments of the invention and an understanding of the various elements and constituents used in making and using the invention, the following terms use din the invention description have the following meanings.

Alzheimer Related Membrane Protein (ARMP) or Presenilin-I (PS1) gene—the chromosome 14 gene which when mutated is associated with familial Alzheimer's Disease and/or other inheritable disease phenotypes (e.g. cerebral hemorrhage, mental retardation, schizophrenia, psychosis, and depression). This definition is understood to include sequence polymorphisms wherein nucleotide substitutions in the gene sequence do not affect the essential function of the gene product, as well as functional equivalents of the nucleotide sequences of SEQ ID NO:1, SEQ ID NO:133, and SEQ ID NO:5. This term primarily relates to an isolated coding sequence, but can also include some or all of the flanking regulatory elements and/or introns. The term PS1 gene includes genes in other species analogous to this human gene which when mutated is associated with Alzheimer's Disease. This gene is also referred to as the ARMP gene, and sometimes as the S182 gene.

Alzheimer Related Membrane Protein (ARMP) or Presenilin-I Protein—the protein encoded by the PS1 gene. This protein is also referred to as ARMP. The preferred source of protein is the mammalian protein as isolated from human or other animal cells. Alternatively, functionally equivalent proteins may exist in plants, insects and invertebrates (such as *C. elegans*). The protein may be produced by recombinant organisms, or chemically or enzymatically synthesized. This definition is understood to include the amino acid sequences of SEQ ID NO:2 and SEQ ID NO:134 and also the various polymorphic forms of the protein wherein amino acid substitutions or deletions within the amino acid sequence do not affect the essential functioning of the protein. The term also includes functional fragments of PS1 and functional equivalents of the PS1 amino acid sequence.

Mutant PS1 gene—The PS1 gene containing one or more mutations which typically lead to Alzheimer's Disease and/or other inheritable disease phenotypes (e.g. cerebral hemorrhage, mental retardation, schizophrenia, psychosis, and depression). This definition is understood to include the various mutations that exist, wherein nucleotide substitutions in the gene sequence affect the essential function of the gene product, as well as mutations of functional equivalents of the nucleotide sequences of SEQ ID NO:1, SEQ ID NO:133 and ID NO:5. This term primarily relates to an isolated coding sequence, but can also include some or all of the flanking regulatory elements and/or introns.

Mutant PS1—a mammalian protein that is highly analogous to PS1 in terms of primary structure, but wherein one or more amino acid insertions, deletions and/or substitutions result in impairment of its essential function, so that mammals, especially humans, whose PS1 producing cells express mutant PS1 rather than the normal PS1, are predisposed to demonstrate the symptoms of Alzheimer's Disease and/or other relevant inheritable phenotypes (e.g. cerebral hemorrhage, mental retardation, schizophrenia, psychosis, and depression).

mPS1 gene—mouse gene analogous to the human PS1 gene. This definition is understood to include sequence polymorphisms wherein nucleotide substitutions in the gene sequence do not affect the essential function of the gene product, as well as functional equivalents of the nucleotide sequence of SEQ ID NO:135. This term primarily relates to an isolated coding sequence, but can also include some or all of the flanking regulatory elements and/or introns.

mPS1—mouse Alzheimer related membrane protein, encoded by the mPS1 gene and analogous to the human PS1. This definition is understood to include the amino acid sequence of SEQ ID NO:134 and also the various polymorphic forms of the protein wherein amino acid substitutions, insertions, or deletions within the amino acid sequence do not affect the essential functioning of the protein. The term also includes functional fragments of the protein and functional equivalents of its amino acid sequence.

Mutant mPS1 gene—the mPS1 gene containing one or more mutations which typically lead to one or more amino acid insertions, deletions and/or substitutions resulting in impairment of the function of the mPS1 protein. This definition is understood to include the amino acid sequence of SEQ ID NO:134 and also the various polymorphic forms of the protein wherein amino acid substitutions or deletions within the amino acid sequence do not affect the essential functioning of the protein. The term also includes functional fragments of the protein and functional equivalents of its amino acid sequence.

Mutant mPS1—a mouse protein which is highly analogous to mPS1 in terms of primary structure, but wherein one or more amino acid insertions, deletions and/or substitutions result in impairment of its essential function, so that mice, whose mPS1 producing cells express mutant mPS1 rather than the normal mPS1, are predisposed to demonstrate the symptoms of Alzheimer's Disease and/or other relevant inheritable phenotypes, or other phenotypes and behaviours as manifested in mice.

PS1 or PS2 carrier—a mammal in apparent good health whose chromosomes contain a mutant PS1 or PS2 gene that may be transmitted to offspring and which will, in most cases, develop Alzheimer's Disease in mid to late adult life.

Missense mutation—A mutation of nucleic acid sequence which alters a codon to that of another amino acid, causing an altered translation product to be made.

Pedigree—In human genetics, a diagram showing the ancestral relationships and transmission of genetic traits over several generations in a family.

PS2 gene—the chromosome 1 gene which shows homology to the PS1 gene and which when mutated is associated with familial Alzheimer's Disease and/or other inheritable disease phenotypes. This definition is understood to include sequence polymorphisms wherein nucleotide substitutions in the gene sequence do not affect the essential function of the gene product, as well as functional equivalents of the nucleotide SEQ ID NO:136. This term primarily relates to an isolated coding sequence, but can also include some or all of the flanking regulatory elements and/or intros. This term also includes the gene in other species analogous to the human gene described herein. This gene is also referred to as the E5-1 gene.

PS2 protein—the protein encoded by the PS2 gene. This protein is also referred to as E5-1. The term PS2 protein includes the protein of SEQ ID NO:137 and also the various polymorphic and splice variant forms of the protein wherein amino acid substitutions or deletions within the amino acid sequence do not affect the essential functioning of the protein. The term also includes functional fragments of the protein and functional equivalents of its amino acid sequence.

Mutant PS2 gene—the PS2 gene containing one or more mutations which typically lead to Alzheimer's Disease. This term is understood to include the various mutations that exist, wherein nucleotide substitutions, insertions, or deletions in the gene sequence affect the essential function of the gene product. This term primarily relates to an isolated coding sequence but can also include some or all of the flanking regulatory elements and/or introns.

Mutant PS2 protein—a protein analogous to PS2 protein but wherein one or more amino acid insertions, deletions and/or substitutions result in impairment of its essential function such that mammals, especially humans, whose PS2-producing cells express mutant PS2 protein, are predisposed to demonstrate the symptoms of Alzheimer's Disease.

DmPS gene—*Drosophila melanogaster* gene analogous to the human PS1 and PS2 genes. This definition is understood to include the amino acid sequence polymorphisms wherein nucleotide substitutions, insertions or deletions in the gene sequence do not affect the essential function of the gene product, as well as functional equivalents of the nucleotide sequence, SEQ ID NO:165. This term primarily relates to an isolated coding sequence but can also include some or all of the flanking regulatory elements and/or introns.

DmPS protein—The protein encoded by the DmPS gene and analogous to the human presenilins. This definition is understood to include the amino acid sequence of SEQ ID NO:166 and also the various polymorphic forms of the protein wherein amino acid substitutions, insertions or deletions within the amino acid sequence do not affect the essential functioning of the protein. The term also includes functional fragments of the protein and functional equivalents of its amino acid sequence.

Mutant DmPS Gene—the DmPS gene containing one or more mutations which lead to one or more amino acid insertions, deletions and/or substitutions resulting in impairment of the function of the DmPS protein.

Mutant DmPS Protein—a *D. melanogaster* protein which is highly analogous to DmPS protein in terms of primary structure, wherein one or more amino acid insertions, deletions and/or substitutions result in impairment of its essential function.

Functional Equivalent—as used in describing gene sequences and amino acid sequences means that a recited sequence need not be identical to the definitive sequence of the SEQ ID NOs but need only provide a sequence which functions biologically and/or chemically as the equivalent of the definitive sequence. Hence sequences which correspond to a definitive sequence may also be considered as functionally equivalent sequence.

Linkage analysis—Analysis of co-segregation of a disease trait or disease gene with polymorphic genetic markers of defined chromosomal location.

hPS1 gene—human PS1 gene
ORF—open reading frame
PCR—polymerase chain reaction
contig—contiguous cloned regions
YAC—yeast artificial chromosome
RT-PCR—reverse transcription polymerase chain reaction.
SSR—Simple sequence repeat polymorphism.

Homology—typically measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various insertions, deletions, substitutions, and other modifications. Conservative substitutions typically include substitutions within the following groups: glycine, alanine; valine, isoleucine; leucine; aspartic acid, glutamic acid, asparagine, glutamine; serine, threonine; lysine, arginine; and phenylalanine, tyrosine.

Percent Identity—is a measure of the identity of any two amino acid or nucleic acid sequences over a defined length.

Protein and polypeptide—any chain of amino acids, regardless of length or post-translational modification (e.g., glycosylation or phosphorylation).

Substantially pure preparation—is a preparation which is at least 60% by weight (dry weight) the compound of interest. Preferably the preparation is at least 75%, more preferably at least 90%, and most preferably at least 99%, by weight the compound of interest. Purity can be measured by any appropriate method, e.g., column chromatography, polyacrylamide gel electrophoresis, or HPLC analysis.

Isolated DNA—is DNA that is not immediately contiguous with both of the coding sequences with which it is immediately contiguous (one on the 5' end and one on the 3' end) in the naturally occuring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA which is part of a hybrid gene encoding additional polypeptide sequence.

Substantially identical amino acid sequence—is an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein (assayed, e.g., as described herein). Preferably, such a sequence is at least 85%, more preferably 90%, and most preferably 95% identical at the amino acid level to the sequence of the protein or peptide to which it is being compared. For nucleic acids, the length of comparison sequences will generally be at least 50 nucleotides, preferably at least 60 nucleotides, more preferably at least 75 nucleotides, and most preferably 110 nucleotides. A "substantially identical" nucleic acid sequence codes for a substantially identical amino acid sequence as defined above.

Transformed cell—is a cell into which (or into an ancestor of which) has been introduced, by means of recombinant DNA techniques, a DNA molecule encoding a protein of interest.

Operably Joined. A coding sequence and a regulatory region are said to be operably joined when they are covalently linked in such a way as to place the expression or transcription of the coding sequence under the influence or control of the regulatory region. If it is desired that the coding sequences be translated into a functional protein, two DNA sequences are said to be operably joined if induction of promoter function results in the transcription of the coding sequence and if the nature of the linkage between the two DNA sequences dose not (1) result in the introduction of a frame-shift mutation, (2) interfere with the ability of the regulatory region to direct the transcription of the coding sequences, or (3) interfere with the ability of the corresponding RNA transcript to be translated into a protein. Thus, a regulatory region would be operably joined to a coding sequence if the regulatory region were capable of effecting transcription of that DNA sequence such that the resulting transcript might be translated into the desired protein or polypeptide.

Stringent Hybridization Conditions. Stringent hybridization conditions is a term of art understood by those of ordinary skill in the art. For any given nucleic acid sequence, stringent hybridization conditions are those conditions of temperature and buffer solution which will permit hybridization of that nucleic acid sequence to its complementary sequence and not to substantially different sequences. The exact conditions which constitute "stringent" conditions, depend upon the length of the nucleic acid sequence and the frequency of occurrence of subsets of that sequence within other non-identical sequences. By varying hybridization conditions from a level of stringency at which no hybridization occurs to a level at which hybridization is first observed, one of ordinary skill in the art can, without undue experimentations, determine conditions which will allow a given sequence to hybridize only with identical sequences. Suitable ranges of such stringency conditions are described in Krause, M. H., and S. A. Aaronson, *Methods in Enzymology,* 200:546–556 (1991). Stringent hybridization conditions, depending upon the length and commonality of a sequence, may include hybridization conditions of 30 C.–60 C. and from 5× to 0.1× SSC. Highly stringent hybridization conditions may include hybridization at 45 C. and 0.1× SSC. Less than stringent hybridization conditions are employed to isolate nucleic acid sequences which are substantially similar, allelic or homologous to any given sequence.

Purified antibody—is an antibody which is at least 60%, by weight, free from the proteins and naturally-occurring organic molecules with which it is naturally associated. Preferably, the preparation is at least 75%, more preferably at least 90%, and most preferably at least 99%, by weight, antibody.

Specifically binds—means an antibody which recognizes and binds the protein of interest but which does not substantially recognize and bind other molecules in a sample, e.g., a biological sample, which naturally includes the protein of interest.

The present invention is concerned with the identification and sequencing of the mammalian ARMP or presenilin I gene in order to gain insight into the cause and etiology of Alzheimer's Disease, and to provide screening methods and therapies for the diagnosis and treatment of the disease can be developed. The gene has been identified, cDNA isolated and cloned, and its transcripts and gene products identified and sequenced. During such identification of the gene, considerable sequence information has also been developed on intron information in the PS1 gene, flanking untranslated information and signal information and information involving neighbouring genes in the AD3 chromosome region. Direct sequencing of overlapping RT-PCR products spanning the human gene isolated from affected members of large pedigrees linked to chromosome 14 has led to the discovery of missense mutations which co-segregate with the disease.

Although it is generally understood that Alzheimer's Disease is a neurological disorder, most likely in the brain, expression of PS1 has been found in a variety of human tissues such as heart, brain, placenta, lung, liver, skeletal muscle, kidney and pancreas. Although this gene is expressed widely, the clinically apparent phenotype exists in brain although it is conceivable that biochemical phenotypes may exist in these other tissues. As with other genetic diseases such as Huntington's Disease and APP—Alzheimer's, the clinical disease manifestation may reflect the different biochemistries of different cell types and tissues (which stem from genetics and the protein). Such findings suggest that AD may not be solely a neurological disorder but may also be a systemic disorder, hence requiring alternative therapeutic strategies which may be targeted to other tissues or organs or generally in addition or separately from neuronal or brain tissues.

The PS1 mutations identified have been related to Alzheimer's Disease pathology. With the identification and sequencing of the gene and the gene product, probes and antibodies raised to the gene product can be used in a variety of hybridization and immunological assays to screen for and detect the present of either a normal or mutated gene or gene product.

Patient therapy through removal or blocking of the mutant gene product, as well as supplementation with the normal gene product by amplification, by genetic and recombinant techniques or by immunotherapy can now be achieved. Correction or modification of the defective gene product by protein treatment immunotherapy (using antibodies to the defective protein) or knock-out of the mutated gene is now also possible. Familial Alzheimer's Disease could also be controlled by gene therapy in which the gene defect is corrected in situ or by the use of recombinant or other vehicles to deliver a DNA sequence capable of expressing the normal gene product, or a deliverately mutated version of the gene product whose effect counterbalances the deleterious consequences of the disease mutation to the affected cells of the patient.

The present invention is also concerned with the identification and sequencing of a second human gene, the PS2 or presenilin II gene on chromosome 1, which is associated with Alzheimer's Disease.

Disease mechanism insights and therapies analogous to those described above in relation to the PS1 gene also are nonavailable as a result of the identification and isolation of the PS2 gene.

A homologue of the human presenilin I gene, mPS1, has been identified in mice and has been cloned and sequenced. Additionally, a homologue of the human presenilin genes, DmPS1, has been identified in *D. melanogaster* and its sequence determined.

The remainder of the "Description of the Preferred Embodiments" is organized as follows.
1. Isolation of the Human PS1 (ARMP) Gene
   a. Genetic mapping of the AD3 locue
   b. Construction of a physical contig spanning the AD3 Region
   c. Transcription mapping and preliminary analysis of candidate genes
   d. Recovery of potential candidate genes
2. Characterization of the Human PS1 (ARMP) Gene
3. Identification of an alternate splice form of the PS1 (ARMP) gene product
4. Functional Domains of PS1 Protein
5. PS1 (ARMP) Protein
6. Mutations in the S182 (PS1) transcript
7. Isolation and Purification of PS1 (ARMP) Protein
8. Expression of PS1 (ARMP)
9. Antibodies to PS1 (ARMP)
10. Isolation of the Murine PS1 Gene
11. Transgenic Mouse Model of Alzheimer's Disease
12. Isolation of the Human PS2 (E5-1) Gene—A Homologue of the PS1 Gene
13. Mutations of the PS2 (E5-1) Gene associated with Alzheimer's Disease
14. PS2 (E5-1) Protein
15. Isolation and Purification of PS2 (ARMP) Protein
16. Antibodies to PS2 (E5-1)
17. Transgenic Mouse Model of PS2 (E5-1)-related Alzheimer's Disease 18. Functional Domains of Presenilins
19. Isolation of Presenilin Binding Proteins
   a. direct extraction by affinity chromatography using GST-fusion proteins and synthetic peptides
   b. co-isolation of presenilins and bound proteins by immunoprecipitation
   c. Biomolecular Interaction Assay (BIAcore) utilizing a GST-fusion capture system
   d. Two-Hybrid yeast systems
20. Identification of Small Molecules with Presenilin Binding Capacity
21. Assays for identifying Drugs Which Affect Presenilin Expression
22. Identification of a homologue of the ARMP (PS1) gene in C. elegans
23. Identification of a homologue of the PS1 (ARMP) gene in D. melanogaster
24. Screening for and Diagnosis of Alzheimer's Disease
   a. General diagnostic Methods
   b. Screening for Alzheimer's Disease Linked to Chromosome 14
   c. Screening for Alzheimer's Disease Linked to Chromosome 1
25. Therapies
   a. Rationale for Therapeutic, Diagnostic, and Investigational Applications of the PS1 and PS2 Genes and Gene Products as they Relate to the Amyloid Precursor Protein
   b. Rationale for Therapeutic, Diagnostic, and Investigational Applications of the PS1 and PS2 Genes and the Products Thereof
   c. Protein Therapy
   d. Gene Therapy
26. EXAMPLES
   a. Example 1: Development of the genetic, physical, "contig" and transcriptional map of the minimal co-segregating region
   b. Example 2: Cumulative two point lod scores for chromosome 14q24.3 markers
   c. Example 3: Haplotypes between flanking markers segregated with AD3 in FAD pedigrees
   d. Example 4: Recovery of transcribed sequences from the AD3 interval
   e. Example 5: Locating mutations in the ARMP (PS1) gene using restriction enzymes
   f. Example 6: Locating mutations in the ARMP (PS1) gene using allele specific oligonucleotides
   g. Example 7: Northern hybridization demonstrating the expression of ARMP (PS1) mRNA in a variety of tissues
   h. Example 8: Eukaryotic and prokaryotic expression vector systems
   i. Example 9: Locating additional mutations in the ARMP (PS1) gene
   j. Example 10: Antibody production
   k. Example 11: Identification of mutations in the (PS2) E5-1 gene
   l. Example 12: Transgenic Mice
   m. Example 13: Expression of Recombinant PS1 and PS2 in Eukaryotic Cells
   n. Example 14: Isolation of Presenilin Binding Proteins by Affinity Chromatography
   o. Example 15: Isolation of Presenilin Biding Proteins by Two-Hybrid Yeast System
   p. Example 16: Transgenic C. elegans
   q. Example 17: Cloning of a Drosophila melanogaster homologue, DmPS, for the Human Presenilin Genes Isolation of the Human PS1 (ARMP) Gene Genetic mapping of the AD3 locus After the initial regional mapping of the AD3 gene locus to 14q24.3 near the anonymous microsatellite markers D14S43 and D14S53 (Schellenberg, GD et al., 1992; St George-Hyslop. P et al., 1992: Van Broeckhoven. C et al., 1992), twenty one pedigrees were used to segregate AD as a putative autosomal dominant trait (St George-Hyslop, P et al., 1992) and to investigate the segregation of 18 additional genetic markers from the 14q24.3 region which had been organized into a high density genetic linkage map (FIG. 1B) (Weissenbach et al., 1992; Gyapay et al., 1994). Pairwise maximum likelihood analyses previously published confirmed substantial cumulative evidence for linkage between familial Alzheimer's Disease (FAD) and all of these markers (Table 1). However, much of the genetic data supporting linkage to these markers were derived from six large early onset pedigrees, FAD1 (Nee et al., 1983), FAD2 (Frommelt et al., 1991), FAD3 (Goudsmit et al., 1981; Pollen, 1993), FAD4 (Foncin et al., 1985), TOR1.1 (Bergamini, 1991) and 603 (Pericak-Vance et al., 1988) each of which provides at least one anonymous genetic marker from 14q24.3 (St. George-Hyslop, P. et al 1992).

In order to define more precisely the location of the AD3 gene relative to the known locations of the genetic markers from 14q24.3, recombinational landmarks were sought by direct inspection of the raw haplotype data from those genotyped affected members of the six pedigrees showing definitive linkage to chromosome 14. This selective strategy in this particular instance necessarily discards data from the reconstructed genotypes of deceased affected members as well as from elderly asymptomatic members of the large pedigrees, and takes no account of the smaller pedigrees of uncertain linkage status. However, this strategy is very sound because it also avoids the acquisition of potentially misleading genotype data acquired either through errors in the reconstructed genotypes of deceased affected members arising from non-paternity or sampling errors or from the inclusion of unlinked pedigrees.

Upon inspection of the haplotype data for affected subjects, members of the six large pedigrees whose genotypes were directly determined revealed obligate recombinants at D14S48 and D14S53, and at D14S258 and D14S63. The single recombinant at D14S53, which depicts a telomeric boundary for the FAD region, occurred in the same AD affected subject of the FAD1 pedigree who had previously been found to be recombinant at several other markers located telomeric to D14S53 including D14S48 (St George-Hyslop, P et al., 1992). conversely, the single recombinant at D14S258, which marks a centromeric boundary of the FAD region, occurred in an affected member of the FAD3 pedigree who was also recombinant at several other markers centromeric to D14S258 including D14S63. Both recombinant subjects had unequivocal evidence of Alzheimer's Disease confirmed through standard clinical tests for the illness in other affected members of their families, and the genotype of both recombinant subjects was informative and co-segregating at multiple loci within the interval centromeric to D14S53 and telomeric to D14S258.

When the haplotype analyses were enlarged to include the reconstructed genotypes of deceased affected members of the six large pedigrees as well as data from the remaining fifteen pedigrees with probabilities for linkage of less than 0.95, several additional recombinants were detected at one or more marker loci within the interval between D14S53 and D14S258. Thus, one additional recombinant was detected in the reconstructed genotype of a deceased affected member of each of three of the larger FAD pedigrees (FAD1, FAD2 and other related families), and eight additional recombinants were detected in affected members of five smaller FAD pedigrees. However, while some of these recombinants might have correctly placed the AD3 gene within a more defined target region, it was necessary to regard these potentially closer "internal recombinants" as unreliable not only for the reasons discussed earlier, but also because they provided mutually inconsistent locations for the AD3 gene within the D14S53–D14S258 interval.

Construction of a physical contig spanning the AD3 region

As an initial step towards cloning the AD3 gene, a contig of overlapping genomic DNA fragments cloned into yeast artificial chromosome vectors, phage artificial chromosome vectors and cosmid vectors was constructed (FIG. 1B). FISH mapping studies using cosmids derived from the YAC clones 932c7 and 964f5 suggested that the interval most likely to carry the AD3 gene was at least five megabases in size. Because the large size of this minimal co-segregating region would make positional cloning strategies intractable, additional genetic pointers were sought which focused the search for the AD3 gene to one or more subregions within the interval flanked by D14S53 and D14S258. Haplotype analyses at the markers between D14S53 and D14S258 failed to detect statistically significant evidence for linkage disequilibrium and/or allelic association between the FAD trait and alleles at any of these markers, irrespective of whether the analyses were restricted to those pedigrees with early onset forms of FAD, or were generalized to include all pedigrees. This result was not unexpected given the diverse ethnic origins of our pedigrees. However, when pedigrees of similar ethnic descent were collated, direct inspection of the haplotypes observed on the disease-bearing chromosome segregating in different pedigrees of similar ethnic origin revealed two clusters of marker loci (Table 2). The first of these clusters located centromeric to D14S77 (D14S786, D14S277 and D14S268) and spanned the 0.95 Mb physical interval contained in YAC 78842 (depicted as region B in FIG. 1C). The second cluster was located telomeric to D14S77 (D14S43, D14S273, and D14S76) and spanned the ~1 Mb physical interval included within the overlapping YAC clones 964c2, 74163, 797d11 and part of 854f5 (depicted as region A in FIG. 1C). Identical alleles were observed in at least two pedigrees from the same ethnic origin (Table 2). As part the strategy, it was reasoned that the presence of shared alleles at one of these groups of physically clustered marker loci might reflect the co-inheritance of a small physical region surrounding the PS1 gene on the original founder chromosome in each ethnic population. Significantly, each of the shared extended haplotypes were rare in normal Caucasian populations and allele sharing was not observed at other groups of markers spanning similar genetic intervals elsewhere on chromosome 14q24.3.

Transcription mapping and preliminary analysis of candidate genes

To isolate expressed sequences encoded within both critical intervals, a direct selection strategy was used involving immobilized, cloned, human genomic DNA as the hybridization target to recover transcribed sequences from primary complementary DNA pools derived from human brain mRNA (Rommens et al., 1993). Approximately 900 putative cDNA fragments of size 100 to 600 base pairs were recovered from regions A and B in FIG. 1C. These fragments were hybridized to Southern blots containing genomic DNAs from each of the overlapping YAC clones and genomic DNAs from humans and other mammals. This identified a subset of 151 clones which showed evidence for evolutionary conservation and/or for a complex structure which suggested that they were derived from spliced mRNA. The clones within this subset were collated on the basis of physical map location, cross-hybridization and nucleotide sequence, and were used to screen conventional human brian cDNA libraries for longer cDNAs. At least 19 independent cDNA clones over 1 kg in length were isolated and then aligned into a partial transcription map of the AD3 region (FIG. 1D). Only three of these transcripts corresponded to known characterized genes (cFOS, dihydrolipoamide succinyl transferase and latent transforming growth-factor binding protein 2).

Recovery of Potential Candidate Genes

Each of the open reading frame portions of the candidate genes were recovered by RT-PCR from mRNA isolated from post-mortem brain tissue of normal control subjects and from either post-mortem brain tissue or cultured fibroblast cell lines of affected members of six pedigrees definitively linked to chromosome 14. The RT-PCR products were then screened for mutations using chemical cleavage and restriction endonuclease fingerprinting single-strand sequence conformational polymorphism methods (Saleeba and Cotton, 1993; Liu and Sommer, 1995), and by direct nucleotide sequencing. With one exception, all of the genes examined, although of interest, were not unique to affected subjects, and did not co-segregate with the disease. The single exception was the candidate gene represented by clone S182 which contained a series of nucleotide changes not observed in normal subjects, but which altered the predicted amino acid sequence in affected subjects. Although nucleotide sequence differences were also observed in some of the other genes, most were in the 3' untranslated regions and none were unique to AD-affected subjects.

The remaining sequences, a subset of which are mapped in FIG. 1B, together with additional putative transcriptional sequences not identified in FIG. 1C, are identified in the sequence listings as Nos. 14 to 43. The sequences identified by SEQ ID NOs: 14 to 43 represent neighbouring genes or fragments of neighbouring genes adjacent to the hPS1 gene or possibly additional coding fragments arising from alternative splicing of the hPS1. Sequences identified by SEQ ID NOs: 44–126 and 150–160 represent neighboring genomic fragments containing both exon and intron information. Such sequences are useful for creating primers, for creating diagnostic tests, creating altered regulatory sequences and use of adjacent genomic sequences to create better animal models.

Characterization of the Human PS1 (ARMP) gene

Hybridization of the S182 clone to northern blots identified a transcript expressed widely in many areas of brain and peripheral tissues as a major 3.0 kb transcript and a minor transcripto of 7.0 kg. Although the identity of the ~7.0 kb transcript is unclear, two observations suggest that the ~3.0 kg transcript represents an active product of the gene. Hybridization of the S182 clone to northern blots containing mRNA from a variety of murine tissues, including brain, identifies only a single transcript identical in size to the ~3.0 kg human transcripto. All of the longer cDNA clones recovered to date (2.6–2.8 kg), which include both 5' and 3' UTRs and which account for the ~3.0 kg band on the northern blot, have mapped exclusively to the same physical region of chromosome 14. From these experiments the ~7.0 kb transcript could represent either a rare alternately spliced or polyadenylated isoform of the ~3.0 kb transcript or could represent another gene with homology to S182.

The nucleotide sequence of the major transcript was determined from the consensus of eleven independent longer cDNA clones and from 3 independent clones recovered by standard 5' rapid amplification of cDNA ends and bears no significant homology to other human genes. The cDNA of the sequenced transcript is provided in SEQ ID NO:1 and the predicted amino acid sequence is provided in SEQ ID NO:2. The cDNA sequence of another sequenced human clone is also provided as SEQ ID NO:133 and its predicted amino acid sequence is provide din SEQ ID NO:134.

Analysis of the 5' end of multiple cDNA clones and RT-PCR products as well as corresponding genomic clones indicates that the 5' UTR is contained within at least two exons and that transcription either begins from two different start sites and/or that one of the early 5' untranslated exons is alternatively spliced (Table 6). The longest predicted open reading frame contains 467 amino acids with a small alternatively spliced exon of 4 amino acids at 25 codons from the putative start codon (Table 3). This putative start codon is the first in phase ATG located 63 bp downstream of a TGA stop codon and lacks a classical Kozak consensus sequences around the first two in-phase ATG sequences (Sherrington, 1995). Like other genes lacking classical 'strong' start codons, the putative 5' UTR of the human transcripts is rich in GC.

Further investigation of the PS1 gene has revealed a host of sequence fragments which form the PS1 gene and include intron sequence information, 5' end untranslated sequence information and 3' end untranslated sequence information (Table 6). Such sequence fragments are identified as SEQ ID NOs:6 to 13.

The DNA sequence of the PS1 gene as cloned has been incorporated into a plasmid Bluescript. This stable vector has been deposited at ATCC, Rockville, Md., under ATCC accession number 97124 on Apr. 28, 1995.

Identification of an Alternate Splice Form of the PS1 (ARMP) Gene Product

During sequencing studies of RT-PCR products for the PS1 gene recovered from a variety of tissues, it was discovered that some peripheral tissues (principally white blood cells) demonstrated two alternative splice forms of the PS1 gene. One form is identical to the (putatively 467 amino acid) isoform constitutively expressed in all brain regions. The alternative splice form results from the exclusion of the segment of the cDNA comprising base pairs 1018 to 1116, and results in a truncated isoform of the PS1 protein wherein the hydrophobic part of the hydrophilic acidically-charged loop immediately C-terminal to TM6 is removed. This alternatively spliced isoform therefore is characterized by preservation of the sequence N-terminal to and including the tyrosine at position 256, changing of the aspartate at 257 to alanine, and splicing on to the C-terminal part of the protein from and including tyrosine 291. Such splicing differences are often associated with important functional domains of the proteins. This argues that this hydrophilic loop (and consequently the N-terminal hydrophilic loop with similar amino acid charge) is/are active functional domains of the PS1 product and thus sites for therapeutic targeting.

Functional Domains of the PS1 (ARMP) Protein

With respect to DNA SEQ ID NO:1 and DNA SEQ ID NO:133, analysis of the sequence of overlapping cDNA clones predicted an ORF protein of 467 amino acids when read from the first in phase ATG start codon, and a molecular mass of approximately 52.6 kDa. The molecular weight of the protein can vary due to possible substitutions, insertions or deletions of amino acids or due either to polymorphisms in the protein or alternate splicing of the transcript.

Analysis of the predicted amino acid sequence using the Hopp and Woods algorithm suggested that the PS1 protein product is a multispanning integral membrane protein such as a receptor, a channel protein, or a structural membrane protein. The absence of recognizable signal peptide and the paucity of glycosylation sites are noteworthy, and the hydropathy profile suggests that the protein is less likely to be a soluble protein with a highly compact three-dimensional structure.

The protein may be a cellular protein with a highly compact three dimensional structure in which respect it may be similar to APOE which is also related to Alzheimer's Disease. As mutations in this protein are associated with early onset (presenilin) Alzheimer's Disease, the protein has been designated presenilin I (PS1).

The protein also contains a number of potential phosphorylation sites, one of which is the consensus site for MAP-kinase which is also involved in the hyperphosphorylation of tau during the conversion of normal tau to neurofibrillary tangles. This consensus sequence may provide a putative common pathway linking this protein and other known biochemical aspects of Alzheimer's Disease and would represent a likely therapeutic target. Review of the protein structure reveals two sequences YTPF (residues 115–119) and STPE (residues 353–356) which represent the 5/T-P motif which is the MAP kinase consensus sequence. Several other phosphorylation sites exist with consensus sequences for Protein Kinase C (PKC) activity. Because PKC activity is associated with differences in the metabolism of APP which are relevant to Alzheimer's Disease, these sites on the PS1 protein and homologues are sites for therapeutic targeting.

Figure 3A:
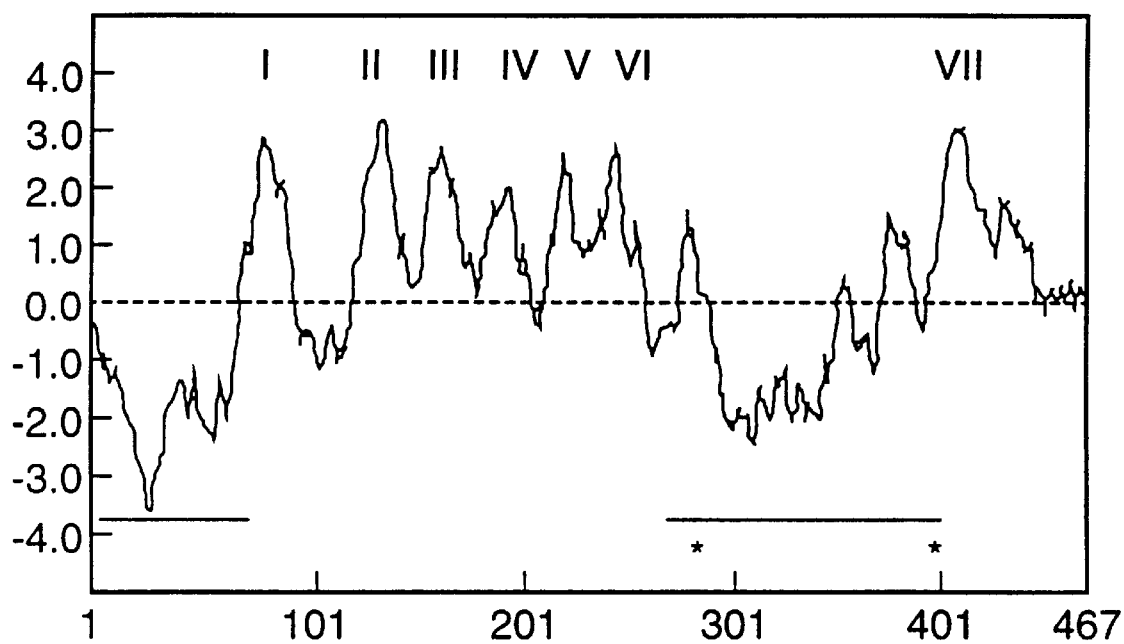
Figure 3B:
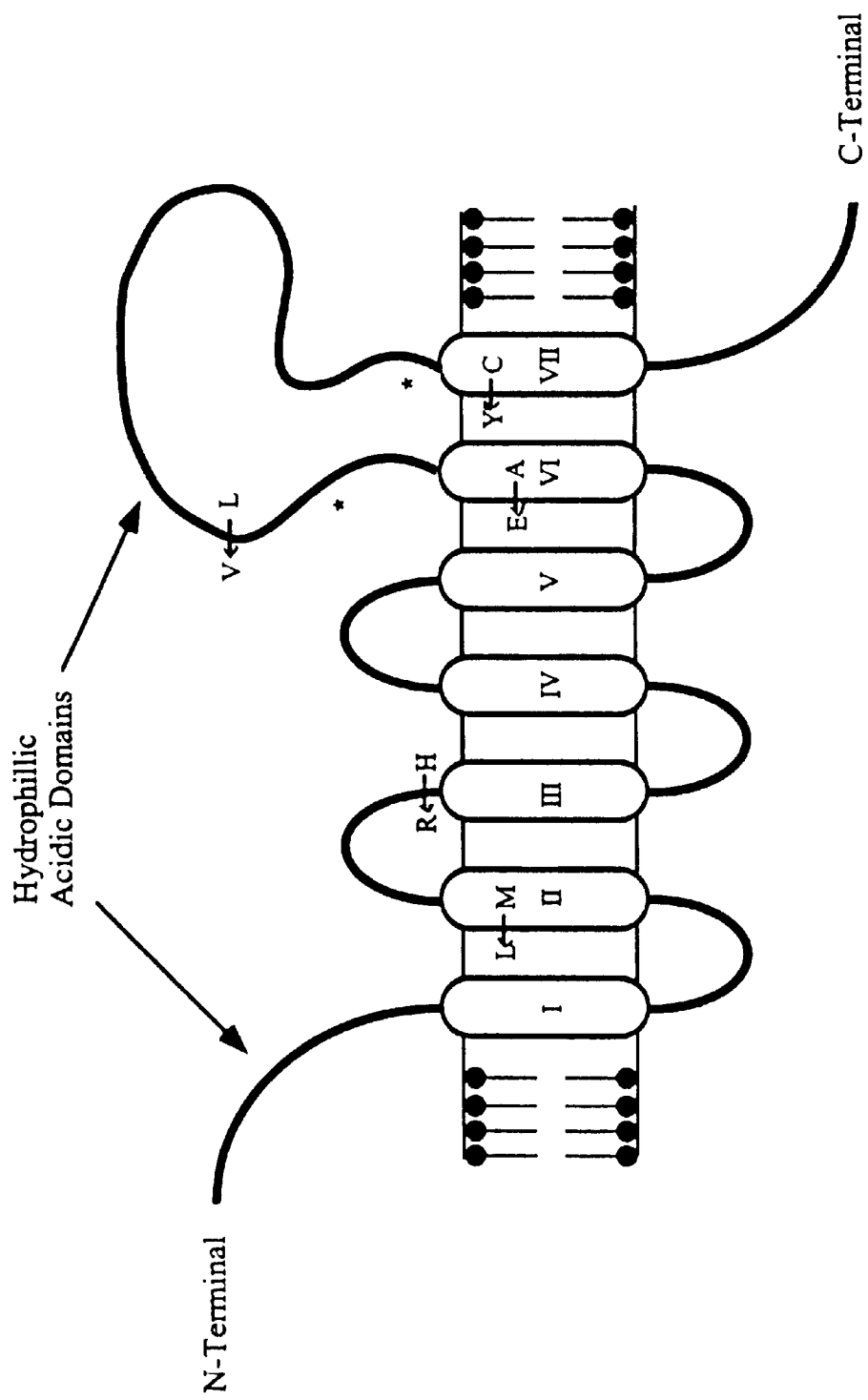
Figure 4:
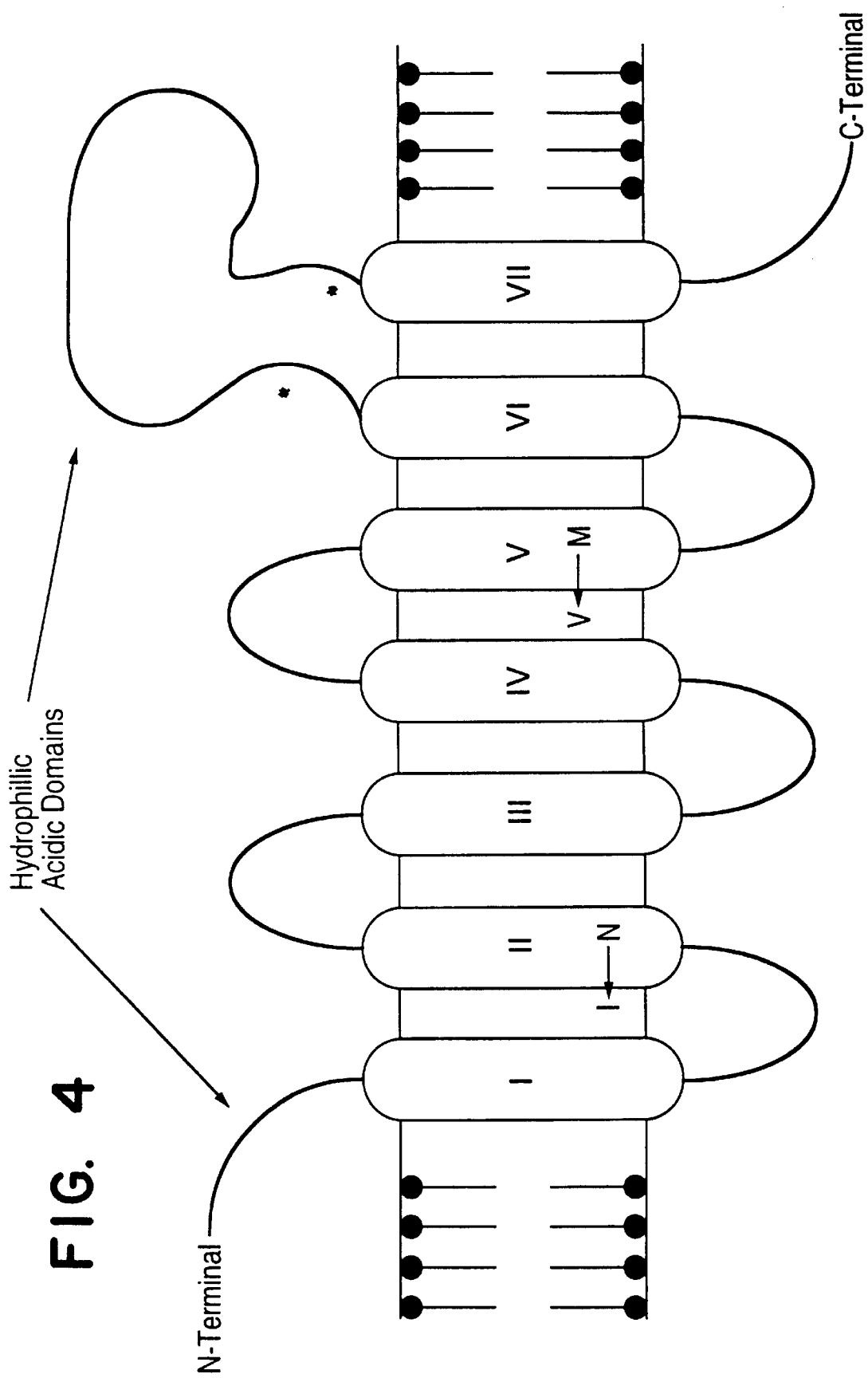
FIG. 4 is a schematic drawing of the predicted structure of the PS2 protein.
Figure 5A:
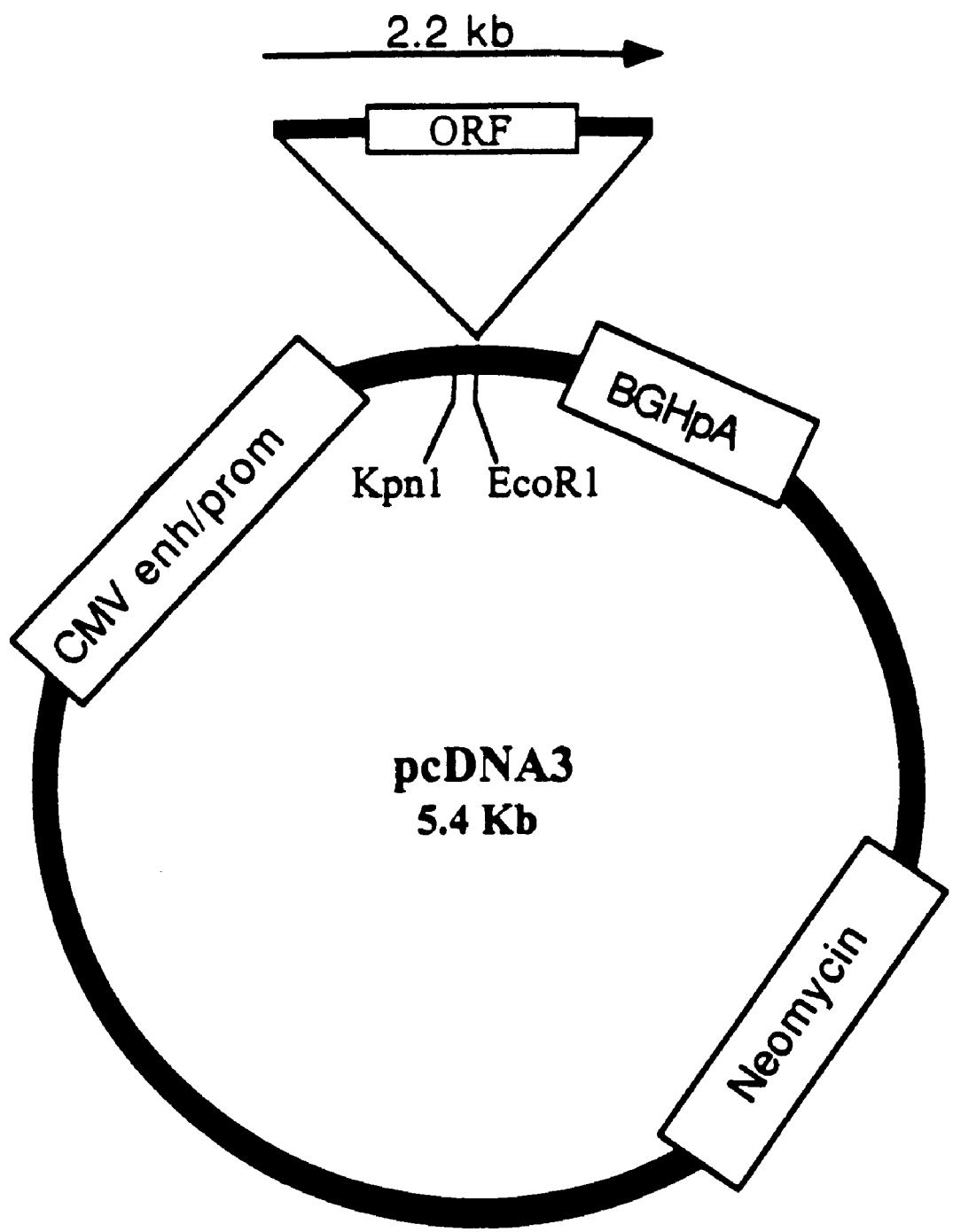
FIG. 5A depicts an expression vector containing the entire ARMP cDNA sequence and includes the 5' untranslated region.
Figure 5B:
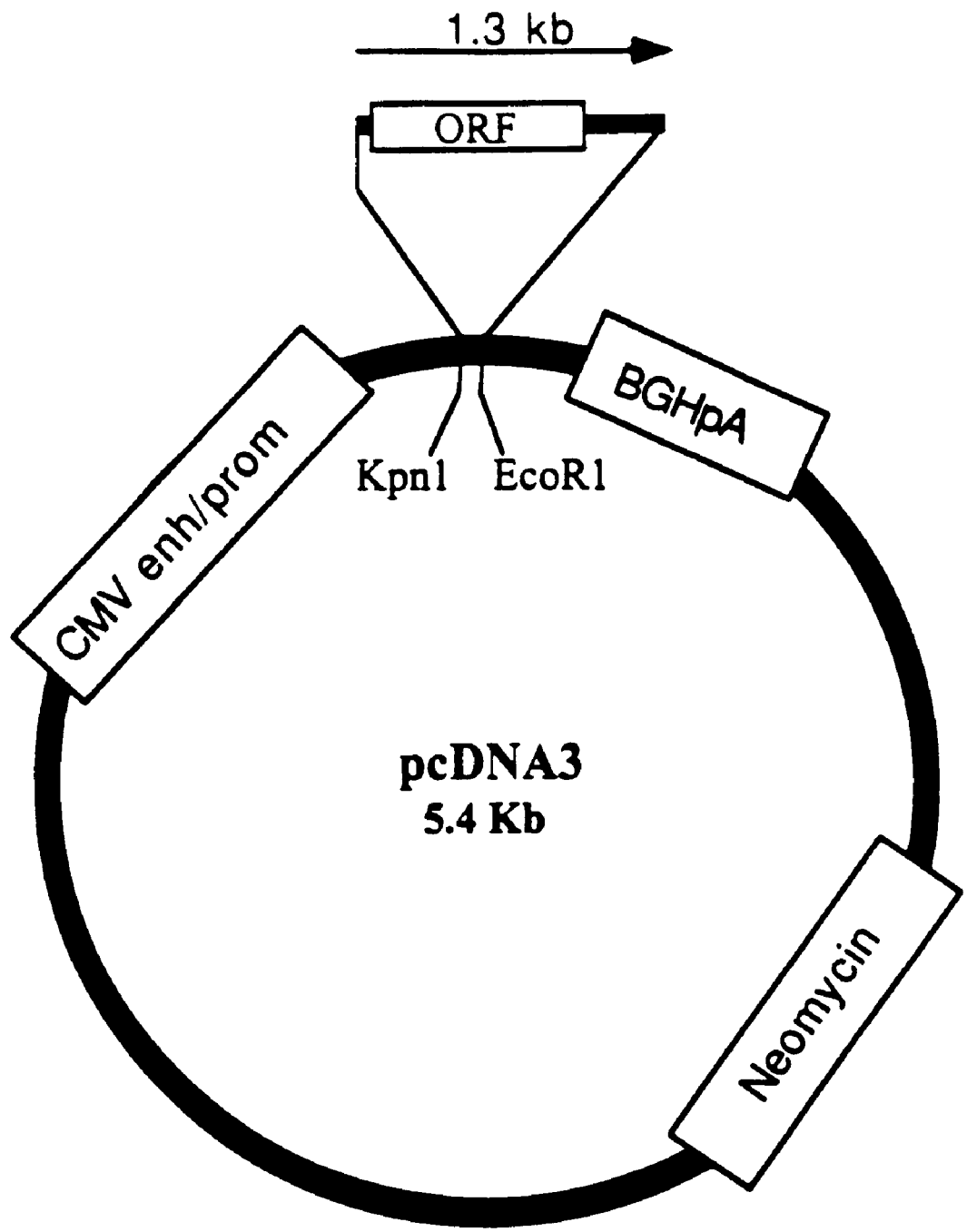
FIG. 5B depicts an expression vector containing a truncated ARMP cDNA in which the 5' untranslated region is replaced with an artificial Kozak consensus sequence around the 5' cloning site.

The N-terminal is characterized by a highly hydrophilic acidic charged domain with several potential phosphorylation domains, followed sequentially by a hydrophobic membrane spanning domain of 19 residues, a charged hydrophilic loop, five additional hydrophobic membrane spanning domains interspersed with short (5–20 residue) hydrophilic domains, an additional larger acidic hydrophilic charged loop and at least one, and possibly two, other hydrophobic potentially membrane-spanning domains, culminating in a polar domain at the C-terminus (Table 4 and FIG. 3B). The presence of seven membrane spanning domains is characteristic of several classes of G-coupled receptor proteins but is also observed with other proteins including channel proteins.

PS1 (ARMP) Protein

The PS1 (ARMP) protein is a member of a novel class of transmembrane proteins which share substantial amino acid homology. The homology is sufficient that certain nucleotide probes and antibodies raised against one can identify other members of this gene family. The major differences between members of this family reside in the amino acid and nucleotide sequence homologous to the hydrophilic acid loop domain between putative transmembrane 6 and transmembrane 7 domains of the PS1 gene and gene product. This region is alternatively spliced in some non-neural tissues, and is also the site of several pathogenic disease-causing mutations in the PS1 gene. The variable splicing of this hydrophilic loop, the presence of a high density of pathogenic mutations within this loop, and the fact that the amino acid sequences of the loop differs between members of the gene family suggest that this loop is an important functional domain of the protein and may confer some specificity to the physiologic and pathogenic interactions which the PS1 gene product undergoes. Because the N-terminal hydrophilic domain shares the same acidic charge as the hydrophilic acid loop domain between TM6 and TM7, and has the same orientation with respect to the membrane, it is very likely that these two domains share functionality either in a coordinated (together) or independent fashion (e.g. different ligands or functional properties). As a result everything said about the hydrophilic loop applies also the N-terminal hydrophilic domain.

Knowledge of the specificity of the loop can be used to identify ligands and functional properties of the PS1 gene product (e.g. sites of interactions with APP, cytosolic proteins such as kinases, Tau, and MAP, etc.).

Comparison of the nucleic acid and predicted aminoacid sequences of PS1 with available databases using the BLAST alignment paradigms revealed modest amino acid similarity with the C. elegans sperm integral membrane protein SPE-4 ($p=1.5$ $e^{-25}$, 24–37% identity over three groups of at least fifty residues) and weaker similarity to portions of several other membrane spanning proteins including mammalian chromogranin A and the alpha subunit of mammalian voltage dependent calcium channels (Altschul et al., 1990). This clearly established that they are not the same gene. The amino-acid sequence similarities across putative transmembrane domains may occasionally yield alignment that simply arises from the limited number of hydrophobic amino acids, but there is also extended sequence alignment between S182 protein and SPE-4 at several hydrophilic domains. Both the putative PS1 protein and SPE-4 are predicted to be of comparable size (467 and 465 residues, respectively) and to contain at least seven transmembrane domains with a large acidic domain preceding the final predicted transmembrane domain. The PS1 protein does have a longer predicted hydrophilic region at the N terminus.

The similarity between the putative products of the SPE-4 and PS1 genes implies that they may have similar activities. The SPE-4 protein of C. elegans appears to be involved in the formation and stabilization of the fibrous body-membrane organelle (FBMO) complex during spermatogenesis. The FBMO is a specialized Golgi-derived organelle, consisting of a membrane bound vesicle attached to and partly surrounding a complex of parallel protein fibers and may be involved in the transport and storage of soluble and membrane-bound polypeptides. Mutations in SPE-4 disrupt the FBMO complexes and arrest spermatogenesis. Therefore the physiologic function of SPE-4 may be either to stabilize interactions between integral membrane budding and fusion events, or to stabilize interactions between the membrane and fibrillary proteins during the intracellular transport of the FBMO complex during spermatogenesis. Comparable functions could be envisaged for PS1. The PS1 could be involved either in the docking of other membrane-bound proteins such as βAPP, or the axonal transport and fusion budding of membrane-bound vesicles during protein transport such as in the Golgi apparatus or endosome-lysosome system. If correct, then mutations might be expected to result in aberrant transport and processing of βAPP and/or abnormal interactions with cytoskeletal proteins such as the microtubule-associated protein Tau. Abnormalities in the intracellular and in the extracellular disposition of both βAPP and Tau are in fact an integral part of the neuropathologic features of Alzheimer's Disease. Although the location of the PS1 mutations in highly conserved residues within conserved domains of the putative proteins suggests that they are pathogenic, at least three of these mutations are conservative which is commensurate with the onset of disease in adult life. Because none of the mutations observed so far are deletions or nonsense mutations that would be expected to cause a loss of function, we cannot predict whether these mutations will have a dominant gain-of-function effect and promote aberrant processing of βAPP or a dominant loss-of-function effect causing arrest of normal βAPP processing.

An alternate possibility is that the ARMP gene product may represent a receptor or channel protein. Mutations of such proteins have been causally related to several other dominant neurological disorders in both vertebrate (e.g., malignant hyperthermia, hyperkalemic periodic paralysis in humans) and in invertebrate organisms (deg-1(d) mutants in C. elegans). Although the pathology of these other disorders does not resemble that of Alzheimer's Disease. For example, anomalies have been reported in ion channels in Alzheimer's Disease. For example, anomalies have been reported in the tetra-ethylammonium-sensitive 113 pS potassium channel and in calcium homeostasis. Perturbations in transmembrane calcium fluxes might be especially relevant in view of the weak homology between PS1 and the α-ID subunit of voltage-dependent calcium channels and the observation that increases in intracellular calcium in cultured cells can replicate some of the biochemical features of Alzheimer's Disease such as alteration in the phosphorylation of Tau-microtubule-associated protein and increased production of Aβ peptides.

The normal PS1 protein, substantially free of other proteins, is encoded by the aforementioned SEQ ID NO:1 and SEQ ID NO:133. As will be later discussed, PS1 protein and fragments thereof may be made by a variety of methods. Purified mutant PS1 protein is characterized by FAD—associated phenotype (necrotic death, apoptotic death, granulovascular degeneration, neurofibrillary degeneration, abnormalities or changes in the metabolism of APP, $Ca^{2+}$, $K^+$, and glucose, mitochondrial function and energy metabolism neurotransmitter metabolism, all of which have been found to be abnormal in human brain, and/or peripheral tissue cells in subjects with Alzheimer's Disease) in a variety of cells. The mutant PS1, free of other proteins, is encoded by the mutant DNA sequence.

Mutations in the S182 (PS1) transcript

Several mutations in the ARMP gene have been identified which cause a severe type of familial Alzheimer's Disease. One or a combination of these mutations may be responsible for this form of Alzheimer's Disease as well as several other neurological disorders. The mutations may be any form of nucleotide sequence alteration or substitution. Specific disease causing mutations in the form of nucleotide and/or amino acid substitutions have been located, although it is anticipated that additional mutations will be found in other families.

Direct sequencing of overlapping RT-PCR products spanning the 3.0 kb S182 transcript isolated from affected members of the six large pedigrees linked to chromosome 14 led to the discovery of eight missense mutations in each of the six pedigrees (Table 7, FIG. 2). Each of these mutations co-segregated with the disease in the respective pedigrees, and were absent from upwards of 142 unrelated neurologically normal subjects drawn from the same ethnic origins as the FAD pedigrees (284 unrelated chromosomes).

The location of the gene within the physical interval segregating with AD3 trait, the presence of eight different missense mutations which co-segregate with the disease trait in six pedigrees definitively linked to chromosome 14, and the absence of these mutations in 284 independent normal chromosomes cumulatively confirms that the PS1 gene is the AD3 locus. Further biologic support for this hypothesis arises both from the fact that the residues mutated in FAD kindreds are conserved in evolution (Table 3) and occur in domains of the protein which are also highly conserved, and from the fact that the PS1 gene product is expressed at high levels in most regions of the brain including those most severally affected by AD.

Each of the observed nucleotide substitutions occurred within the putative ORF of the PS1 transcript, and would be predicted to change the encoded amino acid at the following positions, numbering from the first putative initiation codon. The mutations are listed both with reference to their nucleotide locations in SEQ ID NO:1 and SEQ ID NO:133 (an additional human clone) and to their amino acid locations in SEQ ID NO:2 and SEQ ID NO:134 (the additional human clone).

| | | | | |
|---|---|---|---|---|
| i) 685, A→C | Met | 146 | Leu |
| ii) 737, A→G | His | 163 | Arg |
| iii) 986, C→A | Ala | 246 | Glu |
| iv) 1105, C→G | Leu | 286 | Val |
| v) 1478, G→A | Cys | 410 | Tyr |
| vi) 1027, C→T | Ala | 260 | Val |
| vii) 1102, C→T | Ala | 285 | Val |
| viii) 1422, C→G | Leu | 392 | Val |

The Met146Leu, Ala246Glu and Cys410Tyr mutations have not been detected in the genomic DNA of affected members of the eight remaining small early onset autosomal dominant FAD pedigrees or six additional families in our collection which express late FAD onset. We predict that such mutations would not commonly occur in late onset FAD which has been excluded by genetic linkage studies from the more aggressive form of AD linked to chromosome 14q24.3 (St George-Hyslop, P et al., 1992; Schellenberg et al., 1993). The His163Arg mutation has been found in the genomic DNA of affected members of one additional FAD pedigree for which positive but significant statistical evidence for linkage to 14 becomes established. Age of onset of affected members was consistent with affected individuals from families linked to chromosome 14.

Mutations Ala260Val, Ala285Val, and Leu392Val all occur within the acidic hydrophilic loop between putative transmembrane domains 6 (TM6) and transmembrane domain 7 (TM7) (FIG. 3). Two of these mutations (A260V; A285V) and the L286V mutation are also located in the alternate splice domain.

All nine mutations can be assayed by a variety of strategies (direct nucleotide sequencing, allele specific oligos, ligation polymerase chain reaction, SSCP, RFLPs etc.) using RT-PCR products representing the mature mRNA/cDNA sequence or genomic DNA.

Of all the nucleotide substitutions co-segregating with the disease in their respective pedigrees, none were seen in asymptomatic family members aged more than two standard deviations beyond the mean age of onset, and none were present on 284 chromosomes from unrelated neurologically normal subjects drawn from comparable ethnic origins.

Table 9 shows the above-noted PS1 mutations and other published mutations of this gene.

Isolation and Purification of PS1 (ARMP) Protein

The PS1 protein may be isolated and purified by methods selected on the basis of properties revealed by its sequence. Since the protein possesses properties of a membrane-spanning protein, a membrane fraction of cells in which the protein is highly expressed (e.g. central nervous system cells or cells from other tissues) is isolated and the proteins extracted by detergent solubilization.

Purification can be achieved using protein purification procedures such as chromatography methods (gel-filtration, ion-exchange and immunoaffinity), by high-performance liquid chromatography (RP-HPLC, ion-exchange HPLC, size-exclusion HPLC, high-performance chromatofocusing and hydrophobic interaction chromatography) or by precipitation (immunoprecipitation). Polyacrylamide gel electrophoresis can also be used to isolate the PS1 protein based on its molecular weight, charge properties and hydrophobicity.

Similar procedures to those just mentioned could be used to purify the protein from cells transfected with vectors containing the PS1 gene (e.g. baculovirus systems, yeast expression systems, eukaryotic expression systems).

Purified protein can be used in further biochemical analyses to establish secondary and tertiary structure which may aid in the design of pharmaceuticals to interact with the protein, alter protein charge configuration or charge interaction with other proteins, lipid or saccharide moieties, alter its function in membranes as a transporter channel or receptor and/or in cells as an enzyme or structural protein and treat the disease.

The protein can also be purified by creating a fusion protein by ligating the PS1 cDNA sequence to a vector which contains a sequence for another peptide (e.g. GST-glutathione succinyl transferase). The fusion protein is expressed and recovered from prokaryotic (e.g. bacterial or baculovirus) or eukaryotic cells. The fusion protein can then be purified by affinity chromatography based upon the fusion vector sequence. The PS1 protein can then be further purified from the fusion protein by enzymatic cleavage of the fusion protein.

Expression of PS1 (ARMP)

As an embodiment of the present invention, PS1 protein may be expressed using eukaryotic and prokaryotic expression systems. Eukaryotic expression systems can be used for many studies of the PS1 gene and gene product including determination of proper expression and post-translational modifications for full biological activity, identifying regulatory elements located in the 5' region of the PS1 gene and their role in tissue regulation of protein expression, and production of large amounts of the normal and mutant protein for isolation and purification. Cells expressing the PS1 protein may be used as functional assay system for antibodies generated against the protein or to test effectiveness of pharmacological agents. Expressed and purified PS1 protein may be used to examine its role as a component of a signal transduction system and to study the function of the normal complete protein, specific portions of the protein, or of naturally occurring and artificially produced mutant proteins.

Prokaryotic expression systems allow the holo-protein, or various important functional domains of the protein, to be recovered as fusion proteins and used for binding studies, structure studies, functional studies, and for the generation of appropriate antibodies.

Expression of the PS1 gene in heterologous cell systems can be used to demonstrate structure-function relationships. Ligating the PS1 DNA sequence into a plasmid expression vector to transfect cells is a useful method to test the influence of PS1 on various cellular biochemical parameters. Plasmid expression vectors containing either the entire normal or mutant human or mouse PS1 sequence or portions thereof, can be used in in vitro mutagenesis experiments which will identify portions of the protein crucial for regulatory function.

The DNA sequence can be manipulated in studies to understand the expression of the gene and its product, to achieve production of large quantities of the protein for functional analysis, for antibody production, and for patient therapy. Changes in the sequence may or may not alter the expression pattern in terms of relative quantities, tissue-specificity and functional properties. Partial or full-length DNA sequences which encode for the PS1 protein, modified or unmodified, may be ligated to bacterial expression vectors. *E. coli* can be used with a variety of expression vector systems, e.g. the T7 RNA polymerase/promoter system using two plasmids or by labelling of plasmid-encoded proteins, or by expression by infection with M13 Phage mGPI-2. *E. coli* vectors can also be used with Phage lambda regulatory sequences, by fusion protein vectors (e.g. lacZ and trpE), by maltose-binding protein fusions, and by glutathione-S-transferase fusion proteins, etc., all of which, together with many other prokaryotic expression systems, are widely available commercially.

Alternatively, the PS1 protein can be expressed in insect cells using baculoviral vectors, or in mammalian cells using vaccinia virus or specialised eukaryotic expression vectors. For expression in mammalian cells, the cDNA sequence may be ligated to heterologous promoters, such as the simian virus (SV40) promoter in the pSV2 vector or other similar vectors and introduced into cultured eukaryotic cells such as COS cells to achieve transient or long-term expression. The stable integration of the chimeric gene construct may be maintained in mammalian cells by biochemical selection, such as neomycin and mycophoenolic acid.

The PS1 DNA sequence can be altered using procedures such as restriction enzyme digestion, fill-in with DNA polymerase, deletion by exonuclease, extension by terminal deoxynucleotide transferase, ligation of synthetic or cloned DNA sequences and site-directed sequence alteration with the use of specific oligonucleotides together with PCR.

The cDNA sequence or portions thereof, or a mini gene consisting of a cDNA with an intron and its own promoter, is introduced into eukaryotic expression vectors by conventional techniques. These vectors permit the transcription of the cDNA in eukaryotic cells by providing regulatory sequences that initiate and enhance the transcription of the cDNA and ensure its proper splicing and polyadenylation. The endogenous PS1 gene promoter can also be used. Different promoters within vectors have different activities which alters the level of expression of the cDNA. In addition, certain promoters can also modulate function such as the glucocorticoid-responsive promoter from the mouse mammary tumor virus.

Some of the vectors listed contain selectable markers or neo bacterial genes that permit isolation of cells by chemical selection. Stable long-term vectors can be maintained in cells as episomal, freely replicating entities by using regulatory elements of viruses. Cell lines can also be produced which have integrated the vector into the genomic DNA. In this manner, the gene product is produced on a continuous basis.

Vectors are introduced into recipient cells by various methods including calcium phosphate, strontium phosphate, electroporation, lipofection, DEAE dextran, microinjection, or by protoplast fusion. Alternatively, the cDNA can be introduced by infection using viral vectors.

Using the techniques mentioned, the expression vectors containing the PS1 gene or portions thereof can be introduced into a variety of mammalian cells from other species or into non-mammalian cells as described in Example 8.

The recombinant expression vector, according to this invention, comprises the selected DNA of the DNA sequences of this invention for expression in a suitable host. The DNA is operatively joined in the vector to an expression control sequence in the recombinant DNA molecule so that normal or mutant PS1 protein can be expressed. The expression control sequence may be selected from the group consisting of sequences that control the expression of genes by prokaryotic or eukaryotic cells and their viruses and combinations thereof. The expression control sequence may be selected from the group consisting of the lac system, the trp system, the tac system, the trc system, major operator and promoter regions of phage lambda, the control region of the fd coat protein, early and late promoters of SV40, promoters derived from polyoma, adenovirus, retrovirus, baculovirus, simian virus, 3-phosphoglycerate kinase promoter, yeast acid phosphatase promoters, yeast alpha-mating factors and combinations thereof.

The host cells to be transfected with the vectors of this invention may be from a host selected from the group consisting of *E. coli,* Pseudomonas, *Bacillus subtillus, Bacillus stearothermophilus,* or other bacilli, other bacteria, yeasts, fungi, insects, mice or other animals or plant hosts or may be human tissue cells.

For the mutant PS1 DNA sequence, similar systems are employed to express and produce the mutant protein.

Antibodies to PS1 (ARMP)

Antibodies to epitopes within the PS1 protein can be raised to provide information on the characteristics of the proteins. Generation of antibodies enables the visualization of the protein cells and tissue using Western blotting. In this technique, proteins are separated by polyacrylamide gel electrophoresis and transferred to nitrocellulose membranes. These membranes are then incubated in the presence of a primary antibody, washed and incubated with a secondary antibody to detect the protein-primary antibody complex. Following repeated washing, the entire complex is visualized using colourimetric or chemiluminescent methods.

Antibodies to the PS1 protein also allow for use of immunocytochemistry and immunofluorescence techniques in which the protein can be visualized directly in cells and tissues. This is most helpful in order to establish the subcellular location of the protein and the tissue specificity of the protein.

In order to prepare polyclonal antibodies, fusion proteins containing defined portions or all of the PS1 protein may be synthesized in bacteria by expression of corresponding DNA sequences in a suitable cloning vehicle, as described herein. The protein is then purified, coupled to a carrier protein, mixed with Freund's adjuvant (to help stimulate the antigenic response) and injected into rabbits or other suitable animals. Alternatively, protein can be isolated from cultured cells expressing the protein, Following booster injections at bi-weekly intervals, the rabbits or other suitable animals are bled and the sera isolated. Sera are used directly or purified prior to use, by various methods including affinity chromatography, Protein A-Sepharose, Antigen Sepharose. Anti-mouse-Ig-Sepharose. Sera or purified antibodies are used to probe protein extracts run on a polyacrylamide gel to identify the PS1 protein. Alternatively, antibodies may be obtained by making synthetic peptides corresponding to antigenic portions of the PS1 protein and injecting these into rabbits or other suitable animals.

To produce monoclonal PS1 antibodies, cells actively expressing the protein are cultured or isolated from tissues and the cell membranes isolated. The membranes, extracts, or recombinant protein extracts containing the PS1 protein are injected in Freund's adjuvant into mice. After receiving 9 injections over a three week period, the mice are sacrificed and their spleens are removed and resuspended in phosphate buffered saline (PBS). The spleen cells serve as a source of lymphocytes, some of which are producing antibody of the appropriate specificity. These cells are then fused with a permanently growing myeloma partner cell, and the products of the fusion are plated into a number of tissue culture wells in the presence of a selective agent such as HAT. The wells are screened by ELISA to identify those containing cells making useful antibody and these cells are freshly plated. After a period of growth, these cells are again screened to identify antibody-producing cells. Several cloning procedures are carried out until over 90% of the wells contain single clones which are positive for antibody production. By this procedure, a stable line of monoclonal antibody-producing clones is established. Monoclonal antibody produced by such clones is purified by methods such as affinity chromatography using Protein A Sepharose or ion-exchange chromatography or by variations and combinations of these techniques.

Antibodies may also be used coupled to other compounds or materials for diagnostic and/or therapeutic uses. For example, they may be coupled to radionuclides for imaging and therapy, or to liposomes for the targeting of compounds contained in the liposomes to a specific tissue location.

Isolation of Murine PS1 Gene

In order to characterize the physiological significance of the normal and mutant human PS1 gene and gene products in a transgenic mouse model, it was necessary to recover a mouse homologue of the human PS1 gene. A murine homologue of the human PS1 gene was recovered by screening a mouse cDNA library with a labelled human DNA probe. In this manner, a 2 kb partial transcript (representing the 3' end of the gene) and several RT-PCR products representing the 5' end were recovered. Sequencing of the consensus cDNA transcript of the murine homologue revealed substantial amino acid identity. The mouse cDNA sequence is identified as SEQ ID NO:3 and the predicted amino acid sequence is identified as SEQ ID NO:4. Further sequencing of the mouse cDNA transcript has provided the complete coding sequence, identified as SEQ ID NO:135; the predicted amino acid sequence is identified as SEQ ID NO:134. More importantly, all of the amino acids that were mutated in the FAD pedigrees were conserved between the murine homologue and the normal human variant (Table 3). This conservation of the PS1 gene, as is shown in Table 3, indicates that an orthologous gene exists in the mouse (mPS1), and it is now possible to clone mouse genomic libraries using human PS1 probes. This will also make is possible to identify and characterize the PS1 gene in other species. This also provides evidence of animals with various disease states or disorders currently known or yet to be elucidated.

Transgenic Mouse Mold

The creation of a mouse model for Alzheimer's Disease is important to the understanding of the disease and for the testing of possible therapies. Currently no unambigous viable animal model for Alzheimer's Disease exists.

There are several ways in which to create an animal model for Alzheimer's Disease. One strategy is the generation, in the mouse gene, of a specific mutation such as one of the identified human PS1 gene mutations. Secondly, a wild type human gene could be inserted and/or the murine gene could be humanized by homologous recombination. Thirdly, it is possible to insert a mutant (single or multiple) human gene as a genomic or minigene cDNA construct using wild type, mutant or artificial promoter elements. Fourthly, knock-out of the endogenous murine genes may be accomplished by the insertion of artificially modified fragments of the endogenous gene by homologous recombination. The modifications include insertion of mutant stop codons, the deletion of DNA sequences, or the inclusion of recombination elements (lox p sites) recognized by enzymes such as Cre recombinase.

To inactivate the mPS1 gene, chemical or x-ray mutagenesis of mouse gametes, followed by fertilization, can be applied. Heterozygous offspring may be identified by Southern blotting to demonstrate loss of one allele by dosage, or failure to inherit one parental allele using RFLP markers.

To create a transgenic mouse, a mutant version of PS1 or mPS1 can be inserted into a mouse germ line using standard techniques of oocyte microinjection, or transfection or microinjection into stem cells. Alternatively, if it is desired to inactivate or replace the endogenous mPS1 gene, homologous recombination using embryonic stem cells may be applied.

For oocyte injection, one or more copies of the mutant or wild type PS1 gene can be inserted into the pronucleus of a just-fertilized mouse oocyte. This oocyte is then reimplanted into a pseudo-pregnant foster mother. The liveborn mice are screened for integrants using analysis of tail DNA for the presence of human PS1 gene sequences. The transgene may be either a complete genomic sequence injected as YAC, BAC, PAC or other chromosome DNA fragment, a cDNA with either the natural promoter or a heterologous promoter, or a minigene containing all of the coding region and other elements found to be necessary for optimum expression.

Retroviral infection of early embryos can also be done to insert the mutant or wild type human PS1. In this method, the mutant or wild type PS1 is inserted into a retroviral vector which is used to infect mouse embryos directly during the early stages of development to generate chimeras, some of which will lead to germline transmission. Similar experiments can be conducted in the case of mutant proteins, using mutant murine or other animal PS1 gene sequences.

Homologous recombination using stem cells allows for the screening of gene transfer cells to identify the rare homologous recombination events. Once identified, these can be used to generate chimeras by injection of mouse blastocysts, and a proportion of the resulting mice will show germline transmission from the recombinant line. This methodology is especially useful if inactivation of the mPS1 gene is desired. For example, inactivation of the mPS1 gene can be done by designing a DNA fragment which contains sequences from mPS1 exon flanking a selectable marker. Homologous recombination leads to the insertion of the marker sequences in the middle of an exon, inactivating the mPS1 gene. DNA analysis of individual clones can then be used to recognize the homologous recombination events.

It is also possible to create mutations in the mouse germline by injecting oligonucleotides containing the mutation of interest and screening the resulting cells by PCR.

This embodiment of the invention has the most significant commercial value as a mouse model for Alzheimer's Disease. Because of the high percentage of sequence conservation between human and mouse it is contemplated that an orthologous gene will exist also in many other species. It is thus contemplated that it will be possible to generate other animal models using similar technology.

Isolation of the Human PS2 (E5-1) Gene, A Homologue of the PS1 (ARMP) Gene

A gene, presenilin II (PS2) or E5-1, with substantial nucleotide and amino acid homology to the PS1 gene was identified by using the nucleotide sequence of the cDNA for PS1 to search data bases using the BLASTN paradigm of Altschul et al. 1990. Three expressed sequence tagged sites (ESTs) identified by accession numbers T03796, R14600, and R05907 were located which had substantial homology ($p<1.0e^{-100}$, greater than 97% identity over at least 100 contiguous base pairs).

Oligonucleotide primers were produced from these sequences and used to generate PCR products by reverse transcriptase PCR (RT-PCR). These short RT-PCR products were partially sequenced to confirm their identity with the sequences within the data base and were then used as hybridization probes to screen full-length cDNA libraries. Several different cDNA's ranging in size from 1 Kb to 2.3 Kb were recovered from a cancer cell cDNA library (CaCo-2) and from a human brain cDNA library (E5-1, G1-1, cc54, cc32).

The nucleotide sequence of these clones confirmed that all were derivatives of the same transcript.

The gene encoding the transcript, the PS2 gene, mapped to human chromosome 1 using hybrid mapping panels and to two clusters of CEPH Mega YAC clones which have been placed upon a physical contig map (YAC clones 750g7.921d12 mapped by FISH to 1q41; and YAC clone 787g12 which also contains an EST for the leukemia associated phosphoprotein (LAP18) gene which has been mapped to 1p36.1-p35) (data not shown).

Hybridization of the (E5-1) PS2 cDNA clones to Northern Blots detected an ~2.3 kilobase mRNA band in many tissues including regions of the brain, as well as a ~2.6 mRNA band in muscle, cardiac muscle and pancreas.

In skeletal muscle, cardiac muscle and pancreas, the (E5-1) PS2 gene is expressed at relatively higher levels than in brain and as two different transcripts of ~2.3 Kb and ~2.6 Kb. Both of the transcripts have sizes clearly distinguishable from that of the 2.7 Kb PS1 transcript, and did not cross-hybridize with PS1 probes at high stringency. The cDNA sequence of the (E5-1) PS2 gene is identified as SEQ ID NO:136.

The longest ORF within the (E5-1) PS2 cDNA consensus nucleotide sequence predicts a polypeptide containing 448 amino acids (SEQ ID NO:137) numbering from the first in-phase ATG codon which was surrounded by GCC-agg-GCt-ATG-c Kozak consensus sequence.

Analysis of RT-PCR products from brain and muscle RNA revealed that nucleotides 1153–1250 of the PS2 transcript are alternately spliced.

A splice variant of the (E5-1) PS2 cDNA sequence identified as SEQ ID NO:136 has also been found in all tissue examined. This splice variant lacks the triplet GAA at nucleotide positions 1338–1340.

A further variant has been found in one normal individual whose (E5-1) PS2 cDNA had C replacing T at nucleotide position 626, without any change in the amino acid sequence.

The DNA sequence of the PS2 gene as cloned has been incorporated into a vector and deposited at ATCC, Rockville, Md., under ATCC accession number 97214 on Jun. 28, 1995.

Mutations of the PS2 (E5-1) Gene Associated with Alzheimer's Disease

The strong similarity between PS1 and the (E5-1) PS2 gene product raised the possibility that the (E5-1) PS2 gene might be the site of disease-causing mutations in some of a small number of early onset AD pedigrees in which genetic linkage studies have excluded chromosomes 14, 19 and 21. RT-PCR was used to isolate cDNAs corresponding to the (E5-1) PS2 transcript from lymphoblasts, fibroblasts or post-mortem brain tissue of affected members of eight pedigrees with early onset FAD in which mutations in the βAPP and PS1 gene had previously been excluded by direct sequencing studies.

Examination of these RT-PCR products detected a heterozygous A→G substitution at nucleotide 1080 in all four affected members of an extended pedigree of Italian origin (Flo10) with early onset, pathologically confirmed FAD (onset=50–70 yrs). This mutation would be predicted to cause a Met→Val missense mutation at codon 239 (Table 8).

A second mutation (A→T at nucleotide 787) causing a Asn→Ile substitution at codon 141 was found in affected members of a group of related pedigrees of Volga German ancestry (represented by cell lines AG09369, AG09907, AG09952, and AG09905, Coriell Institute, Camden N.J.). Significantly, one subject (AG09907) was homozygous for this mutation, an observation compatible with the in-bred nature of these pedigrees. Significantly, this subject did not have a significantly different clinical picture from those subjects heterozygous for the Asn141Ile mutation. Neither of the (E5-1) PS2 gene mutations were found in 284 normal Caucasian controls nor were they present in affected members of pedigrees with the AD3 type of AD.

Both of these PS2 mutations would be predicted to cause the substitution of residues which are highly conserved within the PS1/PS2 gene family.

An additional (E5-1) PS2 mutation is caused by a T to C substitution at base pair 1624 causing an Ile to Thr substitution at codon 420. This mutation was found in a further case of early onset (45 years of age) familial AD.

The finding of a gene whose product is predicted to share substantial amino acid and structural similarities with the PS1 gene product suggests that these proteins may be functionally related as independent proteins with overlapping functions but perhaps with slightly different specific activities, as physically associated subunits of a multimeric polypeptide or as independent proteins performing consecutive functions in the same pathway.

The observation of three different missense mutations in conserved domains of the (E5-1) PS2 protein in subjects with a familial form of AD argues that these mutations are, like those in the PS1 gene, causal to AD. This conclusion is significant because, while the disease phenotype associated with mutations in the PS1 gene (onset 30–50 yrs, duration 10 years) is subtly different from that associated with mutations in the (E5-1) PS2 gene (onset 40–70 years; duration up to 20 yrs), the general similarities clearly argue that the biochemical pathway subsumed by members of this gene family is central to the genesis of at least early onset AD. The subtle differences in disease phenotype may reflect a lower level of expression of the (E5-1) PS2 transcript in the CNS, or may reflect a different role for the (E5-1) PS2 gene product.

By analogy to the effects of PS1 mutations, (E5-1) PS2 when mutated may cause aberrant processing of APP (Amyloid Precursor Protein) into Aβ peptide, hyperphosphorylation of Tau microtubule associated protein and abnormalities of intracellular calcium homeostasis. Interference with these anomalous interactions provides a potential therapy for AD.

PS2 (E5-1) Protein

A comparison of the amino acid sequences of human PS1 and (E5-1) PS2 homologue protein is shown in Table 8. Identical residues are indicated by vertical lines. The locations of mutations in the (E5-1) PS2 gene are indicated by downward pointing arrows. The locations of the mutations in the human PS1 gene are indicated by upward pointing arrows. Putative TM domains are in open ended boxes. The alternatively spliced exons are denoted by superscripted (E5-1) PS2 or subscripted (PS1) "*".

BLASTP alignment analyses also detected significant homology with SPE-4 of C. elegans (P=3.5e-26; identity= 20–63% over five domains of at least 22 residues), and weak homologies to brain sodium channels (alpha III subunit) and to the alpha subunit of voltage dependent calcium channels from a variety of species (P=0.02; identities 20–28% over two or more domains each of at least 35 residues) (Altschul, 1990). These alignments are similar to those described above for the PS1 gene. However, the most striking homology to the PS2 protein was found with the amino acid sequence predicted for PS1. PS1 and PS2 proteins share 63% overall amino acid sequence identity, and several domains display virtually complete identity (Table 8). Furthermore, all eight residues mutated in PS1 in subjects with AD3 are conserved in the PS2 protein (Table 8). As would be expected, hydrophobicity analyses suggest that both proteins also share a similar structural organization.

The similarity was greatest in several domains of the protein corresponding to the intervals between transmembrane domain 1 (TM1) and TM6, and from TM7 to the C-terminus of the PS1 gene. The main difference from PS1 is a difference in the size and amino acid sequence of the acidically-charged hydrophilic loop in the position equivalent to the hydrophilic loop between transmembrane domains TM6 and TM7 in the PS1 protein and in the sequence of the N-terminal hydrophilic domains.

Thus, both proteins are predicted to possess seven hydrophobic putative transmembrane domains, and both proteins bear large acidic hydrophilic domains at the N-terminus and between TM6 and TM7 (FIGS. 6 and 8). A further similarity arose from the above-described analysis of RT-PCR products from brain and muscle RNA, which revealed that nucleotides 1153–1250 of the (E5-1) PS2 transcript are alternatively spliced. These nucleotides encode amino acids 263–296, which are located within the TM6–TM7 loop domain of the putative PS2 protein and which share 94% sequence identity with the alternatively spliced amino acids 257–290 in PS1.

The most noticeable differences between the two predicted amino acid sequences occur in the amino acid sequence in the central portion of the TM6→TM7 hydrophilic loop (residues 304–374 of PS1; 310–355 of (PS2), and in the N-terminal hydrophilic domain (Table 8). By analog, this domain is also less highly conserved between the murine and human PS1 genes (identity=47/60 residues), and shows no similarity to the equivalent region of SPE-4.

Isolation and Purification of PS2 (ARMP) Protein

The PS2 protein may be isolated and purified by the type of methods described above for the PS1 protein.

The protein may also be prepared by expression of the (E5-1) PS2 cDNA described herein in a suitable host. The protein is preferably expressed as a fusion protein by ligating its encoding cDNA sequence to a vector containing the coding sequence for another suitable peptide, e.g., GST. The fusion protein is expressed and recovered from prokaryotic cells such as bacterial or baculovirus cells or from eukaryotic cells. Antibodies to PS1, by virtue of portions of amino acid sequence identity with PS2, can be used to purify, attract and bind to PS2 protein and vice versa.

Antibodies to PS2 (E5-1)

Due to its structural similarity with the PS1, the PS2 protein may be used for the development of probes, peptides, or antibodies to various peptides within it which may recognize both the PS2 and the PS1 gene products. As a protein homologue for the PS1, the PS2 protein may be used as a replacement for a defective PS1 gene product. It may also be used to elucidate functions of the PS1 gene in tissue culture and vice versa.

Transgenic Mouse Model of PS2 (E5-1)-Related Alzheimer's Disease

An animal model of Alzheimer's Disease related to mutations of the PS2 gene may be created by methods analogous to those described above for the PS1 gene.

Functional Domains of Presenilins

The mutations in presenilin I (PS1) and presenilin II (PS2) cluster around two domains, suggesting that these domains are the functional domains of these proteins. Five PS1 mutations cluster in the region between codon 82 and codon 146 which comprises the putative first transmembrane domain (TM1), the TM1–TM2 loop, and the TM2 domain in presenilin I; the mutation at codon 141 of PS2 is located in the TM2 domain of presenilin II. These mutations probably destabilize the TM1–TM2 loop domain and its anchor points in TM1 and TM2. Eight PS1 mutations result in the alteration of amino acids between codons 246 and 410, which are involved in TM6, the TM6–TM7 loop, and TM7. The TM6–TM7 loop is located on the opposite face of the membrane from the TM1–TM2 loop. These mutations may modify the structure or stability of the TM6–TM7 loop (either directly or by modifying the conformation of TM6 or TM7). Further evidence for a functional domain residing in the TM6–TM7 loop (amino acids 300 to 371) is the sequence divergence in the central part of the TM6–TM7 loop among different members of the presenilin protein family. Because the amino-terminus sequences of members of the presenilin protein family are divergent, it is likely that the amino-terminus, like the TM6–TM7 loop, plays a role in conferring specificity to the function of each of the different presenilin proteins. These regions may represent ligand binding sites. If this is so, mutations in the TM6–TM7 region are likely to modify ligand binding activity. The TM1–TM2 loop, which is conserved amongst different members of the presenilin protein family, probably represents an effector domain on the opposing membrane face. Both the TM6–TM7 loop and the TM1–TM2 loop can be used as sites to develop specific binding agents to inhibit the effects of the mutations and/or restore the normal function of the presenilin protein in subjects with Alzheimer's Disease.

Isolation of Presenilin Binding Proteins

Isolation of interacting partners of the presenilins allows identification of the biochemical partners for the presenilins and thus the identification of the biochemical pathway disturbed by mutations in PS1 and PS2. Such partners could be for example, enzymes, co-receptors, ligands or stabilizers. By analysing these interactions, it is possible to design compounds which counteract the effect of the mutation interaction, thus providing treatment for abnormal interactions. These treatments might alter the interaction of the presenilins with these partners, they may alter the function of the interacting protein, they may alter the amount of tissue distributions or expression of the interaction partners, or they may alter similar properties of the presenilins themselves.

Soluble recombinant fusion proteins can be made, or the nucleotide sequence coding for amino acids within the loop or parts of the loop can be expressed, in suitable vectors (yeast-2-hybrid, baculovirus, and phage-display systems for instance) and used to identify other proteins which interact with PS1 or PS2 in the pathogenesis of Alzheimer's Disease and other neurological and psychiatric disease. Therapies can be designed to modulate these interactions and thus to modulate Alzheimer's Disease and the other conditions associated with acquired or inherited abnormalities of the PS1 and PS2 genes or their gene products. The potential efficacy of these therapies can be tested by analyzing the affinity and function of these interactions after exposure to the therapeutic agent by standard pharmacokinetic measurements of affinity (Kd and Vmax etc) using synthetic peptides or recombinant proteins corresponding to functional domains of the PS1 gene, the PS2 gene or other presenilin homologues. Another method for assaying the effect of any interactions involving functional domains such as the hydrophilic loop is to monitor changes in the intracellular trafficking and post-translational modification of the relevant genes by in situ hybridization, immunohistochemistry, Western blotting and metabolic pulse-chase labelling studies in the presence of, and in the absence of, the therapeutic agents. A further method is to monitor the effects of "downstream" events including (i) changes in the intracellular metabolism, trafficking and targeting of APP and its products; (ii) changes in second messenger events, e.g., cAMP intracellular $Ca^{++}$, protein kinase activities, etc.

Based on the locations of the familial AD mutations, the position of divergent primary sequence and the general topology of the PS1 and PS2 proteins, it is proposed that at least three domains may provide functional specificity to the presenilins. These functional domains are (1) the N-terminus (unique sequence in PS1 and PS2); (2) the TM6→7 loop (clustered mutations in the flanking conserved hydrophobic sequences and unique internal sequence); (3) the TM1, TM2 domains and TM1→2 linking sequence (concentration of several familial AD mutations) and (4) the C-terminus. To isolate proteins that interact with these functional domains, screening for presenilin binding proteins is carried out using GST-fusion constructs and synthetic peptides corresponding to these regions. For example, for PS2, GST-fusion peptides are made including sequences corresponding to amino acids 1 to 87 (N-terminus) or 272–390 (TM6→7 loop) or a synthetic peptide is made corresponding to amino acids 107 to 134 (TM1→2 link); for PS1, GST-fusion peptides are made including sequences corresponding to amino acids 1 to 81 (N-terminus) or 266 to 410 (TM6→7 loop) or a synthetic peptide is made corresponding to amino acids 101 to 131 (TM1→2 link). The following methods may be employed to isolate presenilin binding proteins:

(1) direct extraction by affinity chromatography using GST-fusion proteins and synthetic peptides;
(2) co-isolation of presenilins and bound proteins by immunoprecipitation;
(3) Biomolecular Interaction Assay (BIAcore) utilizing a GST-fusion capture system; and
(4) Two-Hybrid yeast systems.

1. GST-Presenilin Fusion Protein & Synthetic Peptide Affinity Chromatography

GST-fusion proteins containing the N-terminus and TM6→7 loop sequences for PS1 and PS2 are used to probe human brain homogenates and the isolated collection of proteins is separated by SDS-PAGE and microsequenced (Phizicky and Fields, 1995). To ensure that the band being sequenced contains only one protein species, the presenilin-fusion and binding proteins are separated by 2D gel electrophoresis prior to transfer and sequencing. For proteins with a blocked N-terminus, an additional HPLC purification and cleavage (CNBr and/or trypsin) of the particular binding protein is used to release peptide fragments. Further purification by HPLC and microsequencing by conventional methods provides internal sequence data on such blocked proteins.

The TM1→2 linking sequence is predicted to reside on the opposite side of the membrane to that of the N-terminal and TM6→7 loop and may be important in transmembrane communication. This is supported by the Tyr115 His mutation which was observed in a pedigree with early onset familial AD (30–40 years) and by additional mutations in the TM1/2 helices which might be expected to destabilise the loop. The TM1→2 loop is relatively short (PS1: residues 101–131; PS2: residues 107–134) making these sequence more amenable to conventional peptide synthesis. The PS1 fragment (31-mer) has been synthesised containing an additional C-terminal cysteine residue. This peptide will be used to create an affinity substrate for affinity chromatography (Sulfo-link; Pierce) to isolate binding proteins for microsequencing. A peptide corresponding to the PS2 sequence is similarly synthesised and used to screen for distinct binding proteins.

2. Co-Immunoprecipitation of PS1/PS2 and Bound Proteins

An additional technique for the isolation of the presenilins and their associated proteins is direct immunoprecipitation with antibodies. This procedure has been successfully used, for example, to isolate many of the synaptic vesicle associated proteins (Phizicky & Fields, 1994).

3. Biomolecular Interaction Assay (BIAcore)

A useful method for the detection and isolation of binding proteins is the BIAcore system developed by Pharmacia Biosensor and described in the manufacturer's protocol (LKB Pharmacia, Sweden). This system uses an affinity purified anti-GST antibody to immobilize GST-fusion proteins onto a sensor chip. The sensor utilizes surface plasmon resonance which is an optical phenomenon that detects changes in refractive indices. A homogenate of a tissue of interest is passed over the immobilized fusion protein and protein-protein interactions are registered as changes in the refractive index. This system can be used to determine the kinetics of binding, to assess whether any observed binding is of physiological relevance.

4. Two-Hybrid Yeast System

The Two-Hybrid system takes advantage of transcriptional factors that are composed of two physically separable, functional domains (Phizicky and Fields, 1994, supra). The most commonly used is the yeast GAL4 transcriptional activator consisting of a DNA binding domain and a transcriptional activation domain. Two different cloning vectors are used to generate separate fusions of the GAL4 domains to genes encoding potential binding proteins. The fusion proteins are co-expressed, targeted to the nucleus and, if interactions occur, activation of a reporter gene (e.g. lacZ)

produces a detectable phenotype. For example, the Clontech Matchmaker System-2 may be used to screen the Clontech brain cDNA GAL4 activation domain fusion library with presenilin GAL4 binding domain fusion clones (Clontech, Palo Alto, Calif.).

Identification of Small Molecules with Presenilin Binding Capacity

Small molecule-based therapies are particularly preferred because such molecules are more readily absorbed after oral administration, have fewer potential antigenic determinants, and/or are more likely to cross the blood brain barrier than larger, protein-based pharmaceuticals. In light of the present disclosure, one of ordinary skill in the art is enabled to develop drug screening methodologies which will be useful in the identification of candidate small molecule pharmaceuticals for the treatment of Alzheimer's Disease. In particular, one is enabled to screen large libraries of small molecules in order to identify those which bind to the normal and/or mutant PS1 or PS2 protein and which, therefore, are candidates for modifying the in vivo activity of the normal or mutant presenilin proteins. Furthermore, one is enabled to identify small molecules which selectively or preferentially bind to a mutant form of a presenilin protein and which, therefore, may have particular utility in treating heterozygous victims of this dominant autosomal disease.

Methods for screening small molecule libraries for candidate protein-binding molecules are well known in the art and, in light of the present disclosure, may now be employed to identify compounds which bind to the normal or mutant forms of a presenilin. Briefly, in one embodiment, either a normal or mutant PS1 or PS2 protein may be immobilized on a substrate such as a column or filter, and a solution including the test compound(s) is contacted with the presenilin protein under conditions which are permissive for binding. The substrate is then washed with a solution which substantially reflects physiological conditions to remove unbound or weakly bound small molecules. A second wash may then elute those compounds which strongly bound to the immobilized normal or mutant presenilin. Alternatively, the small molecule test compounds may be immobilized and a solution of normal or mutant PS1 or PS2 may be contacted with the column, filter or other substrate. The ability of the presenilin to bind to the small molecules may be determined as above or a labelled form of presenilin (e.g., radio-labelled or chemiluminescent) may be used to more rapidly assess binding to the substrate-immobilized compound(s). In addition, as both PS1 and PS2 are believed to be membrane associated proteins, it may be preferred that the presenilin proteins be incorporated into lipid bilayers (e.g., liposomes) to promote their proper folding. Such presenilin-liposomes may be immobilized on substrates (either directly or by means of another element in the liposome membrane), passed over substrates with immobilized small molecules, or used in any of a variety of other well known binding assays for membrane proteins. In another series of embodiments, either normal or mutant, free or membrane-bound PS1 or PS2 may be mixed in a solution with the candidate compound(s) under conditions which are permissive for binding, and the presenilin may be immunoprecipitated. Small molecules which co-immunoprecipitate with a presenilin may then be identified. As will be obvious to one of ordinary skill in the art, there are numerous other methods of screening individual small molecules or large libraries of small molecules (e.g., phage display libraries) to identify compounds which bind to normal or mutant presenilins. All of these methods comprise the step of mixing normal or mutant presenilin with test compounds, allowing for binding (if any), and assaying for bound complexes. All such methods are now enabled by the present disclosure of purified the presenilin I and presenilin II proteins.

Because the normal physiological roles of PS1 and PS2 are still unknown, compounds which bind to normal or mutant or both forms of these presenilins may have utility in treatments. Compounds which bind only to a normal presenilin may, for example, act as enhancers of its normal activity and thereby at least partially compensate for the lost or abnormal activity of mutant forms of the presenilin in Alzheimer's Disease victims. Compounds which bind to both normal and mutant forms of a presenilin may have utility if they differentially affect the activities of the two forms so as to alleviate the overall departure from normal function. Alternatively, blocking the activity of both normal and mutant forms of either PS1 or PS2 in heterozygotes may have less severe physiological and clinical consequences than the normal progress of the disease and, therefore, compounds which bind to and inhibit the activity of both normal and mutant forms of a presenilin may have utility. Preferably, however, compounds are identified which have a higher affinity of binding to mutant presenilin than to normal presnilin (e.g., 5–10 fold higher $K_a$) and which selectively or preferentially inhibit the activity of the mutant form. Such compounds may be identified by using any of the techniques described above and by then comparing the binding affinities of the candidate compound(s) for the normal and mutant forms of PS1 or PS2.

Once identified by the methods described above, the candidate compounds may then be produced in quantities sufficient for pharmaceutical administration or testing (e.g., $\mu$g or mg or greater quantities), and formulated in a pharmaceutically acceptable carrier (see, e.g., *Remington's Pharmaceutical Sciences*, Gennaro, A., ed., Mack Pub., 1990, the disclosure of which is incorporated herein by reference). These candidate compounds may then be administered to Alzheimer's patients or animal models of Alzheimer's Disease. The animal models described and enabled herein are of particular utility in further testing candidate small molecules which bind to normal or mutant presnilin for their therapeutic efficacy.

Once identified by the methods described above, the candidate compounds may also serve as "lead compounds" in the design and development of new pharmaceuticals. For example, as is well known in the art, sequential modification of small molecules (e.g., amino acid residue replacement with peptides; functional group replacement with peptide or non-peptide compounds) is a standard approach in the pharmaceutical industry for the development of new pharmaceuticals. Such development generally proceeds from a "lead compound" which is shown to have at least some of the activity (e.g., PS1 binding ability) of the desired pharmaceutical. In particular, when one or more compounds having at least some activity of interest (e.g., PS1 binding) are identified, structural comparison of the molecules can greatly inform the skilled practitioner by suggesting portions of the lead compounds which should be conserved and portions which may be varied in the design of new candidate compounds. Thus, the present invention also provides a means of identifying lead compounds which may be sequentially modified to produce new candidate compounds for use in the treatment of Alzheimer's Disease. These new compounds then may be tested both for presnilin-binding (e.g., in the binding assays described above) and for therapeutic efficacy (e.g., in the animal models described herein). This procedure may be iterated until compounds having the desired therapeutic activity and/or efficacy are identified.

Assays for Identifying Drugs Which Affect Presenilin Expression

In another series of embodiments, the present invention provides asays for identifying small molecules or other compounds which are capable of inducing or inhibiting the expression of PS1, PS2 or other presenilin-related genes and proteins. The assays may be performed in vitro using non-transformed cells, immortalized cell lines, or recombinant cell lines. In addition, the assays may detect the presence of increased or decreased expression of PS1, PS2 or other presenilin-related genes or proteins on the basis of increased or decreased mRNA expression (using, e.g., the nucleic acid probes disclosed and enabled herein), increased or decreased levels of PS1, PS2 or other presenilin-related protein products (using e.g., the anti-presnilin antibodies disclosed and enabled herein), or increased or decreased levels of expression of a reporter gene (e.g., β-galactosidase or luciferase) operatively joined to a presenilin 5' regulatory region in a recombinant construct.

Thus, for example, one may culture cells known to express a particular presenilin and add to the culture medium one or more test compounds. After allowing a sufficient period of time (e.g., 6–72 hours) for the compound to induce or inhibit the expression of the presenilin, may change in levels of expression from an established baseline may be detected using any of the techniques described above and well known in the art. In particularly preferred embodiments, the cells are from an immortalized cell line such as human glioblastoma cell line or a hybridoma x glioma cell line. Using the nucleic acid probes and/or antibodies disclosed and anbled herein, detection of changes in the expression of presenilin, and thus identification of the compound as an inducer or repressor of presenilin expression, requires only routine experimentation.

In particularly preferred embodiments, a recombinant assay is employed in which a reporter gene such as β-galactosidase or luciferase is operably joined to the 5' regulatory regions of a presenilin gene. Such regulatory regions may be easily isolated and cloned by one of ordinary skill in the art in light of the present disclosure of the coding regions of these genes. The reporter gene and regulatory regions are joined in-frame (or in each of the three possible reading frames) so that transcription and translation of the reporter gene may proceed under the control of the presenilin regulatory elements. The recombinant construct may then be introduced into any appropriate cell type although mammalian cells are preferred, and human cells are most preferred. The transformed cells may be grown in culture and, after establishing the baseline level of expression of the reporter gene, test compounds may be added to the medium. The ease of detection of the expression of the reporter gene provides for a rapid, high through-put assay for the identification of inducers and repressors of the presenilin gene.

Compounds identified by this method will have potential utility in modifying the expression of the PS1, PS2 or other presenilin-related genes in vivo. These compounds may be further tested in the animal models disclosed and enabled herein to identify those compounds having the most potent in vivo effects. In addition, as described above with respect to small molecules having presenilin-binding activity, these molecules may serve as :lead compounds" for the further development of pharmaceuticals by, for example, subjecting the compounds to sequential modifications, molecular modeling, and other routine procedures employed in rational drug design.

Identification of a Homologue of the ARMP (PS1) Gene in E. elegans

A homologue of the presenilin genes have been found in C. elegans. This homologue is designated SEL-12. Missense and nonsense mutations in this gene lead to an incompletely penetrant defect in intracellular signal transduction pathways mediated by the Notch/Lin-12 gene (Levitan, 1995). The Notch/Lin-12 gene mediates intercellular signalling and cell fate determination during embryo genesis.

By determining the biology of this C. elegans gene, one obtains a simpler model on which one can study potential therapeutics for manipulation of the system.

By examining the relationship between Notch/Lin-12 genes and the human presenilins, Drosophila DmPS and C. elegans SEL-12, one may elucidate the general biochemical functions of the presenilins and identify upstream and downstream genes in the pathway which can be modified therapeutically by drugs. Notch is involved in cell fate decisions in embryo genesis. These same cell fate decisions may be reactivated after injury due to genetic or environmental agents. If the presenilins, amyeloid precursor protein (APP), or apolipoprotein E (ApoE) are involved in Notch mediated responses to injury, or responses mediated by other genes, which lead to regeneration or degeneration decisions similar to those occurring in embryo genesis (differentiation versus degeneration) then knowledge of this pathway can be exploited to develop drugs to suppress degenerative response and augment normal regenerative response. The C. elegans and D. melanogaster models provide convenient ways to (1) define the genes involved in Notch-presenilin interactions; (2) determine the structural nature of these interactions and effects of mutations on these interactions; and (3) develop and test compounds based on the data from (1) and (2) to modulate these interactions. There is good evidence APP and ApoE are involved in injury repair mechanisms.

This observation suggests that the presenilin genes may have similar functions and that mutations in the presenilin genes may alter the effectiveness of intracellular signalling pathways. Modification of a signalling pathway in the presence of presenilin mutations could be used as a means to define treatments for Alzheimer's Disease (AD). The potential mechanisms by which mutations in the presenilin genes might alter intracellular signalling pathways include the following:

First, the presenilin gene could act as a co-receptor with other receptors such as Notch/Lin-12.

Second, the presenilins could be involved as downstream effectors in the signal pathway (for instance, perhaps acting as a second messenger or amplification system through modification of calcium metabolism, etc.). Alternatively, the presenilin proteins may be involved in the intracellular processing of membrane proteins such as Notch/Lin-12 or the βAPP proteins. This role in protein processing would be in keeping with the intracellular localization of the presenilin proteins in the endoplasmic reticulum and Golgi apparatus. The alteration of protein processing could occur shortly after synthesis of the native membrane proteins (e.g. the presenilins may have a role in chaperone, protein folding, and membrane insertion events). Alternatively, the presenilins might have a function in the processing of other enzymes and intracellular proteins which are necessary for the modification of cell surface proteins such as Notch/Lin-12 and βAPP (e.g. the presenilins may be involved in the processing of α, β and secretase which are involved in βAPP metabolism). The presenilins could also be involved in the intracellular transport of fragments of cell membrane proteins (e.g. the C-terminal stump of Notch/Lin-12 or βAPP), as for instance in the translocation of Notch/Lin-12 fragments into the nucleus where they affect transcription.

Disturbances of function caused by mutations in the presenilin genes could be modified or corrected by drug treatment. These drugs could be screened for by using one or more of the following assays:

PC12 cells (ATCC, Rockville, Md.) are stably transfected by standard lipofectamine or calcium phosphate methods with wild-type and mutant presenilin cDNA's cloned into the vector pcDNA3 (Invitrogen, San Diego, Calif.) and induced to differentiate into neuron-like cell types by the administration of nerve growth factor (Gibco/BRL, Md.) (Obermeier et al., (1994), these cells return to the undifferentiated state after withdrawal of the nerve growth factor. Differences in the rates and degrees of differentiation between PC12 cells transfected with wild-type or mutant presenilin cDNA's can be quantitated and an assay is thereby obtained, in which reversion to the wild-type phenotype is scored after the administration of a variety of chemical compounds available from a pharmaceutical/chemical combinatorial library.

A similar assay can be derived based upon Notch signalling pathways in other cell types including *Drosophila melanogaster* cells (PC or S2 cells) transfected with activated (mutant) Notch cDNA clones, or mammalian P19 cells also transfected with activated Notch cDNA clones.

By double-transfecting the Drosophila or P19 cells with the activated Notch clone, and with either wild-type or mutant presenilin cDNA's, it is possible to discern a difference in the rate of differentiation in cell types transfected with wild-type presenilin compared to cell types co-transfected with the mutant presenilin cDNA. Again, by challenging these cell types and scoring the phenotype of suppression of differentiation into neuronal cells in the presence of chemicals drawn from a chemical combinatorial library, compounds may be identified which reverse the effect of mutant presenilin genes on this Notch-mediated phenotype.

A similar effect can also be achieved in *C. elegans* and *Drosophila melanogaster* whole animals. In this system, animals bearing either wild-type Notch/Lin-12 genes or activated mutations in the Notch/Lin-12 gene also carry either wild-type or mutant human presenilin transgenes.

*C. elegans* and *D. melanogaster* are transformed by microinjection oocytes.

The presenilin transgenes are cloned downstream of the *C. elegans* heat-shock promoter element in an expression vector such as pPD69.78 hsp 16.2 or pPD69.3 hsp 16–41, which are public domain vectors for creating *C. elegans* transgenic lines in which the gene of interest is under the control of an inducible heat shock promoter element.

Identification of a Homologue of the PS1 (ARMP) Gene in *D. melanogaster*

A homologue of the presenilin genes has been found in *D. melanogaster*. This homologue is designated the DmPS gene.

Redundant oligonucleotides coding for highly conserved regions of the presenilin/sel 12 portions were prepared and used to identify relevant mRNAs from adult and embryonic *D. melanogaster*. These mRNAs were sequenced and shown to contain an open reading frame with a putative amino acid sequence highly homologous to that of the human presenilins. The DmPS cDNA is identified as SEQ ID NO:165.

This sequence encodes a polypeptide of 541 amino acids (SEQ ID NO:166) with about 52% identity to the human presenilins.

The DNA sequence of the DmPS gene as cloned has been incorporated into a plasmid Bluescript. This stable vector was been deposited at ATCC, Rockville, Md., under ATCC accession number 97428 on Jan. 26, 1996.

The structure of the *D. melanogaster* homologue is similar to that of the human presenilins with at least seven putative transmembrane domains (Kyte-Doolittle hydrophobicity analyses using window of 15 and cut-off of 1.5). Evidence of at least one alternative splice form was detected in that clone pds 13 contained an ORF of 541 amino acids, while clones pds 7 , pds 14 and pds 1 lacked nucleotides 1300–1341 inclusive. This alternative splicing would result in the alteration of Gly to Ala at residue 384 in the putative TM6–TM7 loop, and in-frame fusion to the Glu residue at codon 399 of the longer ORF. The principal differences between the amino acid sequence of the *D. melanogaster* and human genes were in the N-terminal acid hydrophilic domain and in the acid hydrophilic portion of the TM6–TM7 loop. The residues surrounding the TM6→TM7 loop are especially conserved (residues 220–313 and 451–524) suggesting that these are functionally important domains. Sixteen out of twenty residues mutated in human PS1 or PS2 and giving rise to human FAD are conserved in the *D. melanogaster* homologue.

The *D. malanogaster* presenilin (DmPS) gene can be targeted for null mutations (either spontaneous deletions/ rearrangements or mutations inserted by standard P-element mutagenesis techniques). Wild-type or mutant transgenes can be over-expressed using standard transgenic methods in which cDNA minigene under the control of one or more promoter elements such as the GAL4-UAS system is microinjected into oocytes (Brand and Perrimon, 1993). The presence or absence of a phenotype can be scored by anatomic and pathologic inspection, for example, for defects in Notch mediated developmental pathways (Campos-Ortega, 1991) similar to those seen in *C. elegans* with defects in the sel-12 gene, which is the *C. elegans* homologue of the human presenilin genes (Levitan & Greenwald, 1995), or for behavioural defects, for example defects in memory and learning, using methods used to characterize this in *D. melanogaster* mutants such as "dunce" and "ruderbaker" (Davis, 1996), or by biochemical methods (e.g. detection of defects in the handling of APL-1 which is the *D. melanogaster* homologue of the human APP genes thought to be involved in AD). Drosophila models can be used to explore the general biochemical function of the DmPS gene by analyzing the effect of null (knockout) mutations, the effects, in the *D. melanogaster,* of missense mutations gene similar to those observed in the human presenilin genes in human early onset AD and the effects of over-expressing wild-type or mutant DmPS. Such models can also be used to determine whether the human presenilin genes can complement loss of function mutations in the Drosophila DmPS gene, providing guidance for gene replacement therapy in humans with mutant presenilin genes). These models can also be used to test the efficacy of drugs intended to affect the biochemical processes which cause AD. Such drug screening is carried out by observing which drugs correct or improve a phenotype associated with a DmPS gene mutation.

The DmPS gene can also be used to define other proteins which interact with the Drosophila DmPS homologue. The human equivalents of any interacting proteins identified in *D. melanogaster* can be isolated using a variety of methods including PCR with redundant oligonucleotides, and protein database searches. The function of the interacting protein can also be more conveniently examined in *D. melanogaster* by genetic and biochemical means. Methods for identifying and characterizing such interacting proteins include yeast-2-hybrid, affinity chromatography using the *D. melanogaster* protein as the affinity reagent), and immunoprecipitation (with or without cross-linking) methods (Phizicky & Fields, 1995). The kinetics, biochemistry, and structural basis of this interaction can be verified using BIAcore analysis or crystallography etc and would serve as a basis for the development of compounds to augment defective interactions or impede pathological interactions due to mutations in the *D. melanogaster* presenilin. The function of the interacting protein can also be more easily worked out by genetic and biochemical means in *D. melanogaster* than in a higher animal model.

Additionally, the DmPS gene can be used in genetic paradigms to identify other genes which interact with the presenilins and which can modulate the effect of the mutant isoforms of the presenilins. Cross breeding experiments with other mutant *D. melanogaster* lines provide a means of mapping and cloning other genes which suppress or enhance the phenotype associated with mutations in the *D. melanogaster* presenilin. Subsequent isolation of the human homologues of such modifier genes will identify gene products capable of modulating the effect of mutations in the human presenilin genes. The biochemical effect of these modulating gene products can be modelled and used to develop pharmaceuticals to treat AD. Part of or all of the modulating gene product itself can be administered as a treatment for AD by a variety of means including protein infusion and gene therapy.

SCREENING AND DIAGNOSIS FOR ALZHEIMER'S DISEASE

General Diagnostic Methods

The presenilin and presenilin-related genes and gene products, as well as other products derived therefrom (e.g., probes, antibodies), will be useful in the diagnosis of Alzheimer's Disease, presenile and senile dementias, psychiatric diseases such as schizophrenia, depression, etc., and neurologic diseases such as stroke and cerebral hemorrhage—all of which are seen to a greater or lesser extent in symptomatic subjects bearing mutations in the PS1 or PS2 genes or in the APP gene. Diagnosis of inherited cases of these diseases can be accomplished by methods based upon the nucleic acids (including genomic and mRNA/cDNA sequences), proteins and/or antibodies disclosed and enabled herein. Preferably, the methods and products are based upon the human PS1 or PS2 nucleic acids, proteins or antibodies disclosed herein. As will be obvious to one of ordinary skill in the art, however, the significant evolutionary conservation of large portions of the PS1 and PS2 nucleotide and amino acid sequences, even in species as diverse as humans and *C. elegans* and Drosophila, allow the skilled artisan to make use of such non-human presenilin-homologue nucleic acids, proteins and antibodies even for applications directed toward human or other mammalian subjects. Thus, for brevity of exposition, but without limiting the scope of the invention, the following description will focus upon uses of the human homologues of PS1 and PS2. It will be understood, however, that homologous sequences from other species, including those disclosed herein, will be equivalent for many purposes.

As will be appreciated by one of ordinary skill in the art, the choice of diagnostic methods of the present invention will be influenced by the nature of the available biological samples to be tested and the nature of the information required. PS1, for example, is highly expressed in brain tissue but brain biopsies are invasive and expensive procedures, particularly for routine screening. Other tissues which express PS1 at significant levels, however, may demonstrate alternative splicing (e.g., white blood cells) and, therefore, PS1 mRNA or protein from such cells may be less informative. Thus, assays based upon a subject's genomic DNA may be the preferred methods for PS1 diagnostics as no information will be lost due to alternative splicing and because essentially any nucleate cells may provide a usable sample. Diagnostics based upon other presenilin-related proteins are subject to similar considerations: availability of tissues, levels of expression in various tissues, and alternative translation products resulting from alternative mRNA splicing.

When a diagnostic assay is to be based upon presenilin-related proteins, a variety of approaches are possible. For example, diagnosis can be achieved by monitoring differences in the electrophoretic mobility of normal and mutant proteins. Such an approach will be particularly useful in identifying mutants in which charge substitutions are present, or in which insertions, deletions or substitutions have resulted in a significant change in the molecular mass of the resultant protein. Alternatively, diagnosis may be based upon differences in the proteolytic cleavage patterns of normal and mutant proteins, differences in molar ratios of the various amino acid residues, or by functional assays demonstrating altered function of the gene products. In some preferred embodiments, protein-based diagnostics will employ differences in the ability of antibodies to bind to normal and mutant presenilin-related proteins (especially PS1 or PS2). Such diagnostic tests may employ antibodies which bind to the normal proteins but not to mutant proteins, or vice versa. Because a limited number of mutations have been identified in the PS1 and PS2 genes/proteins, and because these mutations appear to be themselves conserved, it is currently preferred that antibodies capable of selectively binding to mutant proteins be employed. In particular, an assay in which a plurality of monoclonal antibodies each capable of binding to a mutant epitope, may be employed. The levels of anti-mutant antibody binding in a sample obtained from a test subject (visualized by, for example, radiolabelling, ELISA or chemiluminescence) may be compared to the levels of binding to a control sample. Such antibody diagnostics may be used for in situ immunohistochemistry using biopsy samples of CNS tissues obtained antemortem or postmortem, including neuropathological structures associated with these diseases such as neurofibrillary tangles and amyloid plaques, or may be used with fluid samples such a cerebrospinal fluid or with peripheral tissues such as white blood cells.

When the diagnostic assay is to be based upon nucleic acids from a sample, either mRNA or genomic DNA may be used. When mRNA is used from a sample, many of the same considerations apply with respect to source tissues and the possibility of alternative splicing. That is, there may be little or no expression of transcripts unless appropriate tissue sources are chosen or available, and alternative splicing may result in the loss of some information. With either mRNA or DNA, standard methods well known in the art may be used to detect the presence of a particular sequence either in situ or in vitro (see, e.g. Sambrook et al., eds. (1989) Molecular Cloning: A Laboratory Manual, Cold Spring Harbor Press, Cold Spring Harbor, N.Y.).

For in situ detection of a mutant PS1, PS2 or other presenilin-related nucleic acid sequence, a sample of tissue may be prepared by standard techniques and then contacted with a probe, preferably one which is labelled to facilitate detection, and an assay for nucleic acid hybridization is conducted under stringent conditions which permit hybridization only between the probe and highly or perfectly complementary sequences. Because most of the PS1 and PS2 mutations detected to date consist of a single nucleotide substitution, high stringency hybridization conditions will be required to distinguish normal sequences from most mutant sequences. As an example only, the following procedure may be employed on a subject. A rat animal model is anesthetized and transcardially perfused with cold PBS, followed by perfusion with a formaldehyde solution. The brain or other tissue of interest is then removed, frozen in liquid nitrogen, and cut into thin micron sections. The sections are placed on slides and incubated in proteinase K. Following rinsing in DEP, water and ethanol, the slides are placed in prehybridization buffer. A radioactive probe corresponding to the selected oligonucleotide is incubated with the sectioned brain tissue. After incubation and air drying, the labeled areas are visualized by autoradiography. Dark spots on the tissue sample indicate hybridization of the probe with brain mRNA, demonstrating expression of the nucleic acid sequence.

A significant advantage of the use of either DNA or mRNA is the ability to amplify the amount of genetic material using the polymerase chain reaction (PCR), either alone (with genomic DNA) or in combination with reverse transcription (with mRNA to produce cDNA). Because it is contemplated that such PCR-based genetic methods may be preferred commercial embodiments for diagnostic screenings, a detailed description of several embodiments is presented below.

Screening for Alzheimer's Disease Linked to Chromosome 14

Screening for Alzheimer's Disease as linked to chromosome 14 may now be readily carried out because of the knowledge of the mutations in the gene.

Individuals with a high risk for Alzheimer's Disease (present in family pedigree) or, individuals not previously known to be at risk, or people in general may be screened routinely using probes to detect the presence of a mutant PS1 gene by a variety of techniques. Genomic DNA used for the diagnosis may be obtained from body cells, such as those present in the blood, tissue biopsy, surgical specimen, or autopsy material. The DNA may be isolated and used directly for detection of a specific sequence or may be PCR amplified prior to analysis. RNA or cDNA may also be used. To detect a specific nucleic acid sequence, hybridization using specific oligonucleotides, direct nucleotide sequencing, restriction enzyme digest, RNase protection, chemical cleavage, or ligase-mediated detection may be used. Oligonucleotides specific to mutant sequences can be chemically synthesized and labelled radioactively with isotopes, or non-radioactively using biotin tags, and hybridize to individual samples immobilized on membranes or other solid-supports by dot-blot or transfer from gels after electrophoresis. The presence or absence of these mutant sequences is then visualized using methods such as autoradiography, fluorometry, or colorimetric reaction. Examples of suitable PCR primers which are useful for example in amplifying portions of the subject sequence containing the aforementioned mutations are set out in Table 5. This table also sets out changes in restriction enzyme sites to provide a useful diagnostic tool as defined herein. Direct DNA sequencing reveals sequence differences between normal and mutant PS1 DNA. Cloned genomic or cDNA segments may be used as probes to detect specific DNA segments. PCR can be used to enhance the sensitivity of this method. PCR is an enzymatic amplification directed by sequence-specific primers, and involves repeated cycles of heat denaturation of the DNA, annealing of the complementary primers and extension of the annealed primer with a DNA polymerase. This results in an exponential increase of the target DNA.

Other nucleotide sequence amplification techniques may be used, such as ligation-mediated PCR, anchored PCR and enzymatic amplification as will be understood by those skilled in the art.

Sequence alterations may also generate fortuitous restriction enzyme recognition sites which are revealed by the use of appropriate enzyme digestion followed by gel-blot hybridization. DNA fragments carrying the site (normal or mutant) are detected by their increase or reduction in size, or by the increase or decrease of corresponding restriction fragment numbers. Genomic DNA samples may also be amplified by PCR prior to treatment with the appropriate restriction enzyme and the fragments of different sizes are visualize, for example under UV light in the presence of ethidium bromide, after gel electrophoresis.

Genetic testing based on DNA sequence differences may be achieved by detection of alteration in electrophoretic mobility of DNA fragments in gels. Small sequence deletions and insertions can be visualized by high resolution gel electrophoresis of single stranded DNA, or as changes in the migration pattern of DNA heteroduplexes in non-denaturing gel electrophoresis. Alternatively, a single base substitution mutation may be detected based on differential PCR product length in PCR. The PCR products of the normal and mutant gene may be differentially detected in acrylamide gels.

Nuclease protection assays (S1 or ligase-mediated) also reveal sequence changes at specific locations.

Alternatively, to confirm or detect a polymorphism resulting in restriction mapping changes, ligated PCR, ASO, REF-SSCP chemical cleavage, endonuclease cleavage at mismatch sites or SSCP may be used. Both REF-SSCP and SSCP are mobility shift assays which are based upon the change in conformation due to mutations.

DNA fragments may also be visualized by methods in which the individual DNA samples are not immobilized on membranes. The probe and target sequences may be in solution or the probe sequence may be immobilized. Autoradiography, radioactive decay, spectrophotometry and fluorometry may also be used to identify specific individual genotypes. Mutations can also be detected by direct nucleotide sequencing.

According to an embodiment of the invention, the portion of the cDNA or genomic DNA segment that is informative for a mutation can be amplified using PCR. For example, the DNA segment immediately surrounding the C 410 Y mutation acquired from peripheral blood samples from an individual can be screened using the oligonucleotide primers TGGAGACTGGAACACAAC (SEQ ID NO:127) and GTGTGGCCAGGGTAGAGAACT (SEQ ID NO:128). This region would then be amplified by PCR, the products separated by electrophoresis, and transferred to membrane. Normal and mutant PCR products may then be detected using, for example, hybridization of labeled oligonucleotide probes and autoradiography, RFLP analysis, or direct sequencing.

Screening for Alzheimer's Disease Linked to Chromosome 1

Screening for Alzheimer's Disease linked to mutation of the PS2 gene may no be conveniently carried out.

General screening methods are described above in relation to the described mutations in the PS1 gene. These described methods can be readily applied and adapted to detection of the described chromosome 1 mutations, as will be readily understood by those skilled in the art.

In accordance with one embodiment of the invention, the Asn141Ile mutation is screened for by PCR amplification of the surrounding DNA fragment using the primers:

5'-CATTCACTGAGGACACACC (end-labelled)
       and                                 (SEQ ID NO:175)

5'-TGTAGAGCACCACCAAGA (unlabelled)    (SEQ ID NO:176)

Any tissue with nucleated cells may be examined. The amplified products may be separated by, for example, electrophoresis and an autoradiogram or other standard method may be employed to detect mutant sequences.

In accordance with a further embodiment, the Met239Val mutation is screened for by PCR amplification of its surrounding DNA fragment using the primers:

5'-GCATGGTGTGCATCCACT and        (SEQ ID NO:177)

5'-GGACCACTCTGGGAGGTA           (SEQ ID NO:178)

The amplified products are separated and an autoradiogram or other standard method may be employed to detect mutant sequences.

In accordance with a further embodiment, the Ile420Thr mutation is screened for by PCR amplification of genomic DNA using primers 5' TGC TGC TTG CTG TGT TCA 3' (SEQ ID NO:161) and 5' CGA TGT CCC TCA GAT GTA GA 3' (SEQ ID NO:162) to generate a 146 base pair product which can be probed with allele specific oligonucleotides for the wild-type (5' CAT CTC CAT CAC GTT CG 3'; SEQ ID NO:163) and mutant (5' CAT CTC CAC CAC GTT CG 3': SEQ ID NO:164) sequences.

The same primer sets may be used to detect the mutations by means of other methods such a SSCP, chemical cleavage, DGGE, nucleotide sequencing, ligation chain reaction and allele specific oligonucleotides. As will be understood by those skilled in the art, other suitable primer pairs may be devised and used.

In inherited cases, as the primary event, and in non-inherited cases as a secondary event due to the disease state, abnormal processing of PS1, PS2, APP or proteins reacting with PS1, PS2, or APP may occur. This can be detected as abnormal phosphorylation, glycosylation, glycation amidation or proteolytic cleavage products in body tissues or fluids, e.g., CSF or blood.

Diagnosis of non-inherited cases also can be made by observation of alterations in the presenilin transcription, translation, and post-translational modification and processing as well as alterations in the intracellular and extracellular trafficking of presenilin gene products in the brain and peripheral cells. Such changes will include alterations in the amount of presenilin messenger RNA and/or protein, alteration in phosphorylation state, abnormal intracellular location/distribution, abnormal extracellular distribution, etc. Such assays will include: Northern Blots (with presenilin-specific and non-specific nucleotide probes which also cross-react with other members of the gene family), and Western blots and enzyme-linked immunosorbent assays (ELISA) (with antibodies raised specifically to: a presenilin; to various functional domains of a presenilin; to other members of the homologous gene family; and to various post-translational modification states including glycosylated and phosphorylated isoforms). These assays can be performed on peripheral tissues (e.g. blood cells, plasma, cultured or other fibroblast tissues, etc.) as well as on biopsies of CNS tissues obtained antemortem or postmortem, and upon cerebrospinal fluid. Such assays might also include in-situ hybridization and immunohistochemistry (to localized messenger RNA and protein to specific subcellular compartments and/or within neuropathological structures associated with these diseases such as neurofibrilary tangles and amyloid plaques).

In accordance with the present invention, diagnostic kits are also provided which will include the reagents necessary for the above-described diagnostic screens. For example, kits may be provided which include antibodies or sets of antibodies which are specific to one or more mutant epitopes. These antibodies may, in particular, be labelled by any of the standard means which facilitate visualization of binding. Alternatively, kits may be provided in which oligonucleotide probes or PCR primers are present for the detection and/or amplification of mutant PS1, PS2 or other presenilin-related nucleotide sequences. Again, such probes may be labelled for easier detection of specific hybridization. As appropriate to the various diagnostic embodiments described above, the oligonucleotide probes or antibodies in such kits may be immobilized to substrates and appropriate controls may be provided.

Therapies

An important aspect of the biochemical studies using the genetic information of this invention is the development of therapies to circumvent or overcome the PS1 or PS2 gene defect, and thus prevent, treat, control serious symptoms or cure the disease. In view of expression of the PS1 gene in a variety of tissues, one has to recognize that Alzheimer's Disease may not be restricted to the brain, or alternatively that diseases manifest in other tissues may arise from mutations, mis-expression, mis-metabolism or other inherited or acquired alteration in these genes and gene products.

Alzheimer's Disease manifests itself as a neurological disorder which in one of its forms is caused by a mutation in the PS1 gene and in another of its forms by a mutation in the PS2 gene, but such manifestation may be caused by the mutations affecting other organ tissues, such as the liver, releasing factors which affect brain activity and ultimately cause Alzheimer's Disease. Hence, in considering various therapies, it is understood that such therapies may be targeted at tissue other than the brain, such as heart, placenta, lung, liver, skeletal muscle, kidney and pancreas, where PS1 or PS2 is also expressed.

The effect of these mutations in PS1 and PS2 apprently is a gain of a novel function or an acceleration of a normal function which causes aberrant processing of (APP) Amyloid Precursor Protein into Aβ peptide, abnormal phosphorylation homeostasis, and abnormal apoptosis in brain. These effects are direct or indirect and are consistent with dominant inheritance with adult onset of symptoms.

Therapy to reverse this will be by means of small molecules (drugs), recombinant proteins, antibodies or recombinant genes, to block the aberrant function by altering the structure of the mutant protein, by enhancing its metabolic clearance or inhibiting binding of ligands to the mutant protein, or by inhibiting the channel function of the mutant protein. The same effect might be gained by inserting a second mutant protein by gene therapy similar to the correction of the "Deg 1(d)" and "Mec 4(d)" mutations in *C. elegans* by insertion of mutant transgenes. Alternately, overexpression of wild type PS1 protein or wild type PS2 or both may correct the defect. This could be achieved by the administration of drugs or proteins to induce the transcription and translation or inhibit the catabolism of the native PS1 and PS2 proteins. It could also be accomplished by infusion of recombinant proteins or by gene therapy with vectors causing expression of the normal protein at a high level or by modification of interacting proteins by the procedures described elsewhere herein.

Rationale for Therapeutic, Diagnostic, and Investigational Applications of the PS1 Gene and Gene Products as They Related to the Amyloid Precursor Protein The Aβ peptide derivatives of APP are neurotoxic (Selkoe et al. 1994). APP is metabolized by passages through the Golgi network and then to secretory pathways via clathrin-coated vesicles with subsequent passage to the plasma membrane where the mature APP is cleaved by α-secretase to a soluble fraction (Protease Nexin II) plus a non-amyloidogenic C-terminal peptide (Selkoe et al. 1995. Gandy et al. 1993) Alternatively, mature APP can be directed to the endosome-lysosome pathway where it undergoes β and α secretase cleavage to produce the Aβ peptides. The phosphorylation state of the cell determines the relative balance of α-secretase (non-amyloidogenic) or Aβ pathways (amyloidogenic pathway) (Gandy et al. 1993). The phosphorylation state of the cell can be modified pharmacologically by phorbol esters, muscarinic agonists and other agents, and appears to be mediated by cytosolic factors (especially protein kinase C) acting upon an integral membrane protein in the Golgi network, which we propose to be the PS1, and members of the homologous family (all of which carry several phosphorylation consensus sequences for protein kinase C). Mutations in the PS1 gene will cause alterations in the structure and function of the PS1 gene product leading to defective interactions with regulatory elements (e.g. protein kinase C) or with APP, thereby promoting APP to be directed to the amyloidogenic endosome-lysosome pathway. Environmental factors (viruses, toxins, and aging etc) may also have similar effects on PS1. To treat Alzheimer's Disease, the phosphorylation state of PS1 can be altered by chemical and biochemical agents (e.g. drugs, peptides and other compounds) which alter the activity or protein kinase C and other protein kinases, or which alter the activity of protein phosphatases, or which modify the availability of PS1 to be post-translationally modified. The interactions between kinases and phosphatases with the PS1 gene products (and the products of its homologues), and the interactions of the PS1 gene products with other proteins involved in the trafficking of APP within the Golgi network can be modulated to decrease trafficking of Golgi vesicles to the endosome-lysosome pathway thereby promoting Aβ peptide production. Such compounds will include: peptide analogues of APP, PS1, and homologues of PS1 as well as other interacting proteins, lipids, sugars, and agents which promote differential glycosylation of PS1 and its homologues, agents which alter the biologic half-life of messenger RNA or protein of PS1 and homologues including antibodies and antisense oligonucleotides; and agents which act upon PS1 transcription.

The effect of these agents in cell lines and whole animals can be monitored by monitoring: transcription; translation; post-translational modification of PS1 (eg phosphorylation or glycosylation); and intracellular trafficking of PS1 and its homologues through various intracellular and extracellular compartments. Methods for these studies include Western and Northern blots; immunoprecipitation after metabolic labelling (pulse-chase) with radio-labelled methionine and ATP, and immunohistochemistry. The effect of these agents can also be monitored using studies which examine the relative binding affinities and relative amounts of PS1 gene products involved in interactions with protein kinase C and/or APP using either standard binding affinity assays or co-precipitation and Western blots using antibodies to protein kinase C, APP or PS1 and its homologues. The effect of these agents can also be monitored by assessing the production of Aβ peptides by ELISA before and after exposure to the putative therapeutic agent (Huang et al. 1993). The effect can also be monitored by assessing the viability of cell lines after exposure to aluminum salts and to Aβ peptides which are thought to be neurotoxic in Alzheimer's Disease. Finally, the effect of these agents can be monitored by assessing the cognitive function of animals bearing: their normal genotype at APP or PS1 homologues; or bearing human APP transgenes (with or without mutations); or bearing human PS1 transgenes (with or without mutations); or a combination of all of these.

Rationale for Therapeutic, Diagnostic, and Investigational Applications of the PS1 and PS2 Genes and Products The PS1 gene product and the PS2 gene product have amino acid sequence homology to human ion channel proteins and receptors. For instance, the PS2 protein shows substantial homology to the human sodium channel α-subunit (E=0.18, P=0.16, identities=22–27% over two regions of at least 35 amino acid residues) using the BLASTP paradigm of Altschul et al. 1990. Other diseases (such as malignant hyperthermia and hyperkalemic periodic paralysis in humans and the neurodegenerative of mechanosensory neurons in C. elegans) arise through mutations in ion channels or receptor proteins. Mutation of the PS1 gene or the PS2 gene could affect similar functions and lead to Alzheimer's Disease and other psychiatric and neurological diseases. Based upon this, a test for Alzheimer's Disease can be produced to detect an abnormal receptor or an abnormal ion channel function related to abnormalities that are acquired or inherited in the PS1 and gene and its product, or in one of the homologous genes such as PS2 and their products. This test can be accomplished either in vivo or in vitro by measurements of ion channel fluxes and/or transmembrane voltage or current fluxes using patch clamp, voltage clamp and fluorescent dyes sensitive to intracellular calcium or transmembrane voltage. Defective ion channel or receptor function can also be assayed by measurements of activation of second messengers such as cyclic AMP, cGMP tyrosine kinases, phosphates, increases in intracellular $Ca^{2+}$ levels, etc. Recombinantly made proteins may also be reconstructed in artificial membrane systems to study ion channel conductance. Therapies which affect Alzheimer's Disease (due to acquired/inherited defects in the PS1 gene or PS2 gene; due to defects in other pathways leading to this disease such as mutations in APP; and due to environmental agents) can be tested by analysis of their ability to modify an abnormal ion channel or receptor function induced by mutation in the PS1 gene or in one of its homologues. Therapies could also be tested by their ability to modify the normal function of an ion channel or receptor capacity of the PS1 gene products and its homologues. Such assays can be performed on cultured cells expressing endogenous normal or mutant PS1 genes/gene products or PS2 genes/gene products. Such studies can be performed in addition on cells transfected with vectors capable of expressing PS1, parts of the PS1 gene and gene product, mutant PS1, PS2 gene, parts of the PS2 gene and gene product, mutant PS2 gene or another homologue in normal or mutant form. Therapies for Alzheimer's Disease can be devised to modify an abnormal ion channel or receptor function of the PS1 gene or PS2 gene. Such therapies can be conventional drugs, peptides, sugars, or lipids, as well as antibodies or other ligands which affect the properties of the PS1 or PS2 gene product. Such therapies can also be performed by direct replacement of the PS1 gene and/or PS2 gene by gene therapy. In the case of an ion channel, the gene therapy could be performed using either mini-genes (cDNA plus a promoter) or genomic constructs bearing genomic DNA sequences for parts or all of the PS1 gene. Mutant PS1 or homologous gene sequences might also be used to counter the effect of the inherited or acquired abnormalities of the PS1 gene as has recently been done for replacement of the mec 4 and deg 1 in *C. elegans* (Huang and Chalfie, 1994). The therapy might also be directed at augmenting the receptor or ion channel function of the homologous genes such as the PS2 gene, in order that it may potentially take over the functions of the PS2 gene rendered defective by acquired or inherited defects. Therapy using antisense oligonucleotides to block the expression of the mutant PS1 or the mutant PS2 gene, co-ordinated with gene replacement with normal PS1 or PS2 gene can also be applied using standard techniques of either gene therapy or protein replacement therapy.

Protein Therapy

Treatment of Alzheimer's Disease can be performed by replacing the mutant protein with normal protein, or by modulating the function of the mutant protein. Once the biological pathway of the PS1 protein and the PS2 protein has been completely understood, it may also be possible to modify the pathophysiologic pathways or pathways (eg. a signal transduction pathway) in which these proteins participate, in order to correct the physiological defect.

To replace the mutant protein with normal protein, or with a protein bearing a deliberate counterbalancing mutation it is necessary to obtain large amounts of pure PS1 protein or PS2 protein from cultured cell systems which can express the protein. Delivery of the protein to the affected brain areas or other tissues can then be accomplished using appropriate packaging or administrating systems.

Gene Therapy

Gene therapy is another potential therapeutic approach in which normal copies of the PS1 gene or the PS2 gene are introduced into patients to code successfully for normal protein in several different affected cell types. The gene must be delivered to those cells in a form in which it can be taken up and code for sufficient protein to provide effective function. Alternatively, in some neurologic mutants it has been possible to prevent disease by introducing another copy of the homologous gene bearing a second mutation in that gene or to alter the mutation, or use another gene to block its effect.

Retroviral vectors can be used for somatic cell therapy especially because of their high efficiency of infection and stable integration and expression. The targeted cells however must be able to divide and the expression of the levels of normal protein should be high because the disease is a dominant one. The full length PS1 gene can be cloned into a retroviral vector and driven from its endogenous promoter or from the retroviral long terminal repeat or from a promoter specific for the target cell type of interest (such as neurons).

Other viral vectors which can be used include adeno-associated virus, vaccinia virus, bovine papilloma virus, or a herpes virus such as Epstein-Barr virus.

Gene transfer could also be achieved using non-viral means requiring infection in vitro. This would include calcium phosphate, DEAE dextran, electroporation, and protoplast fusion. Liposomes may also be potentially beneficial for delivery of DNA into a cell. Although these methods are available, many of these are lower efficiency.

Antisense based strategies can be employed to explore PS1 gene function and as a basis for therapeutic drug design. The principle is based on the hypothesis that sequence-specific suppression of gene expression can be achieved by intracellular hybridization between mRNA and a complementary antisense species. The formation of a hybrid RNA duplex may then interfere with the processing/transport/translation and/or stability of the target PS1 mRNA. Hybridization is required for the antisense effect to occur however the efficiency of intracellular hybridization is low and therefore the consequences of such an event may not be very successful. Antisense strategies may use a variety of approaches including the use of antisense oligonucleotides, injection of antisense RNA and transfection of antisense RNA expression vectors. Antisense effects can be induced by control (sense) sequences, however, the extent of phenotypic changes are highly variable. Phenotypic effects induced by antisense effects are based on changes in criteria such as protein levels, protein activity measurements, and target mRNA levels. Multidrug resistance is a useful model to study molecular events associated with phenotypic changes due to antisense effects, since the multidrug resistance phenotype can be established by expression of a single gene mdr1 (MDR gene) encoding for P-glycoprotein.

Transplantation of normal genes into the affected area of the patient can also be useful therapy for Alzheimer's Disease. In this procedure, a normal human PS1 gene is transferred into a cultivatable cell type such as glial cells, either exogenously or endogenously to the patient. These cells are then injected serotologically into the disease-affected tissue or tissues. This is a known treatment for Parkinson's disease.

Similar gene therapy strategies may be employed with respect to the PS2 gene in patients suffering from abnormalities in this gene.

Immunotherapy is also possible for Alzheimer's Disease. Antibodies are raised to a mutant PS1 or PS2 protein (or a portion thereof) and are administered to the patient to bind or block the mutant protein and prevent its deleterious effects. Simultaneously, expression of the normal protein product could be encouraged. Alternatively, antibodies are raised to specific complexes between mutant or wild-type PS1 or PS2 and their interaction partners.

A further approach is to stimulate endogenous antibody production to the desired antigen. Administration could be in the form of a one time immunogenic preparation or vaccine immunization. An immunogenic composition may be prepared as injectables, as liquid solutions or emulsions. The PS1 or PS2 protein or other antigen may be mixed with pharmaceutically acceptable excipients compatible with the protein. Such excipients may include water, saline, dextrose, glycerol, ethanol and combinations thereof. The immunogenic composition and vaccine may further contain auxiliary substances such as emulsifying agents or adjuvants to enhance effectiveness. Immunogenic compositions and vaccines may be administered parenterally by injection subcutaneously or intramuscularly.

The immunogenic preparations and vaccines are administered in such amount as will be therapeutically effective, protective and immunogenic. Dosage depends on the route of administration and will vary according to the size of the host.

The above disclosure generally describes the present invention. A more complete understanding can be obtained by reference to the following specific examples. These examples are described solely for purposes of illustration and are not intended to limit the scope of the invention. Changes in the form and substitution of equivalents are contemplated as circumstances may suggest or render expedient. Although specific terms have been employed herein, such terms are intended in a descriptive sense and not for purposes of limitation.

The examples are described for the purposes of illustration and are not intended to limit the scope of the invention.

EXAMPLES

Example 1

Development of the genetic, physical "contig" and transcriptional map of the minimal co-segregating region The CEPH Mega YAC and the RPCI PAC human total genomic DNA libraries were searched for clones containing genomic DNA fragments from the AD3 region of chromosome 14q24.3 using oligonucleotide probes for each of the 12 SSR marker loci used in the genetic linkage studies as well as the additional markers depicted in FIG. 1A (Albertsen et al., 1990; Chumakov et al., 1992; Ioannu et al., 1994). The genetic map distances between each marker are depicted above the contig, and are derived from published data (NIH/CEPH Collaborative Mapping Group, 1992; Wang, 1992; Weissenbach, J et al., 1992; Gyapay, G et al., 1994) Clones recovered for each of the initial marker loci were arranged into an ordered series of partially overlapping clones ("contig") using four independent methods. First, sequences representing the ends of the YAC insert were isolated by inverse PCR (Riley et al., 1990), and hybridized to Southern blot panels containing restriction digests of DNA from all of the YAC clones recovered for all of the initial loci in order to identify other YAC clones bearing overlapping sequences. Second, inter-Alu PCR was performed on each YAC, and the resultant band patterns were compared across the pool of recovered YAC clones in order to identify other clones bearing overlapping sequences (Bellamne-Chartelot et al., 1992; Chumakov et al., 1992). Third, to improve the specificity of the Alu-PCR fingerprinting, the YAC DNA was restricted with HaeIII or RsaI, the restriction products were amplified with both Alu and L1H consensus primers, and the products were resolved by polyacrylamide gel electrophoresis. Finally, as additional STSs were generated during the search for transcribed sequences, these STSs were also used to identify overlaps. The resultant contig was complete except for a single discontinuity between YAC932C7 bearing D14S53 and YAC746B4 containing D14S61. The physical map order of the STSs within the contig was largely in accordance with the genetic linkage map for this region (NIH/CEPH Collaborative Mapping Group, 1992; Wang, Z, Weber, J. L., 1992; Weissenbach, J et al., 1992; Gyapay, G et al., 1994). However, as with the genetic maps, it was not possible to resolve unambiguously the relative order of the loci within the D14S43/D14S71 cluster and the D14S76/D14S273 cluster. PAC1 clones suggested that D14S277 is telomeric to D14S268, whereas genetic maps have suggested the reverse order. Furthermore, a few STS probes failed to detect hybridization patterns in at least one YAC clone which, on the basis of the most parsimonious consensus physical map and from the genetic map, would have been predicted to contain that STS. For instance, the D14S268 (AFM265) and RSCAT7 STSs are absent from YAC788H12. Because these results were reproducible, and occurred with several different STS markers, these results most likely reflect the presence of small interstitial deletions within one of the YAC clones.

Example 2

Cumulative two-point lod scores for chromosome 14q24.3 markers

Genotypes at each polymorphic microsatellite marker locus were determined by PCR from 100 nm of genomic DNA of all available affected and unaffected pedigree members as previously described (St George-Hyslop, P et al., 1992) using primer sequences specific for each microsatellite locus (Weissenbach, J et al., 1992; Gyapay, G et al., 1994). The normal population frequency of each allele was determined using spouses and other neurologically normal subjects from the same ethnic groups, but did not differ significantly from those established for mixed Caucasian populations (Weissenbach, J et al., 1992; Gyapay, G et al., 1994). The maximum likelihood calculations assumed an age of onset correction, marker allele frequencies derived from published series of mixed Caucasian subjects, and an estimated allele frequency for the AD3 mutation of 1:1000 as previously described (St George-Hyslop, P et al., 1992). The analyses were repeated using equal marker allele frequencies, and using phenotype information only from affected pedigree members as previously described to ensure that inaccuracies in the estimated parameters used in the maximum likelihood calculations did not misdirect the analyses (St George-Hyslop, P et al., 1992). These supplemental analyses did not significantly alter either the evidence supporting linkage, or the discovery of recombination events.

Example 3

Haplotypes between flanking markers segregated with AD3 in FAD pedigrees

Extended haplotypes between the centromeric and telomeric flanking markers on the parental copy of chromosome 14 segregating with AD3 in fourteen early onset FAD pedigrees (pedigrees NIH2, MGH1, Tor.1.1, FAD4, FAD1, MEX1, and FAD2 show pedigree specific lod scores ≧+3.00 with at least one marker between D14S258 and D14S53). Identical partial haplotypes (boxed) are observed in two regions of the disease bearing chromosome segregating in several pedigrees of similar ethnic origin. In region A, shared alleles are seen at D14S268 ("B": allele size=126 bp, allele frequency in normal Caucasians=0.04; "C": size=124 bp, frequency=0.38); D14S277 ("B": size=156 bp, frequency=0.19; "C": size=154 bp, frequency=0.33); and RSCAT6 ("D": size=111 bp, frequency 0.25; "E": size=109 bp, frequency=0.20; "F": size=107 bp, frequency=0.47). In region B, alleles of identical size are observed at S14S43 ("A": size=193 bp, frequency=0.01; "D": size=187 bp, frequency=0.12; "E": size=185 bp, frequency=0.26; "I": size=160 bp, frequency=0.38); D14S273 ("3": size=193 bp, frequency=0.38; "4" size=191 bp, frequency=0.16; "5": size=189 bp, frequency=0.34; "6": size=187 bp, frequency= 0.02) and D14S76 ("1": size=bp, frequency=0.01; "5": size= bp, frequency=0.38; "6": size=bp, frequency=0.07; "9": size=bp, frequency=0.38). The ethnic origins of each pedigree are abbreviated as: Ashk=Ashkenazi Jewish; Ital= Southern Italian; Angl=Anglo-Saxon-Celt; FrCan=French Canadian; Jpn=Japanese; Mex=Mexican Caucasian; Ger= German; Am=American Caucasian. The type of mutation detected is depicted by the amino acid substitution and putative codon number or by ND where no mutation has been detected because a comprehensive survey has not been undertaken due to the absence of a source of mRNA for RT-PCR studies.

Example 4
Recovery of transcribed sequences from the AD3 interval

Putative transcribed sequences encoded in the AD3 interval were recovered using a direct hybridization method in which short cDNA fragments generated from human brain mRNA were hybridized to immobilized cloned genomic DNA fragments (Rommens, J M et al., 1993) The resultant short putatively transcribed sequences were used as probes to recover longer transcripts from human brain cDNA libraries (Stratagene, La Jolla). The physical locations of the original short clone and of the subsequently acquired longer cDNA clones were established by analysis of the hybridization pattern generated by hybridizing the probe to Southern blots containing a panel of EcoRI digested total DNA samples isolated from individual YAC clones within the contig. The nucleotide sequence of each of the longer cDNA clones was determined by automated cycle sequencing (Applied Biosystems, Inc., CA), and compared to other sequences in nucleotide and protein databases using the blast algorithm (Altschul, S F et al., 1990). Accession numbers for the transcribed sequences in this report are: L40391, L40392, L40393, L40394, L40395, L40396, L40397, L40398, L40399, L40400, L40401, L40402, and L40403.

Example 5
Locating mutations in the ARMP (PS1) gene using restriction enzymes The presence of Ala 246 Glu mutation which creates a DdeI restriction site was assayed in genomic DNA by PCR using the end labelled primer (5'-ATCTCCGGCAGGCATATCT-3') SEQ ID NO:129 and the unlabelled primer (5'-TGAAATCACAGCCAAGATGAG-3') SEQ ID NO:130 to amplify an 84 bp genomic exon fragment using 100 ng of genomic DNA template, 2 mM $MgCl_2$, 10 pMoles of each primer, 0.5U Taq polymerase, 250 uM dNTPs for 30 cycles of 95° C.×20 seconds, 60° C.×20 seconds, 72° C.×5 seconds. The products were incubated with an excess of DdeI for 2 hours according to the manufacturers protocol, and the resulting restriction fragments were resolved on a 6% nondenaturing polyacrylamide gel and visualized by autoradiography. The presence of the mutation was inferred from the cleavage of the 84 bp fragment to due to the presence of a DdeI restriction site. All affected members of the FAD2 pedigree (filled symbols) and several at-risk members ("R") carried the DdeI site. None of the obligate escapees (those individuals who do not get the disease, age>70 years), and none of the normal controls carried the DdeI mutation.

Example 6
Locating mutations in the ARMP (PS1) gene using allele specific oligonucleotides The presence of the Cys 410 Tyr mutation was assayed using allele specific oligonucleotides. 100 ng of genomic DNA was amplified with the exonic sequence primer (5'-TGGAGACTGGAACACAAC-3') SEQ ID NO:127 and the opposing intronic sequence primer (5'-GTGTGGCCAGGGTAGAGAACT-3') SEQ ID NO:128 using the above reaction conditions except 2.5 mM $MgCl_2$, and cycle conditions of 94° C.×20 second, 58° C.×20 second, and 72° C. for 10 seconds). The resultant 216 bp genomic fragment was denatured by 10-fold dilution in 0.4M NaOH, 25 mM EDTA, and was vacuum slot-blotted to duplicate nylon membranes. The end-labelled "wild type" primer (5'-CCATAGCCTGTTTCGTAGC-3') Seq ID NO:131 and the end-labelled "mutant" primer (5'-CCATAGCCTATTTCGTAGC-3') SEQ ID No:132 were hybridized to separate copies of the slot-blot filters in 5×SSC, 5×Denhardt's, 0.5% SDS for 1 hour at 48° C., and then washed successively in 2×SSC at 23° C. and 2×SSC, 0.1% SDS at 50° C. and then exposed to X-ray film. All testable affected members as well as some at-risk members of the AD3 and NIH2 pedigrees possessed the Cys 410 Tyr mutation. Attempts to detect the Cys 410 Tyr mutation by SSCP revealed that a common intronic sequence polymorphism migrated with the same SSCP pattern.

Example 7
Northern hybridization demonstrating the expression of ARMP (PS1) protein mRNA in a variety of tissues Total cytoplasmic RNA was isolated from various tissue samples (including heart, brain and different regions of, placenta, lung, liver, skeletal muscle, kidney and pancreas) obtained from surgical pathology using standard procedures such as CsCl purification. The RNA was then electrophoresed on a formaldehyde gel to permit size fractionation. The nitrocellulose membrane was prepared and the RNA was then transferred onto the membrane. $^{32}$P-labelled cDNA probes were prepared and added to the membrane in order for hybridization between the probe the RNA to occur. After washing, the membrane was wrapped in plastic film and placed into imaging cassettes containing X-ray film. The autoradiographs were then allowed to develop for one to several days. Sizing was established by comparison to standard RNA markers. Analysis of the autoradiographs revealed a prominent band at 3.0 kb in size. These northern blots demonstrated that the ARMP gene is expressed in all of the tissues examined.

Example 8
Eukaryotic and Prokaryotic Expression Vector Systems

Constructs suitable for use in eukaryotic and prokaryotic expression systems have been generated using two different classes of ARMP nucleotide cDNA sequence inserts. In the first class, termed full-length constructs, the entire ARMP cDNA sequence is inserted into the expression plasmid in the correct orientation, and includes both the natural 5' UTR and 3' UTR sequences as well as the entire open reading frame. The open reading frames bear a nucleotide sequence cassette which allows either the wild type open reading frame to be included in the expression system or alternatively, single or a combination of double mutations can be inserted into the open reading frame. This was accomplished by removing a restriction fragment from the wild type open reading frame using the enzymes NarI and PflmI and replacing it with a similar fragment generated by reverse transcriptase PCR and bearing the nucleotide sequence encoding either the Met146Leu mutation or the His163Arg mutation. A second restriction fragment was removed from the wild type normal nucleotide sequence for the open reading frame by cleavage with the enzymes PflmI and NcoI and replaced with a restriction fragment bearing the nucleotide sequence encoding the Ala246Glu mutation, the Ala260Val mutation, the Ala285Val mutation, the Leu286Val mutation, the Leu392Val mutation or the Cys410Tyr mutation. A third variant, bearing a combination of either the Met146Leu or His163Arg mutation in tandem with one of the remaining mutations, was made by linking a NarI-PflmI fragment bearing one of the former mutations and a PflmI-NcoI fragment bearing one of the latter mutations.

The second class of cDNA inserts, termed truncated constructs, was constructed by removing the 5' UTR and part of the 3' UTR sequences from full length wild type or mutant cDNA sequences. The 5' UTR sequence was replaced with a synthetic oligonucleotide containing a KpnI restriction site and a Kozak initiation site (oligonucleotide GGTACCGCCACCATGACAGAGGTACCTGCAC, SEQ ID NO:139). The 3' UTR was replaced with an oligonucleotide corresponding to position 2566 of the cDNA and bore an artificial EcoRI site (oligonucleotide GAATTCACTGGCTGTAGAAAAAGAC, SEQ ID NO:140). Mutant variants of this construct were then made by inserting the mutant sequences described above at the NarI-PflmI and PsImI-NcoI sites as described above.

For eukaryotic expression, these various cDNA constructs bearing wild type and mutant sequences, as described above, were cloned into the expression vector pZeoSV in which the SV60 promoter cassette had been removed by restriction digestion and replaced with the CMV promoter element of pcDNA3 (Invitrogen). For prokaryotic expression, constructs have been made using the glutathione S-transferase (GST) fusion vector pGEX-kg. The inserts which have been attached to the GST fusion nucleotide sequence are the same nucleotide sequences described above (generated with the oligonucleotide primers, SEQ ID NO:139 and SEQ ID NO:140) bearing either the normal open reading frame nucleotide sequence, or bearing a combination of single and double mutations as described above. These GST fusion constructs allow expression of the partial or full-length protein in prokaryotic cell systems as mutant or wild type GST fusion proteins, thus allowing purification of the full-length protein followed by removal of the GST fusion product by thrombin digestion. A further cDNA construct was made with the GST fusion vector, to allow the production of the amino acid sequence corresponding to the hydrophilic acidic loop domain between TM6 and TM7 of the full-length protein, either as a wild type nucleotide sequence or as a mutant sequence bearing either the Ala285Val mutation, the Leu286Val mutation or the Leu392Val mutation. This was accomplished by recovering wild type or mutant sequence from appropriate sources of RNA using the oligonucleotide primers GGATCCGGTCCACTTCGTATGCTG, SEQ ID NO:141, and TTTTTTGAATTCTTAGGCTATGGTTGTGTTCCA, SEQ ID NO:142 This allowed cloning of the appropriate mutant or wild type nucleotide sequence corresponding to the hydrophilic acidic loop domain at the BamHI and the EcoRI sites within the pGEX-KG vector.

Example 9
Locating additional mutations in the ARMP (PS1) gene

Mutations in the ARMP (PS1) gene can be assayed by a variety of strategies (direct nucleotide sequencing, allele specific oligos, ligation polymerase chain reaction, SSCP RFLPs) using RT-PCR products representing the mature mRNA/cDNA sequence or genomic DNA. For the A260V and the A285V mutations, genomic DNA carrying the exon can be amplified using the same PCR primers and methods as for the L286V mutation.

PCR products were then denatured and slot blotted to duplicate nylon membranes using the slot blot protocol described for the C410T mutation.

The Ala260Val mutation was scored on these blots by using hybridization with end-labelled allele-specific oligonucleotides corresponding to the wild type sequence (GATTAGTGGTTGTTTTGTG) SEQ ID NO:143 or the mutant sequence (GATTAGTGGCTGTTTTGTG) SEQ ID NO:144 by hybridization at 48° C. followed by a wash at 52° C. in 3×SSC buffer containing 0.1% SDS. The Ala285Val mutation was scored on these slot blots as described above but using instead the allele-specific oligonucleotides for the wild type sequence (TTTTTCCAGCTCTCATTTA) SEQ ID NO:145 or the mutant primer (TTTTTCCAGTTCTCATTTA) SEQ ID NO:146 at 48° C. followed by washing at 52° C. as above except that the wash solution was 2×SSC.

The Leu392Val mutation was scored by amplification of the exon from genomic DNA using primers (AAACTTGGATTGGGAGAT) SEQ ID NO:148 and (GTGTGGCCAGGGTAGAGAACT) SEQ ID NO:128 using standard PCR buffer conditions except that the magnesium concentration was 2 mM and cycle conditions were 94° C. time 10 second, 56° C. times 20 seconds, and 72° C. for 10 seconds. The resulting 200 base pair genomic fragment was denatured as described for the Cys410Tyr mutation and slot-blotted in duplicate to nylon membranes. The presence or absence of the mutation was then scored by differential hybridization to either a wild type end-labelled oligonucleotide (TACAGTCTTCTGGTTGGTA) SEQ ID NO:147 or with an end-labelled mutant primer (TACAGTGTTGTGGTTGGTA) SEQ ID NO:149 by hybridization at 45° C. and then successive washing in 2×SSC at 23° C. and then at 68° C.

Example 10
Antibody Production

Peptide antigens corresponding to portions of the PS1 protein were synthesized by solid-phase techniques and purified by reverse phase high pressure liquid chromatography. Peptides were covalently linked to keyhole limpet hemocyanin (KLH) via disulfide linkages that were made possible by the addition of a cysteine residue at the peptide C-terminus. This additional residue does not appear normally in the protein sequence and was included only to facilitate linkage to the KLH molecule.

The specific sequences to which antibodies were raised are as follows:

Polyclonal antibody 1142: NDNRERQEHNDRRSL (C)—residues 30–45 (SEQ ID NO:167);
Polyclonal antibody 519: KDGQLIYTPFTEDTE (C)—residues 109–120 (SEQ ID NO:168);
Polyclonal antibody 520: EAQRRVSKNSKYNAE (C)—residues 304–319 (SEQ ID NO:169);
Polyclonal antibody (1143: SHLGPHRSTPESRAA (C)—residues 346–360 (SEQ ID NO:170).

The non-native cysteine residue is indicated at the C-terminal by (C). These sequences are contained within specific unique domains of the PS1 protein. For example, sequences 167, 169 and 170 are located in potentially functional domains that are exposed to the aqueous media and may be involved in binding to other proteins critical for the development of the disease phenotype. Sequence 168 corresponds to a short linking region situated between the predicted first and second transmembrane helices. The choice of peptides was based on analysis of the protein sequence using the I B I Pustell antigenicity prediction algorithm.

A total of three New Zealand white rabbits were immunized with peptide-KLH complexes for each peptide antigen in combination with Freund's adjuvant and were subsequently given booster injections at seven day intervals. Antisera were collected for each peptide and pooled and IgG precipitated with ammonium sulfate. Antibodies were then affinity with Sulfo-link agarose (Pierce) coupled with the appropriate peptide. This final purification is required to remove non-specific interactions of other antibodies present in either the pre- or post-immune serum.

The specificity of each antibody was confirmed by three tests. First, each detected single predominant bands of the approximate size predicted for presenilin I on Western blots of brain homogenate. Second, each cross-reacted with recombinant fusion proteins bearing the appropriate sequence. Third each could be specifically blocked by pre-absorption with recombinant PS1 or the immunizing peptide.

In addition, two different PS1 peptide glutathione S-transferase (GST) fusion proteins have been used to generate PS1 antibodies. The first fusion protein included amino acids 1–81 (N terminus) of PS1 fused to GST. The second fusion protein included amino acids 266–410 (the TM6–TM7 loop domain) of PS1 fused to GST. Constructs encoding these fusion proteins were generated by inserting the appropriate nucleotide sequences into pGEX-2T expression plasmid (Amrad). The resulting constructs included sequences encoding GST and a site for thrombin sensitive cleavage between GST and the PS1 peptide. The expression constructs were transfected into DH5α E. coli and expression of the fusion proteins was induced using IPTG. The bacterial pellets were lysed and the soluble GST-fusion proteins were purified by single step affinity chromatography on glutathione sepharose beads (Boehringer-Mannheim, Montreal). The GST-fusion proteins were used to immunize mice to generate monoclonal antibodies using standard procedures. Clones obtained from these mice were screened with purified presenilin fragments.

In addition, the GST-fusion proteins were cleaved with thrombin to release PS1 peptide. The released peptides were purified by size exclusion HPLC and used to immunize rabbits for the generation of polyclonal antisera.

By similar methods, GST fusion proteins were made using constructs including nucleotide sequences for amino acids 1 to 87 (N terminus) or 272 to 390 (TM6→TM7 loop) of presenilin II and employed to generate monoclonal antibodies to that protein. The PS2 GST fusion proteins were also cleaved with thrombin and the released, purified peptides used to immunize rabbits to prepare polyclonal antisera.

Example 11
Identification of mutations in E5-1 (PS2) gene

RT-PCR products corresponding to the E5-1 (PS2) ORF were generated from RNA of lymphoblasts or frozen post-mortem brain tissue using oligonucleotide primer pairs 5'-CAGAGGATGGAGAGAATAC (SEQ ID NO:171) and 5'-GGCTCCCCAAAACTGTCAT (SEQ ID NO:172) (product=888 bp) and 5'-GCCCTAGTGTTCATCAAGTA (SEQ ID NO:173) and 5'-AAAGCGGGAGCCAAAGTC (SEQ ID NO:174) (product=826 bp) by PCR using 250 μMol dNTPs, 2.5 mM MgCl2, 10 pMol oligonucleotides in 10 μl cycled for 40 cycles of 94° C.×20 seconds, 58° C.×20 seconds, 72° C.×45 seconds. The PCR products were sequenced by automated cycle sequencing (ABI, Foster City, A) and the fluorescent chromatograms were scanned for heterozygous nucleotide substitutions by direct inspection and by the Factura (ver 1.2.0) and Sequence Navigator (ver 1.0.1b15) software packages (data not shown).

Asn141Ile

The A→T substitution at nucleotide 787 creates a BclI restriction site. The exon bearing this mutation was amplified from 100 ng of genomic DNA using 10 pMol of oligonucleotides 5'-CATTCACTGAGGACAGACC (SEQ ID NO:175) (end-labelled) and 5'-TGTAGAGCACCACCAAGA (SEQ ID NO:176) (unlabelled), and PCR reaction conditions similar to those described below for the Met239Val. 2 μl of the PCR product was restricted with BclI (NEBL, Beverly, Mass.) in 10 μl reaction volume according to the manufacturers' protocol, and the products were resolved by non-denaturing polyacrylamide gel electrophoresis. In subjects with wild type sequences, the 114 bp PCR product is cleaved into 68 bp and 46 bp fragments. Mutant sequences cause the product to be cleaved into 53 bp, 46 bp and 15 bp.

Met239Val

The A→G substitution at nucleotide 1080 deletes a NlaIII restriction site, allowing the presence of the Met 239Val mutation to be detected by amplification from 100 ng of genomic DNA using PCR (10 pMol oligonucleotides 5'GCATGGTGTGCATCCACT (SEQ ID NO:177), 5'-GGACCACTCTGGGAGGTA (SEQ ID NO:178), 0.5 U Taq polymerase, 250 μM dNTPS, 1 μCi alpha $^{32}$P-dCTP, 1.5 mM MgCl$_2$, 10 μl volume; 30 cycles of 94° C.×30 seconds, 58° C.×20 second, 72° C.×20 seconds) to generate a 110 bp product. 2 μl of the PCR reaction were diluted to 10 μl and restricted with 3 U of NlaIII (NEBL, Beverly, Mass.) for 3 hours. The restriction products were resolved by non-denaturing polyacrylamide gel electrophoresis and visualized by autoradiography. Normal subjects show cleavage products of 55, 35, 15 and 6 bp, whereas the mutant sequence gives fragments of 55, 50 and 6 bp.

In accordance with a further embodiment, the Ile 420 Thr mutation is screened for by PCR amplification of genomic DNA using primers 5' TGC TGC TTG CTG TGT TCA 3' (SEQ ID NO:161) and 5' CCA TGT CCC TCA GAT GTA GA 3' (SEQ ID NO:162) to generate a 146 base pair product which can be probed with allele specific oligonucleotides for the wild-type (5' CAT CTC CAT CAC GTT CG 3'; SEQ ID NO:163) and mutant (5' CAT CTC CAC CAC GTT CG 3'; SEQ ID NO:164) sequences.

Example 12
Transgenic Mice

A series of wild type and mutant PS1 and PS2 genes were constructed for use in the preparation of transgenic mice. Mutant versions of PS1 and PS2 were generated by site-directed mutagenesis of the cloned cDNAs CC33 (PS1) and CC32 (PS2) using standard techniques.

cDNAs CC33 and CC32 and their mutant versions were used to prepare two classes of mutant and wild type PS1 and PS2 cDNAs, as described in Example 8. The first class, referred to as "full-length" cDNAs, were prepared by removing approximately 200 bp of the 3' untranslated region immediately before the poly A site by digestion with EcoRI (PS1) or PvuII (PS2). The second class, referred to as "truncated" cDNAs, were prepared by replacing the 5' untranslated region with a ribosome binding site (Kozak consensus sequence) placed immediately 5' of the ATG start codon.

Various full length and truncated wild type and mutant PS1 and PS2 cDNAs, prepared as described above, were introduced into one or more of the following vectors and the resulting constructs were used as a source of gene for the production of transgenic mice.

The cos.TET expression vector

This vector was derived from a cosmid clone containing the Syrian hamster PrP gene. It has been described in detail by Scott et al. (1992) and Hsiao et al. (1995). PS1 and PS2 cDNAs (full length or truncated) were inserted into this vector at its SalI site. The final constructs contain 20 kB of 5' sequence flanking the inserted cDNA. This 5' flaking sequence includes the PrP gene promoter, 50 bp of a PrP gene 5'0 untranslated region exon, a splice donor site, a 1 kB intron, and a splice acceptor site located immediately adjacent to the SalI site into which the PS1 or PS2 cDNA was inserted. The 3' sequence flanking the inserted cDNA includes an approximately 8 kB segment of PrP 3' untranslated region including a polyadenylation signal. Digestion of this construct with NotI (PS1) or FseI (PS2) released a fragment containing a mutant or wild type PS gene under the control of the PrP promoter. The released fragment was gel purified and injected into the pronuclei of fertilized mouse eggs using the method of Hsiao et al., 1995 (Table 12).

Platelet-derived growth factor receptor β-subunit constructs

PS cDNAs were also introduced between the SalI (full length PS1 cDNAs) or HindIII (truncated PS1 cDNAs, full length PS2 cDNAs, and truncated PS2 cDNAs) at the 3' end of the human platelet derived growth factor receptor β-subunit promoter and the EcoRI site at the 5' end of the SV40 poly A sequence and the entire cassette was cloned into the pZeoSV vector (Invitrogen, San Diego, Calif.). Fragments released by ScaI/BamHI digestion were gel purified and injected into the pronuclei of fertilized mouse eggs using the method of Hsiao et al. (supra) (Table 12).

Human β-actin constructs

Certain PS1 and PS2 cDNAs were inserted into the SalI site of pBAcGH. The construct produced by this insertion includes 3.4 kB of the human β actin 5' flaking sequence (the human β actin promoter, a spliced 78 bp human β actin 5' untranslated exon and intron) and the PS1 or PS2 insert followed by 2.2 kB of human growth hormone genomic sequence containing several introns and exons as well as a polyadenylation signal. SfiI was used to release a PS-containing fragment which was gel purified and injected into the pronuclei of fertilized mouse eggs using the method of Hsiao et al. (supra) (Table 12).

Phosphoglycerate kinase constructs

Certain PS1 and PS2 cDNAs were introduced into the pkJ90 vector. The cDNAs were inserted between the KpnI site downstream of the human phosphoglycerate kinase promoter and the XbaI site upstream of the 3' untranslated region of the human phosphoglycerate kinase gene. PvuII/HindIII (PS1 cDNAs) or PvuII (PS2 cDNAs) digestion was used to release a PS-containing fragment which was then gel purified and injected into the pronuclei of fertilized mouse eggs as described above.

Table 10 includes a summary of the preparation of transgenic mice.

Example 13
Expression of Recombinant PS1 and PS2 in Eukaryotic Cells

Recombinant PS1 and PS2 have been expressed in a variety of cell type s(e.g. PC12, neuroblastoma, Chinese hamster ovary, and human embryonic kidney 293 cells) using the pcDNA3 vector (Invitrogen, San Diego, Calif.). The PS1 and PS2 cDNAs inserted into this vector were the same full length and truncated cDNAs described in Example 8.

These cDNAs were inserted between the CMV promoter and the bovine growth hormone polyadenylation site of pcDNA3. The transgenes were expressed at high levels.

In addition, PS1 and PS2 have been expressed in COS cells using the pCMX vector. To facilitate tagging and tracing of the intracellular localization of the presenilin proteins, oligonucleotides encoding an 11 amino acid sequence derived from c-myc (EQKLISEEDLN; SEQ ID NO:183) and recognized by the monoclonal anti-MYC antibody 3E10.2 (ATCC, Rockville, Md.) were ligated in-frame either immediately in front or immediately behind the open reading frame of PS1 and PS2 cDNAs. Untagged pCMX constructs were also prepared. The c-myc-tagged constructs were also introduced into pcDNA3 for transfection into CHO cells.

Transient and stable transfection of these constructs has been achieved using Lipofectamine (Gibco/BRL) according to the manufacturer's protocols. Cultures were assayed for transient expression after 48 hours. Stably transfected lines were selected using 0.5 mg/ml Geneticin (Gibco/BRL).

Expression of transfected PS proteins was assayed by Western blot using the anti-presenilin antibodies 1142, 519 and 520 described above. Briefly, cultured transfected cells were solubilized (2% SDS, 5 mM EDTA, 1 mg/ml leupeptin and aprotinin), and the protein concentration was determined by Lowry. Proteins were separated on SDS-PAGE gradient gels (4–20% Novex) and transferred to PVDF (10 mM CAPS) for 2 hr at a constant voltage (50V). Nonspecific binding was blocked with skim milk (5) for 1 hr. The proteins were then probed with the two rabbit polyclonal antibodies (~1 mg/ml in TBS, pH 7.4) for 12 hrs. Presenilin cross-reactive species were identified using biotinylated goat-anti rabbit secondary antibody which was visualized using horseradish peroxidase-conjugated strepavadin tertiary, 4-chloro-napthol, and hydrogen peroxide. The c-myc-tagged presenilin peptides were assayed by Western blotting using both the anti-presenilin antibodies described above (to detect the presenilin peptide antigen), and culture supernatant from the hybridoma MYC1-3E10.2 (ATCC) diluted 1:10 for western blots and 1:3 for immunocytochemistry (to detect the myc-epitope). A major brand of immunoreactivity of 50–60 kDa was identified by each of the various presenilin antibodies, and by the myc-epitope antibodies (for cell lines transfected with myc-containing plasmids). Minor bands at ~10–19 kDA and at ~70 kDa were detected by some presenilin antibodies.

For immunocytochemistry, transfected cells were fixed with 4% formaldehyde in TRIS buffered saline (TBS), washed extensively with TBS plus 0.1% Triton and non-specific binding blocked with 3% BSA. Fixed cells were probed with the presenilin antibodies (e.g. LL520 and SN1142; typically 5–10 mg/ml), washed and visualized with FITC- or rhodamine-conjugated goat-anti rabbit secondary antibody. For c-myc-tagged presenilin constructs, the hybridoma MYC1-3-E10.2 (ATCC) supernatant diluted 1:3 was used with anti-mouse secondary antibody. Slides were mounted in 90% glycerol with 0.1% phenylenediamine (ICN) to preserve fluorescence. Anti-BIP (or anti-calnexin) (StressGen, Victoria, B.C.) and wheat germ agglutinin (EY Labs, San Mateo, Calif.) were used a markers of endoplasmic reticulum and Golgi respectively. Double-immuno-labelling was also performed with anti-actin (Sigma, St. Louis, Mo.), anti-amyloid precursor protein (22C11, Boehringer Mannheim) and anti-neurofilament (NF-M specific, Sigma) in neuronal line NSC34. These immunofluorescence studies demonstrated that the transfection product is widely distributed within the cell, with a particularly intense peri-nuclear localization suggestive of endoplasmic reticulum and Golgi, which is similar to that observed in untransfected cells but is more intense, sometimes spilling over into the nuclear membrane. Co-immunolocalization of the c-myc and PS epitopes was observed in CHO and COS cells transiently transfected with the myc-tagged presenilin constructs.

Robust expression of the transfected presenilin gene in the transfected cells was thus proved by immunocytochemistry, Northern blot, Western blots (using antibodies to presenilins as above, and using the monoclonal antibody MYC1-9E10.2 to the myc-tag in constructs with 3' or 5' c-myc tags).

Example 14
Isolation of Presenilin Binding Proteins by Affinity Chromatography

To identify the proteins which may be involved in the biochemical function of the presenilins, PS1-binding proteins were isolated using affinity chromatography. A GST-fusion protein containing the PSI TM6–TM7 loop, prepared as described in Example 8, was used to probe human brain extracts, prepared by homogenising brain tissue by Polytron in physiological salt solution. Non-specific binding was eliminated by pre-clearing the brain homogenates of endogenous GST-binding components by incubation with glutathione-Sepharose beads. These GST-free homogenates were then incubated with the GST-PS fusion proteins to produce the desired complexes with functional binding proteins. These complexes were then recovered using the affinity glutathione-Sepharose beads. After extensive washing with phosphate buffered saline, the isolated collection of proteins was separated by SDS-polyacrylamide gel electrophoresis (SDS-PAGE; Tris-tricine gradient gel 4–20%). Two major bands were observed at ~14 and 20 kd in addition to several weaker bands ranging from 50 to 60 kd.

Pharmacologic modification of interaction between these proteins and the TM6–TM7 loop may be employed in the treatment of Alzheimer's Disease. In addition, these proteins which are likely to act within the presenilin biochemical pathway may be novel sites of mutations that cause Alzheimer's Disease.

Example 15
Isolation of Presenilin Binding Proteins by Two-Hybrid Yeast System

To identify proteins interacting with the presenilin proteins, a yeast expression plasmid vector (pAS2-1, Clontech) was generated by ligating an in-frame partial cDNA sequence encoding either residues 266–409 of the PS1 protein or residues 272–390 of the PS2 protein into the EcoR1 and BamHI sites of the vector. The resultant fusion protein contains the GAL4 DNA binding domain coupled in frame either to the TM6–TM7 loop of the PS1 protein or to the TM6–TM7 loop of the PS2 protein. These expression plasmids were co-transformed, along with purified plasmid DNA from the human brain cDNA:pACT library, into yeast using the protocols of the Clontech Matchmaker yeast-two-hybrid kit (Clontech). Yeast clones bearing human brain cDNAs which interact with the TM6–TM7 loop domain were selected by HIS resistance and βgal+ activation. The clones were further selected by cyclohexamide sensitivity and the inserts of the human brain cDNAs were isolated by PCR and sequenced. Of 6 million initial transformants, 200 positive clones were obtained after HIS selection, and 42 after βgal+ colour selection, carried out in accordance with the manufacturer's protocol for selection of positive colonies. Of these 42 clones there were several (5–8) independent clones representing the genes typified by our clones pslly2h-9, pslly2h-6, and pslly2h-29. This indicates that these interactions are biologically real and reproducable.

Analysis of the sequences of these clones identified the proteins listed in Table 13 as interacting with the TM6–TM7 loop of PS1. The biologic relevance of these interactions is described in the table. The effect of mutations in the PS1 or PS2 gene on these interactions can be studies and, by screening of chemical libraries, drugs which will modify these interactions positively or negatively can be identified. These compounds are used to screen for effects in AD by analysis of changes in the frequency and/or rate of development of clinical/neuropathologic/biochemical changes of AD in transgenic/homologous recombination animal models or tissue culture models.

Example 16
Transgenic C. elegans

Transgenic C. elegans were obtained by microinjection of oocytes. The vectors used and the transgenes inserted are shown in Table 11. Transformed animals were detected by assaying expression of human cDNA on northern blots or western blots using human cDNA probe CC32 and antibodies 519, 520 and 1142.

Example 17
Cloning of a Drosophila melanogaster homologue, DmPS, for the human presenilin genes Redundant oligonucleotides 5'ctnccngartggacnygyctgg (SEQ ID NO:179) and 5'rcangc(agt)atngtngtrttcca (SEQ ID NO:180) were designed from published nucleotide sequence data for highly conserved regions of the presenilin/sel-12 proteins ending/beginning with Trp (e.g. at residues Trp247 and Trp404 in PS1; Trp253 and Trp385 in PS2). These primers were used for RT-PCR (50 μl volume, 2 mM MgCl$_2$, 30 cycles of 94° C.×30", 57° C.×20", 72° C.×20") from mRNA from adult and embryonic D. melanogaster. The products were then reamplified using cycle conditions of 94° C.×1', 59° C.×0.5' and 72° C.×1' and internal conserved redundant primer 5'tttttctcgagacngcncargaragaaayga (SEQ ID NO:181) and 5'tttttggatcctaraa(agt)atraartcncc (SEQ ID NO:182). The ~600 bp product was cloned into the BamHI and XhoI sites of pBS. These products were sequenced and shown to contain an open reading frame with a putative amino acid sequence highly homologous to that of the human presenilins. This fragment was then used to screen a conventional D. melanogaster cDNA\zap library (Stratagene, CA.) to recover six independent cDNA clones of size ~2–2.5 kb (clones pds8, pds13, pds1, pds3, pds7 and pds14) which were sequenced. The longest ORF encodes a polypeptide of 541 amino acids with 52% identify to the human presenilins.

Although preferred embodiments of the invention have been described herein in detail, it will be understood by those skilled in the art that variations may be made thereto without departing from the spirit of the invention or the scope of the appended claims.

REFERENCES

Albertsen et al, 1990, *Proc. Natl. Acad. Sci. USA*, v. 87, pp. 4256–4260.
Altschul et al., 1990, *J. Mol. Biol.*, v. 215, pp. 403–410.
Bellamne-Chartelot et al., 1992, *Cell*, v. 70, pp. 1059–1068.
Bergamini, 1991, *Acta Neurol.*, v. 13, pp. 534–538.
Brand, A. H. & Perrimon, N. (1993), *Development*, v. 118, pp. 401–415.
Campion et al., (1995), *Hum. Molec. Genet.* (in the press).
Campos-Ortega, J. A. & Jan, Y. N. (1991), *Ann. Rev. Neurosci.*, v. 14, p. 399.
Canadian Patent Application No. 2,096,911
Canadian Patent Application No. 2,071,105
Chartier-Harlin et al., 1992, *Nature*, v. 353, pp. 844–846.
Chumakov et al., 1992, *Nature*, v. 359, pp. 380–387.
Cruts et al., (1995), *Hum. Molec. genet.*, (in the press).
Davis, R. L., (1996), *Physiol. Reviews* (in press).
Foncin et al., 1985, *Rev. Neurol. (Paris)*, v. 141, pp. 194–202.
Frommelt et al., 1991, *Alzheimer Dis. Assoc. Disorders*, v. 5, pp. 36–43.
Gandy et al. 1993
Goate et al., 1991, *Nature*, v. 349, pp. 704–706.
Goudsmit et al., 1981, *J. Neurol. Sci.*, v. 49, pp. 79–87.
Gyapay et al., 1994, *Nature Genetics*, v. 7, pp. 246–339.
Hsiao et al. (1995), *Neuron.*, in press.
Huang and Chalfie, 1994
Huang et al. 1993,
International Patent Application No. WO 94/23049

International Patent Application No. WO 94/00569
Ioannu et al., 1994, *Nature Genetics*, v. 6, pp. 84–89.
Karlinsky et al., 1992, *Neurology*, v. 42, pp. 1445–1453.
Katzman, 1986, *N. Eng. J. Med.*, v. 314, pp. 964–973.
Levitan, 1995,
Levitan et al., (1995), *Nature*, v. 377, pp. 351–354.
Liu and Sommer 1995, *Biotechniques* in the press.
Martin et al., (1995), *NeuroReport*, v. 7, in press.
Mullan et al., 1992, *Nature Genetics*, v. 1, pp. 345–347.
Murrell et al., 1992, *Science*, v. 254, pp. 97–99.
Nee et al., 1983, *Arc. Neurol.*, v. 40, pp. 203–208.
NIH/CEPH Collaborative Mapping Group, 1992, *Science*, v. 258, pp. 67–86.
Obermeir et al., (1994), *Embo J.*, v. 7, pp. 1585–1590.
Pericak-Vance et al., 1988, *Exp. Neurol.*, v. 102, pp. 271–279.
Phizicky et al., (1995), *Microbiol. Reviews*, v. 59, pp. 94–123.
Phizicky and Fields, 1994,
Pollen, 1993, Oxford, Oxford University Press.
Querfurth et al., (1995), *Molec. Brain Res.*, in press.
Riley et al., 1990, *Nucl. Acid Res.*, v. 18, pp. 2887–2890.
Rogaev et al., 1993, *Neurology*, v. 43, pp. 2275–2279.
Rogaev et al., (1995), *Nature*, v. 376, pp. 775–778.
Rogaev et al., (1995), *Nature*, v. 376, pp. 775–778.
Rommens et al., 1993, *Hum. Molec. Genet.*, v. 2, pp. 901–907.
Saleeba and Cotton, 1993, *Methods in Enzymology*, v. 217, pp. 285–295.
Saunders, A., et al., (1993), *Neurology*, v. 43, pp. 1467–1472/
Schellenberg et al., 1993, *Am. J. Hum. Genet.*, v. 53, pp. 619–628.
Schellenberg et al., 1992, *Science*, v. 258, pp. 668–670.
Scheuner et al. (1995), *Soc. Neurosci. Abstr.*, v. 21, p. 1500.
Scott et al. (1992),
Selkoe et al., 1995,
Selkoe et al, 1994,
Sherrington et al., 1995, *Nature*, v. 375, pp. 754–760.
St. George-Hyslop et al., (1990), *Nature*, v. 347, pp. 194–197.
St. George-Hyslop et al., 1992, *Nature*, v. 347, pp. 194–197.
St. George-Hyslop et al., (1994), *Science*, v. 263, p. 537.
Strittmatter et al., 1993, *Proc. Natl. Acad. Sci. USA*, v. 90, pp. 1977–1981.
U.S. Pat. No. 5,297,562
Van Broeckhoven et al., 1992, *Nature Genetics*, v. 2, pp. 335–339.
Wang, 1992, *Genomics*, v. 13, pp. 532–536.
Weissenbach et al., 1992, *Nature*, v. 359, pp. 794–798.
Wong et al., 1993, *Neurosci. Lett.*, v. 152, pp. 96–98.

---

SEQUENCE LISTING (1) GENERAL INFORMATION:

(iii) NUMBER OF SEQUENCES: 183

(2) INFORMATION FOR SEQ ID NO:1:

(i) SEQUENCE CHARACTERISTICS:
        (A) LENGTH: 2791 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

```
TGGGACAGGC AGCTCCGGGG TCCGCGGTTT CACATCGGAA ACAAAACAGC GGCTGGTCTG      60

GAAGGAACCT GAGCTACGAG CCGCGGCGGC AGCGGGGCGG CGGGGNAAGC GTATACCTAA     120

TCTGGGAGCC TGCAAGTGAC AACAGCCTTT GCGGTCCTTA GACAGCTTGG CCTGGAGGAG     180

AACACATGAA AGAAAGAACC TCAAGAGGCT TTGTTTTCTG TGAAACAGTA TTTCTATACA     240

GTTGCTCCAA TGACAGAGTT ACCTGCACCG TTGTCCTACT TCCAGAATGC ACAGATGTCT     300

GAGGACAACC ACCTGAGCAA TACTGTACGT AGCCAGAATG ACAATAGAGA ACGGCAGGAG     360

CACAACGACA GACGGAGCCT TGGCCACCCT GAGCCATTAT CTAATGGACG ACCCCAGGGT     420

AACTCCCGGC AGGTGGTGGA GCAAGATGAG GAAGAAGATG AGGAGCTGAC ATTGAAATAT     480

GGCGCCAAGC ATGTGATCAT GCTCTTTGTC CCTGTGACTC TCTGCATGGT GGTGGTCGTG     540

GCTACCATTA AGTCAGTCAG CTTTTATACC CGGAAGGATG GGCAGCTAAT CTATACCCCA     600

TTCACAGAAG ATACCGAGAC TGTGGGCCAG AGAGCCCTGC ACTCAATTCT GAATGCTGCC     660

ATCATGATCA GTGTCATTGT TGTCATGACT ATCCTCCTGG TGGTTCTGTA TAAATACAGG     720

TGCTATAAGG TCATCCATGC CTGGCTTATT ATATCATCTC TATTGTTGCT GTTCTTTTTT     780

TCATTCATTT ACTTGGGGGA AGTGTTTAAA ACCTATAACG TTGCTGTGGA CTACATTACT     840
```

```
GTTGCACTCC TGATCTGGAA TTTGGGTGTG GTGGGAATGA TTTCCATTCA CTGGAAAGGT      900

CCACTTCGAC TCCAGCAGGC ATATCTCATT ATGATTAGTG CCCTCATGGC CCTGGTGTTT      960

ATCAAGTACC TCCCTGAATG GACTGCGTGG CTCATCTTGG CTGTGATTTC AGTATATGAT     1020

TTAGTGGCTG TTTTGTGTCC GAAAGGTCCA CTTCGTATGC TGGTTGAAAC AGCTCAGGAG     1080

AGAAATGAAA CGCTTTTTCC AGCTCTCATT TACTCCTCAA CAATGGTGTG GTTGGTGAAT     1140

ATGGCAGAAG GAGACCCGGA AGCTCAAAGG AGAGTATCCA AAAATTCCAA GTATAATGCA     1200

GAAAGCACAG AAAGGGAGTC ACAAGACACT GTTGCAGAGA TGATGATGG CGGGTTCAGT      1260

GAGGAATGGG AAGCCCAGAG GGACAGTCAT CTAGGGCCTC ATCGCTCTAC ACCTGAGTCA     1320

CGAGCTGCTG TCCAGGAACT TTCCAGCAGT ATCCTCGCTG GTGAAGACCC AGAGGAAAGG     1380

GGAGTAAAAC TTGGATTGGG AGATTTCATT TTCTACAGTG TTCTGGTTGG TAAAGCCTCA     1440

GCAACAGCCA GTGAGACTG GAACACAACC ATAGCCTGTT TCGTAGCCAT ATTAATTGGT      1500

TTGTGCCTTA CATTATTACT CCTTGCCATT TCAAGAAAG CATTGCCAGC TCTTCCAATC      1560

TCCATCACCT TTGGGCTTGT TTTCTACTTT GCCACAGATT ATCTTGTACA GCCTTTTATG     1620

GACCAATTAG CATTCCATCA ATTTTATATC TAGCATATTT GCGGTTAGAA TCCCATGGAT     1680

GTTTCTTCTT TGACTATAAC CAAATCTGGG GAGGACAAAG GTGATTTTCC TGTGTCCACA     1740

TCTAACAAAG TCAAGATTCC CGGCTGGACT TTTGCAGCTT CCTTCCAAGT CTTCCTGACC     1800

ACCTTGCACT ATTGGACTTT GGAAGGAGGT GCCTATAGAA AACGATTTTG AACATACTTC     1860

ATCGCAGTGG ACTGTGTCCT CGGTGCAGAA ACTACCAGAT TTGAGGGACG AGGTCAAGGA     1920

GATATGATAG GCCCGGAAGT TGCTGTGCCC CATCAGCAGC TTGACGCGTG GTCACAGGAC     1980

GATTTCACTG ACACTGCGAA CTCTCAGGAC TACCGGTTAC CAAGAGGTTA GGTGAAGTGG     2040

TTTAAACCAA ACGGAACTCT TCATCTTAAA CTACACGTTG AAAATCAACC CAATAATTCT     2100

GTATTAACTG AATTCTGAAC TTTTCAGGAG GTACTGTGAG GAAGAGCAGG CACCAGCAGC     2160

AGAATGGGGA ATGGAGAGGT GGGCAGGGGT TCCAGCTTCC CTTTGATTTT TTGCTGCAGA     2220

CTCATCCTTT TTAAATGAGA CTTGTTTTCC CCTCTCTTTG AGTCAAGTCA AATATGTAGA     2280

TGCCTTTGGC AATTCTTCTT CTCAAGCACT GACACTCATT ACCGTCTGTG ATTGCCATTT     2340

CTTCCCAAGG CCAGTCTGAA CCTGAGGTTG CTTTATCCTA AAAGTTTTAA CCTCAGGTTC     2400

CAAATTCAGT AAATTTTGGA AACAGTACAG CTATTTCTCA TCAATTCTCT ATCATGTTGA     2460

AGTCAAATTT GGATTTTCCA CCAAATTCTG AATTTGTAGA CATACTTGTA CGCTCACTTG     2520

CCCCAGATGC CTCCTCTGTC CTCATTCTTC TCTCCCACAC AAGCAGTCTT TTTCTACAGC     2580

CAGTAAGGCA GCTCTGTCGT GGTAGCAGAT GGTCCCACTT ATTCTAGGGT CTTACTCTTT     2640

GTATGATGAA AAGAATGTGT TATGAATCGG TGCTGTCAGC CCTGCTGTCA GACCTTCTTC     2700

CACAGCAAAT GAGATGTATG CCCAAAGCGG TAGAATTAAA GAAGAGTAAA ATGGCTGTTG     2760

AAGCAAAAAA AAAAAAAAAA AAAAAAAAAA A                                   2791
```

(2) INFORMATION FOR SEQ ID NO:2:

(i) SEQUENCE CHARACTERISTICS:
    (A) LENGTH: 467 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:2:

```
Met Thr Glu Leu Pro Ala Pro Leu Ser Tyr Phe Gln Asn Ala Gln Met
1               5                   10                  15

Ser Glu Asp Asn His Leu Ser Asn Thr Val Arg Ser Gln Asn Asp Asn
            20                  25                  30

Arg Glu Arg Gln Glu His Asn Asp Arg Arg Ser Leu Gly His Pro Glu
        35                  40                  45

Pro Leu Ser Asn Gly Arg Pro Gln Gly Asn Ser Arg Gln Val Val Glu
50                      55                  60

Gln Asp Glu Glu Asp Glu Glu Leu Thr Leu Lys Tyr Gly Ala Lys
65                  70                  75                  80

His Val Ile Met Leu Phe Val Pro Val Thr Leu Cys Met Val Val Val
                85                  90                  95

Val Ala Thr Ile Lys Ser Val Ser Phe Tyr Thr Arg Lys Asp Gly Gln
            100                 105                 110

Leu Ile Tyr Thr Pro Phe Thr Glu Asp Thr Glu Thr Val Gly Gln Arg
            115                 120                 125

Ala Leu His Ser Ile Leu Asn Ala Ala Ile Met Ile Ser Val Ile Val
        130                 135                 140

Val Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
                165                 170                 175

Phe Ser Phe Ile Tyr Leu Gly Glu Val Phe Lys Thr Tyr Asn Val Ala
            180                 185                 190

Val Asp Tyr Ile Thr Val Ala Leu Leu Ile Trp Asn Leu Gly Val Val
        195                 200                 205

Gly Met Ile Ser Ile His Trp Lys Gly Pro Leu Arg Leu Gln Gln Ala
210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
            245                 250                 255

Asp Leu Val Ala Val Leu Cys Pro Lys Gly Pro Leu Arg Met Leu Val
        260                 265                 270

Glu Thr Ala Gln Glu Arg Asn Glu Thr Leu Phe Pro Ala Leu Ile Tyr
        275                 280                 285

Ser Ser Thr Met Val Trp Leu Val Asn Met Ala Glu Gly Asp Pro Glu
290                 295                 300

Ala Gln Arg Arg Val Ser Lys Asn Ser Lys Tyr Asn Ala Glu Ser Thr
305                 310                 315                 320

Glu Arg Glu Ser Gln Asp Thr Val Ala Glu Asn Asp Asp Gly Gly Phe
            325                 330                 335

Ser Glu Glu Trp Glu Ala Gln Arg Asp Ser His Leu Gly Pro His Arg
            340                 345                 350

Ser Thr Pro Glu Ser Arg Ala Ala Val Gln Glu Leu Ser Ser Ser Ile
        355                 360                 365

Leu Ala Gly Glu Asp Pro Glu Glu Arg Gly Val Lys Leu Gly Leu Gly
370                 375                 380

Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Phe Val Ala Ile Leu Ile
            405                 410                 415
```

```
Gly Leu Cys Leu Thr Leu Leu Leu Ala Ile Phe Lys Lys Ala Leu
            420                 425                 430

Pro Ala Leu Pro Ile Ser Ile Thr Phe Gly Leu Val Phe Tyr Phe Ala
            435                 440                 445

Thr Asp Tyr Leu Val Gln Pro Phe Met Asp Gln Leu Ala Phe His Gln
450                 455                 460

Phe Tyr Ile
465

(2) INFORMATION FOR SEQ ID NO:3:

(i) SEQUENCE CHARACTERISTICS:
        (A) LENGTH: 1929 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

ACCANACANC GGCAGCTGAG GCGGAAACCT AGGCTGCGAG CCGGCCGCCC GGGCGCGGAG        60

AGAGAAGGAA CCAACACAAG ACAGCAGCCC TTCGAGGTCT TTAGGCAGCT TGGAGGAGAA       120

CACATGAGAG AAAGAATCCC AAGAGGTTTT GTTTTCTTTG AGAAGGTATT TCTGTCCAGC       180

TGCTCCAATG ACAGAGATAC CTGCACCTTT GTCCTACTTC CAGAATGCCC AGATGTCTGA       240

GGACAGCCAC TCCAGCAGCG CCATCCGGAG CCAGAATGAC AGCCAAGAAC GGCAGCAGCA       300

GCATGACAGG CAGAGACTTG ACAACCCTGA GCCAATATCT AATGGGCGGC CCCAGAGTAA       360

CTCAAGACAG GTGGTGGAAC AAGATGAGGA GGAAGACGAA GAGCTGACAT TGAAATATGG       420

AGCCAAGCAT GTCATCATGC TCTTTGTCCC CGTGACCCTC TGCATGGTCG TCGTCGTGGC       480

CACCATCAAA TCAGTCAGCT TCTATACCCG GAAGGACGGT CAGCTAATCT ACACCCCATT       540

CACAGAAGAC ACTGAGACTG TAGGCCAAAG AGCCCTGCAC TCGATCCTGA ATGCGGCCAT       600

CATGATCAGT GTCATTGTCA TTATGACCAT CCTCCTGGTG GTCCTGTATA AATACAGGTG       660

CTACAAGGTC ATCCACGCCT GGCTTATTAT TTCATCTCTG TTGTTGCTGT TCTTTTTTTC       720

GTTCATTTAC TTAGGGGAAG TATTTAAGAC CTACAATGTC KCCGTGGACT ACGTTACAGT       780

AGCACTCCTA ATCTGGAATT GGGGTGTGGT CGGGATGATT GCCATCCACT GGAAAGGCCC       840

CCTTCGACTG CAGCAGGCGT ATCTCATTAT GATCAGTGCC CTCATGGCCC TGGTATTTAT       900

CAAGTACCTC CCCGAATGGA CCGCATGGCT CATCTTGGCT GTGATTTCAG TATATGATTT       960

GGTGGCTGTT TTATGTCCCA AAGGCCCACT TCGTATGCTG GTTGAAACAG CTCAGGAAAG      1020

AAATGAGACT CTCTTTCCAG CTCTTATCTA TTCCTCAACA ATGGTGTGGT TGGTGAATAT      1080

GGCTGAAGGA GACCCAGAAG CCCAAAGGAG GGTACCCAAG AACCCCAAGT ATAACACACA      1140

AAGAGCGGAG AGAGAGACAC AGGACAGTGG TTCTGGGAAC GATGATGGTG GCTTCAGTGA      1200

GGAGTGGGAG GCCCAAAGAG ACAGTCACCT GGGGCCTCAT CGCTCCACTC CCGAGTCAAG      1260

AGCTGCTGTC CAGGAACTTT CTGGGAGCAT TCTAACGAGT GAAGACCCGG AGGAAAGAGG      1320

AGTAAAACTT GGACTGGGAG ATTTCATTTT CTACAGTGTT CTGGTTGGTA AGGCCTCAGC      1380

AACCGCCAGT GGAGACTGGA ACACAACCAT AGCCTGCTTK GTAGCCATAC TGATCGGCCT      1440

GTGCCTTANA TTACTCCTGC TCGCCATTTA CAAGAAGGG TNGCCAGCCC NCCCATCTC       1500

CATCACCTTC GGGTTCGTGT TCTNCTTCGC CACGGATTAC CTTGTGCAGC CCTTCATGGA      1560

CCAACTTGCA TTCCATCAGT TTTATATCTA GCCTTTCTGC AGTTAGAACA TGGATGTTTC      1620
```

-continued

```
TTCTTTGATT ATCAAAAACA CAAAAACAGA GAGCAAGCCC GAGGAGGAGA CTGGTGACTT        1680

TCCTGTGTCC TCAGCTAACA AAGGCAGGAC TCCAGCTGGA CTTCTGCAGC TTCCTTCCGA        1740

GTCTCCCTAG CCACCCGCAC TACTGGACTG TGGAAGGAAG CGTCTACAGA GGAACGGTTT        1800

CCAACATCCA TCGCTGCAGC AGACGGTGTC CCTCAGTGAC TTGAGAGACA AGGACAAGGA        1860

AATGTGCTGG GCCAAGGAGC TGCCGTGCTC TGCTAGCTTT GGMCCGTGGG CATGGAGATT        1920

TACCCGCAC                                                               1929
```

(2) INFORMATION FOR SEQ ID NO:4:

(i) SEQUENCE CHARACTERISTICS:
        (A) LENGTH: 467 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Met Thr Glu Ile Pro Ala Pro Leu Ser Tyr Phe Gln Asn Ala Gln Met
 1               5                  10                  15

Ser Glu Asp Ser His Ser Ser Ala Ile Arg Ser Gln Asn Asp Ser
            20                  25                  30

Gln Glu Arg Gln Gln Gln His Asp Arg Gln Arg Leu Asp Asn Pro Glu
        35                  40                  45

Pro Ile Ser Asn Gly Arg Pro Gln Ser Asn Ser Arg Gln Val Val Glu
    50                  55                  60

Gln Asp Glu Glu Glu Asp Glu Glu Leu Thr Leu Lys Tyr Gly Ala Lys
65                  70                  75                  80

His Val Ile Met Leu Phe Val Pro Val Thr Leu Cys Met Val Val Val
                85                  90                  95

Val Ala Thr Ile Lys Ser Val Ser Phe Tyr Thr Arg Lys Asp Gly Gln
            100                 105                 110

Leu Ile Tyr Thr Pro Phe Thr Glu Asp Thr Glu Thr Val Gly Gln Arg
        115                 120                 125

Ala Leu His Ser Ile Leu Asn Ala Ala Ile Met Ile Ser Val Ile Val
    130                 135                 140

Ile Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
                165                 170                 175

Phe Ser Phe Ile Tyr Leu Gly Glu Val Phe Lys Thr Tyr Asn Val Xaa
            180                 185                 190

Val Asp Tyr Val Thr Val Ala Leu Leu Ile Trp Asn Trp Gly Val Val
        195                 200                 205

Gly Met Ile Ala Ile His Trp Lys Gly Pro Leu Arg Leu Gln Gln Ala
    210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
                245                 250                 255

Asp Leu Val Ala Val Leu Cys Pro Lys Gly Pro Leu Arg Met Leu Val
            260                 265                 270

Glu Thr Ala Gln Glu Arg Asn Glu Thr Leu Phe Pro Ala Leu Ile Tyr
        275                 280                 285
```

```
Ser Ser Thr Met Val Trp Leu Val Asn Met Ala Glu Gly Asp Pro Glu
    290                 295                 300
Ala Gln Arg Arg Val Pro Lys Asn Pro Lys Tyr Asn Thr Gln Arg Ala
305                 310                 315                 320
Glu Arg Glu Thr Gln Asp Ser Gly Ser Gly Asn Asp Asp Gly Gly Phe
                325                 330                 335
Ser Glu Glu Trp Glu Ala Gln Arg Asp Ser His Leu Gly Pro His Arg
            340                 345                 350
Ser Thr Pro Glu Ser Arg Ala Ala Val Gln Glu Leu Ser Gly Ser Ile
        355                 360                 365
Leu Thr Ser Glu Asp Pro Glu Glu Arg Gly Val Lys Leu Gly Leu Gly
    370                 375                 380
Asp Phe Ile Phe Tyr Ser Val Leu Val Gly Lys Ala Ser Ala Thr Ala
385                 390                 395                 400
Ser Gly Asp Trp Asn Thr Thr Ile Ala Cys Xaa Val Ala Ile Leu Ile
                405                 410                 415
Gly Leu Cys Leu Xaa Leu Leu Leu Leu Ala Ile Tyr Lys Lys Gly Xaa
            420                 425                 430
Pro Ala Xaa Pro Ile Ser Ile Thr Phe Gly Phe Val Phe Xaa Phe Ala
        435                 440                 445
Thr Asp Tyr Leu Val Gln Pro Phe Met Asp Gln Leu Ala Phe His Gln
    450                 455                 460

Phe Tyr Ile
465

(2) INFORMATION FOR SEQ ID NO:5:

(i) SEQUENCE CHARACTERISTICS:
        (A) LENGTH: 3087 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

GAATTCGGCA CGAGGGAAAT GCTGTTTGCT CGAAGACGTC TCAGGGCGCA GGTGCCTTGG      60

GCCGGGATTA GTAGCCGTCT GAACTGGAGT GGAGTAGGAG AAAGAGGAAG CGTCTTGGGC     120

TGGGTCTGCT TGAGCAACTG GTGAAACTCC GCGCCTCACG CCCCGGGTGT GTCCTTGTCC     180

AGGGGCGACG AGCATTCTGG GCGAAGTCCG CACSCCTCTT GTTCGAGGCG AAAGACGGGG     240

TCTGATSCTT TCTCCTTGGT CGGGMCTGTC TCGAGGCATG CATGTCCAGT GACTCTTGTG     300

TTTGCTGCTG CTTCCCTCTC AGATTCTTCT CACCGTTGTG GTCAGCTCTG CTTTAGGCAN     360

TATTAATCCA TAGTGGAGGC TGGGATGGGT GAGAGAATTG AGGTGACTTT TCCATAATTC     420

AGACCTAATC TGGGAGCCTG CAAGTGACAA CAGCCTTTGC GGTCCTTAGA CAGCTTGGCC     480

TGGAGGAGAA CACATGAAAG AAAGAACCTC AAGAGGCTTT GTTTTCTGTG AAACAGTATT     540

TCTATACAGT TGCTCCAATG ACAGAGTTAC CTGCACCGTT GTCCTACTTC AGAATGCAC      600

AGATGTCTGA GGACAACCAC CTGAGCAATA CTAATGACAA TAGAGAACGG CAGGAGCACA     660

ACGACAGACG GAGCCTTGGC CACCCTGAGC CATTATCTAA TGGACGACCC CAGGGTAACT     720

CCCGGCAGGT GGTGGAGCAA GATGAGGAAG AAGATGAGGA GCTGACATTG AAATATGGCG     780

CCAAGCATGT GATCATGCTC TTTGTCCCTG TGACTCTCTG CATGGTGGTG GTCGTGGCTA     840

CCATTAAGTC AGTCAGCTTT TATACCCGGA AGGATGGGCA GCTAATCTAT ACCCCATTCA     900
```

```
CAGAAGATAC CGAGACTGTG GGCCAGAGAG CCCTGCACTC AATTCTGAAT GCTGCCATCA    960

TGATCAGTGT CATTGTTGTC ATGACTATCC TCCTGGTGGT TCTGTATAAA TACAGGTGCT   1020

ATAAGGTCAT CCATGCCTGG CTTATTATAT CATCTCTATT GTTGCTGTTC TTTTTTTCAT   1080

TCATTTACTT GGGGGAAGTG TTTAAAACCT ATAACGTTGC TGTGGACTAC ATTACTGTTG   1140

CACTCCTGAT CTGGAATTTG GGTGTGGTGG GAATGATTTC CATTCACTGG AAAGGTCCAC   1200

TTCGACTCCA GCAGGCATAT CTCATTATGA TTAGTGCCCT CATGGCCCTG GTGTTTATCA   1260

AGTACCTCCC TGAATGGACT GCGTGGCTCA TCTTGGCTGT GATTTCAGTA TATGATTTAG   1320

TGGCTGTTTT GTGTCCGAAA GGTCCACTTC GTATGCTGGT TGAAACAGCT CAGGAGAGAA   1380

ATGAAACGCT TTTTCCAGCT CTCATTTACT CCTCAACAAT GGTGTGGTTG GTGAATATGG   1440

CAGAAGGAGA CCCGGAAGCT CAAAGGAGAG TATCCAAAAA TTCCAAGTAT AATGCAGAAA   1500

GCACAGAAAG GGAGTCACAA GACACTGTTG CAGAGAATGA TGATGGCGGG TTCAGTGAGG   1560

AATGGGAAGC CCAGAGGGAC AGTCATCTAG GGCCTCATCG CTCTACACCT GAGTCACGAG   1620

CTGCTGTCCA GGAACTTTCC AGCAGTATCC TCGCTGGTGA AGACCCAGAG GAAAGGGGAG   1680

TAAAACTTGG ATTGGGAGAT TTCATTTTCT ACAGTGTTCT GGTTGGTAAA GCCTCAGCAA   1740

CAGCCAGTGG AGACTGGAAC ACAACCATAG CCTGTTTCGT AGCCATATTA ATTGGTTTGT   1800

GCCTTACATT ATTACTCCTT GCCATTTTCA AGAAAGCATT GCCAGCTCTT CCAATCTCCA   1860

TCACCTTTGG GCTTGTTTTC TACTTTGCCA CAGATTATCT TGTACAGCCT TTTATGGACC   1920

AATTAGCATT CCATCAATTT TATATCTAGC ATATTTGCGG TTAGAATCCC ATGGATGTTT   1980

CTTCTTTGAC TATAACCAAA TCTGGGGAGG ACAAAGGTGA TTTTCCTGTG TCCACATCTA   2040

ACAAAGTCAA GATTCCCGGC TGGACTTTTG CAGCTTCCTT CCAAGTCTTC CTGACCACCT   2100

TGCACTATTG GACTTTGGAA GGAGGTGCCT ATAGAAAACG ATTTTGAACA TACTTCATCG   2160

CAGTGGACTG TGTCCTCGGT GCAGAAACTA CCAGATTTGA GGGACGAGGT CAAGGAGATA   2220

TGATAGGCCC GGAAGTTGCT GTGCCCCATC AGCAGCTTGA CGCGTGGTCA CAGGACGATT   2280

TCACTGACAC TGCGAACTCT CAGGACTACC GGTTACCAAG AGGTTAGGTG AAGTGGTTTA   2340

AACCAAACGG AACTCTTCAT CTTAAACTAC ACGTTGAAAA TCAACCCAAT AATTCTGTAT   2400

TAACTGAATT CTGAACTTTT CAGGAGGTAC TGTGAGGAAG AGCAGGCACC AGCAGCAGAA   2460

TGGGGAATGG AGAGGTGGGC AGGGGTTCCA GCTTCCCTTT GATTTTTTGC TGCAGACTCA   2520

TCCTTTTTAA ATGAGACTTG TTTTCCCCTC TCTTTGAGTC AAGTCAAATA TGTAGATGCC   2580

TTTGGCAATT CTTCTTCTCA AGCACTGACA CTCATTACCG TCTGTGATTG CCATTTCTTC   2640

CCAAGGCCAG TCTGAACCTG AGGTTGCTTT ATCCTAAAAG TTTTAACCTC AGGTTCCAAA   2700

TTCAGTAAAT TTTGGAAACA GTACAGCTAT TTCTCATCAA TTCTCTATCA TGTTGAAGTC   2760

AAATTTGGAT TTTCCACCAA ATTCTGAATT TGTAGACATA CTTGTACGCT CACTTGCCCC   2820

AGATGCCTCC TCTGTCCTCA TTCTTCTCTC CCACACAAGC AGTCTTTTTC TACAGCCAGT   2880

AAGGCAGCTC TGTCGTGGTA GCAGATGGTC CCACTTATTC TAGGGTCTTA CTCTTTGTAT   2940

GATGAAAAGA ATGTGTTATG AATCGGTGCT GTCAGCCCTG CTGTCAGACC TTCTTCCACA   3000

GCAAATGAGA TGTATGCCCA AAGCGGTAGA ATTAAAGAAG AGTAAAATGG CTGTTGAAGC   3060

AAAAAAAAAA AAAAAAAAA AAAAAA                                        3087
```

(2) INFORMATION FOR SEQ ID NO:6:

(i) SEQUENCE CHARACTERISTICS:
        (A) LENGTH: 945 base pairs (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:6:

GTTNTCCNAA CCAACTTAGG AGNTTGGACC TGGGRAAGAC CNACNTGATC TCCGGGAGGN      60

AAAGACTNCA GTTGAGCCGT GATTGCACCC ACTTTACTCC AAGCCTGGGC AACCAAAATG     120

AGACACTGGC TCCAAACACA AAAACAAAAA CAAAAAAAGA GTAAATTAAT TTANAGGGAA     180

GNATTAAATA AATAATAGCA CAGTTGATAT AGGTTATGGT AAAATTATAA AGGTGGGANA     240

TTAATATCTA ATGTTTGGGA GCCATCACAT TATTCTAAAT AATGTTTTGG TGGAAATTAT     300

TGTACATCTT TTAAAATCTG TGTAATTTTT TTTCAGGGAA GTGTTAAAA CCTATAACGT      360

TGCTGTGGAC TACATTACTG TTNCACTCCT GATCTGGAAT TTTGGTGTGG TGGGAATGAT     420

TTCCATTCAC TGGAAAGGTC CACTTCGACT CCAGCAGGCA TATCTCATTA TGATTAGTGC     480

CCTCATGNCC CTGKTGTTTA TCAAGTACCT CCCTGAATGG ACTGNGTGGC TCATCTTGGC     540

TGTGATTTCA GTATATGGTA AAACCCAAGA CTGATAATTT GTTTGTCACA GGAATGCCCC     600

ACTGGAGTGT TTTCTTTCCT CATCTCTTTA TCTTGATTTA GAGAAAATGG TAACGTGTAC     660

ATCCCATAAC TCTTCAGTAA ATCATTAATT AGCTATAGTA ACTTTTTCAT TTGAAGATTT     720

CGGCTGGGCA TGGTAGCTCA TGCCTGTAAT CTTAGCACTT TGGGAGGCTG AGGCGGGCAG     780

ATCACCTAAG CCCAGAGTTC AAGACCAGCC TGGGCAACAT GGCAAAACCT CGTATCTACA     840

GAAAATACAA AAATTAGCCG GGCATGGTGG TGCACACCTG TAGTTCCAGC TACTTAGGAG     900

GCTGAGGTGG GAGGATCGAT TGATCCCAGG AGGTCAAGNC TGCAG                    945

(2) INFORMATION FOR SEQ ID NO:7:

(i) SEQUENCE CHARACTERISTICS:
            (A) LENGTH: 450 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:7:

GTTGCAAAGT CATGGATTCC TTTAGGTAGC TACATTATCA ACCTTTTTGA GAATAAAATG      60

AATTGAGAGT GTTACAGTCT AATTCTATAT CACATGTAAC TTTTATTTGG ATATATCAGT     120

AATAGTGCTT TTTTTTTTTT TTTTTTTTTT TTTTTTTTTT TTTGGGGANA GAGTCTCGCT     180

CTGTCGCCAG GTTGGAGTGC AATGGTGCGA TCTTGGCTCA CTGAAAGCTC CACCNCCCGG     240

GTTCAAGTGA TTCTCCTGCC TCAGCCNCCC AAGTAGNTGG GACTACAGGG GTGCGCCACC     300

ACGCCTGGGA TAATTTTGGG NTTTTAGTA GAGATGGCGT TTCACCANCT TGGNGCAGGC     360

TGGTCTTGGA ACTCCTGANA TCATGATCTG CCTGCCTTAG CCTCCCCAAA GTGCTGGGAT     420

TNCAGGGGTG AGCCACTGTT CCTGGGCCTC                                     450

(2) INFORMATION FOR SEQ ID NO:8:

(i) SEQUENCE CHARACTERISTICS:
            (A) LENGTH: 516 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:8:

```
GCTCATCATG CTTCACGGGG GAGGCTGTGC GGGAAGAATG CTCCCACACA GNATAAAGAA      60
TGCTCCCGCA CAGGATAGAG AATGCCCCCG CACAGCATAG AAGCCCCC GCACAGCATA       120
GAGAATGCCC CCNCACAGCA TAGAGAAGCC CCCGCACAGC ATAGAGAATG CTCTTCACCT     180
CTGGGTTTTT AACCAGCCAA ACTAAAATCA CAGAGGSCMA CACATCATTT AAGATAGAAA     240
TTTCTGTATC TTTTAATTTY TTTCMAAGTA GTTTTACTTA TTTTCAGATT CTATTTCTTT     300
ACTAGAATTA AGGGATAAAA TAACAATGTG TGCATAATGA ACCCTATGAA ACMAACMMAA     360
GCTAGGTTTT TTTCATAGST CTTCTTCCAG ATTGAATGAA CGTCTGTTCT AAAATTTAAC     420
CCCCCAGGGA AATATTCAGT TAACTATGTT AAAAACCCAG ACTTGTGATT GAGTTTTGCC     480
TGAAAATGCT TTCATAATTA TGTGTGAATG TGTGTC                               516
```

(2) INFORMATION FOR SEQ ID NO:9:

(i) SEQUENCE CHARACTERISTICS:
        (A) LENGTH: 1726 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

```
GGATCCCTCC CCTTTTTAGA CCATACAAGG TAACTTCCGG ACGTTGCCAT GGCATCTGTA      60
AACTGTCATG GTGTTGGCGG GGAGTGTCTT TTAGCATGCT AATGTATTAT AATTAGCGTA     120
TAGTGAGCAG TGAGGATAAC CAGAGGTCAC TCTCCTCACC ATCTTGGTTT TGGTGGGTTT     180
TGGCCAGCTT CTTTATTGCA ACCAGTTTTA TCAGCAAGAT CTTTATGAGC TGTATCTTGT     240
GCTGACTTCC TATCTCATCC CGNAACTAAG AGTACCTAAC CTCCTGCAAA TTGMAGNCCA     300
GNAGGTCTTG GNCTTATTTN ACCCAGCCCC TATTCAARAT AGAGTNGYTC TTGGNCCAAA     360
CGCCYCTGAC ACAAGGATTT TAAAGTCTTA TTAATTAAGG TAAGATAGKT CCTTGSATAT     420
GTGGTCTGAA ATCACAGAAA GCTGAATTTG GAAAAGGTG CTTGGASCTG CAGCCAGTAA      480
ACAAGTTTTC ATGCAGGTGT CAGTATTTAA GGTACATCTC AAAGGATAAG TACAATTGTG     540
TATGTTGGGA TGAACAGAGA GAATGGAGCA ANCCAAGACC CAGGTAAAAG AGAGGACCTG     600
AATGCCTTCA GTGAACAATG ATAGATAATC TAGACTTTTA AACTGCATAC TTCCTGTACA     660
TTGTTTTTTC TTGCTTCAGG TTTTTAGAAC TCATAGTGAC GGGTCTGTTG TTAATCCCAG     720
GTCTAACCGT TACCTTGATT CTGCTGAGAA TCTGATTTAC TGAAAATGTT TTTCTTGTGC     780
TTATAGAATG ACAATAGAGA ACGGCAGGAG CACAACGACA GACGGAGCCT TGGCCACCCT     840
GANCCATTAT CTAATGGACG ACCCAGGGTA ACTCCCGGCA GGTGGTGGAN CAAGATGAGG     900
AAGAAGATGA GGANCTGACA TTGAAATATG NCGSCAAGCA TGTGATCATG CTCTTTGKCC     960
CTGTGACTCT CTGCATGGTG GTGGTCGTGG NTACCATTAA GTCAGTCAGC TTTTATACCC    1020
GGAAGGATGG GCAGCTGTAC GTATGAGTTT KGTTTTATTA TTCTCAAASC CAGTGTGGCT    1080
TTTCTTTACA GCATGTCATC ATCACCTTGA AGGCCTCTNC ATTGAAGGGG CATGACTTAG    1140
CTGGAGAGCC CATCCTCTGT GATGGTCAGG AGCAGTTGAG AGANCGAGGG GTTATTACTT    1200
CATGTTTTAA GTGGAGAAAA GGAACACTGC AGAAGTATGT TTCCTGTATG GTATTACTGG    1260
ATAGGGCTGA AGTTATGCTG AATTGAACAC ATAAATTCTT TTCCACCTCA GGGNCATTGG    1320
GCGCCCATTG NTCTTCTGCC TAGAATATTC TTTCCTTTNC TNACTTKGGN GGATTAAATT    1380
```

```
CCTGTCATCC CCCTCCTCTT GGTGTTATAT ATAAAGTNTT GGTGCCGCAA AGAAGTAGC     1440

ACTCGAATAT AAAATTTTCC TTTTAATTCT CAGCAAGGNA AGTTACTTCT ATATAGAAGG    1500

GTGCACCCNT ACAGATGGAA CAATGGCAAG CGCACATTTG GGACAAGGGA GGGGAAAGGG    1560

TTCTTATCCC TGACACACGT GGTCCCNGCT GNTGTGTNCT NCCCCCACTG ANTAGGGTTA    1620

GACTGGACAG GCTTAAACTA ATTCCAATTG GNTAATTTAA AGAGAATNAT GGGGTGAATG    1680

CTTTGGGAGG AGTCAAGGAA GAGNAGGTAG NAGGTAACTT GAATGA                   1726
```

(2) INFORMATION FOR SEQ ID NO:10:

(i) SEQUENCE CHARACTERISTICS:
        (A) LENGTH: 1883 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

```
CNCGTATAAA AGACCAACAT TGCCANCNAC AACCACAGGC AAGATCTTCT CCTACCTTCC      60

CCCNNGGTGT AATACCAAGT ATTCNCCAAT TTGTGATAAA CTTTCATTGG AAAGTGACCA     120

CCCTCCTTGG TTAATACATT GTCTGTGCCT GCTTTCACAC TACAGTAGCA CAGTTGAGTG     180

TTTGCCCTGG AGACCATATG ACCCATAGAG CTTAAAATAT TCAGTCTGGC TTTTTACAGA    240

GATGTTTCTG ACTTTGTTAA TAGAAAATCA ACCCAACTGG TTTAAATAAT GCACATACTT    300

TCTCTCTCAT AGAGTAGTGC AGAGGTAGNC AGTCCAGATT AGTASGGTGG CTTCACGTTC    360

ATCCAAGGAC TCAATCTCCT TCTTTCTTCT TTAGCTTCTA ACCTCTAGCT TACTTCAGGG    420

TCCAGGCTGG AGCCCTASCC TTCATTTCTG ACAGTAGGAA GGAGTAGGGG AGAAAAGAAC    480

ATAGGACATG TCAGCAGAAT TCTCTCCTTA GAAGTTCCAT ACACAACACA TCTCCCTAGA    540

AGTCATTGCC CTTACTTGTT CTCATAGCCA TCCTAAATAT AAGGGAGTCA GAAGTAAAGT    600

CTKKNTGGCT GGGAATATTG GCACCTGGAA TAAAAATGTT TTTCTGTGAA TGAGAAACAA    660

GGGGAAGATG GATATGTGAC ATTATCTTAA GACAACTCCA GTTGCAATTA CTCTGCAGAT    720

GAGAGGCACT AATTATAAGC CATATTACCT TTCTTCTGAC AACCACTTGT CAGCCCNCGT    780

GGTTTCTGTG GCAGAATCTG GTTCYATAMC AAGTTCCTAA TAANCTGTAS CCNAAAAAAT    840

TTGATGAGGT ATTATAATTA TTTCAATATA AGCACCCAC TAGATGGAGC CAGTGTCTGC     900

TTCACATGTT AAGTCCTTCT TTCCATATGT TAGACATTTT CTTTGAAGCA ATTTTAGAGT    960

GTAGCTGTTT TTCTCAGGTT AAAAATTCTT AGCTAGGATT GGTGAGTTGG GGAAAAGTGA   1020

CTTATAAGAT NCGAATTGAA TTAAGAAAAA GAAAATTCTG TGTTGGAGGT GGTAATGTGG   1080

KTGGTGATCT YCATTAACAC TGANCTAGGG CTTTKGKGTT TGKTTTATTG TAGAATCTAT   1140

ACCCCATTCA NAGAAGATAC CGAGACTGTG GGCCAGAGAG CCCTGCACTC AATTCTGAAT   1200

GCTGCCATCA TGATCAGNGT CATTGTWGTC ATGACTANNC TCCTGGTGGT TCWGTATAAA   1260

TACAGGTGCT ATAAGGTGAG CATGAGACAC AGATCTTTGN TTTCCACCCT GTTCTTCTTA   1320

TGGTTGGGTA TTCTTGTCAC AGTAACTTAA CTGATCTAGG AAAGAAAAAA TGTTTTGTCT   1380

TCTAGAGATA AGTTAATTTT TAGTTTTCTT CCTCCTCACT GTGGAACATT CAAAAAATAC   1440

AAAAAGGAAG CCAGGTGCAT GTGTAATGCC AGGCTCAGAG GCTGAGGCAG GAGGATCGCT   1500

TGGGCCCAGG AGTTCACAAG CAGCTTGGGC AACGTAGCAA GACCCTGCCT CTATTAAAGA   1560

AAACAAAAAA CAAATATTGG AAGTATTTTA TATGCATGGA ATCTATATGT CATGAAAAAA   1620
```

```
TTAGTGTAAA ATATATATAT TATGATTAGN TATCAAGATT TAGTGATAAT TTATGTTATT       1680

TTGGGATTTC AATGCCTTTT TAGGCCATTG TCTCAAMAAA TAAAAGCAGA AAACAAAAAA       1740

AGTTGTAACT GAAAAATAAA CATTTCCATA TAATAGCACA ATCTAAGTGG GTTTTTGNTT       1800

GTTTGTTTGN TTGTTGAAGC AGGGCCTTGC CCTNYCACCC AGGNTGGAGT GAAGTGCAGT       1860

GGCACGATTT TGGCTCACTG CAG                                              1883

(2) INFORMATION FOR SEQ ID NO:11:

(i) SEQUENCE CHARACTERISTICS:
        (A) LENGTH: 823 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

CAGGAGTGGA CTAGGTAAAT GNAAGNTGTT TTAAAGAGAG ATGNGGNCNG GGACATAGTG         60

GTACACANCT GTAATGCTCA NCACTKATGG GGAGTACTGA AGGNGGNSGG ATCACTTGNG        120

GGTCNGGAAT NTGAGANCAG CCTGGGCAAN ATGGCGAAAC CCTGTCTCTA CTAAAAATAG       180

CCANAAWNWA GCCTAGCGTG GTGGCGCRCA CGCGTGGTTC CACCTACTCA GGAGGCNTAA       240

GCACGAGNAN TNCTTGAACC CAGGAGGCAG AGGNTGTGGT GARCTGAGAT CGTGCCACTG       300

CACTCCAGTC TGGGCGACMA AGTGAGACCC TGTCTCCNNN AAGAAAAAAA AAATCTGTAC       360

TTTTTAAGGG TTGTGGGACC TGTTAATTAT ATTGAAATGC TTCTYTTCTA GGTCATCCAT       420

GCCTGGCTTA TTATATCATC TCTATTGTTG CTGCTCTTTT TTACATTCAT TTACTTGGGG       480

TAAGTTGTGA AATTTGGGGT CTGTCTTTCA GAATTAACTA CCTNNGTGCT GTGTAGCTAT       540

CATTTAAAGC CATGTACTTT GNTGATGAAT TACTCTGAAG TTTTAATTGT NTCCACATAT       600

AGGTCATACT TGGTATATAA AAGACTAGNC AGTATTACTA ATTGAGACAT TCTTCTGTNG       660

CTCCTNGCTT ATAATAAGTA GAACTGAAAG NAACTTAAGA CTACAGTTAA TTCTAAGCCT       720

TTGGGGAAGG ATTATATAGC CTTCTAGTAG GAAGTCTTGT GCNATCAGAA TGTTTNTAAA       780

GAAAGGGTNT CAAGGAATNG TATAAANACC AAAAATAATT GAT                        823

(2) INFORMATION FOR SEQ ID NO:12:

(i) SEQUENCE CHARACTERISTICS:
        (A) LENGTH: 736 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

GTCTTTCCCA TCTTCTCCAC AGAGTTTGTG CCTTACATTA TTACTCCTTG CCATTTTCAA         60

GAAAGCATTG TCAGCTCTTC CAATCTCCAT CACCTTTGGG CTTGTTTTCT ACTTTGCCAC       120

AGATTATCTT GTACAGCCTT TTATGGACCA ATTAGCATTC CATCAATTTT ATATCTAGCA       180

TATTTGCGGT TAGAATCCCA TGGATGTTTC TTCTTTGACT ATAACAAAAT CTGGGGAGGA       240

CAAAGGTGAT TTCCTGTGTC CACATCTAAC AAATCAAGAT CCCCGGCTGG ACTTTTGGAG       300

GTTCCTTCCA AGTCTTCCTG ACCACCTTGC ACTATTGGAC TTTGGAAGGA GGTGCCTATA       360

GAAAACGATT TTGAACATAC TTCATCGCAG TGGACTGTGT CCTCGGTGCA GAAACTACCA       420
```

```
GATTTGAGGG ACGAGGTCAA GGAGATATGA TAGGCCCGGA AGTTGCTGTG CCCCATCAGC      480

AGCTTGACGC GTGGTCACAG GACGATTTTC ACTGACACTG CGAACTCTCA GGACTACCGT      540

TACCAAGAGG TTAGGTGAAG TGGTTTAAAC CAAACGGAAC TCTTCATCTT AAACTACACG      600

TTGAAAATCA ACCCAATAAT TCTGTATTAA CTGAATTCTG AACTTTTCAG GAGGTACTGT      660

GAGGAAGAGC AGGCACCACC AGCAGAATGG GGAATGGAGA GGTGGGCAGG GGTTCCAGCT      720

TCCCTTTGAT TTTTTG                                                       736

(2) INFORMATION FOR SEQ ID NO:13:

(i) SEQUENCE CHARACTERISTICS:
         (A) LENGTH: 893 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:13:

GGATCCGCCC GCCTTGGCCT CCCAAAGTGC TGGGATTACA GGCATGAGCC ACCGCTCCTG       60

GCTGAGTCTG CGATTTCTTG CCAGCTCTAC CCAGTTGTGT CATCTTAAGC AAGTCACTGA      120

ACTTCTCTGG ATTCCCTTCT CCTNNWGTAA AATAAGNATG TTATCTGNCC NNCCTGCCTT      180

GGGCATTGTG ATAAGGATAA GATGACATTA TAGAATNTNG CAAAATTAAA AGCGCTAGAC      240

AAATGATTTT ATGAAAATAT AAAGATTAGN TTGAGTTTGG GCCAGCATAG AAAAAGGAAT      300

GTTGAGAACA TTCCNTTAAG GATTACTCAA GCYCCCCTTT TGSTGKNWAA TCAGANNGTC      360

ATNNAMNTAT CNTNTGTGGG YTGAAAATGT TTGGTTGTCT CAGGCGGTTC CTACTTATTG      420

CTAAAGAGTC CTACCTTGAG CTTATAGTAA ATTTGTCAGT TAGTTGAAAG TCGTGACAAA      480

TTAATACATT CCTGGTTTAC AAATTGGTCT TATAAGTATT TGATTGGTNT AAATGNATTT      540

ACTAGGATTT AACTAACAAT GGATGACCTG GTGAAATCCT ATTTCAGACC TAATCTGGGA      600

GCCTGCAAGT GACAACAGCC TTTGCGGTCC TTAGACAGCT TGGCCTGGAG GAGAACACAT      660

GAAAGAAAGG TTTGTTTCTG CTTAATGTAA TCTATGGAAG TGTTTTTTAT AACAGTATAA      720

TTGTAGTGCA CAAAGTTCTG TTTTTCTTTC CCTTTTCAGA ACCTCAAGAG CTTTGTTTT       780

CTGTGAAACA GTATTTCTAT ACAGTNTGCT CCAANTGNAC AGAGTTACCT GCACNNCGTT      840

GTCCNTACTT CCAGAATGCA CAGATGTCTG AGGACAACCA CCTGAGCAAT ACT            893

(2) INFORMATION FOR SEQ ID NO:14:

(i) SEQUENCE CHARACTERISTICS:
         (A) LENGTH: 475 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:14:

TCAGAAAATA CTTTNGGGCA CATGAGAATC ACATGAGAAC AAGCTGATGC ATAATTCCTC       60

CTGTGATGGA ATGTAATAGT AATTTAACAG TGTCCTTTCT TTTTAACTGC CTCAAGGATA      120

CAGCAAAATA AAACAAAAGC AATATGAAGG CTGAGAATAG GTATCAGATT ATCATAAAAA      180

GTATAGATCA AAAGGAATCT GGTKCTNAGG TTGGCGCAGC AGCCTCTAGA AGCGACNAGG      240

GAGACTTTTA GAACTACCAT TCTCCTCTAT AAGTGGATCC NANGCCCAGG RAAACTTGAT      300

ATTGAGNACA ATGGCCTTAC TGAAATAACC TGTGATCCAC TCGGNCTCAT CATCTCCACC      360
```

ACCACCATAA ATTTGATGAG TNCCTATAAT ATTCCANCCA GNGGAAATAC CTGGRAGGTT        420

ACTGAAAGGC NACNATCAGA CNAAAATAAA GNATACCGTA GGTAAATTCT ACAGT            475

(2) INFORMATION FOR SEQ ID NO:15:

(i) SEQUENCE CHARACTERISTICS:
        (A) LENGTH: 180 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

GTTCTCNAGA TCTCTTCAAA ATTCATTNTG CGCTATAGGA GCTGGGATTA CCGCGGGTGC        60

TGGAACCAGA CTTGCNCTCC AATGGATCCT CCANACNGGA NGGGGGGTGG ACTCACACCA       120

TTTACAGGGG GCTCGTAAAG AATCCTGTTT TGANTATTNT NCCGTCAATT ACCNCCCCAA       180

(2) INFORMATION FOR SEQ ID NO:16:

(i) SEQUENCE CHARACTERISTICS:
        (A) LENGTH: 457 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

AATGTAACMA CMAAACCYCA AACTCCTGNA AGAANATGGT TACTTATNGA TNCCATTTNC        60

TTTTTNCACT CTCAGACATA AATATAAACM MANTTTCTAC TGTGGRAAAA CATCTNCAGG       120

GGNCNTTTAN CCATGATCTC TAGNACNANG GGCTNGTGGN TNGTTTTAAT GTCTCTAAGC       180

NACTNGACTA GTTTCTCTTN CACTGAGNAA ACTGCNACAA GTNNTTNCTN CTGNATCTGN       240

ACTGNAATGC TAAGTTNCAA GTNCCAATGA GCTNGTGANT TANYCTTTAT TTNAMCNAAA       300

GTNNTTAATC ANCCNCAGTG TTACTTTGNA AAGCTNCTCC CTGGACAGGC GGCCCNACTT       360

CTAATGTTAT GAATGGGCTG GAGNANCCTC NACNTGAGTT TNNWAAGGNT CAACANCCAA       420

TRGNAANTGT AMCCGACTCT AAATTCCAAC CNATAAT                                457

(2) INFORMATION FOR SEQ ID NO:17:

(i) SEQUENCE CHARACTERISTICS:
        (A) LENGTH: 373 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

ATCTGTGCTA GGTAGTGTAC TAATCATTCA GTTTATCTCA TTTAATCTNN ATGNAACTCT        60

AAGTCATTCG CTNTGANCNA CACATAACAG ATCTCGCAAC TGNAGTTTAG CGAGGCCAGT       120

TAATTTKCCA AAGNTCATAA TNCTAAGNAG TTCTAGNATG GAGATTCMAA GTCCNACTGT       180

TTAGTCAAGA GACCCTACTG TTAACTAGTA CCTTTACACT ACTAACTGGG TAANCCATAA       240

NCAATTAATG ATAAAGATTG AGATTACTKC CACATTCTCA CTGGTTATAA ATTAAAACNT       300

CAAATAAAAA NTCTTGGCAC TTCTATGGTA ATATTTTTAT TAGGATAAAC TTTCAAGNAG       360

TGGATNCTAG GTG                                                          373

(2) INFORMATION FOR SEQ ID NO:18:

(i) SEQUENCE CHARACTERISTICS:
        (A) LENGTH: 422 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

```
CCCACACTGN TGGGCCATGG AAGCCATGAG TGTACCACAT GGCCCTGTCC CACTGGCCAC        60

AGTNGATTGG TTGGNTCGGG AGTAGTCACC TGATTCAAGN TGGGCCAATC AGATCCTACC       120

TCCANGGGGT TNGGAATTAG AAAACAGTGA CCCTAGYTAG TNTAGGCNAC TTGAACTGGA       180

GGGCCCATAC ATTCAGGAGC CTTATGGGGC CATGTACACA TGGAAGCAGG AAGANTGAAG       240

GAGGGAGAAG TAGAGGCCAG AAACCCACCT GGGTTCCTGT TTCCCAATGN TAAGTCCCTG       300

CCATGTYCCT GCTCTTCCTG TGGTTNGGAT CTTCAAAGGT TGCTCAAATT NGGGGCAGTG       360

GCCCTGGCAG CTTTTCAAAT CCTYCCCATT TTTATTGAAG CTGAAAGACC CTTGACTAGA       420

AC                                                                     422
```

(2) INFORMATION FOR SEQ ID NO:19:

(i) SEQUENCE CHARACTERISTICS:
        (A) LENGTH: 395 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

```
ATTGTTATTT TTCGTCACTA CCTCCCCGGG TCGGGAGTGG GTAATTTGCG CGCCTGCTGC        60

CTTCCTTGGA TGTGGTAGCC GTTTCTCAGG CTCCCTCTCC GGAATCGAAC CCTGATTCCC       120

CGTCACCCGT GGTCACCATG GTTAGGCACG GCGACTACCA TCGAAAGTTA ATAGGGCAGA       180

TCTCGAGAAT TCTCGAGATC TCCNTCMAAT TATTACTTCA NTTKCGGTAG TGATCAGNAC       240

NAGGCAGTTC TATTGATTTC TCTCCTTTCA TTCTGAGTTT CTCCATAAAT TAATTGGACC       300

TAATCATGTT TKNAATCCTG TCTTTTAGGG GGNANTTGNA CTNTCAAGTG TTTAAAGGGA       360

GGGNCGGAGN ATGATTNTGG ATTGGAGTGA GAGCA                                  395
```

(2) INFORMATION FOR SEQ ID NO:20:

(i) SEQUENCE CHARACTERISTICS:
        (A) LENGTH: 487 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

```
CAGANTTTCT GGGTNAAAAG GACCTNANAC ATAATATAGT GGACTTNCAA TAAACACTTA        60

CCAAATGGAN AAATGAACCC CTGGTCACCC CGATCTCACT AGTNCCTNCC CTGAAACCCG       120

ANANATCTGA GTCCTTTTCT CCTTTACTAA CCCTTNCTCC AATCCTGCTC ATGGGAATTA       180

ANGNTGTAAA ATANGCCTGG GGNACCTCGG RCCTCTNCCC TGGGNTCTGT GGGTGGGAGN       240

ACTGTGGAAG CCGTWTCAAT CGCCCCCACC TATGAGAGCC TTTCTNCAGG GCCAGCCATG       300
```

```
AACGTCCCCC ATGTNATCAG NATCTNCAGG CTACTGCTGT CCTTCYTGGA TWTTTAACCT        360

GGRGGCGGGC CAGGGACAGA AAARGGAGGT GGCAAGATCC TTGAACAAAA GGAGCTATAA        420

AAGGGCGTTG GGGGAAGCAA GGCAAACGGC AGATTAAACA AGCAGGCACC TCAAGGAAAC       480

GTGACGC                                                                 487
```

(2) INFORMATION FOR SEQ ID NO:21:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

```
CTCGAGATCT GGCCCATCAT TTAGTTTTAT NGCTTGNAGT NTNTAGNAGA TAAAACATCC         60

ACGTGGATCT NCTCTTAGAG AAATCAANTA CTTTAGGNAT NTGATAGTCA GAGANTGGNT        120

ATCAAATNGA AAGGNATNTN GGTNGANCAG TTAGTTNGYN CCNTTNGNNG AGACCACTGG        180

GNTGTNGASA CCAGATTCMK GGGTNCNAAT CTTANGGTAA TCTNAGAGCC AACACATGGG        240

TCATNTTATS CCCCAAACTT AGCCACATCT BGTGGGGYTA TGGNGTCACC CCAAGAGCAG        300

GAGGAGCATG GNTGGATGGA AATCCATCTC CACCACTGGA ACCCCAAWTT CTGAATGNAT        360

CACCTGTTAG AGTTTCTTGT YCATAAAATA GCAGGGAATT TAGGAATTTA GTTTTTTTTT        420

AATAGTTTGG GCCTTTTATC CACACTCTCA GGAGCTTAGG ATACTTTTCT CCTTCAGCTC        480

ACTCTGAAAC TCCCTCTGGA                                                    500
```

(2) INFORMATION FOR SEQ ID NO:22:

(i) SEQUENCE CHARACTERISTICS:
        (A) LENGTH: 406 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

```
TCGAGATCTG TGGTAGTNAC ATGATATTCT GGCAMCTACT TTCATTATCA CCTTTATTAA         60

AATAAATTTA AGAAAAATG GCAGTATGTT TCTGTGRAGN CCACGAGTAC TCATTTTAAA        120

GGACTCMAGA GTTNCAGRNA AGTAAAAAGR AAAGAGTAAA ATCATTTTCT AANTYTYWYY        180

TTCCAGAAAT AACGATGTTG AGCATTAAGT GGACTTCATT TCATACTCTT TCMMAGNTTA        240

TGTAGGCATA WAWATGTGTG TGTATATACA TATATATGGG TACATCCTTA GAGAAGTTGG        300

CTGGCTAGAT AGACACACNT NAAAAATGGR ATCATACTCT AATKCCATTT NNANTTTANA        360

AAATACATAT TCAGANCCNC TGTNCTTATA NACAGAGTAA NTGAAA                      406
```

(2) INFORMATION FOR SEQ ID NO:23:

(i) SEQUENCE CHARACTERISTICS:
        (A) LENGTH: 289 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

```
GACCCAGTAA AACTTATCTC ATGAGCATAA GGCTGAATGG GATTGACAGC CTACAGAACC      60

CGGATTTTAT CATGAGGGCA TTAGTGGGGG TTGGGGGTTA GGTACTGAAA GTTTAAGGAG     120

GTGAAAGGAA AGCAACTTGT GCCTTACAGG GTCAAGCTAG GTCAAGGAAA TTCCCAGGAG     180

CGTGTGGAAG CTCTCTACCT GATAGGTGAG CTCAAGCTTA TGACCGCCCA AGCTTCTCCC     240

CAAGCTTCCC TTCCACTGCT TCCTCTTGAT TGACTTCCAC AGCAAGGTC                 289

(2) INFORMATION FOR SEQ ID NO:24:

(i) SEQUENCE CHARACTERISTICS:
        (A) LENGTH: 367 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

CCATCAGGAT TTACTGAGTA AAAATCTCAG GTNTTAACCA TGCCCCTAAA ATGTGCTATN      60

CCAAAGAGGA ACAGGTTACT TGGGAGGAAA AAAGCTGCCT GGGNAACTCC CCNCAAATGT    120

TTATTTTAAA TAAAAATGGT NGATGGAAAT ATTTTNTAAA AGAACTTGGG GTNTAATATG    180

GNATACTGCC CATCAAACAA AAAAGGAAAT AAAACTTCNT TCCCATTTAT AATAAGTTNC    240

CCACCCTTTA CTATCAAGAT TACAACTTAT TGACCTTTTA TGCTNGCTNG GTTTTTTTGG    300

GACTGCCTAA TCCAATGTTT AAATTTTCTA NGTCTGNATT TCAATGTGGG TAGGAGTNAT    360

TTTTCAA                                                              367

(2) INFORMATION FOR SEQ ID NO:25:

(i) SEQUENCE CHARACTERISTICS:
        (A) LENGTH: 425 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

GAGTATCTGA CAGGTAAGAT TGCTTTTTAA AGTTGTTTTA AATGCATTAC ATGACTGAGA      60

AAAGAAAAAT GCACATTTTA TTGTTGCAGT TTAAAATTTC ATTTNGNGTG AAACTAAACG    120

TGAAACAAAA GGGATAAATG TGTTTTGNTT TTGTTTTGGT TTTACCTGTT TGGGGTATTT    180

TTTTCTGAGT TTGTGTAGAA ACCCGTGTGG NTACACTGGG TAATCTTGTC AGGGNTACMA    240

AMCTTGGGTC TTGANTTTGG TTANTTGGNT TTANTTGGTG NACCCATGTA CTTGCTCTTC    300

CNTCCCAGAA ACATAGCTTG GTAGGCNAGG GTTAANCCAG TGTCGGCGAN CCCATGTCCC    360

TANCACAGCA TCTTGTAAGT TTAATGCACA ATCGTTCCNT CCCAGGATGG ANTTATCATT    420

ATAAA                                                                425

(2) INFORMATION FOR SEQ ID NO:26:

(i) SEQUENCE CHARACTERISTICS:
        (A) LENGTH: 2377 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:
```

-continued

```
GAGAGGCGCA GGAGCCACAA ATAAAGCAAG AGCCAGAATC AGAAGNGGAG GAAGAAGAAA      60

AGCAAGAAAA AGRAGRAANA CGAGAAGAAC CCATGGRAGA GGAAGAGGAN CCAGANCMAA     120

AGCCTTGTCT GAAACCTACT CTGAGGCCCA TCAGCTCTGC TCCATCTGTT TCCTCTGCCA     180

GTGGNAATGC NACACCTAAC ACTCCTGGGG ATGAGTCTCC CTGTGGTATT ATTATTCCTC     240

ATGRAAACTC ACCAGATCAA CAGCAACCTG AGGAGCATAG GCCMAAAATA GGACTAAGTC     300

TTAAACTGGG TGCTTCCAAT AGTCCTGGTC AGCCTAATTC TGTGAAGAGA AAGAAACTAC     360

CTGTAGATAG TGTCTTTAAC AAATTTGAGG ATGAAGACAG TGATGACGTA CCCCGAAAAA     420

GGAAACTGGT TCCCTTGGAT TATGGTGAAG ATGATAAAAA TNCAACCAAA GGCACTGTAA     480

ACACTGAAGA AAAGCGTAAA CACATTAAGA GTCTCATTGA GAAAATCCCT ACAGCCAAAC     540

CTGAGCTCTT CGCTTATCCC CTGGATTGGT CTATTGTGGA TTCTATACTG ATGGAACGTC     600

GAATTAGACC ATGGATTAAT AAGAAAATCA TAGAATATAT AGGTGAAGAA GAAGCTACAT     660

TAGTTGATTT NGTTTGTTCT AAGGTTATGG CTCATAGTNC ACCCCAGAGC ATTTTAGATG     720

ATGTTGCCAT GGTACTTGAT GAAGAAGCAG AAGTTTTTAT AGTCAAAATG TGGAGATTAT     780

TGATATATGA AACAGAAGCC AAGAAAATTG GTCTTGTGAA GTAAAACTTT TTATATTTAG     840

AGTTCCATTT CAGATTTCTT CTTTGCCACC CTTTTAAGGA CTTKGAATTT TTCTTTGTCT     900

TKGAAGACAT TGTGAGATCT GTAATTTTTT TTTTTTGTAG AAAATGTGAA TTTTTTGGTC     960

CTCTAATTTG TTGTTGCCCT GTGTACTCCC TTGGTTGTAA AGTCATCTGA ATCCTTGGTT    1020

CTCTTTATAC TCACCAGGTA CAAATTACTG GTATGTTTTA TAAGCCGCAG CTACTGTACA    1080

CAGCCTATCT GATATAATCT TGTTCTGCTG ATTTGTTTCT TGTAAATATT AAAACGACTC    1140

CCCAATTATT TTGCAGAATT GCACTTAATA TTGAAATGTA CTGTATAGGA ACCAACATGA    1200

ACAATTTTAA TTGAAAACAC CAGTCATCAA CTATTACCAC CCCCACTCTC TTTTCATCAG    1260

AAATGGCAAG CCCTTGTGAA GGCATGGAGT TTAAAATTGG AATGCAAAAA TTAGCAGACA    1320

ATCCATTCCT ACTGTATTTC TGTATGAATG TGTTTGTGAA TGTATGTGTA AAAGTCTTTC    1380

TTTTCCCTAA TTTGCTTTGG TGGGGTCCTT AAAACATTTC CCAACTAAAG AATAGAATTG    1440

TAAAGGAAAA GTGGTACTGT TCCAACCTGA AATGTCTGTT ATAATTAGGT TATTAGTTTC    1500

CCAGAGCATG GTGTTCTCGT GTCGTGAGCA ATGTGGGTTG CTAACTGTAT GGGGTTTTCT    1560

TATTAATAAG ATGGCTGCTT CAGCTTCTCT TTTAAAGGAA TGTGGATCAT AGTGATTTTT    1620

CCTTTTAATT TTATTGCTCA GAAATGAGGC ATATCCCTAA AAATCTCGGA GAGCTGTATT    1680

TAATGCATTT TTGCACTAAT TGGTCCTTAG TTTAATTCTA TTGTATCTGT TTATTTAACA    1740

AAAAATTCAT CATATCAAAA AGTGTAAGTG AAAACCCCCT TTAAAACAAA ACAAAAAAAT    1800

GAAATAAAAT TAGGCAAATT GACAGACAGT GAGAGTTTTA CAAACATGAT AGGTATTCTG    1860

CTCGGCAATT TGTAAGTTTA CATGTTATTT AAGGATAAAG GTAAATCATT CAAGGCAGTT    1920

ACCAACCACT AACTATTTGT TTTCATTTTT GTCTTGTAGA AGGTTTATAT CTTGTTTTAC    1980

CTTGGCTCAT TAGTGTTTAA AAATGTACTG ATGATGTGCT TAGAGAAATT CCTGGGCTT     2040

TCTTCGTTGT AGATCAGAAT TTCACCAGGG AGTAAAATTA CCTGAAAACG TAAGAAGTTT    2100

TAAACAGCTT TCCACACAAA TTAGATGCAA CTGTTCCCAT GTCTGAGGTA CTTATTTAAA    2160

AGAAAGGTAA AGATTGGCCT GTTAGAAAAA GCATAATGTG AGCTTTGGAT TACTGGATTT    2220

TTTTTTTTTT TAAACACACC TGGAGAGGAC ATTTGAAAAC ACTGTTCTTA CCCTCGAACC    2280

CTGATGTGGT TCCATTATGT AAATATTTCA AATATTAAAA ATGTATATAT TTGAAAAAAA    2340
```

```
AAAAAAAAAA AAAATTCCTG CGGCCGCAAG GGAATTC                                  2377

(2) INFORMATION FOR SEQ ID NO:27:

(i) SEQUENCE CHARACTERISTICS:
        (A) LENGTH: 489 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

ATTGGAGCTC CACCGCGGTG GCGGCCGCTC TAGNAACTAG TGGATCCCCC GGGCTGCAGG           60

AATTCTCGAG ATCTCCCCCA AGTAAATGAA TGAAAAAAAG AACAGCAACA ATAGAGATGA          120

TATAATAAGC CAGGCATGGA TGACCTTATA GCACCCTGTA TTTATACAGA ACCACCAGGA          180

GGATAGTCAT GACAACNATG ACACTGATCA TGATNCCAGC ATTCAGAATT GAGTNCAGGG          240

CTCTCTGGCC CACAGTCTCG GTATCTTCTG TGNATGGGGT ATAGATTARC TGTCCATCCT          300

TCCGGGNATA AAANCTGACT GACTTAATGG TANCCACGAC CACCACCCAT KCAGAGAGTC          360

ACAGGGACMA AAGAGCATGA TCAACATGCT TGGCNCCATA TTTCAATNTC ANCTCCTCAT          420

CTTCTTCCTC ATCTTNCTCC ACCACCTNCC GGGAGTTAAC CCTGGGGTCG TCCATTAGAT          480

AATGGCTCA                                                                 489

(2) INFORMATION FOR SEQ ID NO:28:

(i) SEQUENCE CHARACTERISTICS:
        (A) LENGTH: 2307 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

AGGGTGCTTC AGTGTGGCTG ACACAGCAGC ATGGTCTTGA CAAGTTTTCT TCATCCTACC           60

ACAAAATCCC AGTTGGTAAT AGAGACTTTA CTCCTACCTA TCAAAACCAC AAAATGTCCC          120

ATTAGGGGGG GACATGTTGT ACATGTTAGG ATCATTCAAA TAACCAAGAT TATAAGGTGA          180

GGAAAGATGC CCCTAACTGA TTCTTTTGTC TCTCATCTTG TTGGTTCCAG GGACCGAGTG          240

GGGTCAATCT TCTGGTSSTG CCTCTCCAGG TCTCTTCCAG GCCGGTCATA GACGTACTCC          300

CTCTGAGGCC GACCGATGGT TAGAAGAGGT GTCTAAGAGC GTCCGGGCTC AGCAGCCCCA          360

GGCCTCAGCT GCTCCTCTGC AGCCAGTTCT CCAGCCTCCT CCACCCACTG CCATCTCCCA          420

GCCAGCATCA CCTTTCCAAG GGAATGCATT CCTCACCTCT CAGCCTGTGC CAGTGGGTGT          480

GGTCCCAGCC CTGCAACCAG CCTTTGTCCC TGCCCAGTCC TATCCTGTGG CCAATGGAAT          540

GCCCTATCCA GCCCCTAATG TGCCTGTGGT GGGCATCACT CCCTCCCAGA TGGTGGCCAA          600

CGTWTTTGGC ACTGCAGGCC ACCCTCAGGC TGCCCATCCC CATCAGTCAC CCAGCCTGGT          660

CAGGCAGCAG ACATTCCCTC ACTACGAGGC AAGCAGTGCT ACCACCAGTC CCTTCTTTAA          720

GCCTCCTGCT CAGCACCTCA ACGGTTCTGC AGCTTTCAAT GGTGTAGATG ATGGCAGGTT          780

GGCCTCAGCA GACAGGCATA CAGAGGTTCC TACAGGCACC TGCCCAGTGG ATCCTTTTGA          840

AGCCCAGTGG GCTGCATTAG AAAATAAGTC CAAGCAGCGT ACTAATCCCT CCCCTACCAA          900

CCCTTTCTCC AGTGACTTAC AGAAGACGTT TGAAATTGAA CTTTAAGCAA TCATTATGGC          960

TATGTATCTT GTCCATACCA GACAGGGAGC AGGGGGTAGC GGTCAAAGGA GCMAAACAGA         1020
```

```
YTTTGTCTCC TGATTAGTAC TCTTTTCACT AATCCCAAAG GTCCCAAGGA ACAAGTCCAG   1080

GCCCAGAGTA CTGTGAGGGG TGATTTTGAA AGACATGGGA AAAAGCATTC CTAGAGAAAA   1140

GCTGCCTTGC AATTAGGCTA AAGAAGTCAA GGAAATGTTG CTTTCTGTAC TCCCTCTTCC   1200

CTTACCCCCT TACAAATCTC TGGCAACAGA GAGGCAAAGT ATCTGAACAA GAATCTATAT   1260

TCCAAGCACA TTTACTGAAA TGTAAAACAC AACAGGAAGC AAAGCAATGT CCCTTTGTTT   1320

TTCAGGCCAT TCACCTGCCT CCTGTCAGTA GTGGCCTGTA TTAGAGATCA AGAAGAGTGG   1380

TTTGTGCTCA GGCTGGGAAC AGAGAGGCAC GCTATGCTGC CAGAATTCCC AGGAGGGCAT   1440

ATCAGCAACT GCCCAGCAGA GCTATATTTT GGGGGAGAAG TTGAGCTTCC ATTTTGAGTA   1500

ACAGAATAAA TATTATATAT ATCAAAAGCC AAAATCTTTA TTTTTATGCA TTTAGAATAT   1560

TTTAAATAGT TCTCAGATAT TAAGAAGTTG TATGAGTTGT AAGTAATCTT GCCAAAGGTA   1620

AAGGGGCTAG TTGTAAGAAA TTGTACATRA GATTGATTTA TCATTGATGC CTACTGAAAT   1680

AAAAAGAGGA AAGGCTGGAA GCATGCAGAC AGGATCCCTA GCTTGTTTTC TGTCAGTCAT   1740

TCATTGTAAG TAGCACATTG CAACAACAAT CATGCTTATG ACCAATACAG TCACTAGGTT   1800

GTAGTTTTTT TTAAATAAAG GAAAAGCAGT ATTGTCCTGG TTTTAAACCT ATGATGGAAT   1860

TCTAATGTCA TTATTTTAAT GGAATCAATC GAAATATGCT CTATAGAGAA TATATCTTTT   1920

ATATATTGCT GCAGTTTCCT TATGTTAATC CTTTAACACT AAGGTAACAT GACATAATCA   1980

TACCATAGAA GGGAACACAG GTTACCATAT TGGTTTGTAA TATGGGTCTT GGTGGGTTTT   2040

GTTTTATCCT TTAAATTTTG TTCCCATGAG TTTTGTGGGG ATGGGGATTC TGGTTTTATT   2100

AGCTTTGTGT GTGTCCTCTT CCCCCAAACC CCCTTTTGGT GAGAACATCC CCTTGACAGT   2160

TGCAGCCTCT TGACCTCGGA TAACAATAAG AGAGCTCATC TCATTTTTAC TTTTGAACGT   2220

TGGCGCTTAC AATCAAATGT AAGTTATATA TATTTGTACT GATGAAAATT TATAATCTGC   2280

TTTAACAAAA ATAAATGTTC ATGGTAG                                      2307

(2) INFORMATION FOR SEQ ID NO:29:

(i) SEQUENCE CHARACTERISTICS:
        (A) LENGTH: 343 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

GGCAGCTATT TACATGGCCT CACAGGCATC AGCTGAAAAG AGGACCCMAA AAGAAATTGG     60

AGATATTGCT GGTGTTGCTG ATGTTACAAT CAGRCAGTTC TATAGACTGA TCTATCCTCG    120

AGCCCCAGAT CTGTTCCTTA CAGACTTCMA ATTKGACACC CCAGTGGACA AACTACCACA    180

GCTATAAATT GAGGCAGYTA ACGTCMAATT CTTGANNACM AAACTTKNCC TGTTGTACAT    240

AGCCTATACM AAATGCTGGG TTGAGCCTTT CATAAGGNAA AACMNAAGAC ATGGNTACGC    300

ATTCCAGGGC TKGANTACTT ATTGCTTGGC ATTCTTGTAT GTA                      343

(2) INFORMATION FOR SEQ ID NO:30:

(i) SEQUENCE CHARACTERISTICS:
        (A) LENGTH: 363 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO:30:

| | | | | | |
|---|---|---|---|---|---|
| AAAGGGCTAA | CCAGCCACTG | CACCAAAATT | AGTCCTTACA | TTATAATACT | CTGGCCATTG | 60 |
| GAAGAGAAAA | ATGGGAAAAT | TCAACAATTT | GAAAGACTAT | GATCCCTCTG | GCTCATGATC | 120 |
| TACTGACCAG | AATGAAGTCC | TGAAGGATTT | CCTTCTGTTA | TGTTATCTAC | CCAGCTAATC | 180 |
| TCAAACAAGA | GGAGCTGGAA | AGAACAAAGC | CCCATGAAGC | TACCCCTAGA | CCCAGAAAGC | 240 |
| CAAGAACAGG | GCCAAGAAAA | TGAACAGCAG | ACAAGCCTGA | AATAGAAGTG | GNACAGACAT | 300 |
| GTGGNAAGAC | CAAGTACACC | CAGTTNGGTG | GTAAAGATTC | CGATATCAAG | CTTATCGATA | 360 |
| CCG | | | | | | 363 |

(2) INFORMATION FOR SEQ ID NO:31:

(i) SEQUENCE CHARACTERISTICS:
        (A) LENGTH: 362 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

| | | | | | |
|---|---|---|---|---|---|
| AGTACATGGT | TTCTTGNCCA | CCCCASCCAC | CTTTCCCCAT | CTCTACCGGY | TGATAGTCTC | 60 |
| TCAGNTAGTA | GACCTTTTCT | NGTTTAGRCA | GGGCCACNTT | TTTAAAAACT | CCAGACGGGT | 120 |
| ACCCTCCATG | TKGMAGGCGA | CGTGGCCCTG | GATCACTCAA | CTGANTGTCA | TNKGANTGGT | 180 |
| GCCCCCAGAG | TGAGGACAAT | GGTGNAGCCC | TCCTAAGGCC | CTNCCTGAGT | GTCCCTCCTT | 240 |
| CATGAAGATG | ATTCTGAGGN | TTCCCAGGCC | TNCACCCTTC | TTKGAAARCC | CATAGNAGTT | 300 |
| CATATGNACT | NCTCTNCTAT | GCTCACCAAA | CTCTNCCTTC | ATCATACTTG | GGGGATGTGT | 360 |
| GT | | | | | | 362 |

(2) INFORMATION FOR SEQ ID NO:32:

(i) SEQUENCE CHARACTERISTICS:
        (A) LENGTH: 475 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

| | | | | | |
|---|---|---|---|---|---|
| GTGCATGTAA | TTACAGTTAC | GATATATGAA | ACGTACAAAA | TATTATGAGT | ATATAATATG | 60 |
| GGGAGACTTA | ATCTAGTTTG | GGGGATCAGG | GCACATTTCT | CTAAGAAAGT | GACATTTGAA | 120 |
| TTGAGCTCTG | AAGGATAAAT | AGACATTACC | CAGAAGAATA | AAATGATGGG | GAAGAAGGAG | 180 |
| GACATTTTCC | GTAGATTTCC | AGTGGCCCCN | CTTGATCCCT | TATCCACTCA | TCACTNAGGA | 240 |
| GGATATTAAA | TKCTATAGAA | ATGGRAGRAA | GACMMAAAGA | GACCCTNATA | TCTCGAGAGG | 300 |
| ATCCAGCMAA | ATTCCAAGAG | ACACAACAWT | AAGAAACTNG | GAAGGAAGAG | AAAAGGCMMN | 360 |
| NNAGGNAAAA | GAAAGACAAG | GAAATTNWNN | NAGNACGGAG | AGAAAGAGAG | AGGGAGCGTN | 420 |
| NAAGGGNACG | AGAAAGGCGA | GNACGGGGAC | GAGAAAGGGN | AAGAGNACGT | AAACG | 475 |

(2) INFORMATION FOR SEQ ID NO:33:

(i) SEQUENCE CHARACTERISTICS:
        (A) LENGTH: 346 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

GGAAATAAAT GAGATCTCAG TGGTGGTATG GATTGGACTG ATCTCTGTAA CTGTGTNTGG     60

AAAAAGGACC GGAAAATGAA AGCCAGATCC CAGTAAGGGG TAGAGAGGGG CCAAGAGAAC    120

TGAACATCTG GGCTGCCGGA GAAATCAAAG TCTAGGAAGT AAGAGGTAAG AGTGTACTAC    180

AGGGGACATA CCCCAATCTC TTGGTTCCCT CCCTCTNCCT TCCTCTCCCA GAGACCCAGG    240

TCCCTGGGAC TATNTTGGAT CTGTCTCTGA AGCTGAAAAA CAAAAGGCAG AGGAGACAGT    300

CGGNTCTAAG TGACCAATCT CAAGCCAGCT TGGTCAGAAN TCCTAA                   346

(2) INFORMATION FOR SEQ ID NO:34:

(i) SEQUENCE CHARACTERISTICS:
        (A) LENGTH: 433 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:34:

AAATCCAGTG CAGGCAACAT TATGTGGAAA TAGAAACAGG GCTCCTGCTA GGAGATTGAN     60

ATTCTGGCTT TCCTTTGGAA CCCCTCACTG ACTCATCGCC CCTGAANCAG GANCCANCAG    120

GTNCCAAGGC TCCCCTGCTC CTNTCCCTNC CCCAGGGCGA GATAGGAARC CGGAARCCTG    180

GGCAGGCTGA RCCCANCCGA CTGGAACCAG GGNAGANCCT GTGGGTGGGT GGNAGGGAGG    240

GAAGGAGGCC AGATTCCTCC AGAACTGGGG RAGAGAACAG GTTTTGGAAG TTGGGGGAGG    300

GTTTGGGTTT CACAGTGATG GTTTCATGAN ACCCTGGAGG GTTNCACACT CCTGGTKCAN    360

TTTTGNTANT CGTNCTTTGA ANACARNCCG CTTCCTTTCA ACCCTCCNCN TAAAAAGTTT    420

TGATNTTTTA AGG                                                      433

(2) INFORMATION FOR SEQ ID NO:35:

(i) SEQUENCE CHARACTERISTICS:
        (A) LENGTH: 350 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:35:

ACCAAGAGCC CCCAGTTTAT GNTAACTCTC ATGACAAACA CAATTTTAGT ACCTCTCACT     60

ACCAACTATC CAGGAACCAG GANTCACCTA TTACTACGGT TCCAGCAGAA TGGGAATCCC    120

ATTCTCGGAT ATCCAGGGTA AATCCCTGAC CATGTGAGAG GAATCCTAGT GCCCCAACAA    180

CCTCACCCCC TGACTCCTCC TCAANGGCTC TGCCAAGTCA ACAAAAAAAT CCTCTACATT    240

TACACTATCT GTAAAGCCAA AGACCAGCGT CAACCTAAAT GTCCATCAAT AAGGGAATGG    300

TTGGATAAGT AAAAATTATG CAGCTGTAGG AAGGAATGAA GAATGTCTAT               350

(2) INFORMATION FOR SEQ ID NO:36:

(i) SEQUENCE CHARACTERISTICS:
        (A) LENGTH: 512 base pairs

```
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:36:

AAAGGGAACA AAAGCTGGTA CCGGGCCCCC CCTCGAGGTC GACGGTATCG ATAAGCTGGA      60

TATCGAATCC TCGAGATCTA CCTAAAAAAA AAAAATTAAC TTCCCAAATG TGGGAGTCTA     120

CTCTGTTCCC TCCTNGTNTT TATTNCTGTN TACTTTYCTA ANATGGTTAA AATGTGTAAN     180

CAATATGTGT CCTTTNACTN KGGKGTGAAC ATTTTTYCTA TTATAAATYC TWAGAAAATA     240

TTNCTATGGN TATGAGATAT TKGATTCCAA GTGCCTKGTA ATTTACTYCT CAAATGTCCC     300

TGATGTKGGA NATTKGTTNC TAGTGTTYCA CTATTTAAAA AAACAGNAAT ATCTGTCTNT     360

ATGCTNAGAG CTTNTYCAGT TTYCAAATTA TTNCCTTAGG GTAAAATCCT AGAAGTAGAA     420

TTTTTGGGGC AAATTATCTA CATATTTATA ATTGTCTTGG TATTCCAAAT CTCGTTTTCC     480

AAAAGCTTAT ATCAATTTGT ACTTAACACC AG                                   512

(2) INFORMATION FOR SEQ ID NO:37:

(i) SEQUENCE CHARACTERISTICS:
        (A) LENGTH: 450 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:37:

ATTTAAGATG ACTGGGGGTC TCTNCCTAAT CCCATACTCC ACTGGAGAGG ANAAGTGGGA      60

AAGGTTGGTC TAGTTARGGT NGNTGGGGAC CCTCCCAAGA GCTGNAGAAG CAGAGATAAG     120

NAGAGCCTNC TNCTAAATCC ACATGGNCCT YCCAAGGNTC TCATCCTCTA GGACCTACCA     180

CTNCTCAGTC TACTTACTTG TCTYCTGANA TGCTTTCTNG AGGGNAGAA AACAAAGGAA      240

GAGTAATAAC AAGCAGNAGA AACTGCAGAG AATGNAAAAT AAGTCCATAG GAGAATGTTG     300

NAAATAGAAT CATCCNCCTT TACATATTGT CACTCCAGGA AAACTGCCAA GAACCACTCA     360

TTCCTCTAGA TACAMTTCCT GTAGGATCCY CCCAGACTTC CTCCCTTAAG CACGTCAGTA     420

TTCTCCTTAT TCTCCCTTCA TTTCAACCCT                                      450

(2) INFORMATION FOR SEQ ID NO:38:

(i) SEQUENCE CHARACTERISTICS:
        (A) LENGTH: 766 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:38:

CGAGATCTGC CCCAGCCCAC ATTTCCTTTG TTGAATGAGT AGAGAAGACT GAGAAGTATC      60

ACTCACCCGT GATGTGGTTT GTCCCTTTTC CAGCCAGTGT GTTGGTAATA AAAGTCACCT     120

TTCAGAGCTT TGGTCCCCGT AATGCCCGTC TTTCCTGTGT CCAGGAATAA CCTTTGNTAC     180

TAGGCAGTCC TCTGAAAGAT TTGTAGAAGG TTAAAGTGGA AAGGGACTTG GAAGCTCATA     240

GAATCCATGC CTCTTCTTTT AGCATCAAGG AATTAGAAGT CCTGAGAGAT GAAGAATGTT     300

GTCTTCCCAA CTCAAACCCA TTTCTTGAAG CCATTTCCCT GGTTACTGNA TTGGCCACAA     360
```

```
CCCTTCCCCC TTGNTATCCT CATCCTGCTA ATGCTGTTTT TAATGGCCTG CCAGTCTGGA    420

TTTGTCTTTG GCAACCAAAC AATTTTGCTT CACAAGATTC CTACTTAAGG GAAGAGAGGG    480

GCTCCTCATT TNTCACTTGT ACAAGAGCAG GGCTGGTCAG CTTTACACAG GTGTCAGATG    540

AACCGTCACA ANCCAGANTT NCATGTTGGC CTCAGGAGGG CTTCNAGGTC CAACATCTCG    600

ACGTAAGGAG CGTTCCCAGT TCTTTCATGC TCAGATAACA GTNCTAACTN CAGCTGTTTC    660

ATCCCNAATC CCTANTTGAG GTCTTAACAT CTATTCCATT TTKCCNACMA GGGTTATNCT    720

GTTAACCCTC TNCACCAGAN TTAGANCTGA CTGATNCACT TCCTAG                   766

(2) INFORMATION FOR SEQ ID NO:39:

(i) SEQUENCE CHARACTERISTICS:
        (A) LENGTH: 327 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:39:

TCATACTTGT ATAGTTCKNT AAGATAATCA CTCTCTCACT CAGACATNNG GNGRARNGCC    60

CNTCGATCAC TTGGGANAGG NGACTTGCMA TGTTTAATGA TTGTCANCCM NANAANTAAG    120

CTNACAGGGC AAAAACAGCC TYANGTCAGT TCTNTCTCCC TAATCCTCTA GRAKNAAATC    180

NNAWRNTRNN ACTCTGNNTC TGTGCCATNA NANATNTTNC ANTTGTATTT ATGNACTCCA    240

CATNGAGTAC ACCTCACTAA WTNTNCTNCT GGGNAACNCC CSCMCCANTT TTTNNTTGNT    300

GANANACARC AATGCTGGCA TACNGTG                                       327

(2) INFORMATION FOR SEQ ID NO:40:

(i) SEQUENCE CHARACTERISTICS:
        (A) LENGTH: 431 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

CCAGACTTTC ATAACTNGTG TTATTATGAA GATTAGAGTN CTGAAGCTTA CTGGATTAGA    60

AGAGNACGAG GGGGTAGCTG CCCCAATATA TTCTAATTTC TCTKGAGGAC CACCAAATNG    120

GMAGAGTGTC TCTGATAGGG AAAAGGAAGA GTTGGAAGGN ATCTTAGCCT CTAGGANAAA    180

AGAACCATTT TTATTGGCCA CCAAAGTTAC ATCTAGTKGC CTACAAATTT ATNTCCAAAC    240

TCCTTATCCT GCCAATTCAG GGTCCTGNAA ACTGATGCCA AACTATAGTT TAGTCTNCTA    300

TCACATGACT GCATTATACA TACCCAATTA TCTGGGMAAA CAGACCTGAT CCAAACACAG    360

TTKGGTNCTT TCCTTNCCTT NCCTTKGTTT AGCCTGTYCC GTCTACTNGG GGTGTCTTKG    420

ATTTGCTCCA G                                                        431

(2) INFORMATION FOR SEQ ID NO:41:

(i) SEQUENCE CHARACTERISTICS:
        (A) LENGTH: 276 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:41:

```
TTTTTTTCCA CCAGACTTAC CAAATTTTAG ATGNATGGAA GAACTGTAAA TNCCCATAAA      60
GNTAATCTAT NCATNGACCC CCACCATTAT GATAGAGATC ATNTGGTGAN TAATGAAAGA     120
TGAAACTCTC AGCTGGGAAA GTAANAAGGA ATAGGATGTA AGTATGAGCT CCTGTTTTTT     180
ATTATNTTTA TGGATGCCCC CTCAGAAAAA TATGNAANGG GGTAACTGAC TNGGAAATGG     240
GTNTTTTATG NATAGTAAGT CCCACTCACG AGGTTT                              276
```

(2) INFORMATION FOR SEQ ID NO:42:

(i) SEQUENCE CHARACTERISTICS:
        (A) LENGTH: 270 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

```
TCGAGATCTA AAGCAGATGN AGACTTTNCA CNAAATAAAT TTACTGCTTT TTTYCTGTGA      60
NATAAGTTNC GAGAAGGAAA GCTTTKGATT NCTRNATGAG TYCAGTGGAT TATYCTNAGN     120
ACTAGAGTKG NKGTKGAAGN CATGGNACAT TTATATAGWT YWTTCAGTTC TACACTAAAT     180
GATGGAAGAA TGAAAATCC TATATGACAA ATAGAAAAGT YCATYCTYCA TAATTGAGAA      240
CATTGAGCAG TTGGATTACC AAGATCTCGA                                     270
```

(2) INFORMATION FOR SEQ ID NO:43:

(i) SEQUENCE CHARACTERISTICS:
        (A) LENGTH: 580 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:43:

```
CTTAGTTTTA GACTAGTTTC ATTATACTAC CAGTTTCTAA TATGTTGGTT TTTTATTCAC      60
TATTTGATAT ATTTGTTTTA ATATATGTTC TTGTTTTAGC AGGTAAAAGA ATCATAACAA     120
ATGTTTTTAA AAGAACATTA TTATTCTTTA ATAACTGTCT TTTTATGCAT TTGGCATGCC     180
AACTTTTTTC ATTAACATCT TGGGTATTTT ATAAAAAGAG GGAAAGCTCA ATGTTTAACA     240
GGTAGCTTTT CTTAGGAGCT AAATTAAATA TTTAACAAAT CTCCTTCCCT TCNCCCTTCC     300
CCATCCCTCA AAGNATGGGT GNANTTATCT TTAACTTTTG GGCTNGCATC CNTGNAAGCT     360
TATGGNTANT CATAGTCTNA CMAAACTAGG GTCACCNAAC TTGGCAGCAG AAATAATCTA     420
GTCTTACTGT GATAACTACC CAATTACTTT ATTATTTTTC CAGTTNCAGT TCCAAATGTT     480
TTGTGGNAAN AATTTTTNCT GTTTGTGATT TTCCAAGCTT AGAGGGGAA ACCAACTTTC      540
CAGTGTTGGA GAGCACTGNA TAGTTTATGN ATTGTGTAAA                          580
```

(2) INFORMATION FOR SEQ ID NO:44:

(i) SEQUENCE CHARACTERISTICS:
        (A) LENGTH: 347 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:44:

```
TGTTTCTTAA NACAGAAAAA AATTTACTGA TNGGACATTG TTCTAAGTGT ATTATTGTAT      60

TAAATGGATC ATTTAATTTA ATCTTCATAA CTGACATAGG AGTTGAGTAA CTTGTGTGGT     120

CAAATAGCTA GTAAGTGATG AGTAGGCTGG GCGCAGTGGC TCAAGCCTGT AATCCCAGCA     180

CTCTGGGAGG CTGAGGCAGG CAGATCACTT GAGGTCAGGA GTTTGAGACC AGCCTGGNCA     240

ACATGGNAAA ACCTCGTCTC TACTAAAAAT ACAAAAATTA GCTGGGCGTG GTGGGNGCGC     300

ACTTGTAGNC CCAGNTACTC GGAAGGCTGA GGCAGGAGGA ATCGCTT                  347
```

(2) INFORMATION FOR SEQ ID NO:45:

(i) SEQUENCE CHARACTERISTICS:
        (A) LENGTH: 430 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:45:

```
GCTCATCATG CTTCACGGGG GAGGCTGTGC GGGAAGAATG CTCCCACACA GNATAAAGAA      60

TGCTCCCGCA CAGGATAGAG AATGCCCCCG CACAGCATAG AGAAGCCCCC GCACAGCATA     120

GAGAATGCCC CCNCACAGCA TAGAGAAGCC CCCGCACAGN ATAGAGAATG CTCTTCACCT     180

CTGGGTTTTT AACCAGCCAA ACTAAAATCA CAGAGGGCAA CACATCATTT AAGATAGAAA     240

TTTCTGTATC TTTTAATTTC TTTCAAAGTA GTTTTACTTA TTTNCAGATT CTATTTCTTT     300

ACTAGAATTA AGGGATAAAA TAACAATGTG TGCATAATGA ACCCTATGAA ACAAACAAAA     360

GCTAGGTTTT NTNCATAGGT CTNCTTCCNN ATTGAATGAA CGTCTNTCCT CAAATTTANC     420

CCCCCAGGGA                                                           430
```

(2) INFORMATION FOR SEQ ID NO:46:

(i) SEQUENCE CHARACTERISTICS:
        (A) LENGTH: 400 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:46:

```
CAAACCCTAT GNGAAATGGA AAGGAAACTA TTCTAAAGCA TAAAAGGTAG AAATATATAT      60

ACCACCCATC AAGAAAGATT ATTTTTGNTG AACTCAAGTC ACCAGAGTGG CTAAAGCCCA     120

GTAGAATGGA AATGATTATA TGGAAGGTGA GGCCAACGGG ACCAGAACAT ACTGTGATAG     180

ACAGNAAGGA GCTGTCTATC TTCTATTCTC CCACAGAAGG AGGTGACTAA GTCANCTGCC     240

CAAGCAATGT TATATCTGCA ATTGATGTNC AGCAGTACAA GTCTGAACAA CTTGGATTGG     300

NTGATTAATG TCCACANTAA ACATACAAGT CNTAATAGCT ATCTCTATAT AGTCTTTGGG     360

TNTTTACAAG GCACTGNCAC ATNATCTCAC CTATTCCTCC                          400
```

(2) INFORMATION FOR SEQ ID NO:47:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:47:

| | | | | | |
|---|---|---|---|---|---|
| AGNATCCAGA | ATTGAGTGNA | GNGTTCTCTG | GNCCACAGTC | TCGGTATCTN | CTGTGAAATG | 60 |
| GGGTATAGAT | TCTACAATAA | AACAAACACA | NNGGCCCTAG | GTCAGTGTTA | ATGGAGATCA | 120 |
| CCANCCACAT | TACCACCTCC | AACACAGAAT | TTTCTTTTTC | TTAATNCAAT | NCGTNTCTTA | 180 |
| TAAGTCACTT | TNCCCCAACT | CACCAATCTA | GNTAAGAATT | TTTACCCTGA | GAAAAACAGC | 240 |
| TACACTCTAA | AATTGCTNCA | AAGAAAATGT | CTAACATNTG | GAAAGAAGGA | CTTAACATGT | 300 |
| GANGNAGACA | CTGGCTCCAT | CTAGNGGGTG | CTTTNTTTTG | AAATAATTAT | AATNCCNCAT | 360 |
| CAAATTTTNG | GGGGNTACAG | CTTATTAGGA | ACTTGTTATA | GAACCAGATT | CTGCCACAGA | 420 |
| ANCCACGTGG | GTTGACAAGT | GGTTGNCAGA | AGAAAGGTAA | TATGGCTTAT | NATTAGGGNC | 480 |
| TCNCATCTGC | AGAGTAATTG | | | | | 500 |

(2) INFORMATION FOR SEQ ID NO:48:

(i) SEQUENCE CHARACTERISTICS:
        (A) LENGTH: 460 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:48:

| | | | | | |
|---|---|---|---|---|---|
| AAAATGCTTG | ANNCAAATGT | CATCTAGTTC | CATCTCTACG | ACTCTCATGG | GGTCCAAAGA | 60 |
| AGAGTTTTAN | TTGAGTTTTA | GAATGTGAAG | TTGTGAAGTG | TCTGAAAAAC | TACATGGTGN | 120 |
| TCTGAAAGNC | AAACTTTTAG | CCTTGGGGGA | GAGCATCTAA | GACAGNAGGT | GAAGGGNAGG | 180 |
| GGTTAGAACT | AGAGGGATTG | AAGAATATTA | TCCATATAGG | TTAGGGTTAG | GTNNGGCAAC | 240 |
| GTTTTATAGA | ACAAACATTG | GCAAGCTACA | GCCACAGGCC | AGATCTGTCT | NCTACCTTCC | 300 |
| CACAAAGGTG | TAATAACAAA | GTTATTCACA | AATGTGTGAA | TAAACTNNCA | TTGGAAAGTG | 360 |
| CCCACGCTCC | TNGGTTTATA | CATTGTCTGT | GGCTGCTTTC | ACACTACAGT | AGCACAGGTG | 420 |
| AGTGTNTGCA | CTGGAGACCA | TATGCCCCAT | AGAGCTTTAA | | | 460 |

(2) INFORMATION FOR SEQ ID NO:49:

(i) SEQUENCE CHARACTERISTICS:
        (A) LENGTH: 370 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:49:

| | | | | | |
|---|---|---|---|---|---|
| ATCAAGCAAC | AGTGTGTTAT | GCCTATACTC | CATGTTTATA | TGTGTGTATT | AAAAAATGTA | 60 |
| TTTGTATATA | TGTGTATGTA | TAAGTGTGTG | TGTGTGTATG | ATGATTCTNC | TCCCGNTTTG | 120 |
| AAGGTGAAAG | AAAGCACACC | TTTATTTAAG | CATAAACTTT | GGGTTTCAGA | TACTGTCTGG | 180 |
| AAAAATGATT | TATCTCCCAC | TTTGAAATTC | CAAAATACGT | ACATATATTT | TTTTTTTCTT | 240 |
| TTCTTTTTTA | GTTTNAGGGT | CTTGCTGTGT | TGCCCAGGCT | GGAGTGCAGT | AGTGTGATCA | 300 |
| TAGNTCACAC | AGNCTCTAAC | TCCCAGGNTC | AAGNTATCTT | CCTGCCCCAG | NCTCCTGAGT | 360 |
| AGNTGGGACT | | | | | | 370 |

(2) INFORMATION FOR SEQ ID NO:50:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:50:

```
CAAAAAATCA AAGGGAAGNT GGAACCCCTG CCCACCTCTC CATTCCCCAT TCTGCTGGTG    60
GTGNCTGCTC TTCCTCACAG TACCTCCTGA AAAGTTCAGA ATTCAGTTAA TACAGAATTA   120
TTGGGTTGAT TTTCAACGTG TAGTTTAAGA TGAAGAGTTC CGNTTGGTTT AAACCACTTC   180
ACCTAACCTC TTGGTAACGG TAGTCCTGAG AGTTCGCAGT GTCANTGAAA ATCGTCCTGT   240
GACCACGCGT CAAGCTGCTG ATGGGGACA GAAACTTCCG GGNCTATCAT ATCTCCTTGA   300
NCTCGGCCCT CAAATCTGGT AGTTTCTGCA CCGAGGGACA CAGTCCACTG CGATGAAGTA   360
TGTTCAAAAT CGNTTTCTTT AGGGAACTCC TTCCAAAGTC CAATAGTGNA AGGTGGTCAA   420
GGAAGGATTT GGAAGGAAGN TGNAAAAGTC AGNCGGGAAT CTTGATTTGG NTAGNTGTGG   480
ANANAGGAAA TCACTTGGCC                                              500
```

(2) INFORMATION FOR SEQ ID NO:51:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:51:

```
GGAAAGAGGT CTCCTAACAC CCAGACAGTG TAAAAATCCA GTTTTTCTTC CTTTTGGNNG    60
GAGACAGAGT CTCGCACTGT AGCTCAGGCT GGAGTGCAGT GGCAC                  105
```

(2) INFORMATION FOR SEQ ID NO:52:

(i) SEQUENCE CHARACTERISTICS:
        (A) LENGTH: 386 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:52:

```
AGTCCCAGCT ACTCAGGAGG CTGGGGCAGG AAGATAGCTT GAGCCTGGGA GTTAGAGGCT    60
GTGTGAGCTA TGATCACACT ACTGCACTCC AGCCTGGGCA ACACAGCAAG ACCCTAAAAC   120
TAAAAAAGAA AAGAAAAAAA AAATATATGT ACGTATTTTG GAATTTCAAA GTGGGAGATA   180
AATCATTTTT CCAGACAGTA TCTGAAACCC AAAGTTTATG CTTAAATAAA GGTGTGCTTT   240
CTTTCACCTT CAAAGCGGGA GAAGAATCAT CATACACACA CACACACTTA TACATACACA   300
TATATACAAA ATACATTTTT TAATACACAC ATATAAACAT GGAGTATAGG CATAACACAC   360
TGTTGCTTGA TAAAATATAG GGATCC                                       386
```

(2) INFORMATION FOR SEQ ID NO:53:

(i) SEQUENCE CHARACTERISTICS:

(A) LENGTH: 377 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:53:

TATATTTNAT CAAGCAACAG TGTGTTATGC CTATACTCCA TGTTTATATG TGTGTATTAA        60

AAAATGTATT TGTATATATG TGTATGTATA AGTGTGTGTG TGTGTATGAT GATTCTCCTC       120

CCGNTTGAAG GTGAAAGAAA GCACACCTTT ATTTAAGCAT AAACTTTGGG TTTCAGATAC       180

TGTCTGGAAA AATGATTTAT CTCCCACTTT GAAATTCCAA AATACGTACA TATATTTTTT       240

TTTTCTTTTC TTTTTTAGTT TNAGGGTCTT GCTGTGTTGC CCAGGCTGGA GTGCAGTAGT       300

GTGATCATAG NTCACACAGG CTCTAACTCC CAGGNTCAAG CTATCTTCCT GCCCCAGNCT       360

CCTGAGTAGG TGGGACT                                                     377

(2) INFORMATION FOR SEQ ID NO:54:

(i) SEQUENCE CHARACTERISTICS:
        (A) LENGTH: 521 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:54:

CTGCAGTAAG CCACGTTCAT GCCACTGTAC TCTAGCGTGG ATGACAGAGA GAGATCCTGT        60

CTTTGGAAGA AAAAACAAA AAGAAAAAAA AAAGAGTATG GCCATGGCCT TATAATATAG        120

AAGGGGTCAC ATATTAATCT CTGAAAATGG ATCTCTTGTG GGCTTTCATA CAAGGCAACA       180

GCCACAGAGT ACGTACCTGA AAGCTGCCTG GGNTTAATGG CTGGNAGTAT GTTCTAACTN       240

GTTCAGGNAC CCATGTCACN ACTGGTGGTT ACAGAATGTG AATCTCACAC TGTCCNAAAT       300

CGGTTTTATT TTTAAAANGA ATAATTCTAN TACATTACCT TATAAAAAGT AGGTAACCTA       360

ATTTTGGNTT TTAAAAGTGA ATTGAGGGCA GATGCAAGTG GNTCACACCT ATTAATCCCA       420

AATACCTTGG AGAGGGCAAG GTAGGAGGAT TGGTTGGAGC CCAGGAGTCC AAAGACCAGG       480

CTAGGGAATA TTGNAAGAAN GTCCTCTCTA CAANAAANAA T                          521

(2) INFORMATION FOR SEQ ID NO:55:

(i) SEQUENCE CHARACTERISTICS:
        (A) LENGTH: 516 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:55:

CTGCANGAAG CTTTTNTTNC TTTTNGGNGG AGACAGAGTC TTGCTGTGTC ANCCCAGGCT        60

GGGGTGCAGT GGNACAGTCA TAGCTCACTG CAACCTTGAA CTCCCTGGNT CATGCGATCC       120

TCCCACTTCA GCCTCTCAAG TAGCTAGAAC TACAGGTGTG CACCACCATG CCTGACTAAC       180

TTGTTTATTN GNGGGAGAGA GAACGNTCTT GCTATATTGC CTAGGCTGGT CNTTGAACTC       240

TTGGGNTNCA AGCAATCCTC CTACCTTGGC CTCTNCAAGG TANTTGGGAT TNATAGGTGT       300

GAGCCACNTG CATCTGGCCT CAATTCACTT TTAAAATNCA AAATTAGGTT ACCTACTTTT       360

```
TATAAGGTAA TGTATTAGAA TTATTCTTNN NAAAAATAAA ACCGATTTGG GAAAGNGTGA        420

GANTCACATT CTGTAACCAC CAGTGGTGAA ATGGGTCCCC GAACAAGGTA GAACATACTC        480

CCAGCCATTA ACCCCAGGGA GNGTTCAAGT CCGTNC                                  516
```

(2) INFORMATION FOR SEQ ID NO:56:

(i) SEQUENCE CHARACTERISTICS:
        (A) LENGTH: 505 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:56:

```
GGATCCTGTT TCTTAAAACA GAAAAAAATT TACTGATAGN ACATTGTTCT AAGTGTATTA         60

TTGTATTAAA TGGATCATTT AATTTAATCT TCATAACTGA CATAGGAGTT GAGTAACTTG        120

TGTGGTCAAA TAGCTAGTAA GTGATGAGTA GGCTGGGCGC AGTGGNTCAA GCCTGTAATC        180

CCAGCACTCT GGGAGGCTGA GGCAGGCAGA TCACTTGAGG TCAGGAGTTT GAGACCAGCC        240

TGGCCAACAT GGNAAAACCT CGTCTCTACT AAAAATACAA AAATTAGCTG GCGTGGTGG         300

GTGCGCACTT GTAGTCCCAG CTACTCGGAA GGGTTGAGGC AGGAGGAATC GCTTGGTCCC        360

CGGGAGGGAG AGGTTGNTNG TGNAGCTGAG ATCACGCCAC TNGCACTCCA GGCTGGGNAA        420

CAAAAGGGAG ACCTTTNCTC AAAAAAAAAT NAAAATAAAA AGTGATGAGT AGGATTGGGA        480

CCCNAGACAT CTTTTCTCCA AGACC                                              505
```

(2) INFORMATION FOR SEQ ID NO:57:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:57:

```
CTGCAGNCTC AAACCCTTGT CCTGGGATCA AACAATCCTC CCACCTCAGC CTTCAAAGTA         60

GATAGAACTA CAGGCATGCA CTACCATGCC TAATTTTTTA AAAAAAAATT TTTTTTCAGA        120

GATGAGATCT CACTGTGTTT CCCAGGNTTG TCCGGAACTC CTGGACTCAA GCGATCCTCC        180

CACCTTGGGC TGCCAAAGTG TTGGGATTAC AGGCATGAGC CACCATGCCT GGCCATACAC        240

TTTTTTTTTT TTTTTAANCA AGACGGAGTC TNGTTCTGTC GCCCAGACTG GAGTGCAGGG        300

GCGTNNATCT TGGCTCACTT GAAAGCTTCG CCTCCCAGGG TTCATGCCGT TCTCCTGNCT        360

CAGCCTCCCA AGTNGGTGGG ACTACAGGNA TCTGCACCAC GNCCGGTTAT TTNTTGGGTT        420

TGNNGNAGGG ACGGGGTTTC ACCATGTTAG GCAGGATGAC TTCGGACTTC CNGACCCAAG        480

ATCACCCTGC TCGGCTCCCA                                                    500
```

(2) INFORMATION FOR SEQ ID NO:58:

(i) SEQUENCE CHARACTERISTICS:
        (A) LENGTH: 440 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:58:

```
GAATTCCAGA CGAGCCTGGG CAACACAGTG AGACTCTATC ACTACAAAAA AATTTTAAAA        60

TTAGCTAAAG TTGATGGNAC ATGCCTGCAG TCCCAGCTAC TCAGGAGGCT GGGGCAGGAA       120

GATAGCTTGA GCCTGGGAGT TAGAGGCTGT GTGAGCTATG ATCACACTAC TGCACTCCAG       180

CCTGGGCAAC ACAGCAAGAC CCTAAAACTA AAAAGAAAA GAAAAAAAAA ATATATGTAC        240

GTNTTTGGGG AATTTCAAAG TGGGAGATAA ATCATTTTTC CAGACAGTNT CTTGAAACCC       300

AAAGTTTATG CTTAAATAAA GGTGTGCTTT CTTTCACCTT CAAANGCGGG AGAAGGATCA       360

TCATNCACAC ACACACACTN ATCATNCACA TTTTTACAAA TNCAATTNNN NAATACAACA       420

CATTTTAACA TGGGGTTTTG                                                   440
```

(2) INFORMATION FOR SEQ ID NO:59:

(i) SEQUENCE CHARACTERISTICS:
        (A) LENGTH: 513 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:59:

```
GGATCCTGTT TCTTAAAACA GAAAAAAATT TACTGATAGN ACATTGTTCT AAGTGTATTA        60

TTGTATTAAA TGGATCATTT AATTTAATCT TCATAACTGA CATAGGAGTT GAGTAACTTG       120

TGTGGTCAAA TAGCTAGTAA GTGATGAGTA GGCTGGGCGC AGTGGCTCAA GCCTGTAATC       180

CCAGCACTCT GGGAGGCTGA GGCAGGCAGA TCACTTGAGG TCAGGAGTTT GAGACCAGCC       240

TGGCCAACAT GGNAAAACCT CGTCTCTACT AAAAATACAA AAATTAGCTG GCGTGGTGG       300

NTGCGCACTT GTAGTCCCAG CTACTCGGAA GGCTNGAGGC AGGAGGAATC GCTTGATCCC       360

NGGGAGGGAG AGGTTGGTNG TGANGCTGAG ATCACGNCAC TTGNACTCCA GNCTGGGNAA       420

CAAANGNGAG ATCTTNTCTC AAAAAAAAAT AAAANTAAAA NGTGATGAGT AGGATTTGGA       480

CCCCAGACAT CCTNTCTCCA GGACCTGGNA TTC                                    513
```

(2) INFORMATION FOR SEQ ID NO:60:

(i) SEQUENCE CHARACTERISTICS:
        (A) LENGTH: 390 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:60:

```
GAATTCCTGG NCTCAAGTGA TCCTCTCACC TCAGCCTCCC AAATTGCTGG GATTAGAGTG        60

TGAGCCACTG TGCCTAGCCT GCATATATCT ATTTTTAATG ACTGCTAAAT CTCATTGTAT       120

GAAAATTTAT GTCCTAGCTA TAAAATTTGN TAGCACATGT TTAATTTTTT CTAATTTCAG       180

ATGTTTTAAA CTAATATTTC CCAAAGTATA GTATGGCATT TTAGGTATGA TATGATCTTT       240

NNTCCTCTTC GTACTCATTT TTATAGTTAT GGCCTGTGCA ACTGGTTTCC CATTTATATG       300

AATGATACAG AGCTTCCTAT TAAGAAAAAG TTCAGCTTGG GGAAAAAAAA AGTGAATTGT       360

CAACTTNGAG GGAAAAAAGT GAATTATTGG                                        390
```

(2) INFORMATION FOR SEQ ID NO:61:

(i) SEQUENCE CHARACTERISTICS:
        (A) LENGTH: 366 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:61:

```
TCAAGTACCT CCCTGAATGG ACTGCGTGGC TCATCTTGGC TGTGATTTCA GTATATGGTA      60
AAACCCAAGA CTGATAATTT GTTTGTCACA GGAATGCCCC ACTGGAGTGT TTTCTTTCCT     120
CATCTCTTTA TCTTGATTTA GAGAAAATGG TAACGTGTAC ATCCCATAAC TCTTCAGTAA     180
ATCATTAATT AGCTATAGTA ACTTTTTCAT TTGAAGATTT CGGCTGGGCA TGGTAGCTCA     240
TGCCTGTAAT CTTAGCACTT TGGGAGGCTG AGGCGGGCAG ATCACCTAAG CCCAGAGTTC     300
AAGACCAGCC TGGGCAACAT GGCAAAACCT CGTATCTACA GAAAATACAA AAATTNGNCG     360
GGNATG                                                                366
```

(2) INFORMATION FOR SEQ ID NO:62:

(i) SEQUENCE CHARACTERISTICS:
        (A) LENGTH: 498 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:62:

```
AACACCAGGG NCATGAGGGC ACTAATCATA ATGAGATATG CCTGCTGGAG TCGAAGTGGA      60
CCTTTCCAGT GAATGGAAAT CATTCCCACC ACACCAAAAT TCCAGATCAG GAGTGNAACA     120
GTAATGTAGT CCACAGCAAC GTTATAGGTT TAAACACTT CCCTGAAAAA AAATTACACA     180
GATTTTAAAA GATGTACAAT AATTTCCACC AAAACATTAT TTAGAATAAT GTGATGGCTC     240
CCAAACATTA GATATTAATN TCCCACCTTT ATAATTTTAC CATAACCTAT ATCAACTGTG     300
CTATTATTTA TTTAATNCTT CCCTNTAAAT TAATTTACTC TTTTTTTGTT TTTGTTTTTG     360
NGTTTGGAGC CAGTGTCTCA TTTTGGTTGC CCAGGCTTGG AGTAAAGTGG GTGCAATCAC     420
GGCTCAACTG NAGTCTTTNC CTCCNGGAGA TCAGGTNGGT CTTCCCCAGG TCCAANCTCC     480
TAAGTTGGTT NGGANAAC                                                   498
```

(2) INFORMATION FOR SEQ ID NO:63:

(i) SEQUENCE CHARACTERISTICS:
        (A) LENGTH: 469 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:63:

```
TAAACAACAG GGNCATGAGG GCACTAATCA TAATGAGATA TGCCTGCTGG AGTCGAAGTG      60
GACCTTTCCA GTGAATGGAA ATCATTCCCA CCACACCAAA ATTCCAGATC AGGAGTGAAA     120
CAGTAATGTA GTCCACAGCA ACGTTATAGG TTTTAAACAC TTCCCTGAAA AAAAATTACA     180
CAGATTTTAA AAGATGTACA ATAATTTCCA CCAAAACATT ATTTAGAATA ATGTGATGGC     240
TCCCAAACAT TAGATATTAA TNTCCCACCT TTATAATTTT ACCATAACCT ATATCAACTG     300
TGCTATTATT TATTTAATNC TTCCCTCTAA ATTAATTTAC TCTTTTTTTG TTTTTGTTTT     360
```

```
TGTGTTTGGA GCCAGTGTCT CATTTTGGTT GCCCAGGCTT GGAGTAAAGT GGGTGCAATC        420

ACGGCTCAAC TGNAGTCTTT ACCTCCCGGA GATCANGTTG GTCTTTCCC                    469

(2) INFORMATION FOR SEQ ID NO:64:

(i) SEQUENCE CHARACTERISTICS:
        (A) LENGTH: 370 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:64:

GTTTATCAAG TACCTCCCTG AATGGACTGN GTGGCTCATC TTGGCTGTGA TTTCAGTATA         60

TGGTAAAACC CAAGACTGAT AATTTGTTTG TCACAGGAAT GCCCCACTGG AGTGTTTTCT        120

TTCCTCATCT CTTTATCTTG ATTTAGAGAA AATGGTAACG TGTACATCCC ATAACTCTTC        180

AGTAAATCAT TAATTAGCTA TAGTAACTTT TTCATTTGAA GATTTCGGCT GGGCATGGTA        240

GCTCATGCCT GTAATCTTAG CACTTTGGGA GGCTGAGGCG GGCAGATCAC CTAAGCCCAG        300

AGTTCAAGAC CAGCCTGGGC AACATGGCAA AACCTCGTAT CTACAGAAAA TACAAAAATT        360

AGCCNGGNAT                                                               370

(2) INFORMATION FOR SEQ ID NO:65:

(i) SEQUENCE CHARACTERISTICS:
        (A) LENGTH: 316 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:65:

GTCATGGTGT TGGCGGGGAG TGTCTTTTAG CATGCTAATG TATTATAATT AGCGTATAGT         60

GAGCAGTGAG GATAACCAGA GGTCACTCTC CTCACCATCT TGGTTTTGGT GGGTTTTGGC        120

CAGCTTCTTT ATTGCAACCA GTTTTATCAG CAAGATCTTT ATGAGCTGTA TCTTGTGCTG        180

ACTTCCTATC TCATCCCGNA ACTAAGAGTA CCTAACCTCC TGNAAATTGA AGNCCAGNAG        240

GTCTTGGCCT TATTTNACCC AGCCCCTATT CAAAATAGAG TNGTTCTTGG NCCAAACGCC        300

CCTGACACAA GGATTT                                                        316

(2) INFORMATION FOR SEQ ID NO:66:

(i) SEQUENCE CHARACTERISTICS:
        (A) LENGTH: 448 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:66:

CTGCAGNCCG GGGGATCCTG GTAAAAGTCA CAAGGTCAGC CTACTAAAGC AGGGAAAACT         60

AAAGGCAAGT AAACACGTGC AGACAAAAAA AGGGATAAAG AAAAGGAATT AAGAAACTAG        120

CATTTTTAAN GTGGGGGAGG TGAATGCTTC CCAGAATGGG TTTATATCAC TTGCTTGNGG        180

GCCTTCTGAG TGTTGGNAAC AACCTGTCAT CATCACACAT ACCTGTCATC TTTAATGGTC        240

TCCATACATT ACTAATAGAT TATACAGATG GCCATCACTT AACACTTCCA CTCACTCAAT        300
```

```
TTGTNCAACA TGCAAGGTTA CCCTCTTTTT TNGCTTACNG CCACAAAGCA TTGGANAAGG      360

TTTGTGATTT TTACTAGCCN CCACTTCATC AAATTTAAGC ATTTTCTTTT TCCTNTTAAC      420

ANCCAGGACA GGNTTNAACN AAGGAAAT                                        448
```

(2) INFORMATION FOR SEQ ID NO:67:

(i) SEQUENCE CHARACTERISTICS:
        (A) LENGTH: 450 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:67:

```
CTGCAGCTCC AAGCACCTTT TTCAAATTCA GCTTTCTGTG ATTTCAGACC ACATATGCAA       60

GGAACTATCT TACCTTAATT AATAAGACTT TAAAATCCTT GTGTCAGAGG CGTTTGGACC      120

AGAGCAACTC TATCTTGAAT AGGGGCTGGG TAAAATAAGG CCAAGACCTA CTGGGCTGCA      180

TTTGCAGGAG GTTAGGTACT CTTAGTTACG GGATGAGATA GGAAGTCAGC ACAAGATACA      240

GCTCATAAAG GATCTTGCTG ATAAAACTGG TTGCAATAAA GAAGCTGGNC AAAACCCACC      300

AAAACCAAGA TGGTGAGGAG AGTGACCTCT GGTTATCCTC ACTGNTCACT ATACGNTAAT      360

TATTATACAT TAGCATGCTA AAAGACACTC CCCGCAACAA CCATGANAGG TTTACAAGTT      420

NCCATGGNAA CGNNCCCGGA NGNTANCTTG                                      450
```

(2) INFORMATION FOR SEQ ID NO:68:

(i) SEQUENCE CHARACTERISTICS:
        (A) LENGTH: 388 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:68:

```
CTGNAGCCTC CACCACCCAG GTTCAGGTGA TTCTCCTGCC GTAGNCTCAT GAGTAGNTGG       60

GATTACAGGC ATGTGCCACC ATGCCCGACT AATTTTTATA TTTTTAGTAG AGACGGGGTT      120

TCACCATGTT GGGCAGGCTG GTCTCAAACT CCTGACCTCA AGTGATCTGC CCACCTTGGC      180

CTCCCAAAGT GCTGGGATTT CAGGCGCCTG GCCTGTTACT TGATTATATG CTAAACAAGG      240

GGTGGATTAT TCATGAGTTT TCTGGGAAAG AGGTGGGCAA TTCCCGGAAC TGAGGGATCC      300

CTCCCCTTNN NAGACCATAC AAGGTAACTT CCGGACGTTG GCATGGNATC TTGTTAAACT      360

TGTCATGGNG TTGGGGGGGA GTGTCTTT                                        388
```

(2) INFORMATION FOR SEQ ID NO:69:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:69:

```
CTGCAGAAGT ATGTTTCCTG TATGGTATTA CTGGATAGGG CTGAAGTTAT GCTGAATTGA       60

ACACATAAAT TCTTTTCCAC CTCAGGGNCA TTGGGCGCCC ATTGCTCTTC TGCCTAGAAT      120
```

```
ATTCTTTCCT TTTCTAACTT TGGTGGATTA AATTCCTGTC ATCCCCCTCC TCTTGGTGTT      180

ATATATAAAG TNTTGGTGCC GCAAAAGAAG TAGCACTCGA ATATAAAATT TTCCTTTTAA      240

TTCTCAGCAA GGNAAGTTAC TTCTATATAG AAGGGTGCAC CCNTACAGAT GGAACAATGG      300

CAAGCGCACA TTTGGGACAA GGGAGGGGAA AGGGTTCTTA TCCCTGACAC ACGTGGTCCC      360

NGCTGNTGTG TNCTNCCCCC ACTGANTAGG GTTAGACTGG ACAGGCTTAA ACTAATTCCA      420

ATTGGNTAAT TTAAAGAGAA TNATGGGGTG AATGCTTTGG GAGGAGTCAA GGAAGAGNAG      480

GTAGNAGGTA ACTTGAATGA                                                 500

(2) INFORMATION FOR SEQ ID NO:70:

(i) SEQUENCE CHARACTERISTICS:
        (A) LENGTH: 435 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:70:

CTGCAGAGTA ATTGCAACTG GAGTTGTCTT AAGATAATGT CACATATCCA TCTTCCCCTT       60

GTTTCTCATT CACAGAAAAA CATTTTTATT CCAGGTGCCA ATATTCCCAG CCAAAAAGAC      120

TTTACTTCTG ACTCCCTTAT ATTTAGGATG GCTATGAGAA CAAGTAAGGG CAATGACTTC      180

TAGGGAGATG TGTTGTGTAT GGAACTTCTA AGGAGAGAAT TCTGCTGACA TGTCCTATGT      240

TCTTTTCTCC CCTACTCCTT CCTACTGTCA GAAATGAAGG CTAGGGCTCC AGCCTGGACC      300

CTGAAGTAAG CTAGAGGTTA GAAGCTAAAG AAGAAAGAAG GAGATTGAGT CCTTGGATGA      360

ACGTGAAGCC ACCCTACTAA TCTGGACTGN CTACCTCTGN ACTACTCTAT GAGAGAGAAA      420

GTATGTGCAT TATTT                                                      435

(2) INFORMATION FOR SEQ ID NO:71:

(i) SEQUENCE CHARACTERISTICS:
        (A) LENGTH: 439 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:71:

CATGCTCTTT GTCCCTGTGA CTCTCTGCAT GGTGGTGGTC GTGGNTACCA TTAAGTCAGT       60

CAGCTTTTAT ACCCGGAAGG ATGGGCAGCT GTACGTATGA GTTTGGTTTT ATTATTCTCA      120

AAGCCAGTGT GGCTTTTCTT TACAGCATGT CATCATCACC TTGAAGGCCT CTGCATTGAA      180

GGGGCATGAC TTAGCTGGAG AGCCCATCCT CTGTGATGGT CAGGAGCAGT TGAGAGAGCG      240

AGGGGTTATT ACTTCATGTT TTAAGTGGAG AAAAGGAACA CTGCAGAAGT ATGTTTCCTG      300

TATGGTATTA CTGGATAGGG CTGAAGTTAT GCTGAATTGA ACACATAAAT TCTTTTCCAC      360

CTCAGGGGCA TTGGGCGCCC ATTGNTCTTC TGCCTAGAAT ATTCTTTCCT TTNCTNACTT      420

GGGNGGATTA AATTCCTGT                                                  439

(2) INFORMATION FOR SEQ ID NO:72:

(i) SEQUENCE CHARACTERISTICS:
        (A) LENGTH: 318 base pairs
        (B) TYPE: nucleic acid
```

```
            (C) STRANDEDNESS: single
            (D) TOPOLOGY: linear (ii) MOLECULE TYPE: DNA (genomic)

(xi) SEQUENCE DESCRIPTION: SEQ ID NO:72:

TCCATCTCTA CGACTCTCAT GGGGTCCAAA GAAGAGTTTT AATTGAGTTT TAGAATGTGN      60

AGTTGTGAAG TGTCTGAAAA ACTACATGGT GNTCTGAAAG NCAAACTTTT AGCCTTGGGG     120

GAGAGCATCT AAGACAGNAG GTGAAGGGGA GGGGTTAGAN CTAGAGGGAT TGAAGAATAT     180

TATCCATATA GGTTAGGGTT AGGTGTGGCA ACGTTTTATA GAACAAACAT TGGNAAGCTA     240

CAGACACAGG CCAGNTCTGT CTNCTACCTN TCCACAAAGG TGTNATAACA AAGTTANNCA     300

CAAATGTGTG AATAAACT                                                  318

(2) INFORMATION FOR SEQ ID NO:73:

(i) SEQUENCE CHARACTERISTICS:
        (A) LENGTH: 450 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:73:

GTTGCAAAGT CATGGATTCC TTTAGGTAGC TACATTATCA ACCTTTTTGA GAATAAAATG      60

AATTGAGAGT GTTACAGTCT AATTCTATAT CACATGTAAC TTTTATTTGG ATATATCAGT     120

AATAGTGCTT TTTCNTTTTT TTTTTTTNTT TTTTTTNNTT TTNGGGGANA GAGTCTCGCT     180

CTGTCGCCAG GTTGGAGTGC AATGGTGCGA TCTTGGCTCA CTGAAAGCTC CACCNCCCGG     240

GTTCAAGTGA TTCTCCTGCC TCAGCCNCCC AAGTAGNTGG GACTACAGGG GTGCGCCACC    300

ACGCCTGGGA TAATTTTGGG NTTTTTAGTA GAGATGGCGT TTCACCANCT TGGNGCAGGC     360

TGGTCTTGGA ACTCCTGANA TCATGATCTG CCTGCCTTAG CCTCCCCAAA GTGCTGGGAT     420

TNCAGGGGTG AGCCACTGTT CCTGGGCCTC                                    450

(2) INFORMATION FOR SEQ ID NO:74:

(i) SEQUENCE CHARACTERISTICS:
        (A) LENGTH: 489 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:74:

CTGCAGNTGA GCCGTGATTG CANCCACTTT ACTCCNAGCC TGGGCAANCA AAATGAGACA      60

CTGGCTNCAA ACACAAAAAC AAAAACAAAA AAAGAGTAAA TTAATTTAAA GGGAAGTATT     120

AAATAAATAA TAGCACAGTT GATATAGGTT ATGGTAAAAT TATAAAGGTG GGATATTAAT     180

ATCTAATGTT TGGGAGCCAT CACATTATTC TAAATAATGT TTTGGTGGAA ATTATTGTAC     240

ATCTTTTAAA ATCTGTGTAA TTTTTTTTCA GGGAAGTGTT TAAAACCTAT AACGTTGCTG     300

TGGACTACAT TACTGTTGCA CTCCTGATCT GGAATTTTGG TGTGGTGGGA ATGATTTCCA     360

TTCACTGGAA AGGTCCACTT CGACTCCAGC AGGCATATCT CATTATGATT AGTGCCCTCA     420

TGGCCCTGGT GTTTATCAAG TACCNCCCTG AATGGACTGG GTGGCTCATC TTGGCTGTGA     480

TTTCAGTAT                                                           489
```

(2) INFORMATION FOR SEQ ID NO:75:

(i) SEQUENCE CHARACTERISTICS:
        (A) LENGTH: 449 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:75:

```
CTGCAGNCTT GACCTCCTGG GATCAATCGA TCCTCCCACC TCAGCCTCCT AAGTAGCTGG      60
AACTACAGGT GTGCACCACC ATGCCCGGCT AATTTTTGTA TTTTCTGTAG ATACGAGGTT     120
TTGCCATGTT GCCCAGGCTG GTCTTGAACT CTGGGCTTAG GTGATCTGCC CGCCTCAGCC     180
TCCCAAAGTG CTAAGATTAC AGGCATGAGC TACCATGCCC AGCCGAAATC TTCAAATGAA     240
AAAGTTACTA TAGCTAATTA ATGATTTACT GAAGAGTTAT GGGATGTACA CGTTACCATT     300
TTCTCTAAAT CAAGATAAAG AGATGAGGAA AGAAAACACT CCAGTGGGGC ATTCCTGTGA     360
CAAACAAATT ATCAGTCTTG GGTTTTACNA TATACTGAAA TCACAGCCAA GATGAGCCAC     420
GCAGTCCATT CAGGGAGGTA CTTGATAAA                                       449
```

(2) INFORMATION FOR SEQ ID NO:76:

(i) SEQUENCE CHARACTERISTICS:
        (A) LENGTH: 490 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:76:

```
TTCTTGCCGT TCCCGACCCG AGCCTGGTGC CCCTTCCCCA TTATGATCCT TNTCGCTTCC      60
GGCGGCATCG GGATGCCCCG CGTTGCAGGC CATNCTGTCC CAGNCAGGTA GATGACGACC     120
ATCAGGGACA GCTTCAAGGA TCGCTCGCGG CTCTTACCAG CCTAACTTCG ATCATTGGAC     180
CGCTGATCGT CACGGCGATT TATCCCGCCT CGGCGAGCAC ATGGAACGGG TTGGCATGGA     240
TTGTAGGCGC CGCCCTATAC CTTGTCTGCC TCCCCCGCGT TGCGTCGCGG TGCATGGAGC     300
CGGNCCACCT CGACCTGAAT GGAANCCGGC GGCACCTCGC TAACGGATTC ACCACTCCAA     360
GAATTGGAGC CAATCAATTC TTGCGGAGAA CTGTGAATGC NCAAACCAAC CCTTGGCAGA     420
ACATATCCAT CGCGTCCGCC ATCTCCANCA GCCGCACGCG GCGCATCTCG GGCAGCGTTG     480
GGTCCTGCAG                                                            490
```

(2) INFORMATION FOR SEQ ID NO:77:

(i) SEQUENCE CHARACTERISTICS:
        (A) LENGTH: 470 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:77:

```
CTGCAGTGTT TAAAAAATAA AATAAACTAA AAGTTTATTT ATGAGGAGTA CACTGCTTTC      60
TTGTAAACAC ATGTACAAGC CATATAATAG AGTTCATTTC NNACCCTAGT TACGGAAACA     120
CTAGAAAGTC TNCACCCGGC CAAGATAACA CATCTTTAGG TAAAAATAGC AAGAAATATT     180
```

```
TTATGGGTTG TTTACTTAAA TCATAGTTTT CAGGTTGGGC ACAGTGGNTC ATGCCTGTAA        240

TCCCAGCACT TTATGCGGCT GAGGCAGGCA GATCAGTTGA GGTCAGAAGT TTGAGACCAG        300

CCTGGGCAAT GTGGCAAAAC CTCATCTCCA CTAAAAATAC AAAAATTAGC CAGGCATGGT        360

GGTGCACACA TGTTAATTCC CAGCTACTTG GGAGGNTTGA GACAGGAGGG TCGCTTGGNC        420

CTAGGAGGGA AGAAGTTGNA GGGANCTTAA TGTCACTGCA CTCTAGNTTG                   470

(2) INFORMATION FOR SEQ ID NO:78:

(i) SEQUENCE CHARACTERISTICS:
          (A) LENGTH: 445 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:78:

CACTCAATTC TGAATGCTGC CATCATGATC AGTGTCATTG TTGTCATGAC TANNCTCCTG         60

GTGGTTCTGT ATAAATACAG GTGCTATAAG GTGAGCATGA GACACAGATC TTTGNTTTCC        120

ACCCTGTTCT TCTTATGGTT GGGTATTCTT GTCACAGTAA CTTAACTGAT CTAGGAAAGA        180

AAAAATGTTT TGTCTTCTAG AGATAAGTTA ATTTTTAGTT TTCTTCCTCC TCACTGTGGA        240

ACATTCAAAA AATACAAAAA GGAAGCCAGG TGCATGTGTA ATGCCAGGCT CAGAGGCTGA        300

GGCAGGAGGA TCGCTTGGGC CCAGGAGTTC ACAAGCAGCT TGGGCAACGT AGCAAGACCC        360

TGCCTCTATT AAAGAAAACA AAAAACAAAT ATTGGAAGTA TTTTATATGC ATGGAATCTA        420

TATGTCATGA AAAAATTAGT GTAAA                                              445

(2) INFORMATION FOR SEQ ID NO:79:

(i) SEQUENCE CHARACTERISTICS:
          (A) LENGTH: 496 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:79:

CCTGTATTTA TACTGAACCA CCAGGAGGAT AGTCATGACT ACAATGACNC TGATCATGAT         60

GGCAGCATTC AGAATTGAGT GCAGGGCTCT CTGGCCCACA GTCTCGGTAT CTTCTGTGAA        120

TGGGGTATAG ATTCTACAAT AAAACAAACA CAAAAGCCCT AGGTCAGTGT TAATGGAGAT        180

CACCAACCAC ATTACCACCT CCAACACAGA ATTTTCTTTT TCTTAATTCA ATTCGNATCT        240

TATAAGTCAC TTTTCCCCAA CTCACCAATN CTAGCTAAGA ATTTTTAACC TGAGAAAAAC        300

AGCTACACTC TAAAATTGCT TCAAAGAAAA TGTCTAACAT ATGGAAAGAA GGACTTAACA        360

TGTGAAGCAG ACACTGGCTC CATCTAGTGG GTGCTTTATA TTGAAATAAT TATAATACCT        420

CATCAAATTT TTTNGGGTAC AGNTTATTAG GAACTTGGTA TGGAACCAGA TTCTGCCACA        480

GAAACCACGN GGGCTG                                                        496

(2) INFORMATION FOR SEQ ID NO:80:

(i) SEQUENCE CHARACTERISTICS:
          (A) LENGTH: 496 base pairs
          (B) TYPE: nucleic acid
          (C) STRANDEDNESS: single
          (D) TOPOLOGY: linear
```

(ii) MOLECULE TYPE: DNA (genomic)

(xi) SEQUENCE DESCRIPTION: SEQ ID NO:80:

| CATTAGATAA | TGGNTCAGGG | TGGCCAAGGC | TCCGTCTGTC | GTTGTGCTCC | TGCCGTTCTC | 60 |
| TATTGTCATT | CTATAAGCAC | AAGAAAAACA | TTTTCAGTAA | ATCAGATTCT | CAGCAGAATC | 120 |
| AAGGTAACGG | TTAGACCTGG | GATTAACAAC | AGACCCGTCA | CTATGAGTTC | TAAAAACCTG | 180 |
| AAGCAAGAAA | AAACAATGTA | CAGGAAGTAT | GCAGTTTAAA | AGTCTAGATT | ATCTATCATT | 240 |
| GTTCACTGAA | GGCATTCAGG | TCCTCTCTTT | TACCTGGGTC | TTGGNTTGCT | CCATTCTCTC | 300 |
| TGTTCATCCC | AACATACACA | ATTGTACTTA | TCCTTTGAGA | TGTACCTTAA | ATACTGACAC | 360 |
| CTGCATGAAA | ACTTGTTTAC | TGGCTGCAGG | TCCAAGCACC | TTTTTCNAAA | TTCAGCTTTC | 420 |
| TGTGATTTCA | GACCACATAT | GCAAGGAACT | ATCTTACCTT | AATTAATAAG | ANTTTAAAAT | 480 |
| CCTTGTGTCA | GAGGCG | | | | | 496 |

(2) INFORMATION FOR SEQ ID NO:81:

(i) SEQUENCE CHARACTERISTICS:
           (A) LENGTH: 368 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:81:

| AGGANCGCTT | GGGCCCAGGA | GTTCACAAGC | AGCTTGGGCA | ACGTAGCAAG | ACCCTGCCTC | 60 |
| TATTAAAGAA | ACAAAAAAC | AAATATTGGA | AGTATTTTAT | ATGCATGGAA | TCTATATGTC | 120 |
| ATGAAAAAAT | TAGTGTAAAA | TATATATATT | ATGATTAGNT | ATCAAGATTT | AGTGATAATT | 180 |
| TATGTTATNN | NGGGATTTCA | ATGCCTTTTT | AGGCCATTGT | CTCAAAAAAT | AAAAGCAGAA | 240 |
| AACAAAAAAA | GTTGTAACTG | AAAAATAAAC | ATTTCCATAT | AATAGCACAA | TCTAAGTGGG | 300 |
| TTTTTGNTTG | TTTGTTTGNT | TGTTGAAGCA | GGGCCTTGCC | CTNCCACCCA | GGNTGGAGTG | 360 |
| AAGTGCAG | | | | | | 368 |

(2) INFORMATION FOR SEQ ID NO:82:

(i) SEQUENCE CHARACTERISTICS:
           (A) LENGTH: 500 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:82:

| GAATTCCTTT | TTTTTTTTT | TTTTTTTTT | TTNCTCCTAA | TGTTTTTATT | GTNCCTTAGA | 60 |
| TAACTGGATA | GNACAAAGTT | NGNCTTNGTT | TTTTACTTAA | AAAACGTACT | TTCCGCATAC | 120 |
| TGTNGCCCGT | ATGACTTTCC | TGTCCCATCG | GAAACCAGAG | TTTCCCCAGG | TGAGCCCTTC | 180 |
| CTATCTGNGG | NTACATGATT | TAGCTAATTT | AACAAGAAGA | GAGTAATTCC | TTNGGATTAT | 240 |
| TATCAACATG | AAACTTGGAC | TATGTCTCTA | TAAGGGTGAA | CACTGATTTT | TTTTTTCTTT | 300 |
| TTAGAAACAA | AAACCATCCA | CTTATTAATC | CAAACTACGG | GATTGGATTT | ACAACAATCA | 360 |
| TCGCATNAAC | TGAACATACG | AAGTTACCAC | TCAAGGGAAT | NACAGAAGAA | CGTTGNACAA | 420 |
| TNTNTCTTAC | GGGGTACGNG | AATTCAAACA | ATGTGGGGAN | AGGAACTTCA | NTCTACAAAN | 480 |
| TCTGACCATC | GNTTCAGTAT | | | | | 500 |

(2) INFORMATION FOR SEQ ID NO:83:

(i) SEQUENCE CHARACTERISTICS:
        (A) LENGTH: 450 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:83:

```
GAATTCCTTT ACTCTTCTTT AATTCTACCG TCTTTGGGCA TACATCTCAT TTGNTGTGGA        60

AGAAGGTCTG ACAGNAGGGC TGACAGCACC GATTCATAAC ACATTCTTTT CATCATACAA       120

AGAGTAAGAC CCTAGAATAA TGGGACCATC TGCTACCACG ACAGAGCTGC CTTACTGGCT       180

GTAGAAAAAG ACTGCTTGTG TGGGAGAGAA GAATGAGGAC AGAGGAGGCA TCTGGGCAA        240

GTGAGCGTAC AAGTATNTCT ACAAATTCAG AATTTGGTGG AAAATCCAAA TTTGNCTTCA       300

ACATGATAGA GAATTGATGA GAAAATAGCT GTNCTGTTTC CAAAATTTAC TGAATTTGGG       360

AACCTGAGGT TAAAACTTTT AGGATNAAGC AACTCAGGTT CAAGACTTNG NCTNGGGAAG       420

GAATGGAAAC ACAGACGGGA ATGAGTNTCA                                        450
```

(2) INFORMATION FOR SEQ ID NO:84:

(i) SEQUENCE CHARACTERISTICS:
        (A) LENGTH: 450 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:84:

```
CAACTGTATT TATACAGNAA CCACCAGGAG GATAGTCATG ACAACAATGA CAAACTAGGA        60

ATAGCCCCCT TTCACTTCTG AGTCCCAGAG GTTACCCAAG GCACCCCTCT GACATCCGGC       120

CTGCTTCTTC TCACATGANA AAAACTAGCC CCCAGTNTGA TCCGCAGGTN GAGGAATNCC       180

CCGGGTCGAG GTTCGGATCC TGGATGACAG ACCCTCTCGC CCCTGAAGGN GATAACCGGG       240

TGTGGTACAT GGACGGNTAT CACAACAACC GCTTCGNACG TGAGTACAAG TCCATGGTTG       300

ACTTCATGAA CACGGACAAT TTCACCTCCC ACCGTCTCCC CCACCCCTGG TCGGGCACGG       360

GGNAGGTGGT CTNCAACGGT TCTTTCTNCT TCAACAAGTT CCAGAGCCAC ATCATCATCA       420

GGTTTGGACC TGAAGANAGA GAACATCCTC                                        450
```

(2) INFORMATION FOR SEQ ID NO:85:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:85:

```
GGATCCCTCC CCTTTTTAGA CCATACAAGG TAACTTCCGG ACGTTGCCAT GGCATCTGTA        60

AACTGTCATG GTGTTGGCGG GGAGTGTCTT TTAGCATGCT AATGTATTAT AATTAGCGTA       120

TAGTGAGCAG TGAGGATAAC CAGAGGTCAC TCTCCTCACC ATCTTGGTTT TGGTGGGTTT       180

TGGCCAGCTT CTTTATTGCA ACCAGTTTTA TCAGCAAGAT CTTTATGAGC TGTATCTTGT       240
```

```
GCTGACTTCC TATCTCATCC CGTAACTAAG AGTACCTAAC CTCCTGCAAA TNGCAGCCCA        300

GTAGGTCTTG GNCTTATTTT ACCCAGCCCC TATTCAAGAT AGAGTTGCTC NTGGTCCAAA        360

CGCCTCTGAC ACAAGGATTT TAAAGTCTTA TTAATTAAGG TAAGATAGGT CCTTGGATAT        420

GTGGTCTGAA ATCACAGAAA GCTGAATTTG GAAAAGGTG CTTGGAGCTG CAGCCAGTAA         480

ACAAGTTTTC ATGCAGGTGT                                                   500
```

(2) INFORMATION FOR SEQ ID NO:86:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:86:

```
CTGCAGTGAG CCAAAATCGT GCCACTGCAC TTCACTCCAG CCTGGGTGAC AGGGCAAGGC        60

CCTGCTTCAA CAAACAAACA AACAAACAAA AACCCACTTA GATTGTGCTA TTATATGGAA        120

ATGTTTATTT TTCAGTTACA ACTTTTTTTG TTTTCTGCTT TTATTTGTTG AGACAATGGC        180

CTAAAAAGGC ATTGAAATNC CAAAATAACA TAAATTATCA CTAAATCTTG ATAACTAATC        240

ATAATATATA TATTTTACAC TAATTTTTTC ATGACATATA GATTCCATGC ATATAAAATA        300

CTTCCAATAT TTGTTTTTTG TTTTCTTTAA TAGAGGCAGG GTCTTGCTAC GTTGCCCAAG       360

CTGCTTGTGA ACTCCTGGGC CCAAGCGATC CTCCTGCCTC AGCCTCTGAG CCTGGCATTA      420

CACATGCACC TGGCTTCCTT TTTGTNTTTT TTGAATGTTC CACAGTGAGG AGGAAGAAAA      480

CTNAAAATTA ACTTATCTCT                                                  500
```

(2) INFORMATION FOR SEQ ID NO:87:

(i) SEQUENCE CHARACTERISTICS:
        (A) LENGTH: 450 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:87:

```
CTGCAGATGA GAGGCACTAA TTATAAGCCA TATTACCTTT CTTCTGACAA CCACTTGTCA        60

GCCCACGTGG TTTCTGTGGC AGAATCTGGT TCTATAACAA GTTCCTAATA AGCTGTAGCC       120

AAAAAAATTT GATGAGGTAT TATAATTATT TCAATATAAA GCACCCACTA GATGGAGCCA       180

GTGTCTGCTT CACATGTTAA GTCCTTCTTT CCATATGTTA GACATTTTCT TTGAAGCAAT      240

TTTAGAGTGT AGCTGTTTTT CTCAGGTTAA AAATTCTTAG CTAGGATTGG TGAGTTGGGG      300

AAAAGTGACT TATAAGATAC GAATTGAATT AAGAAAAAGA AAATTCTGTG TTGGAGGTGG     360

TAATGTGGGT GGTGATCTTC ATTAACACTG ANCTAGGGNT TTGGGGTTTG GTTTATTGTA    420

GAATCTATAC CCCATTCANA GAAGATACCG                                      450
```

(2) INFORMATION FOR SEQ ID NO:88:

(i) SEQUENCE CHARACTERISTICS:
        (A) LENGTH: 502 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:88:

| | | | | | |
|---|---|---|---|---|---|
| CTGCAGCCAG | TAAACAAGTT | TTCATGCAGG | TGTCAGTATT | TAAGGTACAT | CTCAAAGGAT | 60 |
| AAGTACAATT | GTGTATGTTG | GGATGAACAG | AGAGAATGGA | GCAAGCCAAG | ACCCAGGTAA | 120 |
| AAGAGAGGAC | CTGAATGCCT | TCAGTGAACA | ATGATAGATA | ATCTAGACTT | TTAAACTGCA | 180 |
| TACTTCCTGT | ACATTGTTTT | TTCTTGCTTC | AGGTTTTTAG | AACTCATAGT | GACGGGTCTG | 240 |
| TTGTTAATCC | CAGGTCTAAC | CGTTACCTTG | ATTCTGCTGA | GAATCTGATT | TACTGAAAAT | 300 |
| GTTTTTCTTG | TGCTTATAGA | ATGACAATAG | AGAACGGCAG | GAGCACAACG | ACAGACGGAG | 360 |
| CCTTGGCCAC | CCTGAGCCAT | TATCTAATGG | ACGACCCAGG | GTAACTCCCG | GCAGGTGGTG | 420 |
| GAGCAAGATG | AGGAAGAAGA | TGAGGAGCTG | ACATTGAAAT | ATGGCGGCNA | GCATGTGATC | 480 |
| ATGCTCNTTG | GCCCTGTGAN | TC | | | | 502 |

(2) INFORMATION FOR SEQ ID NO:89:

(i) SEQUENCE CHARACTERISTICS:
            (A) LENGTH: 499 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:89:

| | | | | | |
|---|---|---|---|---|---|
| CTGCAGTGTT | CCTTTTCTCC | ACTTAAAACA | TGAAGTAATA | ACCCCTCGNT | CTCTCAACTG | 60 |
| CTCCTGACCA | TCACAGAGGA | TGGGCTCTCC | AGCTAAGTCA | TGCCCCTTCA | ATGNAGAGGC | 120 |
| CTTCAAGGTG | ATGATGACAT | GCTGTAAAGA | AAAGCCACAC | TGGGTTTGAG | AATAATAAAA | 180 |
| CAAAACTCAT | ACGTACAGCT | GCCCATCCTT | CCGGGTATAA | AAGCTGACTG | ACTTAATGGT | 240 |
| AGCCACGACC | ACCACCATGC | AGAGAGTCAC | AGGGACAAAG | AGCATGATCA | CATGCTTGGC | 300 |
| GNCATATTTC | AATGTCAGNT | CCTCATCTTC | TTCCTCATCT | TGNTCCACCA | CCTGCCGGGA | 360 |
| GTTACCNTGG | GTCGTCCATT | AGATAATGGG | TCAGGGTGGC | CAAGGCTCCG | TCTGTCGTTG | 420 |
| TGCTCCTGCC | GTTCTCTATT | GTCATTCTAT | AAGCACAAGA | AAAACATTTN | CAGTAAATCA | 480 |
| GATNCTCAGC | AGAATCAAG | | | | | 499 |

(2) INFORMATION FOR SEQ ID NO:90:

(i) SEQUENCE CHARACTERISTICS:
            (A) LENGTH: 500 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:90:

| | | | | | |
|---|---|---|---|---|---|
| TAACTCCCAG | GNTCAAGATN | TCTNCCTGCG | TTAGCCTCCT | GAGTAGCTGG | GACTATAGGT | 60 |
| ATGTGCCACT | ATTCCTGAAA | ACATAATCAG | TTTTGAAGGT | AGTGTCTGGG | CTGGGCGCAG | 120 |
| TGGNTCACGC | CTTCAATCCC | AGCACTTTGG | GAGGNCGAGG | TGGGCGGATC | ACCTGAGGTC | 180 |
| AGGAGTTCGA | GACCAGCCTG | ACCAACATGG | GATAAGACTC | CATCTCTACT | AAAAATACAA | 240 |
| AAAATTAGCC | AGGCATGGTG | GNGCATGCCT | GTAATCCCAG | CTACTCAGGA | GGNTGAGGNA | 300 |
| GGAGAATTGG | TTGGAACCTA | GGAAGCAGAG | GCTGTGGTGG | AGCCGAGATC | GCACCATTGG | 360 |

| | | | | |
|---|---|---|---|---|
| ACTCCAGGCT | GGGNAACAAG | AGTGAAAATC | CNTCTTAAAA | AAAAAAAAAA AAAGGTAGNG | 420 |
| TTTTGNCCGG | NGCGGGGGGT | CACGCCTGTA | ATCCCAGNAT | TGGGGANGGC AAGGNGGGGG | 480 |
| GTCANNANGN | NAGNAGTCCG | | | | 500 |

(2) INFORMATION FOR SEQ ID NO:91:

(i) SEQUENCE CHARACTERISTICS:
        (A) LENGTH: 502 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:91:

| | | | | |
|---|---|---|---|---|
| GAATTCTGCT | GACATGTCCT | ATGTTCTTTT | CTCCCCTACT | CCTTCCTACT GTCAGNAATG | 60 |
| AAGGGTAGGG | CTCCAGCCTG | GACCCTGAAG | TAAGCTAGAG | GTTAGAAGCT AAAGAAGAAA | 120 |
| GAAGGAGATT | GAGTCCTTNG | ATGAACGTGA | AGCCACCGTA | CTAATCTGGA CTGCCTACCT | 180 |
| CTGCACTACT | CTATGAGAGA | GAAAGTATGT | GCATTATTTA | AACCAGTTGG GTTGATTTTC | 240 |
| TATTAACAAA | GTCAGAAACA | TCTCTGTAAA | AAGCCAGACT | GAATATTTTA AGCTCTATGG | 300 |
| GTCATATGGT | CTCCAGGGCA | AACACTCAAC | TGTGCTACTG | TAGTGTGAAA GCAGGCACAG | 360 |
| ACAATGTATT | AACCAAGGAG | GGTGGTCACT | TTCCAATGAA | AGTTTATCAC AAATTGGNGA | 420 |
| ATACTTGGTA | TTACACCNNG | GGGGAAGGTA | GGAGAAGATC | TTGCCTGTGG TTGTNGNTGG | 480 |
| CAATGTTGGT | CTTTTATACG | NG | | | 502 |

(2) INFORMATION FOR SEQ ID NO:92:

(i) SEQUENCE CHARACTERISTICS:
        (A) LENGTH: 495 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:92:

| | | | | |
|---|---|---|---|---|
| GAATTCTCTC | CTTAGAAGTT | CCATACACAA | CACATCTCCC | TAGAAGTCAT TGCCCTTACT | 60 |
| TGTTCTCATA | GCCATCCTAA | ATATAAGGGA | GTCAGAAGTA | AAGTCTGGNT GGCTGGGAAT | 120 |
| ATTGGCACCT | GGAATAAAAA | TGTTTTTCTG | TGAATGAGAA | ACAAGGGGAA GATGGATATG | 180 |
| TGACATTATC | TTAAGACAAC | TCCAGTTGCA | ATTACTCTGC | AGATGAGAGG CACTAATTAT | 240 |
| AAGCCATATT | ACCTTTCTTC | TGACAACCAC | TTGTCAGCCC | ACGTGGTTTC TGTGGCAGAA | 300 |
| TCTGGTTCTA | TAACAAGTTC | CTAATAAGCT | GTAGCCAAAA | AAATTTGATG AGGTATTATA | 360 |
| ATTATTTCAA | TATAAAGCAC | CCACTAGATG | GAGCCAGTGT | CTGCTTCACA TGTTAAGTCC | 420 |
| TTCTTTCCAT | ATGTTAGACA | TTTCTTTGAA | GCAATTTTAG | AGTGTAGCTG TTTCTCAGGT | 480 |
| TAAAATTCTT | AGTAG | | | | 495 |

(2) INFORMATION FOR SEQ ID NO:93:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:93:

```
TATGGTTGCC TATTCTTGTC ACAGTAACTN AACTGATCTA GGAAAGAAAA AATGTTTTGT        60

CTTCTAGAGA TAAGTTAATT TTTAGTTTTC TTCCTCCTCA CTGTGGAACA TTCAAAAAAT       120

ACAAAAAGGA AGCCAGGTGC ATGTGTAATG CCAGGCTCAG AGGCTGAGGC AGGAGGATCG       180

CTTGGGCCCA GGAGTTCACA AGCAGCTTGG GCAACGTAGC AAGACCCTGC CTCTATTAAA       240

GAAAACAAAA AACAAATATT GGAAGTATTT TATATGCATG GAATCTATAT GTCATGAAAA       300

AATTAGTGTA AAATATATAT ATTATGATTA GTTATCAAGA TTTAGTGATA ATTTATGTTA       360

TTTTGGGATT TCAATGCCTT TTTAGGCCAT TGTCTCAAAA AAATAAAAGC AGGAAAACAA       420

AAAAAGTTGT AACTTGAAAA ATAAACATTT CCATATTTAT AGCCAACTAA GTGGGTTTNG       480

GGTNGGTTGG GTTGGTTGGT                                                  500
```

(2) INFORMATION FOR SEQ ID NO:94:

(i) SEQUENCE CHARACTERISTICS:
        (A) LENGTH: 385 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:94:

```
TTATCATTAA CAGGTCCCAC AACCCTTAAA AAGTACAGAT TTTTTTTTTC TTNGTGGAGA        60

CAGGGTCTCA CTTGGTCGCC CAGACTGGAG TGCAGTGGCA CGATCTCAGT TCACCACAAC       120

CTCTGCCTCC TGGGTTCAAG CAATNCTCGT GCTTAAGCCT CCTGAGTAGG TGGAACCACG       180

CGTGCGCGCC ACCACGCTAG GTTNATTGTG GCTTTTTTAG TAGAGACAGG GTTTCGCCAT       240

GTTGCCCAGG CTGGTCTCAN ATTCCNGACC TCAAGTGATC CGNCCGCCTC AGACTCCCAA       300

AGTGNTGAGC ATTACAGNTG TGTACCACTA TGTCCCNGNC CNCATCTCTC TTTAAAACAN       360

CTTNCATTTA CCTAGTCCAC TCCTG                                            385
```

(2) INFORMATION FOR SEQ ID NO:95:

(i) SEQUENCE CHARACTERISTICS:
        (A) LENGTH: 330 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:95:

```
GACCTAGAAA AGAAAGCATT TCAANNTAAT TAACAGGTCC CACAACCCTT AAAAAGTACA        60

GATTTTTTTT TTCTTTNNGG AGACAGGGTC TCACTTTGTC GCCCAGACTG GAGTGCAGTG       120

GCACGATCTC AGCTCACCAC ANCCTCTGCC TCCTGGGTTC AAGNANTTCT CGTGCTTANG       180

CCTCCTGAGT AGGTGGAACC ACGCGTGTGC GCCACCACGC TAGGCTACTT TNTGTATTTT       240

TAGTAGAGAC AGGGTTTCGC CATNTTGCCC AGGCTGNTCT CAAATTCCTG ACCCNCAAGT       300

GATCCCCCCN CCTTCAGTAC TCCCCATCAG                                       330
```

(2) INFORMATION FOR SEQ ID NO:96:

(i) SEQUENCE CHARACTERISTICS:
        (A) LENGTH: 382 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO:96:

| | | | | | |
|---|---|---|---|---|---|
| GGTGGNCGTT | CTAGAACTAG | TGGCNCCCAA | GGNAGAAGAA | GTTTTCTTAG TACAGAACAA | 60 |
| AATGAAANGT | CTCCCATGTC | TACTTCTTTC | TACACAGACA | CGGCATCCAT CCGTTTTTCT | 120 |
| CANTCTTTCC | NCCACCTTTC | CCGTCTTTCT | ATTCCACAAA | GCCGNCATTG TCATCCTGGC | 180 |
| CCNTTCTCAA | TGAGCTGTTG | NNTACACCTC | CCAGACGGCG | TGGTGGNCGG TCAGAGGGGC | 240 |
| TCCTCACTTC | CCAGTAGGGG | TGGCCGNGCA | GGNGGTGCCC | CNCACCCCCC GGGCGGGGTG | 300 |
| GTTNGTCCNN | CCGGNGGGNT | GCACCNCCCC | CACCCCTCCC | CNCTCTNCTA CTGGCGGTCG | 360 |
| TNTATTNCAN | NATCTTTAAG | CA | | | 382 |

(2) INFORMATION FOR SEQ ID NO:97:

(i) SEQUENCE CHARACTERISTICS:
        (A) LENGTH: 360 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:97:

| | | | | | |
|---|---|---|---|---|---|
| GGATCCAAAG | GAAGTTAGAG | GCCAGCTCAG | TCTACACCTG | CTACTGNTCA GTGCCCACCC | 60 |
| GGTCAAGGGA | GACCAACACA | TGGTAAAGGT | CAAGGGCTTC | TTGGAAGGCA GTCAGCAGCC | 120 |
| TGTGCAAGAT | GTTCTCCACA | CTGCTCAGNT | TAAGGGGAGC | TGGGGGCAGG ACCTCAGCTG | 180 |
| GNATCTCTGC | TTCACCAGTG | TCCAGGGGTT | GCACAATTCT | TGTTTACTCG TAGGATATTT | 240 |
| AATCTTGGNN | GGTGCTATCA | TAAATGGGAC | TTATCCNCTN | ATTATGTTTT CTTACTAGTT | 300 |
| GTTTATGTGA | AGGTTATTGA | TTTGGGTTTC | ACTTTATTTN | GTGGNAATGG AGTTTCACTC | 360 |

(2) INFORMATION FOR SEQ ID NO:98:

(i) SEQUENCE CHARACTERISTICS:
        (A) LENGTH: 208 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:98:

| | | | | | |
|---|---|---|---|---|---|
| AATGTCACGG | ATTCCTTTAG | GTAGNTACAC | CCATCAACCT | TTTTGAGAAT AAAATGAATT | 60 |
| GAGAGTGTTA | CAGTCTAATT | CTATATCACA | TGTAACTTTT | ATTTGGATAT ATCAGTAATA | 120 |
| GTGCTTTTTT | TTTTTTTTTT | TTTTTTTTTT | TTTTTTTTNG | GNGANAGAGT CTCGCTCTGT | 180 |
| CGCCAGGTTG | GAGTGNAATG | GTGCGATC | | | 208 |

(2) INFORMATION FOR SEQ ID NO:99:

(i) SEQUENCE CHARACTERISTICS:
        (A) LENGTH: 470 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:99:

-continued

```
AACAAGGTTT CTCGGTCGGC GGTGAATATA CCGGGGCGTC GATATTTGTT GCGGAATACT        60

CCCCTGACCG TAAACGTGGC TTTATGGGCA GCTGGCTGGA CTTCGGTTCT ATTGCCGGGT       120

TTGTGCTGGG TGCGGGCGTG GTGGTGTTAA TTTCGACCAT TGTCGGCGAA GCGAACTTCC       180

TCGATTGGGG CTGGCGTATT CCGTTCTTTA TCGCTCTGCC GTTAGGGATT ATCGGGCTTT       240

ACCTGCGCCA TGCGCTGGAA GAGACTCCGG CGTTCCAGCA GNATGTCGAT AAACTGGAAC       300

AGGGCGACCG TGAAGGTTTG GAGGATGGCC CGAAAGTCTC GTTTAAAGAG ATTGGCACTA       360

AATACTGGNG CAGNCTGTTG AATGTTTGGG CTTGGTAATT GGCAACCAAC GTGATTACTA       420

NATGTTGGTG ACCTATATTG CCGAGTTATT GGCGGATAAC CTGAATTATC                 470
```

(2) INFORMATION FOR SEQ ID NO:100:

(i) SEQUENCE CHARACTERISTICS:
        (A) LENGTH: 440 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:100:

```
TAATTATATT GAAATGCTTC TCNTCTAGGT CATCCATGNC TGGNTTATTA TATCATCTCT        60

ATTGNTGNTG CTCTTTTTTA CATNCATTTA CTTGGGGTAA GTTGTGAAAT TTGGGGTCTG       120

TCTTTCAGAA TTAACTACCT NNGTGCTGTG TAGCTATCAT TTAAAGCCAT GTACTTTGNT       180

GATGAATTAC TCTGAAGTTT TAATTGTNTC CACATATAGG TCATACTTGG TATATAAAAG       240

ACTAGNCAGT ATTACTAATT GAGACATTCT TCTGTNGCTC CTNGCTTATA ATAAGTAGAA       300

CTGAAAGNAA CTTAAGACTA CAGTTAATTC TAAGCCTTTG GGGAAGGATT ATATAGCCTT       360

CTAGTAGGAA GTCTTGTGCN ATCAGAATGT TTNTAAAGAA AGGGTNTCAA GGAATNGTAT       420

AAANACCAAA AATAATTGAT                                                   440
```

(2) INFORMATION FOR SEQ ID NO:101:

(i) SEQUENCE CHARACTERISTICS:
        (A) LENGTH: 449 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:101:

```
AAAACAAAGC CTCTTGAGGT TCTGAAAAGG GAAAGAAAAA CAGAACTTTG TGCACTACAA        60

TTATACTGTT ATAAAAAACA CTTCCATAGA TTACATTAAG CAGAAACAAA CCTTTCTTTC       120

ATGTGTTCTC CTCCAGGCCA AGCTGTCTAA GGACCGCAAA GGCTGTTGTC ACTTGCAGGC       180

TCCCAGATTA GGTCTGAAAT AGGATTTCAC CAGGTCATCC ATTGTTAGTT AAATCCTAGT       240

AAATTCATTT ANACCAATCA AATACTTATA AGACCAATTT GTAAACCAGG AATGTATTAA       300

TTTGTCACGA CTTTCAACTA ACTGACAAAT TTACTATAAG CTCAAGGTAG GACTCTTTAG       360

CAATAAGTAG GAACCGCCTG AGACAACCAA ACATTTTCAA CCCACAAANG ATACTTTAAT       420

GACTTTCTGA TTTNCCAGCA AAAGGGGGG                                         449
```

(2) INFORMATION FOR SEQ ID NO:102:

(i) SEQUENCE CHARACTERISTICS:
        (A) LENGTH: 425 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:102:

GGATCCGCCC TCCTCGGCCT CCCAAAGTGT TGGGATTACA GGCGTGAGCC ACCGCACCTG     60

GCTTTTTTTT TTTTTTTTTT TGGNGGAGAC AGAGTCTTAC TCTGTTGCCC AAGCTGGAGT    120

GCAGTGGTGC AATCTTGGTT CACTGNAACC TCCACCTCCA GAGTTCAAGC AATTCTCTGC    180

CTCAGTTTCT GGAGTAGCTG GGATTACAGG TGCCTGCCAT CACGCCTGGC TAAATTTGGN    240

ATTTTTTTTT AGTAGAGACA GGGTTTCACC ATGTTGGCCA GGCTGGTCTT GAACTCCTGA    300

CCTTGTGATC CACCAGCCTC GGCCTCCCAA ATTGNTGGGA TTACAGGCGT GAGCCACCAC    360

AACCAGGCTA AGTTTTAAA ACATGCCAAG TGTATTTACA TAATGCGATA CGANTTATGT    420

ACATA                                                               425

(2) INFORMATION FOR SEQ ID NO:103:

(i) SEQUENCE CHARACTERISTICS:
        (A) LENGTH: 386 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:103:

GGATCCGCCC GCCTTGGCCT CCCAAAGTGC TGGGATTACA GGCATGAGCC ACCGCTCCTG     60

GCTGAGTCTG CGATTTCTTG CCAGCTCTAC CCAGTTGTGT CATCTTAAGC AAGTCACTGA    120

ACTTCTCTGG ATTCCCTTCT CCTNTTGTAA AATAAGCATG TTATCTGTCC NNCCTGCCTT    180

GGGCATTGTG ATAAGGATAA GATGACATTA TAGAATNTNG CAAAATTAAA AGCGCTAGAC    240

AAATGATTTT ATGAAAATAT AAAGATTAGN TTGAGTTTGG GCCAGCATAG AAAAAGGAAT    300

GTTGAGAACA TTCCNTTAAG GATTACTCAA GCTCCCTTTG GTGTATATCA GNNGTCANNA    360

CNTATCTTNG GGGCTGAAAA ATGTTT                                        386

(2) INFORMATION FOR SEQ ID NO:104:

(i) SEQUENCE CHARACTERISTICS:
        (A) LENGTH: 224 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:104:

GAAAAGGGAA AGAAAAACAG AACTTTGTGC ACTACAATTA TACTGTTATA AAAACACTT     60

CCATAGATTA CATTAAGCAG AAACAAACCT TTCTTTCATG TGTTCTCCTC CAGGCCAAGC    120

TGTCTAAGGA CCGCAAAGGC TGTTGTCACT TGCAGGCTCC CAGATTAGGT CTGAAATAGG    180

ATTTCACCAG GTCATCCATT GTTAGTTAAA TCCTAGTAAA TNCA                    224

(2) INFORMATION FOR SEQ ID NO:105:

(i) SEQUENCE CHARACTERISTICS:
        (A) LENGTH: 440 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO:105:

GGATCCGCCC TCCTCGGCCT CCCAAAGTGT TGGGATTACA GGCGTGAGCC ACCGCACCTG      60

GCTTTTTTTT TTTTTTTTTT TGGNGGAGAC AGAGTCTTAC TCTGTTGCCC AAGCTGGAGT     120

GCAGTGGTGC AATCTTGGTT CACTGCAACC TCCACCTCCA GAGTTCAAGC AATTCTCTGC     180

CTCAGTTTCT GGAGTAGCTG GGATTACAGG TGCCTGCCAT CACGCCTGGN TAAATTTGGG     240

ATTTTTTTTT AGTAGAGACA GGGTTTCANC ATGTTGGCCA GGNTGGTCTT GGACTCCTGA     300

CCTGGTGAAC CACCAGGCTC GGGCTCCAAA TTTGGTTGGG ATTACAGGGG GTNAANCAAC     360

CACAACCCAG NCTAAAGTTT TNAAAACATN CAAAGTGTTT TAAAATNATG NGATACGATT     420

TATTGTACAA TTAATTTTAT                                                440

(2) INFORMATION FOR SEQ ID NO:106:

(i) SEQUENCE CHARACTERISTICS:
           (A) LENGTH: 448 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:106:

GTCTTTCCCA TCTTCTCCAC AGAGTTTGTG CCTTACATTA TTACTCCTTG CCATTTTCAA      60

GAAAGCATTG TCAGCTCTTC CAATCTCCAT CACCTTTGGG CTTGTTTTCT ACTTTGCCAC     120

AGATTATCTT GTACAGCCTT TTATGGACCA ATTAGCATTC CATCAATTTT ATATCTAGCA     180

TATTTGCGGN TAGAATCCCA TGGATGTTTC TTCTTTGACT ATAACAAAAT CTGGGGAGGA     240

CAAAGGTGAT TTTCCTGTGT CCACATCTAA CAAAGTCAAG ATCCCCGGCT GGACTTTTGG     300

AGGTTCCTTC CAAGTCTTCC TGACCACCTT GCACTATTGG ACTTTGGNAA GGAGGTGCCT     360

ATAGAAAACG ATTTTGGAAC ATACTTCATC GCAGGGGAC TGTGTCCCCC GGTGGCAGAA     420

NCTACCAAGA TTTGCGGGNC GAGGTCAA                                       448

(2) INFORMATION FOR SEQ ID NO:107:

(i) SEQUENCE CHARACTERISTICS:
           (A) LENGTH: 198 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:107:

GGATCCGCCC GCCTTGGCCT CCCAAAGTGC TGGGATTACA GGCATGAGCC ACCGCTCCTG      60

GCTGAGTCTG CGATTTCTTG CCAGCTCTAC CCAGTTGTGT CATCTTAAGC AAGTCACTGA     120

ACTTCTCTGG ATTCCCTTCT CCTTNAGTAA AATAAGNATG TTATCTGNCC GCCCTGCCTN     180

GGNNATTGNG ATAAGGAT                                                  198

(2) INFORMATION FOR SEQ ID NO:108:

(i) SEQUENCE CHARACTERISTICS:
           (A) LENGTH: 500 base pairs
           (B) TYPE: nucleic acid
           (C) STRANDEDNESS: single (D) TOPOLOGY: linear (ii) MOLECULE TYPE: DNA (genomic)

(xi) SEQUENCE DESCRIPTION: SEQ ID NO:108:

| | |
|---|---|
| CTGCAGTGAG CCGTGATTGC ACCACTTTAC TCCAGCCTGG GCAACAAAAT GAGACCCTGG | 60 |
| CTCAAAAACA AAAACAAAAA CAAAAAAAGA GTAAATTAAT TTAAAGGGAA GTATTAAATA | 120 |
| AATAATAGCA CAGTTGATAT AGGTTATGGT AAAATTATAA AGGTGGGATA TTAATATCTA | 180 |
| ATGTTTGGGA GCCATCACAT TATTCTAAAT AATGTNTTGG TGAAAATTAT TGTACATCTT | 240 |
| TTAAAATCTG TGTAATTTTT TTTCAGGGAA GTGTTTAAAA CCTATAACGT TGCTGTGGAC | 300 |
| TACATTACTG TTGCACTCCT GATCTGGAAT TTTGGGTGTG GTGGGAATGA TTTCCATTCA | 360 |
| CTGGAAAGGT CCACTTCGAC TCCAGCAGGC ATATCTCATT ATGATTAGTG CCTCATGGNC | 420 |
| CTGGTGTTTA TCAAAGTACC TCCCTGAATG GACTGCGTGG GTCATCTTGG NTGTGATTCA | 480 |
| GTATATGGTA AAACCCAAGA | 500 |

(2) INFORMATION FOR SEQ ID NO:109:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:109:

| | |
|---|---|
| CTGCAGCCTT GACCTCCTGG GATCAATCGA TCCTCCCACC TCAGCCTCCT AAGTAGCTGG | 60 |
| AACTACAGGT GTGCACCACC ATGCCCGGCT AATNGNTGTA TTTTCTGTAG ATACGAGGTN | 120 |
| TNGCCATGTT GCCCAGGCTG GTCTTGAACT CTGGGCTTAG GTGATCTGCC CGCCTCAGCC | 180 |
| TCCCAAAGTG CTAAGATTAC AGGCATGAGC TACCATGCCC AGCCGAAATC TTCAAATGAA | 240 |
| AAAGTTACTA TAGCTAATTA ATGATTTACT GAAGAGTTAT GGGATGTACA CGTTACCATT | 300 |
| TTCTCTAAAT CAAGATAAAG AGATGAGGAA AGAAAACACT CCAGTGGGGC ATTCCTGTNA | 360 |
| CAAAACAAAT TATCAGTCTT GGGGTTTNAC CATATACTGA AATCACAGGC AAGATGAGCC | 420 |
| ACGCAGTCCA TNCAGGGAGG TACTGGATAA CACCAGGGNC ATGAGGGACT AATCATAATG | 480 |
| AGATATGCTG CTGGAGTCGA | 500 |

(2) INFORMATION FOR SEQ ID NO:110:

(i) SEQUENCE CHARACTERISTICS:
        (A) LENGTH: 550 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:110:

| | |
|---|---|
| CTGCAGGATG AGAGCGATCT CTTNTTNCAT TTCCTGCGCT ACGCGCTGCG GGCGACCAAA | 60 |
| TTCTTTCGCC ATAATAAATT CTCCTGACNA AAAAGGGGCT GTTAGCCCCT TTTTAAAATT | 120 |
| AATTTCAGGT GGAAGGGCTG TTCACGTTGA CCTGATAAGA CGCGCCAGCG TCACATCAGG | 180 |
| CAATCCATGC CGGATGCAGC GTAAACGCCT TATCCCGCAT GGAACCCTAA AAACCTTAAG | 240 |
| CAATGGTACG TTGGATCTCG ATGATTTCGA ATACTTCGAT CACATCGNCA GTGCGGACGT | 300 |
| CGTTGTAGTT CTTAACGCCG ATACCACATT CCATACCGTT ACGGGACTTC GTTAACGTCA | 360 |

```
TCTTTGGAAG CGGGGCAGGG ACTCCAGCTC GNCTTCGTAG ATAACCACGT TGGCACGCAG      420

GAACGCGGGT CGGGTTGTGA CGTTTAACAC AACTTCCGGG TAACCATACA GGCTGNGATG      480

GNACCAAATT TCGGGGGATT TGGACAAGTC AAGAACTTCC CGCCAGACCG ATAATCTTGT      540

TGTTCAGTTC                                                            550
```

(2) INFORMATION FOR SEQ ID NO:111:

(i) SEQUENCE CHARACTERISTICS:
        (A) LENGTH: 541 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:111:

```
CTGCAGCTTT CCTTTAAACT AGGAAGACTT GTTCCTATAC CCCAGTAACG ATACACTGTA       60

CACTAAGCAA ATAGCAGTCA AACCCAAATG AAATTTNTAC AGATGTTCTG TGTCATTTTA      120

TNTTGTTTAT GTTGTCTCCC CCACCCCCAC CAGTTCACCT GCCATTTATT TCATATTCAT      180

TCAACGTCTN NNTGTGTAAA AAGAGACAAA AAACATTAAA CTTTTTTCCT TCGTTAATTC      240

CTCCCTACCA CCCATTTACA AGTTTAGCCC ATACATTTTA TTAGATGTCT TTTATGTTTT      300

TCTTTTNCTA GATTTAGTGG CTGNGTTGTG TCCGAAAGGT CCACTTCGTA TTGCTGGTTG      360

AAACAGCTCA GGAGAGAAAT GAAACGCTTT TTCCAGCTCT CATTTACTCC TGTAAGTATT      420

TGGAGAATGA TATTGAATTA GTAATCAGNG TAGAATTTAT CGGGAACTTG AAGANATGTN      480

ACTATGGCAA TTTCANGGNA CTTGTCTCAT CTTAAATGAN AGNATCCCTG GACTCCTGNA      540

G                                                                     541
```

(2) INFORMATION FOR SEQ ID NO:112:

(i) SEQUENCE CHARACTERISTICS:
        (A) LENGTH: 241 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:112:

```
NNCCCNCNCN NNNNNNNTTN NTNTTGCCCG ATAACTATAG GGNGACTTGG AGATCCACCG       60

CGGTGGCGGN CGNTCTAGAA CTAGTGGATC CCCCGGGNTG CAGGACCCAA CGCTGCCCGA      120

GATGCGCCGC GTGCGGTTGC TGGAGATGGC GGACGCGATG GATATGTTCT GCCAAGGGTT      180

GGTTTGCGCA TTCACAGTTC TCCGCAAGAA TTGATTGGCT CCAATTCTTG GAGTGGTGAA      240

T                                                                     241
```

(2) INFORMATION FOR SEQ ID NO:113:

(i) SEQUENCE CHARACTERISTICS:
        (A) LENGTH: 834 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:113:

```
CCCCCCCNCC NNNNNTTTTN NGCAGCCCGT AATTACCCTC ACTNCCGGGA ACAAAAGCTG       60
```

```
GGTACCGGGC CCCCCCTCGA GGTCGACGGT ATCGATAAGC TTGATATCGA ATTCCTGCAG    120

TGTTTAAAAA ATAAAATAAA CTAAAAGTTT ATTTATGAGG AGTACACTGC TTTCTTGTAA    180

ACACATGTAC AAGCCATATA ATAGAGTTCA TTTTTTACCC TAGTTACGGA AACACTAGAA    240

AGTCTTCACC CGGCCAAGAT AACACATCTT TAGTAAAAAT AGCAAGAAAT ATTTTATGGG    300

TTGTTTACTT AAATCATAGT TTTCAGGTTG GGCACAGTGG NTCATGCCTG TAATCCCAGC    360

ACTTTATGCG GNTGAGGCAG GCAGATCAGT TGAGGTCAGA AGTTTGGAGA CCAGNCTGGG    420

CAATGTGGNA AAACCTCATC TCCACTAAAA ATACAAAAAT TAGNCAGGCA TGGTGGTGCA    480

CACATGTAAT TCCAGNTACT TGGGGAGGCT GAGACAGGAG GATCGNTTGA ACCTAGGGAG    540

GGAGGAGTTG GAGTGAGCTA ATGTCAATGC ACTCTTGGTT GGGGCGANAG AGCAAGATCT    600

TTCTTCCAAA AAAAAAAAAA AAAAAAAAGC CAGGTGNGGN GGTCAAGGCT GTAATCCAGA    660

ATTNGGGAGG CCGNGGAGGN NATCANTGNG GNAGGNGTCA AGNGGGGCNG GCCACATGGG    720

GAACCCGTTN TTNTTAAATN AAAATTAGCC GGGGNGGGGG AGGACTNTAT CCNGTTCCGG    780

NGGTGNGGAG GATCNTTATT NTGGNGGAGG GTGGATGNNC CAGTTGACNC CCCC          834
```

(2) INFORMATION FOR SEQ ID NO:114:

(i) SEQUENCE CHARACTERISTICS:
        (A) LENGTH: 838 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:114:

```
TTGGGCNCNC GCCCCTTAAN TTTTTATNGN TTNCTANAAA AANANNNGGC NCNNTAAAAT     60

ATATTTTTTN TTGTGACCCC TTTTAAAAGG GACCCNCTAA AAAATTTTNT GGTTNNTTTN    120

GATTTANGTG GGTGNTTTTN TTATATTTTT GGNGAGNNTC TGTAGTCNTC NCCCTCAAAC    180

ANNTCNTACN ATNGGNANCG TGACTCTGTC NTTNGTANAN NTCGNTNTCN NGTNATTCNA    240

GGNNCCTCGC GCNNCNCGGG CNNNGTTTTT TTTNNCNNTT TTTAAGCCNA ANNCTCAGTA    300

NCNTCCAACG GNGCTNNGAC ANNNGNNNCT NTCGNGGGTN CCCTCTNTNT NGNNCNNGGC    360

TNNNGNNNNC NGNCNGCNGN GCCNTGCGNN NNGNNNGNGG NNNGNTNNCA TANGGATNGN    420

GNTGCTCNNC NCNNGNGTNN TNAGTAGGNA NTTTTNTNNT ACTTGCCNNC NNNTNGCTGC    480

GAGNANAGCN ANNTNGNNGN AGNGNNGNTG CGCGGANNTT CCCCTGATNA NCTCGAGCNG    540

NTTACNGGNG CNNCCTNGAA NAAGNGNNGT ANNGTGCCGA GNCGCTANNC TGAGCCTGAG    600

TNTCGACNGG NATNGTGNNT CNTACNGTTA NGGGNNGCNN GANCGGGNTG ANTCNCCGGN    660

NGANCNAGCG ACTGCCTNTC ANGCGAANCG TNTCANGNNN GTAGAGCANA GGGTNANNNG    720

TCNNNNAAGC NTNNAGTGAN TGTCNTNACN NGTGANTTAC GGCNTAGNCT TGATNTNNAN    780

NCGAGGNNNN ATNNANNNTT GGANANTTNN TNNNNTCNCN TCGCGGNGNG NCNNGCCG     838
```

(2) INFORMATION FOR SEQ ID NO:115:

(i) SEQUENCE CHARACTERISTICS:
        (A) LENGTH: 803 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:115:

| | | | | | |
|---|---|---|---|---|---|
| ATTCGCGCGT | AGCCCGATAA | CTATAGGGCG | ACNTGGAGNT | CCACCGCGGT | GGCGGCCGCT | 60 |
| CTAGNAACTA | GTGGATCCCC | CGGGCTGCAG | GAATTCACGG | ACTAATCCTC | TACAGATCTT | 120 |
| GCTGGAGTGG | CCTTTCAGCC | TTTTGTGACT | GTTTGTAGTG | AAATGTACAC | ACAAGCCTAC | 180 |
| AAGGCAGCCC | AGATGTACCA | TAACTGTGGG | AAAATTAAAA | AAAAAAAAAC | ACAGAACCTC | 240 |
| TCTATGTTGC | CCATGCTGGA | CTCAAACTCT | TAGACAAGCA | ATCCTCGTAC | CTCAGCCTCC | 300 |
| TGAGTTCCTG | AGTAGCTGGG | ACTACAAGCA | TGCACCACCA | TGCCAGGCTA | TGAGAAAGTT | 360 |
| CTTTTTATTG | ATCCAGACCT | TATTGCCTGG | TAACTTCCAC | CACTGTTCCT | AGCTCTGNTC | 420 |
| TCTGGTCCTA | ACAGAGGAAA | ATCTTGACCC | CACACCTAGT | GCAACTGGAT | AGCTTATNGT | 480 |
| TGGGCTNGTG | TTTCCTCTAT | TCTGGGTCCA | CCCTAAAATC | CNATAGATAC | TCCAACTGCT | 540 |
| CANAGNAAAC | CAAGCTCTCT | CTCTNNCTTN | CTTTCTTNNN | CTCTATTNAT | TNATGGGNNA | 600 |
| TNATTNATTN | NGGGGATGGN | GTTCGGTCGC | CGCCCGGCTG | GNGTGAAATG | GGGGAGGCAA | 660 |
| TCAATTTAAC | CCCACCCNGG | GTCCAGGGAT | CTCGTTNAAA | CCGNNNNNNN | NNNNNNNNNA | 720 |
| NGNNCNNCNC | NNNCCNNTNN | NNNGGTTTNN | NNGNNNNGGG | NNNCCNNNNN | NANNNNNNTN | 780 |
| NNNCCNCCNA | NNNTNCNNNN | CCC | | | | 803 |

(2) INFORMATION FOR SEQ ID NO:116:

(i) SEQUENCE CHARACTERISTICS:
        (A) LENGTH: 780 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:116:

| | | | | | |
|---|---|---|---|---|---|
| CNNNNNNNCC | CNNNTNATTNT | ACGCCAGCCG | CGTAATTAAC | CCTCACTAAA | GGGAACAAAA | 60 |
| GCTGGGTACC | GGGCCCCCCC | TCGAGGTCGA | CGGTATCGAT | AAGCTTGATA | TCGAATTCCA | 120 |
| ACTCCTCACT | TGCCAGATGT | GACCTTAAGC | AAGTGAACTT | CTGTGTGCCA | CACTGTTTTC | 180 |
| ATCTGTAAAA | GGATAAAGGG | AATATCATAA | ATTAGNTTGT | TAAGCCTTAG | TTTAATAATG | 240 |
| TCTCTAAGTT | TTACATATAA | GTAGACAGTG | TCTTTCTTGT | TTAGTGAATA | ATCATTCTTA | 300 |
| TTATTTAATA | GTATCTCTAC | TAAATTTATT | GTGTAAGATT | ATACTAATCT | TGTTTAGTGC | 360 |
| GTGGTAATCA | CTTCTGCTCA | TATTTAACCT | ATAAGCATAA | TATAGTTTAT | TTATATACCA | 420 |
| NTTATTTATT | TTATTTTATT | TGNNGAGATG | CAGCTTGTCT | TTTNCAACCC | AGGGNTGNGG | 480 |
| NGNAGNNGNG | NAANCTTGNT | TCACTGNAAC | CNCCACCNCC | CAGGTNCAAG | NGATTCTCCT | 540 |
| GNTCAAGCCN | CCTNAGNAGN | TGGNATTACA | GNACGANTAC | ANNCCAGNTA | NNNNGGNTNT | 600 |
| NNGNTNGNNA | GGNNNCACAN | NNGNCAGGTN | NNTCGNCTCC | NNGCCANTNA | CTNNNNCCAN | 660 |
| CCCCNNNGNN | NNNNATANAG | NATNANCANN | NNCCNCNNNN | NCNNNNNNNG | GNGGANNCCN | 720 |
| NNTNGCNGNN | ANNGNNANNN | NNTNNNNNNN | NNGGNCNNNG | NNNNNNNNCC | NNNNNNCCCC | 780 |

(2) INFORMATION FOR SEQ ID NO:117:

(i) SEQUENCE CHARACTERISTICS:
        (A) LENGTH: 803 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:117:

| | | | | | |
|---|---|---|---|---|---|
| NNNNNNNNNC | CNNNNNNTTC | GNNCGTAACN | CGANTCACTA | TAGGGCGACT | TGGAGCTCCA | 60
| CCGCGGTGGC | GGCCGCTCTA | GAACTAGTGG | ATCCCCCGGG | CTGCAGGAAT | TCGATATCAA | 120
| GCTTTNGTGT | GTAAAAAGTA | TTAGAATCTC | ATGTTTTTGA | ACAAGGTTGG | CAGTGGGTTG | 180
| GGAGGAGGGA | TTGGAGATTG | ATGCGATAGG | AATGTGAAGG | GATAGCTTGG | GGTGGATTTT | 240
| ATTTTTTAAT | TTTAATTTTT | ATTTNTTGAG | ATGGAGTCTT | GCTCTGTCTC | CCAGGCTGGA | 300
| GTGCAGTGGT | GTGATCTCAG | CTCACGGGTT | CAAGCGATTC | TCCTGCTGCA | GCCTCCCGAG | 360
| TAGCTGGGAT | TACAGGAGCG | CGCCACCACA | CCCGGNTAAT | TTNNTTGTAT | TTTTAGTAGA | 420
| GACGGGGTTT | CACCATGTTG | GTTAGGCTGG | TCTAGAACTC | CCAACCTCAT | GATCCGCCTG | 480
| CTTCGGCCTC | CCAAAGTGCC | GGAATTACAG | GCGTGAGCGA | CTGCACCCGG | CCGCTTGGGG | 540
| GTGGATTTTT | AAAGAAATTT | AGAAGAATGT | AACTTGGCCA | GATACCATGT | ACCCGTTAAT | 600
| TCATTTNCGG | TTTTTTGGAT | ACCCATTTTG | NNATTCTCCC | NCCACTGGAT | AAATAAGGGN | 660
| GGTTCATTNT | NGNTTAGTTT | GGGTNTTTTT | NAGTGTGGNT | TCTGCTTATN | ATTAGAATGG | 720
| NCTNCTTTNC | CAANCTGGAA | AGGGAGGAGT | TAAAATCANT | ACCAGAANCA | GAAATTCTTT | 780
| TCANTTGTTG | CNCNAGAAAT | GCC | | | | 803

(2) INFORMATION FOR SEQ ID NO:118:

(i) SEQUENCE CHARACTERISTICS:
      (A) LENGTH: 819 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:118:

| | | | | | |
|---|---|---|---|---|---|
| TNCCNNNNCN | NNNNNAATTT | TNGCAGNCGC | GTAATTAACC | TCACTAAAGG | GAACAAAAGC | 60
| TGGGTACCGG | GCCCCCCCTC | GAGGTCGACG | GTATCGATAA | GCTTCCCTCC | CCTTCCTCAG | 120
| CTCTGGCGAC | CCTGCGCTGT | GGTGGTTCTC | CAACCACACT | CATTCTCCTC | AGCTGGCTCC | 180
| TTGCTCTTCT | TCCACCCCCT | CGTTGGAAGT | GTTCCTAAGT | GTTTGGCTTG | GCCTCCTCTT | 240
| CCCCTTCCTT | AGNTTAGACT | TCTCCACTGC | TCCAACATCA | ACTGGAAATC | TATGGAATTG | 300
| ATTCCTGTTT | TCAGCTCCAG | TCCTGTTCAC | AGGGCATTTT | CACCTGCTGG | CACTTCCAAA | 360
| GTGACACTTC | CAAACCACTT | CCTCGCCCTC | CTCTCTAAAC | CAGGTCTTTC | TTCCTAACTT | 420
| CCTTATTTCT | GAGAATGTCT | CTGNCATGTT | CTAAACTGAA | AACTCCTAGT | CAACTNCACA | 480
| CTTTATTCCC | TGGATCCTCA | ATTGGGTTCC | CATGTNCCGT | TAGTGTTTCT | TGGTAAGNCT | 540
| CTGCCANCAC | CGNAGGATCG | ACTCTAATCA | CATCTCAACT | GAATTATGGN | AAAGTCAACT | 600
| CAATTCTCTC | AACCATCCCA | GGCTCCACTA | TGGNTAATAT | GCTAAGGAGA | GCTGACCCAA | 660
| CGGGGAGAAG | ATCTGNGGGG | GAGGAGAGAA | ACAAAGNTAA | TGGAATNATT | CTCGAAAAGC | 720
| CCACAAGGNG | AAGGATAACC | CNCTTCCNCT | CGAAAGAGGG | GGGATCGCCA | GATNTCGCGC | 780
| CCGGAAAGAA | ACCGGGNGA | GGGGGTTACA | NTGTAAGNC | | | 819

(2) INFORMATION FOR SEQ ID NO:119:

(i) SEQUENCE CHARACTERISTICS:
      (A) LENGTH: 796 base pairs
      (B) TYPE: nucleic acid
      (C) STRANDEDNESS: single (D) TOPOLOGY: linear (ii) MOLECULE TYPE: DNA (genomic)

(xi) SEQUENCE DESCRIPTION: SEQ ID NO:119:

```
TNTTGGCTGG TACTGCTTGA GCAACTGGTG AAACTCCGCG CCTCACGCCC CGGGTGTGTC        60
CTTGTCCAGG GGCGACGAGC ATTCTGGGCG AAGTCCGCAC GCCTCTTGTT CGAGGCGGAA       120
GACGGGGTCT GATGCTTTCT CCTTGGTCGG GACTGTCTCG AGGCATGCAT GTCCAGTGAC       180
TCTTGTGTTT GCTGCTGCTT CCCTCTCAGA TTCTTCTCAC CGTTGTGGTC AGCTCTGCTT       240
TAGGCATATT AATCCATAGT GGAGGCTGGG ATGGGTGAGA GAATTGAGGT GACTTTTCCA       300
TAATTCAGGT GAGATGTGAT TAGAGTTCGA TCTGCGGTGG TGGCAGAGGC TTACAAGAAA       360
CACTAACGGG ACATGGGAAC CAATTGAGGA TCAGGGAATA AAGTGTGAAG TTGACTAGGA       420
GGTTTTCAGT TTAGAACATG GCAGAGACAT TCTCAGAAAT AAGGAAGTTA GGAAGAAAGA       480
CTGGTTTAGA GAGGAGGGCG ANGAAGTGGT TTGGGAAGTG TCACTTTGGG AAGTGCCAGC       540
AGGTGAAAAT GCCTGTGACA GGATGGAGCT GAAAACAGGA TCAATTCCAT AGATTCCAGT       600
TGATGTNGGA GCAGGGGAGA AGTCTTAGCT AAGGAAGGGG AAGAGGAGGC CAAGGNAACA       660
CTTAGGACAA TTGNAACGAN GGGGGGGGAG AAGAGNAAGG GCCACTTAGG GGAATAATNT       720
GGTGGGGGAC CCCCAAGNNA GGGCGCANNN TTAGGAGGGG GGGANNTCAN AGGAAAGTGG       780
AAGNTTGGGT TTANCT                                                      796
```

(2) INFORMATION FOR SEQ ID NO:120:

(i) SEQUENCE CHARACTERISTICS:
        (A) LENGTH: 802 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:120:

```
ATTCGTCGTA NCCCGATNAC TATAGGGCGA CTTGGAGCTC CACCGCGGTG GCGGNCGCGG        60
GCAGGGNCCG GNCCTTTGTG GCCGCCCGGG CCGCGAAGCC GGTGTCCTAA AAGATGAGGG       120
GCGGGGCGCG GNCGGTTGGG GCTGGGGAAC CCCGTGTGGG AAACCAGGAG GGGCGGCCCG       180
TTTCTCGGGC TTCGGGCGCG GCCGGGTGGA GAGAGATTCC GGGGAGCCTT GGTCCGGAAA       240
TGCTGTTTGC TCGAAGACGT CTCAGGGCGC AGGTGCCTTG GGCCGGGATT AGTAGCCGTC       300
TGAACTGGAG TGGAGTAGGA GAAAGAGGAA GCGTCTTGGG CTGGGTCTGC TTGAGCAACT       360
GGTGAAACTC CGCGCCTCAC GCCCCGGGTG TGTCCTTGTC CAGGGGCGAC GAGCATTCTG       420
GGCGAAGTCC GCACGCCTCT TGTTCGAGGC GGAAGACGGG GTCTTGATGC TTTCTCCTTG       480
GGTCGGGGAC TGTCTCGAGG CATGCATGTC CAGTGACTCT TGTGTTTGGT GNTGCTTCCC       540
TCTCAGATCT TCTCACCGNG GTGGGCAACT CTGTTTAGGC ATATTATCCA TAGNGGAGGC       600
TGGATGGTTG AAANAATTGA GGTNATTTTC CATAATCAAG TGAAATTTGA TAGAGTCCGN       660
CTTTNGGGGT GNAAGGGTTA AAAAAAAATA ACGGAAATGG AACAATGAGG TCAAGGATTA       720
GTTGAGTTGN TAGNGGTTCA ATTAGANATG AAGGNATCTA AAATAGGAGT AGAGAANNNG       780
TTNAAAGAGG GAAAATTTTG CC                                               802
```

(2) INFORMATION FOR SEQ ID NO:121:

(i) SEQUENCE CHARACTERISTICS:

(A) LENGTH: 793 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:121:

ATATGCAGCC GCGTAATTAA CCTCACTAAA GGGAACAAAA GCTGGGTACC GGGCCCCCCC      60

TCGAGGTCGA CGGTATCGAT AAGCTTGATA TCGAATTCCT GCAGCCCGGG GGATCCGCCC     120

CGCGGCCTCC CAAAGTGCTG GGATTACAGG CGTGAGCCAC CGCCCCGGGN CTCACATTTT     180

ATTTCTATTG GCTAGCGCTG CTCTAAATCT TCTGTTCCTT CTGCTACACC AGGCCTAACA     240

CTCAAAATCC CTGCCAACCT TTTCCTTCCT GAAGCTTCCC TCCCCTTCCT CAGCTCTGGC     300

GACCCTGCGC TGTGGTGGTT CTCCAACCAC ACTCATTCTC CTCAGCTGGC TCCTTGCTCT     360

TCTTCCACCC CCTCGNTGGA AGTGTTCCTA AGTGTTTGGC TTGGCCTCCT CTTCCCCTTC     420

CTTAGCTTAG ACTTCTCCAC TGCTCCAACA TCAACTGGAA ATCTATGGAA TTGATTCCTG     480

TTTCAGCTCC AGTCCTGTTC ACAGGGGATT TTCANCTGGT GGCATTTCCA AAGTGAAATT     540

CCAAACCACT TCCTCGGCCT CCTCTTCTAA ANCAGGTCTT TCTTCCTAAC TTCCTTATTC     600

TTGAGAATGT CTCTGCATGT TCTTAAANTG AAAACTCCTA GTCAAATTCA AATTTATCCC     660

TGATCCCAAA TGGTCCCATT CCCGTAGGGT TTNTGTAGCC TGCACACCGA GGTCGGANTT     720

TATNNATTCA CCGATTATGG AAAGTAACCA ATCTTNACCA NCCAGCTCAT TTGTTNTNTG     780

CTAAGAGGGT NCC                                                      793

(2) INFORMATION FOR SEQ ID NO:122:

(i) SEQUENCE CHARACTERISTICS:
        (A) LENGTH: 440 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:122:

AAAGTCATGG ATTCCTTTAG GTAGCTACAT TATCAACCTT TTTGAGAATA AAATGAATTG      60

AGAGTGTTAC AGTCTAATTC TATATCACAT GTAACTTTTA TTTGGATATA TCAGTAATAG     120

TGCTTTTTCN TTTTTTTTTT TTNTTTTTTT TNNTTTTNGG GGANAGAGTC TCGCTCTGTC     180

GCCAGGTTGG AGTGCAATGG TGCGATCTTG GCTCACTGAA AGCTCCACCN CCCGGGTTCA     240

AGTGATTCTC CTGCCTCAGC CNCCCAAGTA GNTGGGACTA CAGGGGTGCG CCACCACGCC     300

TGGGATAATT TTGGGNTTTT TAGTAGAGAT GGCGTTTCAC CANCTTGGNG CAGGCTGGTC     360

TTGGAACTCC TGANATCATG ATCTGCCTGC CTTAGCCTCC CCAAAGTGCT GGGATTNCAG     420

GGGTGAGCCA CTGTTCCTGG                                               440

(2) INFORMATION FOR SEQ ID NO:123:

(i) SEQUENCE CHARACTERISTICS:
        (A) LENGTH: 453 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:123:

```
CTTAGTCTGT NTCGTAGTCA TATTAATTGT AAGTNTACAC TAATAAGAAT GTGTCAGAGC      60

TCTTAATGTC AAAACTTTGA TTACACAGTC CCTTTAAGGC AGTTCTGTTT TAACCCCAGG     120

TGGGTTAAAT ATTCCAGCTA TCTGAGGAGC TTTTNGATAA TTGGACCTCA CCTTAGTAGT     180

TCTCTACCCT GGCCACACAT TAGAATCACT TGGGAGCTTT TAAAACTGTA AGCTCTGCCC     240

TGAGATATTC TTACTCAATT TAATTGTGTA GTTTTTAAAA TTCCCCAGGA AATTCTGGTA     300

TTTCTGTTTA GGAACCGCTG CCTCAAGCCT AGCAGNACAG ATATGTAGGA AATTAGCTCT     360

GTAAGGTTGG TCTTACAGGG GATAAACAGA TCCTTCCTTA GNCCCTGGGA CTTAATCACT     420

GAGAGTTTGG GTGGNGGTTT NGNATTTAAT GAC                                 453
```

(2) INFORMATION FOR SEQ ID NO:124:

(i) SEQUENCE CHARACTERISTICS:
        (A) LENGTH: 369 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:124:

```
GACACACATT CACACATAAT TATGAAAGCA TTTTCAGGCA AAACTCAATC ACAAGTCTGG      60

GTTTTTAACA TAGTTAACTG AATATTTCCC TTGGGGGGTT AAATTTTAGA ACAGACGTNC     120

ATNCAATCTG GAAGAAGAGC TATGAAAAAA ACCTAGCTTG GGTNGGTTTC ATAGGGTNCA     180

TTATGNACAC ATTGTTATTT TATCCCTTAA TNCTAGTAAA GAAATAGAAT CTGAAAATAA     240

GTAAAACTAC TTGGAAAAAA NTTAAAAGAT ACAGAAATTT CTATCTTAAA TGATGTGTGG     300

GCCNCTGTGA TTTTAGTNGG GNTGGTTAAA ANCCCAGAGG TGAAGAGNAT NCTCTATGCT     360

GTGNGGGGG                                                            369
```

(2) INFORMATION FOR SEQ ID NO:125:

(i) SEQUENCE CHARACTERISTICS:
        (A) LENGTH: 516 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:125:

```
GCTCATCATG CTTCACGGGG GAGGCTGTGC GGGAAGAATG CTCCCACACA GNATAAAGAA      60

TGCTCCCGCA CAGGATAGAG AATGCCCCCG CACAGCATAG AGAAGCCCCC GCACAGCATA     120

GAGAATGCCC CCNCACAGCA TAGAGAAGCC CCCGCACAGC ATAGAGAATG CTCTTCACCT     180

CTGGGTTTTT AACCAGCCAA ACTAAAATCA CAGAGGSCMA CACATCATTT AAGATAGAAA     240

TTTCTGTATC TTTTAATTTY TTTCMAAGTA GTTTTACTTA TTTTCAGATT CTATTTCTTT     300

ACTAGAATTA AGGGATAAAA TAACAATGTG TGCATAATGA ACCCTATGAA ACMAACMMAA     360

GCTAGGTTTT TTTCATAGST CTTCTTCCAG ATTGAATGAA CGTCTGTTCT AAAATTTAAC     420

CCCCAGGGA AATATTCAGT TAACTATGTT AAAAACCCAG ACTTGTGATT GAGTTTTGCC     480

TGAAAATGCT TCATAATTA TGTGTGAATG TGTGTC                               516
```

(2) INFORMATION FOR SEQ ID NO:126:

(i) SEQUENCE CHARACTERISTICS:
        (A) LENGTH: 121 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:126:

GTATAATGCA GGTGCTATAA GGTGAGCATG AGACACAGAT CTTTGCTTTC CACCCTGTTC    60

TTCTTATGGT TGGGTATTCT TGTCACAGTA ACTTAACTGA TCTAGGAAAG AAAAAATGTT   120

T                                                                  121

(2) INFORMATION FOR SEQ ID NO:127:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:127:

TGGAGACTGG AACACAAC                                                  18

(2) INFORMATION FOR SEQ ID NO:128:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:128:

GTGTGGCCAG GGTAGAGAAC T                                              21

(2) INFORMATION FOR SEQ ID NO:129:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:129:

ATCTCCGGCA GGCATATCT                                                 19

(2) INFORMATION FOR SEQ ID NO:130:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:130:

TGAAATCACA GCCAAGATGA G                                              21

(2) INFORMATION FOR SEQ ID NO:131:

(i) SEQUENCE CHARACTERISTICS:
        (A) LENGTH: 19 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:131:

CCATAGCCTG TTTCGTAGC                                                    19

(2) INFORMATION FOR SEQ ID NO:132:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:132:

CCATAGCCTA TTTCGTAGC                                                    19

(2) INFORMATION FOR SEQ ID NO:133:

(i) SEQUENCE CHARACTERISTICS:
        (A) LENGTH: 2791 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:133:

TGGGACAGGC AGCTCCGGGG TCCGCGGTTT CACATCGGAA ACAAAACAGC GGCTGGTCTG        60

GAAGGAACCT GAGCTACGAG CCGCGGCGGC AGCGGGGCGG CGGGGAAGCG TATACCTAAT       120

CTGGGAGCCT GCAAGTGACA ACAGCCTTTG CGGTCCTTAG ACAGCTTGGC CTGGAGGAGA       180

ACACATGAAA GAAAGAACCT CAAGAGGCTT TGTTTTCTGT GAAACAGTAT TTCTATACAG       240

TTGCTCCAAT GACAGAGTTA CCTGCACCGT TGTCCTACTT CCAGAATGCA CAGATGTCTG       300

AGGACAACCA CCTGAGCAAT ACTGTACGTA GCCAGAATGA CAATAGAGAA CGGCAGGAGC       360

ACAACGACAG ACGGAGCCTT GGCCACCCTG AGCCATTATC TAATGGACGA CCCCAGGGTA       420

ACTCCCGGCA GGTGGTGGAG CAAGATGAGG AAGAAGATGA GGAGCTGACA TTGAAATATG       480

GCGCCAAGCA TGTGATCATG CTCTTTGTCC CTGTGACTCT CTGCATGGTG GTGGTCGTGG       540

CTACCATTAA GTCAGTCAGC TTTTATACCC GGAAGGATGG GCAGCTAATC TATACCCCAT       600

TCACAGAAGA TACCGAGACT GTGGGCCAGA GAGCCCTGCA CTCAATTCTG AATGCTGCCA       660

TCATGATCAG TGTCATTGTT GTCATGACTA TCCTCCTGGT GGTTCTGTAT AAATACAGGT       720

GCTATAAGGT CATCCATGCC TGGCTTATTA TATCATCTCT ATTGTTGCTG TTCTTTTTTT       780

CATTCATTTA CTTGGGGGAA GTGTTTAAAA CCTATAACGT TGCTGTGGAC TACATTACTG       840

TTGCACTCCT GATCTGGAAT TTTGGTGTGG TGGGAATGAT TTCCATTCAC TGGAAAGGTC       900

CACTTCGACT CCAGCAGGCA TATCTCATTA TGATTAGTGC CCTCATGGCC CTGGTGTTTA       960

TCAAGTACCT CCCTGAATGG ACTGCGTGGC TCATCTTGGC TGTGATTTCA GTATATGATT      1020

TAGTGGCTGT TTTGTGTCCG AAAGGTCCAC TTCGTATGCT GGTTGAAACA GCTCAGGAGA      1080

GAAATGAAAC GCTTTTTCCA GCTCTCATTT ACTCCTCAAC AATGGTGTGG TTGGTGAATA      1140

TGGCAGAAGG AGACCCGGAA GCTCAAAGGA GAGTATCCAA AAATTCCAAG TATAATGCAG      1200

AAAGCACAGA AAGGGAGTCA CAAGACACTG TTGCAGAGAA TGATGATGGC GGGTTCAGTG      1260

-continued

```
AGGAATGGGA AGCCCAGAGG GACAGTCATC TAGGGCCTCA TCGCTCTACA CCTGAGTCAC   1320

GAGCTGCTGT CCAGGAACTT TCCAGCAGTA TCCTCGCTGG TGAAGACCCA GAGGAAAGGG   1380

GAGTAAAACT TGGATTGGGA GATTTCATTT TCTACAGTGT TCTGGTTGGT AAAGCCTCAG   1440

CAACAGCCAG TGGAGACTGG AACACAACCA TAGCCTGTTT CGTAGCCATA TTAATTGGTT   1500

TGTGCCTTAC ATTATTACTC CTTGCCATTT TCAAGAAAGC ATTGCCAGCT CTTCCAATCT   1560

CCATCACCTT TGGGCTTGTT TTCTACTTTG CCACAGATTA TCTTGTACAG CCTTTTATGG   1620

ACCAATTAGC ATTCCATCAA TTTTATATCT AGCATATTTG CGGTTAGAAT CCCATGGATG   1680

TTTCTTCTTT GACTATAACC AAATCTGGGG AGGACAAAGG TGATTTTCCT GTGTCCACAT   1740

CTAACAAAGT CAAGATTCCC GGCTGGACTT TTGCAGCTTC CTTCCAAGTC TTCCTGACCA   1800

CCTTGCACTA TTGGACTTTG GAAGGAGGTG CCTATAGAAA ACGATTTTGA ACATACTTCA   1860

TCGCAGTGGA CTGTGTCCCT CGGTGCAGAA ACTACCAGAT TTGAGGGACG AGGTCAAGGA   1920

GATATGATAG GCCCGGAAGT TGCTGTGCCC CATCAGCAGC TTGACGCGTG GTCACAGGAC   1980

GATTTCACTG ACACTGCGAA CTCTCAGGAC TACCGGTTAC CAAGAGGTTA GGTGAAGTGG   2040

TTTAAACCAA ACGGAACTCT TCATCTTAAA CTACACGTTG AAAATCAACC CAATAATTCT   2100

GTATTAACTG AATTCTGAAC TTTTCAGGAG GTACTGTGAG GAAGAGCAGG CACCAGCAGC   2160

AGAATGGGGA ATGGAGAGGT GGGCAGGGGT TCCAGCTTCC CTTTGATTTT TTGCTGCAGA   2220

CTCATCCTTT TTAAATGAGA CTTGTTTTCC CCTCTCTTTG AGTCAAGTCA AATATGTAGA   2280

TTGCCTTTGG CAATTCTTCT TCTCAAGCAC TGACACTCAT TACCGTCTGT GATTGCCATT   2340

TCTTCCCAAG GCCAGTCTGA ACCTGAGGTT GCTTTATCCT AAAAGTTTTA ACCTCAGGTT   2400

CCAAATTCAG TAAATTTTGG AAACAGTACA GCTATTTCTC ATCAATTCTC TATCATGTTG   2460

AAGTCAAATT TGGATTTTCC ACCAAATTCT GAATTTGTAG ACATACTTGT ACGCTCACTT   2520

GCCCCCAGAT GCCTCCTCTG TCCTCATTCT TCTCTCCCAC ACAAGCAGTC TTTTTCTACA   2580

GCCAGTAAGG CAGCTCTGTC TGGTAGCAGA TGGTCCCATT ATTCTAGGGT CTTACTCTTT   2640

GTATGATGAA AAGAATGTGT TATGAATCGG TGCTGTCAGC CCTGCTGTCA GACCTTCTTC   2700

CACAGCAAAT GAGATGTATG CCCAAAGCGG TAGAATTAAA GAAGAGTAAA ATGGCTGTTG   2760

AAGCAAAAAA AAAAAAAAAA AAAAAAAAA A                                 2791
```

(2) INFORMATION FOR SEQ ID NO:134:

(i) SEQUENCE CHARACTERISTICS:
        (A) LENGTH: 467 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:134:

```
Met Thr Glu Leu Pro Ala Pro Leu Ser Tyr Phe Gln Asn Ala Gln Met
1               5                   10                  15

Ser Glu Asp Asn His Leu Ser Asn Thr Val Arg Ser Gln Asn Asp Asn
            20                  25                  30

Arg Glu Arg Gln Glu His Asn Asp Arg Arg Ser Leu Gly His Pro Glu
        35                  40                  45

Pro Leu Ser Asn Gly Arg Pro Gln Gly Asn Ser Arg Gln Val Val Glu
    50                  55                  60

Gln Asp Glu Glu Glu Asp Glu Glu Leu Thr Leu Lys Tyr Gly Ala Lys
```

-continued

```
            65                  70                  75                  80
His Val Ile Met Leu Phe Val Pro Val Thr Leu Cys Met Val Val
                    85                  90                  95
Val Ala Thr Ile Lys Ser Val Ser Phe Tyr Thr Arg Lys Asp Gly Gln
                100                 105                 110
Leu Ile Tyr Thr Pro Phe Thr Glu Asp Thr Glu Thr Val Gly Gln Arg
                115                 120                 125
Ala Leu His Ser Ile Leu Asn Ala Ala Ile Met Ile Ser Val Ile Val
            130                 135                 140
Val Met Thr Ile Leu Leu Val Val Leu Tyr Lys Tyr Arg Cys Tyr Lys
145                 150                 155                 160
Val Ile His Ala Trp Leu Ile Ile Ser Ser Leu Leu Leu Phe Phe
                165                 170                 175
Phe Ser Phe Ile Tyr Leu Gly Glu Val Phe Lys Thr Tyr Asn Val Ala
                180                 185                 190
Val Asp Tyr Ile Thr Val Ala Leu Leu Ile Trp Asn Phe Gly Val Val
                195                 200                 205
Gly Met Ile Ser Ile His Trp Lys Gly Pro Leu Arg Leu Gln Gln Ala
            210                 215                 220
Tyr Leu Ile Met Ile Ser Ala Leu Met Ala Leu Val Phe Ile Lys Tyr
225                 230                 235                 240
Leu Pro Glu Trp Thr Ala Trp Leu Ile Leu Ala Val Ile Ser Val Tyr
                245                 250                 255
Asp Leu Val Ala Val Leu Cys Pro Lys Gly Pro Leu Arg Met Leu Val
                260                 265                 270
Glu Thr Ala Gln Glu Arg Asn Glu Thr Leu Phe Pro Ala Leu Ile Tyr
            275                 280                 285
Ser Ser Thr Met Val Trp Leu Val Asn Met Ala Glu Gly Asp Pro Glu
290                 295                 300
Ala Gln Arg Arg Val Ser Lys Asn Ser Lys Tyr Asn Ala Glu Ser Thr
305                 310                 315                 320
Glu Arg Glu Ser Gln Asp Thr Val Ala Glu Asn Asp Asp Gly Gly Phe
                325                 330                 335
Ser Glu Glu Trp Glu Ala Gln Arg Asp Ser His Leu Gly Pro His Arg
                340                 345                 350
Ser Thr Pro Glu Ser Arg Ala Ala Val Gln Glu Leu Ser Ser Ser Ile
                355                 360                 365
Leu Ala Gly Glu Asp Pro Glu Glu Arg Gly Val Lys Leu Gly Leu Gly
            370                 375                 380
Asp Phe Ile Phe Tyr Ser Val Leu Val Gly Lys Ala Ser Ala Thr Ala
385                 390                 395                 400
Ser Gly Asp Trp Asn Thr Thr Ile Ala Cys Phe Val Ala Ile Leu Ile
                405                 410                 415
Gly Leu Cys Leu Thr Leu Leu Leu Ala Ile Phe Lys Lys Ala Leu
            420                 425                 430
Pro Ala Leu Pro Ile Ser Ile Thr Phe Gly Leu Val Phe Tyr Phe Ala
                435                 440                 445
Thr Asp Tyr Leu Val Gln Pro Phe Met Asp Gln Leu Ala Phe His Gln
            450                 455                 460
Phe Tyr Ile
465
```

(2) INFORMATION FOR SEQ ID NO:135:

(i) SEQUENCE CHARACTERISTICS:
    (A) LENGTH: 1962 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:135:

```
ACCAACACGG CAGCTGAGGC GGAAACCTAG GCTGCGAGCC GGCCGCCCGG GCGCGGAGAG      60
AGAAGGAACC AACACAAGAC AGCAGCCCTT CGAGGTCTTT AGGCAGCTTG GAGGAGAACA     120
CATGAGAGAA AGAATCCCAA GAGGTTTTGT TTTCTTTGAG AAGGTATTTC TGTCCAGCTG     180
CTCCAATGAC AGAGATACCT GCACCTTTGT CCTACTTCCA GAATGCCCAG ATGTCTGAGG     240
ACAGCCACTC CAGCAGCGCC ATCCGGAGCC AGAATGACAG CCAAGAACGG CAGCAGCAGC     300
ATGACAGGCA GAGACTTGAC AACCCTGAGC CAATATCTAA TGGGCGGCCC CAGAGTAACT     360
CAAGACAGGT GGTGGAACAA GATGAGGAGG AAGACGAAGA GCTGACATTG AAATATGGAG     420
CCAAGCATGT CATCATGCTC TTTGTCCCCG TGACCCTCTG CATGGTCGTC GTCGTGGCCA     480
CCATCAAATC AGTCAGCTTC TATACCCGGA AGGACGGTCA GCTAATCTAC ACCCCATTCA     540
CAGAAGACAC TGAGACTGTA GGCCAAAGAG CCCTGCACTC GATCCTGAAT GCGGCCATCA     600
TGATCAGTGT CATTGTCATT ATGACCATCC TCCTGGTGGT CCTGTATAAA TACAGGTGCT     660
ACAAGGTCAT CCACGCCTGG CTTATTATTT CATCTCTGTT GTTGCTGTTC TTTTTTTCGT     720
TCATTTACTT AGGGGAAGTA TTTAAGACCT ACAATGTCGC CGTGGACTAC GTTACAGTAG     780
CACTCCTAAT CTGGAATTTT GGTGTGGTCG GGATGATTGC CATCCACTGG AAAGCCCCC     840
TTCGACTGCA GCAGGCGTAT CTCATTATGA TCAGTGCCCT CATGGCCCTG GTATTTATCA     900
AGTACCTCCC CGAATGGACC GCATGGCTCA TCTTGGCTGT GATTTCAGTA TATGATTTGG     960
TGGCTGTTTT ATGTCCCAAA GGCCCACTTC GTATGCTGGT TGAAACAGCT CAGGAAAGAA    1020
ATGAGACTCT CTTTCCAGCT CTTATCTATT CCTCAACAAT GGTGTGGTTG GTGAATATGG    1080
CTGAAGGAGA CCCAGAAGCC CAAAGGAGGG TACCCAAGAA CCCCAAGTAT AACACACAAA    1140
GAGCGGAGAG AGAGACACAG GACAGTGGTT CTGGGAACGA TGATGGTGGC TTCAGTGAGG    1200
AGTGGGAGGC CCAAAGAGAC AGTCACCTGG GGCCTCATCG CTCCACTCCC GAGTCAAGAG    1260
CTGCTGTCCA GGAACTTTCT GGGAGCATTC TAACGAGTGA AGACCCGGAG GAAAGAGGAG    1320
TAAAACTTGG ACTGGGAGAT TTCATTTTCT ACAGTGTTCT GGTTGGTAAG GCCTCAGCAA    1380
CCGCCAGTGG AGACTGGAAC ACAACCATAG CCTGCTTTGT AGCCATACTG ATCGGCCTGT    1440
GCCTTACATT ACTCCTGCTC GCCATTTTCA AGAAAGCGTT GCCAGCCCTC CCCATCTCCA    1500
TCACCTTCGG GCTCGTGTTC TACTTCGCCA CGGATTACCT TGTGCAGCCC TTCATGGACC    1560
AACTTGCATT CCATCAGTTT TATATCTAGC CTTTCTGCAG TTAGAACATG GATGTTTCTT    1620
CTTTGATTAT CAAAAACACA AAAACAGAGA GCAAGCCCGA GGAGGAGACT GGTGACTTTC    1680
CTGTGTCCTC AGCTAACAAA GGCAGGACTC CAGCTGGACT TCTGCAGCTT CCTTCCGAGT    1740
CTCCCTAGCC ACCCGCACTA CTGGACTGTG GAAGGAAGCG TCTACAGAGG AACGGTTTCC    1800
AACATCCATC GCTGCAGCAG ACGGTGTCCC TCAGTGACTT GAGAGACAAG GACAAGGAAA    1860
TGTGCTGGGC CAAGGAGCTG CCGTGCTCTG CTAGCTTTGA CCGTGGGCAT GGAGATTTAC    1920
CCGCACTGTG AACTCTCTAA GGTAAACAAA GTGAGGTGAA CC                       1962
```

(2) INFORMATION FOR SEQ ID NO:136:

(i) SEQUENCE CHARACTERISTICS:
    (A) LENGTH: 2285 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:136:

| | | | | | |
|---|---|---|---|---|---|
| GAATTCGGCA | CGAGGGCATT | TCCAGCAGTG | AGGAGACAGC | CAGAAGCAAG | CTTTTGGAGC | 60 |
| TGAAGGAACC | TGAGACAGAA | GCTAGTCCCC | CCTCTGAATT | TTACTGATGA | AGAAACTGAG | 120 |
| GCCACAGAGC | TAAAGTGACT | TTTCCCAAGG | TCGCCCAGCG | AGGACGTGGG | ACTTCTCAGA | 180 |
| CGTCAGGAGA | GTGATGTGAG | GGAGCTGTGT | GACCATAGAA | AGTGACGTGT | TAAAAACCAG | 240 |
| CGCTGCCCTC | TTTGAAAGCC | AGGGAGCATC | ATTCATTTAG | CCTGCTGAGA | AGAAGAAACC | 300 |
| AAGTGTCCGG | GATTCAAGAC | CTCTCTGCGG | CCCCAAGTGT | TCGTGGTGCT | TCCAGAGGCA | 360 |
| GGGCTATGCT | CACATTCATG | GCCTCTGACA | GCGAGGAAGA | AGTGTGTGAT | GAGCGGACGT | 420 |
| CCCTAATGTC | GGCCGAGAGC | CCCACGCCGC | GCTCCTGCCA | GGAGGGCAGG | CAGGGCCCAG | 480 |
| AGGATGGAGA | GAATACTGCC | CAGTGGAGAA | GCCAGGAGAA | CGAGGAGGAC | GGTGAGGAGG | 540 |
| ACCCTGACCG | CTATGTCTGT | AGTGGGGTTC | CCGGGCGGCC | GCCAGGCCTG | GAGGAAGAGC | 600 |
| TGACCCTCAA | ATACGGAGCG | AAGCATGTGA | TCATGCTGTT | TGTGCCTGTC | ACTCTGTGCA | 660 |
| TGATCGTGGT | GGTAGCCACC | ATCAAGTCTG | TGCGCTTCTA | CACAGAGAAG | AATGGACAGC | 720 |
| TCATCTACAC | GCCATTCACT | GAGGACACAC | CCTCGGTGGG | CCAGCGCCTC | CTCAACTCCG | 780 |
| TGCTGAACAC | CCTCATCATG | ATCAGCGTCA | TCGTGGTTAT | GACCATCTTC | TTGGTGGTGC | 840 |
| TCTACAAGTA | CCGCTGCTAC | AAGTTCATCC | ATGGCTGGTT | GATCATGTCT | TCACTGATGC | 900 |
| TGCTGTTCCT | CTTCACCTAT | ATCTACCTTG | GGGAAGTGCT | CAAGACCTAC | AATGTGGCCA | 960 |
| TGGACTACCC | CACCCTCTTG | CTGACTGTCT | GGAACTTCGG | GGCAGTGGGC | ATGGTGTGCA | 1020 |
| TCCACTGGAA | GGGCCCTCTG | GTGCTGCAGC | AGGCCTACCT | CATCATGATC | AGTGCGCTCA | 1080 |
| TGGCCCTAGT | GTTCATCAAG | TACCTCCCAG | AGTGGTCCGC | GTGGGTCATC | CTGGGCGCCA | 1140 |
| TCTCTGTGTA | TGATCTCGTG | GCTGTGCTGT | GTCCCAAAGG | GCCTCTGAGA | ATGCTGGTAG | 1200 |
| AAACTGCCCA | GGAGAGAAAT | GAGCCCATAT | TCCCTGCCCT | GATATACTCA | TCTGCCATGG | 1260 |
| TGTGGACGGT | TGGCATGGCG | AAGCTGGACC | CCTCCTCTCA | GGGTGCCCTC | CAGCTCCCCT | 1320 |
| ACGACCCGGA | GATGGAAGAA | GACTCCTATG | ACAGTTTTGG | GGAGCCTTCA | TACCCCGAAG | 1380 |
| TCTTTGAGCC | TCCCTTGACT | GGCTACCCAG | GGGAGGAGCT | GGAGGAAGAG | GAGGAAAGGG | 1440 |
| GCGTGAAGCT | TGGCCTCGGG | GACTTCATCT | TCTACAGTGT | GCTGGTGGGC | AAGGCGGCTG | 1500 |
| CCACGGGCAG | CGGGGACTGG | AATACCACGC | TGGCCTGCTT | CGTGGCCATC | CTCATTGGCT | 1560 |
| TGTGTCTGAC | CCTCCTGCTG | CTTGCTGTGT | TCAAGAAGGC | GCTGCCCGCC | CTCCCCATCT | 1620 |
| CCATCACGTT | CGGGCTCATC | TTTTACTTCT | CCACGGACAA | CCTGGTGCGG | CCGTTCATGG | 1680 |
| ACACCCTGGC | CTCCCATCAG | CTCTACATCT | GAGGGACATG | GTGTGCCACA | GGCTGCAAGC | 1740 |
| TGCAGGGAAT | TTTCATTGGA | TGCAGTTGTA | TAGTTTTACA | CTCTAGTGCC | ATATATTTTT | 1800 |
| AAGACTTTTC | TTTCCTTAAA | AAATAAAGTA | CGTGTTTACT | TGGTGAGGAG | GAGGCAGAAC | 1860 |
| CAGCTCTTTG | GTGCCAGCTG | TTTCATCACC | AGACTTTGGC | TCCCGCTTTG | GGGAGCGCCT | 1920 |
| CGCTTCACGG | ACAGGAAGCA | CAGCAGGTTT | ATCCAGATGA | ACTGAGAAGG | TCAGATTAGG | 1980 |
| GTGGGGAGAA | GAGCATCCGG | CATGAGGGCT | GAGATGCCCA | AAGAGTGTGC | TCGGGAGTGG | 2040 |

```
CCCCTGGCAC CTGGGTGCTC TGGCTGGAGA GGAAAAGCCA GTTCCCTACG AGGAGTGTTC    2100

CCAATGCTTT GTCCATGATG TCCTTGTTAT TTTATTNCCY TTANAAACTG ANTCCTNTTN    2160

TTNTTDCGGC AGTCACMCTN CTGGGRAGTG GCTTAATAGT AANATCAATA AANAGNTGAG    2220

TCCTNTTAGA AAAAAAAAAA AAAAAAAAAA AAAAAAAAAA AAAAAAAAAA AAAAAAAAAA    2280

AAAAA                                                                2285
```

(2) INFORMATION FOR SEQ ID NO:137:

(i) SEQUENCE CHARACTERISTICS:
        (A) LENGTH: 448 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:137:

```
Met Leu Thr Phe Met Ala Ser Asp Ser Glu Glu Val Cys Asp Glu
1               5                   10                  15

Arg Thr Ser Leu Met Ser Ala Glu Ser Pro Thr Pro Arg Ser Cys Gln
            20                  25                  30

Glu Gly Arg Gln Gly Pro Glu Asp Gly Glu Asn Thr Ala Gln Trp Arg
        35                  40                  45

Ser Gln Glu Asn Glu Glu Asp Gly Glu Glu Asp Pro Asp Arg Tyr Val
    50                  55                  60

Cys Ser Gly Val Pro Gly Arg Pro Pro Gly Leu Glu Glu Glu Leu Thr
65                  70                  75                  80

Leu Lys Tyr Gly Ala Lys His Val Ile Met Leu Phe Val Pro Val Thr
                85                  90                  95

Leu Cys Met Ile Val Val Val Ala Thr Ile Lys Ser Val Arg Phe Tyr
            100                 105                 110

Thr Glu Lys Asn Gly Gln Leu Ile Tyr Thr Pro Phe Thr Glu Asp Thr
        115                 120                 125

Pro Ser Val Gly Gln Arg Leu Leu Asn Ser Val Leu Asn Thr Leu Ile
    130                 135                 140

Met Ile Ser Val Ile Val Val Met Thr Ile Phe Leu Val Val Leu Tyr
145                 150                 155                 160

Lys Tyr Arg Cys Tyr Lys Phe Ile His Gly Trp Leu Ile Met Ser Ser
                165                 170                 175

Leu Met Leu Leu Phe Leu Phe Thr Tyr Ile Tyr Leu Gly Glu Val Leu
            180                 185                 190

Lys Thr Tyr Asn Val Ala Met Asp Tyr Pro Thr Leu Leu Leu Thr Val
        195                 200                 205

Trp Asn Phe Gly Ala Val Gly Met Val Cys Ile His Trp Lys Gly Pro
    210                 215                 220

Leu Val Leu Gln Gln Ala Tyr Leu Ile Met Ile Ser Ala Leu Met Ala
225                 230                 235                 240

Leu Val Phe Ile Lys Tyr Leu Pro Glu Trp Ser Ala Trp Val Ile Leu
                245                 250                 255

Gly Ala Ile Ser Val Tyr Asp Leu Val Ala Val Leu Cys Pro Lys Gly
            260                 265                 270

Pro Leu Arg Met Leu Val Glu Thr Ala Gln Glu Arg Asn Glu Pro Ile
        275                 280                 285

Phe Pro Ala Leu Ile Tyr Ser Ser Ala Met Val Trp Thr Val Gly Met
    290                 295                 300
```

```
Ala Lys Leu Asp Pro Ser Ser Gln Gly Ala Leu Gln Leu Pro Tyr Asp
305                 310                 315                 320

Pro Glu Met Glu Glu Asp Ser Tyr Asp Ser Phe Gly Glu Pro Ser Tyr
            325                 330                 335

Pro Glu Val Phe Glu Pro Pro Leu Thr Gly Tyr Pro Gly Glu Glu Leu
            340                 345                 350

Glu Glu Glu Glu Glu Arg Gly Val Lys Leu Gly Leu Gly Asp Phe Ile
            355                 360                 365

Phe Tyr Ser Val Leu Val Gly Lys Ala Ala Thr Gly Ser Gly Asp
    370                 375                 380

Trp Asn Thr Thr Leu Ala Cys Phe Val Ala Ile Leu Ile Gly Leu Cys
385                 390                 395                 400

Leu Thr Leu Leu Leu Leu Ala Val Phe Lys Lys Ala Leu Pro Ala Leu
                405                 410                 415

Pro Ile Ser Ile Thr Phe Gly Leu Ile Phe Tyr Phe Ser Thr Asp Asn
            420                 425                 430

Leu Val Arg Pro Phe Met Asp Thr Leu Ala Ser His Gln Leu Tyr Ile
            435                 440                 445
```

(2) INFORMATION FOR SEQ ID NO:138:

(i) SEQUENCE CHARACTERISTICS:
        (A) LENGTH: 372 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:138:

```
Glu Glu Leu Thr Leu Lys Tyr Gly Ala Lys His Val Ile Met Leu Phe
1               5                   10                  15

Val Pro Val Thr Leu Cys Met Ile Val Val Ala Thr Ile Lys Ser
            20                  25                  30

Val Arg Phe Tyr Thr Glu Lys Asn Gly Gln Leu Ile Tyr Thr Pro Phe
            35                  40                  45

Thr Glu Asp Thr Pro Ser Val Gly Gln Arg Leu Leu Asn Ser Val Leu
    50                  55                  60

Asn Thr Leu Ile Met Ile Ser Val Ile Val Met Thr Ile Phe Leu
65                  70                  75                  80

Val Val Leu Tyr Lys Tyr Arg Cys Tyr Lys Phe Ile His Gly Trp Leu
                85                  90                  95

Ile Met Ser Ser Leu Met Leu Leu Phe Leu Phe Thr Tyr Ile Tyr Leu
            100                 105                 110

Gly Glu Val Leu Lys Thr Tyr Asn Val Ala Met Asp Tyr Pro Thr Leu
            115                 120                 125

Leu Leu Thr Val Trp Asn Phe Gly Ala Val Gly Met Val Cys Ile His
            130                 135                 140

Trp Lys Gly Pro Leu Val Leu Gln Gln Ala Tyr Leu Ile Met Ile Ser
145                 150                 155                 160

Ala Leu Met Ala Leu Val Phe Ile Lys Tyr Leu Pro Glu Trp Ser Ala
                165                 170                 175

Trp Val Ile Leu Gly Ala Ile Ser Val Tyr Asp Leu Val Ala Val Leu
            180                 185                 190

Cys Pro Lys Gly Pro Leu Arg Met Leu Val Glu Thr Ala Gln Glu Arg
            195                 200                 205
```

Asn Glu Pro Ile Phe Pro Ala Leu Ile Tyr Ser Ser Ala Met Val Trp
    210                 215                 220

Thr Val Gly Met Ala Lys Leu Asp Pro Ser Ser Gln Gly Ala Leu Gln
225                 230                 235                 240

Leu Pro Tyr Asp Pro Glu Met Glu Asp Ser Tyr Asp Ser Phe Gly
            245                 250                 255

Glu Pro Ser Tyr Pro Glu Val Phe Glu Pro Pro Leu Thr Gly Tyr Pro
            260                 265                 270

Gly Glu Glu Leu Glu Glu Glu Glu Arg Gly Val Lys Leu Gly Leu
    275                 280                 285

Gly Asp Phe Ile Phe Tyr Ser Val Leu Val Gly Lys Ala Ala Ala Thr
    290                 295                 300

Gly Ser Gly Asp Trp Asn Thr Thr Leu Ala Cys Phe Val Ala Ile Leu
305                 310                 315                 320

Ile Gly Leu Cys Leu Thr Leu Leu Leu Ala Val Phe Lys Lys Ala
            325                 330                 335

Leu Pro Ala Leu Pro Ile Ser Ile Thr Phe Gly Leu Ile Phe Tyr Phe
            340                 345                 350

Ser Thr Asp Asn Leu Val Arg Pro Phe Met Asp Thr Leu Ala Ser His
            355                 360                 365

Gln Leu Tyr Ile
    370

(2) INFORMATION FOR SEQ ID NO:139:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:139:

GGTACCGCCA CCATGACAGA GGTACCTGCA C                               31

(2) INFORMATION FOR SEQ ID NO:140:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:140:

GAATTCACTG GCTGTAGAAA AAGAC                                      25

(2) INFORMATION FOR SEQ ID NO:141:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:141:

```
GGATCCGGTC CACTTCGTAT GCTG                                              24

(2) INFORMATION FOR SEQ ID NO:142:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:142:

TTTTTTGAAT TCTTAGGCTA TGGTTGTGTT CCA                                    33

(2) INFORMATION FOR SEQ ID NO:143:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:143:

GATTAGTGGT TGTTTTGTG                                                    19

(2) INFORMATION FOR SEQ ID NO:144:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:144:

GATTAGTGGC TGTTTTGTG                                                    19

(2) INFORMATION FOR SEQ ID NO:145:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:145:

TTTTTCCAGC TCTCATTTA                                                    19

(2) INFORMATION FOR SEQ ID NO:146:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"
```

(xi) SEQUENCE DESCRIPTION: SEQ ID NO:146:

TTTTTCCAGT TCTCATTTA                                                    19

(2) INFORMATION FOR SEQ ID NO:147:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:147:

TACAGTGTTC TGGTTGGTA                                                    19

(2) INFORMATION FOR SEQ ID NO:148:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:148:

TACAGTGTTC TGGTTGGTA                                                    19

(2) INFORMATION FOR SEQ ID NO:149:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:149:

TACAGTGTTG TGGTTGGTA                                                    19

(2) INFORMATION FOR SEQ ID NO:150:

(i) SEQUENCE CHARACTERISTICS:
        (A) LENGTH: 1092 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:150:

GTCTAGATAA GNCAACATTC AGGGGTAGAA GGGGACTGTT TATTTTTTCC TTTAGTCTCT         60

CTTAAAGAGT GAGAAAAATT TTCCCAGGAA TCCCGGTGGA CTTTGCTTCA CCACTCATAG        120

GTTCATACCA AGTTACAACC CCACAACCTT AGAGCTTTTG TTAGGAAGAG GCTTGGTGGG        180

ATTACCGTGC TTGGCTTGGC TTGGTCAGGA TTCACCACCA GAGTCATGTG GGAGGGGGTG        240

GGAACCCAAA CAATTCAGGA TTCTGCCCTC AGGAAATAAA GGAGAAAATA GCTGTTGGAT        300

AAACTACCAG CAGGCACTGC TACAGCCCAT GCTTTGTGGT TTAAGGGCCA GCTAGTTACA        360

ATGACAGCTA GTTACTGTTT CCATGTAATT TTCTTAAAGG TATTAAATTT TTCTAAATAT        420

-continued

```
TAGAGCTGTA ACTTCCACTT TCTCTTGAAG GCACAGWAAG GGAGTCACAA GACACTGTTG    480

CAGAGAATGA TGATGGCGGG TTCAGTGAGG AATGGGAASC CCAGRGGGAC ANTCATCTAG    540

GGCCTCATCG CTCTACACCT GAGTCACGAG CTKCTNTCCA GGRACTTTCC ANCAGTATCC    600

TCGCTGGTGA AGACCCAGAG GAAAGNATGT TCANTTCTCC ATNTTTCAAA GTCATGGATT    660

CCTTTAGGTA GCTACATTAT CAACCTTTTT GAGAATAAAA TGAATTGAGA GTGTTACAGT    720

CTAATTCTAT ATCACATGTA ACTTTTATTT GGATATATCA GTAATAGTGC TTTTTYNTTT    780

TTTTTTTTTT TTTTTTTTTT TTTTNGGNGA NAGAGTCTCG CTCTGTCGCC AGGTTGGAGT    840

GCAATGGTGC GATCTTGGCT CACTGAAAGC TCCACCNCCC GGGTTCAAGT GATTCTCCTG    900

CCTCAGCCNC CCAAGTAGNT GGGACTACAG GGGTGCGCCA CCACGCCTGG GATAATTTTG    960

GGNTTTTTAG TAGAGATGGC GTTTCACCAN CTTGGNGCAG GCTGGTCTTG GAACTCCTGA   1020

NATCATGATC TGCCTGCCTT AGCCTCCCCA AAGTGCTGGG ATTNCAGGGG TGAGCCACTG   1080

TTCCTGGGCC TC                                                      1092
```

(2) INFORMATION FOR SEQ ID NO:151:

(i) SEQUENCE CHARACTERISTICS:
        (A) LENGTH: 1003 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:151:

```
CTGCAGTGAG CCGAGATCAT GCTGCTGTAC TCCAGCCTGG GCCACAGAGC CAAACTCCAT     60

CTCCCAAAAA AAAAAAATAT TAATTAATAT GATNAAATGA TGCCTATCTC AGAATTCTTG    120

TAAGGATTTC TTAGKACAAG TGCTGGGTAT AAACTATANA TTCRATAGAT GNCGATTATT    180

ACTTAYTATT GTTATTGATA AATAACAGCA GCATCTACAG TTAAGACTCC AGAGTCAGTC    240

ACATAGAATC TGGNACTCCT ATTGTAGNAA ACCCCNMMAG AAAGAAAACA CAGCTGAAGC    300

CTAATTTTGT ATATCATTTA CTGACTTCTC TCATTCATTG TGGGGTTGAG TAGGGCAGTG    360

ATATTTTTGA ATTGTGAAAT CATANCAAAG AGTGACCAAC TTTTTAATAT TTGTAACCTT    420

TCCTTTTTAG GGGGAGTAAA ACTTGGATTG GGAGATTTCA TTTTCTACAG TGTTCTGGTT    480

GGTAAAGCCT CAGCAACAGC CAGTGGGAC TGGAACACAA CCATAGCCTG TTTCGTAGCC     540

ATATTAATTG TMMSTATACA CTAATAAGAA TGTGTCAGAG CTCTTAATGT CMAAACTTTG    600

ATTACACAGT CCCTTTAAGG CAGTTCTGTT TTAACCCCAG GTGGGTTAAA TATTCCAGCT    660

ATCTGAGGAG CTTTTNGATA ATTGGACCTC ACCTTAGTAG TTCTCTACCC TGGCCACACA    720

TTAGAATCAC TTGGGAGCTT TTAAAACTGT AAGCTCTGCC CTGAGATATT CTTACTCAAT    780

TTAATTGTGT AGTTTTTAAA ATTCCCCAGG AAATTCTGGT ATTTCTGTTT AGGAACCGCT    840

GCCTCAAGCC TAGCAGCACA GATATGTAGG AAATTAGCTC TGTAAGGTTG GTCTTACAGG    900

GATAAACAGA TCCTTCCTTA GTCCCTGGAC TTAATCACTG AGAGTTTGGG TGGTGGTTTT    960

GGATTTAATG ACACAACCTG TAGCATGCAG TGTTACTTAA GAC                     1003
```

(2) INFORMATION FOR SEQ ID NO:152:

(i) SEQUENCE CHARACTERISTICS:
        (A) LENGTH: 1726 base pairs
        (B) TYPE: nucleic acid
        (C) STRANDEDNESS: single
        (D) TOPOLOGY: linear -continued (ii) MOLECULE TYPE: cDNA (xi) SEQUENCE DESCRIPTION: SEQ ID NO:152:

GGATCCCTCC CCTTTTTAGA CCATACAAGG TAACTTCCGG ACGTTGCCAT GGCATCTGTA     60

AACTGTCATG GTGTTGGCGG GGAGTGTCTT TTAGCATGCT AATGTATTAT AATTAGCGTA    120

TAGTGAGCAG TGAGGATAAC CAGAGGTCAC TCTCCTCACC ATCTTGGTTT TGGTGGGTTT    180

TGGCCAGCTT CTTTATTGCA ACCAGTTTTA TCAGCAAGAT CTTTATGAGC TGTATCTTGT    240

GCTGACTTCC TATCTCATCC CGNAACTAAG AGTACCTAAC CTCCTGCAAA TTGMAGNCCA    300

GNAGGTCTTG GNCTTATTTN ACCCAGCCCC TATTCAARAT AGAGTNGYTC TTGGNCCAAA    360

CGCCYCTGAC ACAAGGATTT TAAAGTCTTA TTAATTAAGG TAAGATAGKT CCTTGSATAT    420

GTGGTCTGAA ATCACAGAAA GCTGAATTTG GAAAAAGGTG CTTGGASCTG CAGCCAGTAA    480

ACAAGTTTTC ATGCAGGTGT CAGTATTTAA GGTACATCTC AAAGGATAAG TACAATTGTG    540

TATGTTGGGA TGAACAGAGA GAATGGAGCA ANCCAAGACC CAGGTAAAAG AGAGGACCTG    600

AATGCCTTCA GTGAACAATG ATAGATAATC TAGACTTTTA AACTGCATAC TTCCTGTACA    660

TTGTTTTTTC TTGCTTCAGG TTTTTAGAAC TCATAGTGAC GGGTCTGTTG TTAATCCCAG    720

GTCTAACCGT TACCTTGATT CTGCTGAGAA TCTGATTTAC TGAAAATGTT TTTCTTGTGC    780

TTATAGAATG ACAATAGAGA ACGGCAGGAG CACAACGACA GACGGAGCCT TGGCCACCCT    840

GANCCATTAT CTAATGGACG ACCCAGGGTA ACTCCCGGCA GGTGGTGGAN CAAGATGAGG    900

AAGAAGATGA GGANCTGACA TTGAAATATG NCGSCAAGCA TGTGATCATG CTCTTTGKCC    960

CTGTGACTCT CTGCATGGTG GTGGTCGTGG NTACCATTAA GTCAGTCAGC TTTTATACCC   1020

GGAAGGATGG GCAGCTGTAC GTATGAGTTT KGTTTTATTA TTCTCAAASC CAGTGTGGCT   1080

TTTCTTTACA GCATGTCATC ATCACCTTGA AGGCCTCTNC ATTGAAGGGG CATGACTTAG   1140

CTGGAGAGCC CATCCTCTGT GATGGTCAGG AGCAGTTGAG AGANCGAGGG GTTATTACTT   1200

CATGTTTTAA GTGGAGAAAA GGAACACTGC AGAAGTATGT TTCCTGTATG GTATTACTGG   1260

ATAGGGCTGA AGTTATGCTG AATTGAACAC ATAAATTCTT TTCCACCTCA GGGNCATTGG   1320

GCGCCCATTG NTCTTCTGCC TAGAATATTC TTTCCTTTNC TNACTTKGGN GGATTAAATT   1380

CCTGTCATCC CCCTCCTCTT GGTGTTATAT ATAAAGTNTT GGTGCCGCAA AAGAAGTAGC   1440

ACTCGAATAT AAAATTTTCC TTTTAATTCT CAGCAAGGNA AGTTACTTCT ATATAGAAGG   1500

GTGCACCCNT ACAGATGGAA CAATGGCAAG CGCACATTTG GGACAAGGGA GGGGAAAGGG   1560

TTCTTATCCC TGACACACGT GGTCCCNGCT GNTGTGTNCT NCCCCCACTG ANTAGGGTTA   1620

GACTGGACAG GCTTAAACTA ATTCCAATTG GNTAATTTAA AGAGAATNAT GGGGTGAATG   1680

CTTTGGGAGG AGTCAAGGAA GAGNAGGTAG NAGGTAACTT GAATGA                 1726

(2) INFORMATION FOR SEQ ID NO:153:

(i) SEQUENCE CHARACTERISTICS:
        (A) LENGTH: 1883 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:153:

CNCGTATAAA AGACCAACAT TGCCANCNAC AACCACAGGC AAGATCTTCT CCTACCTTCC     60

CCCNNGGTGT AATACCAAGT ATTCNCCAAT TTGTGATAAA CTTTCATTGG AAAGTGACCA    120

```
CCCTCCTTGG TTAATACATT GTCTGTGCCT GCTTTCACAC TACAGTAGCA CAGTTGAGTG      180

TTTGCCCTGG AGACCATATG ACCCATAGAG CTTAAAATAT TCAGTCTGGC TTTTTACAGA      240

GATGTTTCTG ACTTTGTTAA TAGAAAATCA ACCCAACTGG TTTAAATAAT GCACATACTT      300

TCTCTCTCAT AGAGTAGTGC AGAGGTAGNC AGTCCAGATT AGTASGGTGG CTTCACGTTC      360

ATCCAAGGAC TCAATCTCCT TCTTTCTTCT TTAGCTTCTA ACCTCTAGCT TACTTCAGGG      420

TCCAGGCTGG AGCCCTASCC TTCATTTCTG ACAGTAGGAA GGAGTAGGGG AGAAAAGAAC      480

ATAGGACATG TCAGCAGAAT TCTCTCCTTA GAAGTTCCAT ACACAACACA TCTCCCTAGA      540

AGTCATTGCC CTTACTTGTT CTCATAGCCA TCCTAAATAT AAGGGAGTCA GAAGTAAAGT      600

CTKKNTGGCT GGGAATATTG GCACCTGGAA TAAAAATGTT TTTCTGTGAA TGAGAAACAA      660

GGGGAAGATG GATATGTGAC ATTATCTTAA GACAACTCCA GTTGCAATTA CTCTGCAGAT      720

GAGAGGCACT AATTATAAGC CATATTACCT TTCTTCTGAC AACCACTTGT CAGCCCNCGT      780

GGTTTCTGTG GCAGAATCTG GTTCYATAMC AAGTTCCTAA TAANCTGTAS CCNAAAAAAT      840

TTGATGAGGT ATTATAATTA TTTCAATATA AAGCACCCAC TAGATGGAGC CAGTGTCTGC      900

TTCACATGTT AAGTCCTTCT TTCCATATGT TAGACATTTT CTTTGAAGCA ATTTTAGAGT      960

GTAGCTGTTT TTCTCAGGTT AAAAATTCTT AGCTAGGATT GGTGAGTTGG GGAAAAGTGA     1020

CTTATAAGAT NCGAATTGAA TTAAGAAAAA GAAAATTCTG TGTTGGAGGT GGTAATGTGG     1080

KTGGTGATCT YCATTAACAC TGANCTAGGG CTTTKGKGTT TGKTTTATTG TAGAATCTAT     1140

ACCCCATTCA NAGAAGATAC CGAGACTGTG GGCCAGAGAG CCCTGCACTC AATTCTGAAT     1200

GCTGCCATCA TGATCAGNGT CATTGTWGTC ATGACTANNC TCCTGGTGGT TCWGTATAAA     1260

TACAGGTGCT ATAAGGTGAG CATGAGACAC AGATCTTTGN TTTCCACCCT GTTCTTCTTA     1320

TGGTTGGGTA TTCTTGTCAC AGTAACTTAA CTGATCTAGG AAAGAAAAAA TGTTTTGTCT     1380

TCTAGAGATA AGTTAATTTT TAGTTTTCTT CCTCCTCACT GTGGAACATT CAAAAAATAC     1440

AAAAAGGAAG CCAGGTGCAT GTGTAATGCC AGGCTCAGAG GCTGAGGCAG GAGGATCGCT     1500

TGGGCCCAGG AGTTCACAAG CAGCTTGGGC AACGTAGCAA GACCCTGCCT CTATTAAAGA     1560

AAACAAAAAA CAAATATTGG AAGTATTTTA TATGCATGGA ATCTATATGT CATGAAAAAA     1620

TTAGTGTAAA ATATATATAT TATGATTAGN TATCAAGATT TAGTGATAAT TTATGTTATT     1680

TTGGGATTTC AATGCCTTTT TAGGCCATTG TCTCAAMAAA TAAAAGCAGA AAACAAAAAA     1740

AGTTGTAACT GAAAAATAAA CATTTCCATA TAATAGCACA ATCAAGTGG GTTTTTGNTT      1800

GTTTGTTTGN TTGTTGAAGC AGGGCCTTGC CCTNYCACCC AGGNTGGAGT GAAGTGCAGT     1860

GGCACGATTT TGGCTCACTG CAG                                             1883
```

(2) INFORMATION FOR SEQ ID NO:154:

(i) SEQUENCE CHARACTERISTICS:
        (A) LENGTH: 1990 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:154:

```
ATGTTTGACA ATTTCTCCGT TCCACCCTTG ATTAAATAAG GTAGTATTCA TTTTTTAAGT       60

TTTAGCTTTT GGATATATGT GTAAGTGTGG TATGCTGTCT AATGAATTAA GACAATTGGT      120

NCTKTCTTTA CCCMACANCT GGACMAAGAG CAGGCAAGAT NCAANAATCA AGTGACCCAG      180
```

```
NCAAACCAGA CACATTTTCT GCTCTCAGCT AGCTTGCCAC CTAGAAAGAC TGGTTGTCNA      240

AGTTGGAGTC CAAGAATCGC GGAGGATGTT TAAAATGCAG TTTCTCAGGT TCTCNCCACC      300

CACCAGAAGT TTTGATTCAT TGAGTGGTGG GAGAGGGCAG AGATATTTGC GATTTTAACA      360

GCATTCTCTT GATTGTGATG CAGCTGGTTC SCAAATAGGT ACCCTAAAGA AATGACAGGT      420

GTTAAATTTA GGATGGCCAT CGCTTGTATG CCGGGAGAAG CACACGCTGG GCCCAATTTA      480

TATAGGGGCT TTCGTCCTCA GCTCGAGCAR CCTCAGAACC CCGACAACCY ACGCCAGCKC      540

TCTGGGCGGA TTCCRTCAGK TGGGGAAGSC CAGGTGGAGC TCTGGKTTCT CCCCGCAATC      600

GTTTCTCCAG GCCGGAGGCC CCGCCCCCTT CCTCCTGGCT CCTCCCCTCC TCCGTGGGCC      660

GNCCGCCAAC GACGCCAGAG CCGGAAATGA CGACAACGGT GAGGGTTCTC GGGCGGGGCC      720

TGGGACAGGC AGCTCCGGGG TCCNCGNNWT NACATCGGAA ACAAAACAGC GGCTGGTCTG      780

GAAGGAACCT GAKCTACGAC CCGCGGCGGC AGCGGGGCGG CGGGGAAGCG TATGTGCGTG      840

ATGGGGAGTC CGGGCAAGCC AGGAAGGCAC CGCGGACATG GCGGCCGCG GGCAGGGNCC       900

GGNCCTTTGT GGCCGCCCGG GCCGCGAAGC CGGTGTCCTA AAAGATGAGG GGCGGGGCGC      960

GGCCGGTTGG GGCTGGGGAA CCCCGTGTGG GAAACCAGGA GGGGCGGCCC GTTTCTCGGG     1020

CTTCGGGCGC GGCCGGGTGG AGAGAGATTC CGGGGAGCCT TGGTCCGGAA ATGCTGTTTG     1080

CTCGAAGACG TCTCAGGGCG CAGGTGCCTT GGGCCGGGAT TAGTAGCCGT CTGAACTGGA     1140

GTGGAGTAGG AGAAAGAGGA AGCGTCTTGG GCTGGGTCTG CTTGAGCAAC TGGTGAAACT     1200

CCGCGCCTCA CGCCCCGGGT GTGTCCTTGT CCAGGGGCGA CGAGCATTCT GGGCGAAGTC     1260

CGCACGCCTC TTGTTCGAGG CGGAAGACGG GGTCTTGATG CTTTCTCCTT GGTCGGGACT     1320

GTCTCGAGGC ATGCATGTCC AGTGACTCTT GTGTTTGCTG CTGCTTCCCT CTCAGATTCT     1380

TCTCACCGTT GTGGTCAGCT CTGCTTTAGG CATATTAATC CATAGTGGAG CTGGGATGG      1440

GTGAGAGAAT TGAGGTGACT TTTCCATAAT TCAGGTGAGA TGTGATTAGA GTYCGGATCC     1500

TNCGGTGGTG GCAGAGGCTT ACCAAGAAAC ACTAACGGGA CATGGGAACC AATTGAGGAT     1560

CCAGGGAATA AAGTGTGAAG TTGACTAGGA GGTTTTCAGT TTAAGAACAT GGCAGAGACA     1620

TTCTCAGAAA TAAGGAAGTT AGGAAGAAAG ACCTGGTTTA GAGAGGAGGG CGAGGAAGTG     1680

GTTTGGAAGT GTCACTTTGG AAGTGCCAGC AGGTGAAAAT GCCCTGTGAA CAGGACTGGA     1740

GCTGAAAACA GGAATCAATT CCATAGATTT CCAGTTGATG TTGGAGCAGT GGAGAAGTCT     1800

AANCTAAGGA AGGGAAGAG GAGGCCAAGC CAAACACTTA GGAACACTTN CNACGAGGGG      1860

GTGGAAGAAG AGCAAGGAGC CAGCTGAGGA GAATGAGTGT GGTTGGAGAA CCACCACAGC     1920

NCAGGGTCGC CAGANCTGAG GAAGGGGAGG GAAGCTTATC GAGKAMSGWC RACMKCGAGT     1980

TGGCAGGGAT                                                            1990

(2) INFORMATION FOR SEQ ID NO:155:

(i) SEQUENCE CHARACTERISTICS:
        (A) LENGTH: 736 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:155:

GTCTTTCCCA TCTTCTCCAC AGAGTTTGTG CCTTACATTA TTACTCCTTG CCATTTTCAA       60

GAAAGCATTG TCAGCTCTTC CAATCTCCAT CACCTTTGGG CTTGTTTTCT ACTTTGCCAC      120
```

```
AGATTATCTT GTACAGCCTT TTATGGACCA ATTAGCATTC CATCAATTTT ATATCTAGCA    180

TATTTGCGGT TAGAATCCCA TGGATGTTTC TTCTTTGACT ATAACAAAAT CTGGGGAGGA    240

CAAAGGTGAT TTCCTGTGTC CACATCTAAC AAATCAAGAT CCCCGGCTGG ACTTTTGGAG    300

GTTCCTTCCA AGTCTTCCTG ACCACCTTGC ACTATTGGAC TTTGGAAGGA GGTGCCTATA    360

GAAAACGATT TTGAACATAC TTCATCGCAG TGGACTGTGT CCTCGGTGCA GAAACTACCA    420

GATTTGAGGG ACGAGGTCAA GGAGATATGA TAGGCCCGGA AGTTGCTGTG CCCCATCAGC    480

AGCTTGACGC GTGGTCACAG GACGATTTTC ACTGACACTG CGAACTCTCA GGACTACCGT    540

TACCAAGAGG TTAGGTGAAG TGGTTTAAAC CAAACGGAAC TCTTCATCTT AAACTACACG    600

TTGAAAATCA ACCCAATAAT TCTGTATTAA CTGAATTCTG AACTTTTCAG GAGGTACTGT    660

GAGGAAGAGC AGGCACCACC AGCAGAATGG GGAATGGAGA GGTGGGCAGG GGTTCCAGCT    720

TCCCTTTGAT TTTTTG                                                    736
```

(2) INFORMATION FOR SEQ ID NO:156:

(i) SEQUENCE CHARACTERISTICS:
        (A) LENGTH: 1117 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:156:

```
GGATCCGCCC GCCTTGGCCT CCCAAAGTGC TGGGATTACA GGCATGAGCC ACCGCTCCTG     60

GCTGAGTCTG CGATTTCTTG CCAGCTCTAC CCAGTTGTGT CATCTTAAGC AAGTCACTGA    120

ACTTCTCTGG ATTCCCTTCT CCTNNWGTAA AATAAGNATG TTATCTGNCC NNCCTGCCTT    180

GGGCATTGTG ATAAGGATAA GATGACATTA TAGAATNTNG CAAAATTAAA AGCGCTAGAC    240

AAATGATTTT ATGAAAATAT AAAGATTAGN TTGAGTTTGG GCCAGCATAG AAAAAGGAAT    300

GTTGAGAACA TTCCNTTAAG GATTACTCAA GCYCCCCTTT TGSTGKNWAA TCAGANNGTC    360

ATNNAMNTAT CNTNTGTGGG YTGAAAATGT TTGGTTGTCT CAGGCGGTTC CTACTTATTG    420

CTAAAGAGTC CTACCTTGAG CTTATAGTAA ATTTGTCAGT TAGTTGAAAG TCGTGACAAA    480

TTAATACATT CCTGGTTTAC AAATTGGTCT TATAAGTATT TGATTGGTNT AAATGNATTT    540

ACTAGGATTT AACTAACAAT GGATGACCTG GTGAAATCCT ATTTCAGACC TAATCTGGGA    600

GCCTGCAAGT GACAACAGCC TTTGCGGTCC TTAGACAGCT TGGCCTGGAG GAGAACACAT    660

GAAAGAMMGG TTTGWNTCTG NTTAWTGTAA TCTATGRAAG TGTTTTTWAT MACAGTATAA    720

TTGTMTGMAC AAAGTTCTGT TTTTCTTTCC CTTTNCAGAA CCTCAAGAGG CTTTGTTTTC    780

TGTGAAACAG TATTTCTATA CAGNTGCTCC AATGACAGAG TNACCTGCAC CGTTGTCCTA    840

CTTCCAGAAT GCACAGATGT CTGAGGACAA CCACCTGAGC AATACTGTAC GTAGCCAGGT    900

ACAGCGTCAG TYTCTNAAAC TGCCTYYGNC AGACTGGATT CACTTATCAT CTCCCCTCAC    960

CTCTGAGAAA TGCTGAGGGG GSTAGGNAGG GCTTTCTCTA CTTNACCACA TTTNATAATT   1020

ATTTTTGGGT GACCTTCAGC TGATCGCTGG GAGGGACACA GGGCTTNTTT AACACATAGG   1080

GTGTTGGATA CAGNCCCTCC CTAATTCACA TTTCANC                            1117
```

(2) INFORMATION FOR SEQ ID NO:157:

(i) SEQUENCE CHARACTERISTICS:
        (A) LENGTH: 540 base pairs (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:157:

| | | | | | |
|---|---|---|---|---|---|
| CTGCAGCTTT | CCTTTAAACT | AGGAAGACTT | GTTCCTATAC | CCCAGTAACG | ATACACTGTA | 60 |
| CACTAAGCAA | ATAGCAGTCA | AACCCAAATG | AAATTTNTAC | AGATGTTCTG | TGTCATTTTA | 120 |
| TNTTGTTTAT | GTTGTCTCCC | CCACCCCCAC | CAGTTCACCT | GCCATTTATT | TCATATTCAT | 180 |
| TCAACGTCTN | NNTGTGTAAA | AAGAGACAAA | AAACATTAAA | CTTTTTTCCT | TCGTTAATTC | 240 |
| CTCCCTACCA | CCCATTTACA | AGTTTAGCCC | ATACATTTTA | TTAGATGTCT | TTTATGTTTT | 300 |
| TCTTTTNCTA | GATTTAGTGG | CTGTTTNGTG | TCCGAAAGGT | CCACTTCGTA | TGCTGGTTGA | 360 |
| AACAGCTCAG | GAGAGAAATG | AAACGCTTTT | TCCAGCTCTC | ATTTACTCCT | GTAAGTATTT | 420 |
| GGAGAATGAT | ATTGAATTAG | TAATCAGNGT | AGAATTTATC | GGGAACTTGA | AGANATGTNA | 480 |
| CTATGGCAAT | TTCANGGNAC | TTGTCTCATC | TTAAATGANA | GNATCCCTGG | ACTCCTGNAG | 540 |

(2) INFORMATION FOR SEQ ID NO:158:

(i) SEQUENCE CHARACTERISTICS:
    (A) LENGTH: 509 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:158:

| | | | | | |
|---|---|---|---|---|---|
| CCCCGTCNAT | GCATACTTTG | TGTGTCCAGT | GCTTACCTGG | AATCCNGTCT | TTCCCAACAG | 60 |
| CAACAATGGT | GTGGTTGGTG | AATATGGCAG | AAGGAGACCC | GGAAGCTCAA | AGGAGAGTAT | 120 |
| CCAAAAATTC | CAAGTATAAT | GCAGAAAGTA | GGTAACTYYY | NTTAGATAMN | ATCTTGATTT | 180 |
| TNCAGGGTCA | CTGTTATAAG | CTAACAGTAT | AGNAATGTTT | TTATCGTCTT | TCTNKGGNCA | 240 |
| TAGACTCCTN | KGAGAATCTC | TTGAGAACTA | TGATAATGCC | CAGTAAATAC | NCAGATAAGT | 300 |
| ATTTAAGGAG | TNCAGATACT | CAAANCCCAA | CAATACNGTC | AAAGCATCCT | AGGTTAAGAC | 360 |
| AMCNCCCATT | AAATACAGAA | TACCAGCATG | GAAAGGTTCA | GGCTGAGGTT | ATGATTGGGT | 420 |
| TTGGGTTTTG | GGNNNGTTTT | TTATAAGTCA | TGATTTTAAA | AAGAAAAAAT | AAACTCTCTC | 480 |
| CAAACATGTA | AAAGTAAGAA | TCTCCTAAA | | | | 509 |

(2) INFORMATION FOR SEQ ID NO:159:

(i) SEQUENCE CHARACTERISTICS:
    (A) LENGTH: 823 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:159:

| | | | | | |
|---|---|---|---|---|---|
| CAGGAGTGGA | CTAGGTAAAT | GNAAGNTGTT | TTAAAGAGAG | ATGNGGNCNG | GGACATAGTG | 60 |
| GTACACANCT | GTAATGCTCA | NCACTKATGG | GGAGTACTGA | AGGNGGNSGG | ATCACTTGNG | 120 |
| GGTCNGGAAT | NTGAGANCAG | CCTGGGCAAN | ATGGCGAAAC | CCTGTCTCTA | CTAAAAATAG | 180 |
| CCANAAWNWA | GCCTAGCGTG | GTGGCGCRCA | CGCGTGGTTC | CACCTACTCA | GGAGGCNTAA | 240 |
| GCACGAGNAN | TNCTTGAACC | CAGGAGGCAG | AGGNTGTGGT | GARCTGAGAT | CGTGCCACTG | 300 |

```
CACTCCAGTC TGGGCGACMA AGTGAGACCC TGTCTCCNNN AAGAAAAAAA AAATCTGTAC      360

TTTTTAAGGG TTGTGGGACC TGTTAATTAT ATTGAAATGC TTCTYTTCTA GGTCATCCAT      420

GCCTGGCTTA TTATATCATC TCTATTGTTG CTGCTCTTTT TTACATTCAT TTACTTGGGG      480

TAAGTTGTGA AATTTGGGGT CTGTCTTTCA GAATTAACTA CCTNNGTGCT GTGTAGCTAT      540

CATTTAAAGC CATGTACTTT GNTGATGAAT TACTCTGAAG TTTTAATTGT NTCCACATAT      600

AGGTCATACT TGGTATATAA AAGACTAGNC AGTATTACTA ATTGAGACAT TCTTCTGTNG      660

CTCCTNGCTT ATAATAAGTA GAACTGAAAG NAACTTAAGA CTACAGTTAA TTCTAAGCCT      720

TTGGGGAAGG ATTATATAGC CTTCTAGTAG GAAGTCTTGT GCNATCAGAA TGTTTNTAAA      780

GAAAGGGTNT CAAGGAATNG TATAAANACC AAAAATAATT GAT                       823

(2) INFORMATION FOR SEQ ID NO:160:

(i) SEQUENCE CHARACTERISTICS:
          (A) LENGTH: 945 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:160:

GTTNTCCNAA CCAACTTAGG AGNTTGGACC TGGGRAAGAC CNACNTGATC TCCGGGAGGN       60

AAAGACTNCA GTTGAGCCGT GATTGCACCC ACTTTACTCC AAGCCTGGGC AACCAAAATG      120

AGACACTGGC TCCAAACACA AAAACAAAAA CAAAAAAAGA GTAAATTAAT TTANAGGGAA      180

GNATTAAATA AATAATAGCA CAGTTGATAT AGGTTATGGT AAAATTATAA AGGTGGGANA      240

TTAATATCTA ATGTTTGGGA GCCATCACAT TATTCTAAAT AATGTTTTGG TGGAAATTAT      300

TGTACATCTT TTAAAATCTG TGTAATTTTT TTTCAGGGAA GTGTTAAAA CCTATAACGT       360

TGCTGTGGAC TACATTACTG TTNCACTCCT GATCTGGAAT TTTGGTGTGG TGGGAATGAT      420

TTCCATTCAC TGGAAAGGTC CACTTCGACT CCAGCAGGCA TATCTCATTA TGATTAGTGC      480

CCTCATGNCC CTGKTGTTTA TCAAGTACCT CCCTGAATGG ACTGNGTGGC TCATCTTGGC      540

TGTGATTTCA GTATATGGTA AAACCCAAGA CTGATAATTT GTTTGTCACA GGAATGCCCC      600

ACTGGAGTGT TTTCTTTCCT CATCTCTTTA TCTTGATTTA GAGAAAATGG TAACGTGTAC      660

ATCCCATAAC TCTTCAGTAA ATCATTAATT AGCTATAGTA ACTTTTTCAT TTGAAGATTT      720

CGGCTGGGCA TGGTAGCTCA TGCCTGTAAT CTTAGCACTT TGGGAGGCTG AGGCGGGCAG      780

ATCACCTAAG CCCAGAGTTC AAGACCAGCC TGGGCAACAT GGCAAAACCT CGTATCTACA      840

GAAAATACAA AAATTAGCCG GGCATGGTGG TGCACACCTG TAGTTCCAGC TACTTAGGAG      900

GCTGAGGTGG GAGGATCGAT TGATCCCAGG AGGTCAAGNC TGCAG                     945

(2) INFORMATION FOR SEQ ID NO:161:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "primer"

(xi) SEQUENCE DESCRIPTION: SEQ ID NO:161:

TGCTGCTTGC TGTGTTCA                                                    18
```

(2) INFORMATION FOR SEQ ID NO:162:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:162:

CCATGTCCCT CAGATGTAGA                                              20

(2) INFORMATION FOR SEQ ID NO:163:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:163:

CATCTCCATC ACGTTCG                                                  17

(2) INFORMATION FOR SEQ ID NO:164:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:164:

CATCTCCACC ACGTTCG                                                  17

(2) INFORMATION FOR SEQ ID NO:165:

(i) SEQUENCE CHARACTERISTICS:
        (A) LENGTH: 1895 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:165:

```
TATATGAGTC GCTTTAAAAC AAAAGAAAGT TTTTACCAGC TACATTCCTT TGGTTTCCTT      60

AACTAAATCC CATCACACAA CTACGGCTTC GCAGGGGGAG GCGTCCAGCG CTACGGAGGC     120

GAACGAACGC ACACCACTGA TGGCTGCTGT CAATCTCCAG GCTTCGTGCT CCTCCGGGCT     180

CGCCTCTGAG GATGACGCCA ATGTGGGCAG CCAGATAGGC GCGGCGGAGC GTTTGGAACG     240

ACCTCCAAGG CGGCAACAGC AGCGGAACAA CTACGGCTCC AGCAATCAGG ATCAACCGGA     300

TGCTGCCATA CTTGCTGTGC CCAATGTGGT GATGCGTGAA CCTTGTGGCT CGCGCCCTTC     360

AAGACTGACC GGTGGAGGAG GCGGCAGTGG TGGTCCGCCC ACAAATGAAA TGGAGGAAGA     420

GCAGGGCCTG AAATACGGGG CCCAGCATGT GATCAAGTTA TTCGTCCCCG TCTCCCTTTG     480

CATGCTGGTA GTGGTGGCTA CCATCAACTC CATCAGCTTC TACAACAGCA CGGATGTCTA     540
```

```
TCTCCTCTAC ACACCTTTCC ATGAACAATC GCCCGAGCCT AGTGTTAAGT TCTGGAGTGC      600

CTTGGCGAAC TCCCTGATCC TGATGAGCGT GGTGGTGGTG ATGACCTTTT TGCTGATTGT      660

TTTGTACAAG AAGCGTTGCT ATCGCATCAT TCACGGCTGG CTGATTCTCT CCTCCTTCAT      720

GTTGTTGTTC ATTTTTACGT ACTTATATTT GGAAGAGCTT CTTCGCGCCT ATAACATACC      780

GATGGACTAC CCTACTGCAC TACTGATTAT GTGGAACTTT GGAGTGGTCG GAATGATGTC      840

CATCCATTGG CAGGGACCTC TGCGGTTGCA GCAAGGATAT CTCATTTTCG TGGCAGCCTT      900

GATGGCCTTG GTGTTCATTA ATACCTGCCT GAATGGACT GCCTGGGCTG TATTGGCTGC       960

CATTTCTATT TGGGATCTTA TTGCTGTCCT TTCGCCAAGA GGACCCCTCC GCATTCTGGT     1020

GGAAACGGCT CAGGAGCGAA ATGAGCAAAT CTTCCCCGCT CTGATTTATT CATCCACTGT     1080

CGTTTACGCA CTTGTAAACA CTGTTACGCC GCAGCAATCG CAGGCCACAG CTTCCTCCTC     1140

GCCGTCGTCC AGCAACTCCA CCACAACCAC GAGGGCCACG CAGAACTCGC TGGCTTCGCC     1200

AGAGGCAGCA GCGGCTAGTG GCCAACGCAC AGGTAACTCC CATCCTCGAC AGAATCAGCG     1260

GGATGACGGC AGTGTACTGG CAACTGAAGG TATGCCACTT GTGACTTTTA AAAGCAATTT     1320

GCGCGGAAAC GCTGAGGCTG CGGGTTTCAC GCAAGAGTGG TCAGCTAACT TGAGCGAACG     1380

TGTGGCTCGT CGCCAGATTG AAGTTCAAAG TACTCAGAGT GGAAACGCTC AGCGCTCCAA     1440

CGAGTATAGG ACAGTAACAG CTCCGGATCA GAATCATCCG GATGGGCAAG AAGAACGTGG     1500

CATAAAGCTT GGCCTCGGCG ACTTCATCTT CTACTCGGTA TTAGTGGGCA AGGCCTCCAG     1560

CTACGGCGAC TGGACGACCA CAATCGCTTG CTTTGTGGCC ATCCTCATTG GACTCTGCCT     1620

CACTCTTCTG CTTCTGGCCA TTTGGCGCAA GGCGCTACCC GCCCTGCCCA TCTCAATAAC     1680

GTTCGGATTG ATATTTTGCT TCGCCACTAG TGCGGTGGTC AAGCCGTTCA TGGAGGATCT     1740

ATCGGCCAAG CAGGTGTTTA TATAAACTTG AAAAGACAAG GACACATCAA GTGTCTTACA     1800

GTATCATAGT CTAACAAAGC TTTTTGTAAT CCAATTCTTT ATTTAACCAA ATGCATAGTA     1860

ACAACCTCGA CTAAAAAAAA AAAAAAAAAA AAAAA                                1895
```

(2) INFORMATION FOR SEQ ID NO:166:

(i) SEQUENCE CHARACTERISTICS:
        (A) LENGTH: 541 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:166:

```
Met Ala Ala Val Asn Leu Gln Ala Ser Cys Ser Ser Gly Leu Ala Ser
1               5                  10                  15

Glu Asp Asp Ala Asn Val Gly Ser Gln Ile Gly Ala Ala Glu Arg Leu
            20                  25                  30

Glu Arg Pro Pro Arg Arg Gln Gln Arg Asn Asn Tyr Gly Ser Ser
        35                  40                  45

Asn Gln Asp Gln Pro Asp Ala Ala Ile Leu Ala Val Pro Asn Val Val
    50                  55                  60

Met Arg Glu Pro Cys Gly Ser Arg Pro Ser Arg Leu Thr Gly Gly Gly
65                  70                  75                  80

Gly Gly Ser Gly Gly Pro Pro Thr Asn Glu Met Glu Glu Glu Gln Gly
                85                  90                  95

Leu Lys Tyr Gly Ala Gln His Val Ile Lys Leu Phe Val Pro Val Ser
```

-continued

```
                100                 105                 110
Leu Cys Met Leu Val Val Ala Thr Ile Asn Ser Ile Ser Phe Tyr
            115                 120                 125
Asn Ser Thr Asp Val Tyr Leu Leu Tyr Thr Pro Phe His Glu Gln Ser
    130                 135                 140
Pro Glu Pro Ser Val Lys Phe Trp Ser Ala Leu Ala Asn Ser Leu Ile
145                 150                 155                 160
Leu Met Ser Val Val Val Met Thr Phe Leu Leu Ile Val Leu Tyr
            165                 170                 175
Lys Lys Arg Cys Tyr Arg Ile Ile His Gly Trp Leu Ile Leu Ser Ser
            180                 185                 190
Phe Met Leu Leu Phe Ile Phe Thr Tyr Leu Tyr Leu Glu Glu Leu Leu
        195                 200                 205
Arg Ala Tyr Asn Ile Pro Met Asp Tyr Pro Thr Ala Leu Leu Ile Met
    210                 215                 220
Trp Asn Phe Gly Val Val Gly Met Met Ser Ile His Trp Gln Gly Pro
225                 230                 235                 240
Leu Arg Leu Gln Gln Gly Tyr Leu Ile Phe Val Ala Ala Leu Met Ala
            245                 250                 255
Leu Val Phe Ile Lys Tyr Leu Pro Glu Trp Thr Ala Trp Ala Val Leu
            260                 265                 270
Ala Ala Ile Ser Ile Trp Asp Leu Ile Ala Val Leu Ser Pro Arg Gly
        275                 280                 285
Pro Leu Arg Ile Leu Val Glu Thr Ala Gln Glu Arg Asn Glu Gln Ile
    290                 295                 300
Phe Pro Ala Leu Ile Tyr Ser Ser Thr Val Val Tyr Ala Leu Val Asn
305                 310                 315                 320
Thr Val Thr Pro Gln Gln Ser Gln Ala Thr Ala Ser Ser Ser Pro Ser
            325                 330                 335
Ser Ser Asn Ser Thr Thr Thr Arg Ala Thr Gln Asn Ser Leu Ala
            340                 345                 350
Ser Pro Glu Ala Ala Ala Ser Gly Gln Arg Thr Gly Asn Ser His
        355                 360                 365
Pro Arg Gln Asn Gln Arg Asp Asp Gly Ser Val Leu Ala Thr Glu Gly
    370                 375                 380
Met Pro Leu Val Thr Phe Lys Ser Asn Leu Arg Gly Asn Ala Glu Ala
385                 390                 395                 400
Ala Gly Phe Thr Gln Glu Trp Ser Ala Asn Leu Ser Glu Arg Val Ala
            405                 410                 415
Arg Arg Gln Ile Glu Val Gln Ser Thr Gln Ser Gly Asn Ala Gln Arg
            420                 425                 430
Ser Asn Glu Tyr Arg Thr Val Thr Ala Pro Asp Gln Asn His Pro Asp
        435                 440                 445
Gly Gln Glu Glu Arg Gly Ile Lys Leu Gly Leu Gly Asp Phe Ile Phe
    450                 455                 460
Tyr Ser Val Leu Val Gly Lys Ala Ser Ser Tyr Gly Asp Trp Thr Thr
465                 470                 475                 480
Thr Ile Ala Cys Phe Val Ala Ile Leu Ile Gly Leu Cys Leu Thr Leu
            485                 490                 495
Leu Leu Leu Ala Ile Trp Arg Lys Ala Leu Pro Ala Leu Pro Ile Ser
        500                 505                 510
Ile Thr Phe Gly Leu Ile Phe Cys Phe Ala Thr Ser Ala Val Val Lys
    515                 520                 525
```

```
Pro Phe Met Glu Asp Leu Ser Ala Lys Gln Val Phe Ile
    530                 535                 540
```

(2) INFORMATION FOR SEQ ID NO:167:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:167:

```
Asn Asp Asn Arg Glu Arg Gln Glu His Asn Asp Arg Arg Ser Leu
1               5                   10                  15
```

(2) INFORMATION FOR SEQ ID NO:168:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:168:

```
Lys Asp Gly Gln Leu Ile Tyr Thr Pro Phe Thr Glu Asp Thr Glu
1               5                   10                  15
```

(2) INFORMATION FOR SEQ ID NO:169:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:169:

```
Glu Ala Gln Arg Arg Val Ser Lys Asn Ser Lys Tyr Asn Ala Glu
1               5                   10                  15
```

(2) INFORMATION FOR SEQ ID NO:170:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:170:

```
Ser His Leu Gly Pro His Arg Ser Thr Pro Glu Ser Arg Ala Ala
1               5                   10                  15
```

(2) INFORMATION FOR SEQ ID NO:171:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:171:

CAGAGGATGG AGAGAATAC                                                     19

(2) INFORMATION FOR SEQ ID NO:172:

(i) SEQUENCE CHARACTERISTICS:
          (A) LENGTH: 19 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "primer"

(xi) SEQUENCE DESCRIPTION: SEQ ID NO:172:

GGCTCCCCAA AACTGTCAT                                                     19

(2) INFORMATION FOR SEQ ID NO:173:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "primer"

(xi) SEQUENCE DESCRIPTION: SEQ ID NO:173:

GCCCTAGTGT TCATCAAGTA                                                    20

(2) INFORMATION FOR SEQ ID NO:174:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "primer"

(xi) SEQUENCE DESCRIPTION: SEQ ID NO:174:

AAAGCGGGAG CCAAAGTC                                                      18

(2) INFORMATION FOR SEQ ID NO:175:

(i) SEQUENCE CHARACTERISTICS:
          (A) LENGTH: 19 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "primer"

(xi) SEQUENCE DESCRIPTION: SEQ ID NO:175:

CATTCACTGA GGACACACC                                                     19

(2) INFORMATION FOR SEQ ID NO:176:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: other nucleic acid (A) DESCRIPTION: /desc = "primer"

(xi) SEQUENCE DESCRIPTION: SEQ ID NO:176:

TGTAGAGCAC CACCAAGA                                                       18

(2) INFORMATION FOR SEQ ID NO:177:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:177:

GCATGGTGTG CATCCACT                                                       18

(2) INFORMATION FOR SEQ ID NO:178:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:178:

GGACCACTCT GGGAGGTA                                                       18

(2) INFORMATION FOR SEQ ID NO:179:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:179:

CTCCGATGGA CGCTGG                                                         16

(2) INFORMATION FOR SEQ ID NO:180:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:180:

CAGCAGTATG TGTTTCCA                                                       18

(2) INFORMATION FOR SEQ ID NO:181:

(i) SEQUENCE CHARACTERISTICS:
        (A) LENGTH: 27 base pairs
        (B) TYPE: nucleic acid
        (C) STRANDEDNESS: single
        (D) TOPOLOGY: linear -continued (ii) MOLECULE TYPE: other nucleic acid
    (A) DESCRIPTION: /desc = "primer"

(xi) SEQUENCE DESCRIPTION: SEQ ID NO:181:

TTTTTTGGAT CCTAAAAGTA TAATCCC                                    27

(2) INFORMATION FOR SEQ ID NO:182:

(i) SEQUENCE CHARACTERISTICS:
       (A) LENGTH: 27 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "primer"

(xi) SEQUENCE DESCRIPTION: SEQ ID NO:182:

TTTTTTGGAT CCTAAAAGTA TAATCCC                                    27

(2) INFORMATION FOR SEQ ID NO:183:

(i) SEQUENCE CHARACTERISTICS:
       (A) LENGTH: 11 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:183:

Glu Gln Lys Leu Ile Ser Glu Glu Asp Leu Asn
1               5                   10

TABLE 1

| | RECOMBINATION FRACTION (θ) | | | | | | |
|---|---|---|---|---|---|---|---|
| LOCUS | 0.00 | 0.05 | 0.10 | 0.15 | 0.20 | 0.30 | 0.40 |
| D14S63 | -∞ | 1.54 | 3.90 | 4.38 | 4.13 | 2.71 | 1.08 |
| D14S258 | -∞ | 21.60 | 19.64 | 17.19 | 14.50 | 8.97 | 3.81 |
| D14S77 | -∞ | 15.18 | 15.53 | 14.35 | 12.50 | 7.82 | 2.92 |
| D14S71 | -∞ | 15.63 | 14.14 | 12.19 | 10.10 | 5.98 | 2.39 |
| D14S43 | -∞ | 19.36 | 17.51 | 15.27 | 12.84 | 7.80 | 3.11 |
| D14S273 | -∞ | 12.30 | 11.52 | 10.12 | 8.48 | 5.04 | 1.91 |

TABLE 1-continued

| | RECOMBINATION FRACTION (θ) | | | | | | |
|---|---|---|---|---|---|---|---|
| LOCUS | 0.00 | 0.05 | 0.10 | 0.15 | 0.20 | 0.30 | 0.40 |
| D14S61 | -∞ | 26.90 | 24.92 | 22.14 | 18.98 | 12.05 | 5.07 |
| D14S53 | -∞ | 11.52 | 11.41 | 10.39 | 8.99 | 5.73 | 2.51 |
| D14S48 | -∞ | 0.50 | 1.05 | 1.14 | 1.04 | 0.60 | 0.18 |

TABLE 2

| | PEDIGREE ID | | | | | | | | | | | | | |
|---|---|---|---|---|---|---|---|---|---|---|---|---|---|---|
| LOCUS | NLH2 | FAD3 | TUR1.1 | FAD4 | RB | FAD1 | B1G12 | BOW | COOK | 683 | TOR42 | QUE | MEX1 | FAD2 |
| D14S63 | 1 | 4 | 7 | 4 | | 5 | | | | | | | 9 | 2 |
| D14S258 | 6 | 6 | 8 | 7 | 4 | 5 | 5 | 6 | 6 | | 7 | 6 | 7 | 6 |
| D14S268 | C | C | B | B | C | C | C | C | C | C | C | B | C | C |
| D14S277 | C | C | C | C | C | C | C | C | C | A | A | C | B | B |
| D14S786 | D | D | E | E | F | E | E | D/F | E | E | E | E | F | D |
| D14S77 | Y | Y | K | S | | P | P | K | H | | C | U | F | A |
| D14S71 | 7 | 7 | 1 | 5 | 7 | 7 | | 6 | 7 | 3 | 7 | 2 | 6 |
| D14S43 | A | A | 1 | 1 | 1 | E | D | 1 | 1 | C | 1 | D | C |
| D14S273 | 6 | 6 | 5 | 5 | 5 | 4 | 4 | 4 | 6 | 6 | 6 | 5 | J |
| D14S76 | 5 | 5 | 5 | 5 | 5 | 6 | 9 | 9 | | 9 | 1 | 5 | 5 |
| D14S41 | E | E | G | F | | I | | | | | D | | L | F |
| D14S53 | F | F | C | F | F | J | C | F | E | | J | D | F | F |
| ETHNIC ORIGIN | Ashk | Ashk | Ital | Ital | Ital | Angl | Angl | Angl | Angl | Amer | FrCan | FrCan | Mex | Ger |
| MUTATION | C410Y | C410Y | M146L | M146L | ND | A246E | ND | ND | ND | H163R | H163R | ND | ND | L286V |

TBALE 3

```
                                                                    Similarities
     No.  Target File                Key   Target  Overlap    Match  Percentage
       1  marmp.con/long(Frame 1)      1        1      467      465      99.57%
       1         10        20        30        40        50        60        70
HUMAN N- MTELPAPLSYFQNAQMSEDNHLSNTVRSQNDNRERQEHNDRRSLGHPEPLSNGRPQGNSRQVVEQDEERD
         ****************************  ****** *** *** ********* ***************
MOUSE N- MTEIPAPLSYFQNAQMSEDSHSSSAIRSQNDSQERQQQHDRQRLDNPEPISNGRPQSNSRQVVEQDEEED
         1         10        20        30        40        50        60        70

71        80        90       100       110       120       130       140
         EELTLKYGAKHVIMLFVPVTLCMVVVVATIKSVSFYTRKDGQLIYTPFTEDTETVGQRALHSILNAAIMI
         **********************************************************************
         EELTLKYGAKHVIMLFVPVTLCMVVVVATIKSVSFYTRKDGQLIYTPFTEDTETVGQRALHSILNAAIMI
        71        80        90       100       110       120       130       140

141       150       160       170       180       190       200       210
         SVIVVMTILLVVLYKYRCYKVIHAWLIISSLLLLFFFSFIYLGEVFRTYNVAVDYITVALLIWNLGVVGM
         ***** ************************************** ***** ****** * *********
         SVIVIMTILLVVLYKYRCYKVIHAWLIISSLLLLFFFSFIYLGEVFRTYNVXVDYVTVALLIWNWGVVGM
       141       150       160       170       180       190       200       210

211       220       230       240       250       260       270       280
         ISIHWKGPLRLQQAYLIMISALMALVFIKYLPEWTAWLILAVISVYDLVAVLCPKGPLRMLVETAQERNE
         * ********************************************************************
         IAIHWKGPLRLQQAYLIMISALMALVFIKYLPEWTAWLILAVISVYDLVAVLCPKGPLRMLVETAQERNE
       211       220       230       240       250       260       270       280

281       290       300       310       320       330       340       350
         TLFPALIYSSTMVWLVNMAEGDPEAQRRVSKNSKYNAESTERESQDTVAENDDGGFSEEWEAQRDSHLGP
         ****************************** ** ************************************
         TLFPALIYSSTMVWLVNMAEGDPEAQRRVPKNPKYNTQRAERETQDSGSGNDDGGFSEEWEAQRDSHLGP
       281       290       300       310       320       330       340       350

351       360       370       380       390       400       410       420
         HRSTPESRAAVQELSSSILAGEDPEERGVKLGLGDFIFYSVLVGKASATASGDWNTTIACFVAILIGLCL
         **************** *** *************************************** *********
         HRSTPESRAAVQELSGSILTSEDPEERGVKLGLGDFIFYSVLVGKASATASGDWNTTIACXVAILIGLCL
       351       360       370       380       390       400       410       420

421       430       440       450       460
         TLLLLAIFKKALPALPISITFGLVFYFATDYLVQPFMDQLAFHQFYI -C
          ****** *** **  ************* ********************
         XLLLLAIYKKGXPAXPISITFGLVFXFATDYLVQPFMDQLAFHQFYI -C
       421       430       440       450       460
```

TABLE 4

HUMAN ARMP FUNCTIONAL DOMAINS

| Domains (Amino Acid Residue) | Functional Characteristic |
|---|---|
| 82–100 AA | Hydrophobic |
| 132–154 AA | Hydrophobic |
| 164–183 AA | Hydrophobic |
| 195–213 AA | Hydrophobic |
| 244–256 AA | Hydrophobic |
| 281–299 AA | Hydrophobic |
| 404–428 AA | Hydrophobic |
| 431–449 AA | Hydrophobic |
| 115–119 AA (YTPF) | Phosphorylation Site |
| 353–356 AA (STPC) | Phosphorylation Site |
| 300–385 AA | Acid Rich Domain Possible Metal Binding Domain |

ANTIGENIC SITES INCLUDING AMINO ACID RESIDUES

27–44
46–48
50–60
66–67
107–111
120–121
125–126
155–160
185–189
214–223
220–230
240–245
267–269
273–282
300–370
400–420

TABLE 5

| MUTATION | ENZYME (effect of mutation) | AMPLIFICATION 0440 #1 | AMPLIFICATION 0440 #2 | ALLELE SPECIFIC 0440 |
|---|---|---|---|---|
| M146LEU | Bsphl (destroy) | 910 (170-S182 F) TCACAGAAGATA CCGAGACT | 911 (170-S182) R CCCAACCATAAGA AGAACAG | |
| MIS 163 Ary | Nla III (destroy) | 927 (intronic) TCTGTACTTTTT AAGGGTTGTG | 928 ACTTCAGAGTAATT CATCANCA | |
| Ala 246 | Dlc I (create) | 849 * GACTCCAGCAGG CATATCT | 892 TGAAATCACAGCC AAGATGAG | |
| Leu 286 Val. | Pvu II (create) | 952 GATGAGACAAGT NCCNTGAA 945 TTAGTGGCTGTT TNGTGTCC | 951 CACCCATTTACAAG TTTAGC | |
| Cys 410 Tys | Allele specific iligo | 893 GTGTGGCCAGGG TAGAGAACT | 885 TGGAGACTGGAAC ACAAC | CCATAGCCTGTTTCGTAGC 890 = WT CCATAGCCTATTTCGTAGC 891 = MUT |

TABLE 6

POSITION OF EXONS AND INTRON-EXON BOUNDARIES OF THE ARMP GENE

| cDNA/mRNA SEQUENCE | | CORRESPONDING GENOMIC SEQUENCE | |
|---|---|---|---|
| ARMP (917 ver) | Transcript ID CC44 ver | Genomic sequence file ID & position of exon | Comments |
| 1–113 bp | N/A | 917–936.gen @ 731–834 bp | Alternate 5'UTR |
| N/A | 1–422 bp | 917–036.gen @ 1067–1475 bp | Alternate 5'UTR |
| 114–195 bp | 423–500 bp | 932–943.gen @ 589–671 bp | |
| 196–335 bp | 501–632 bp | 932–943.gen @ 759–899 bp | 12 bp Variable spliced |
| 337–586 bp | 633–883 bp | 901–912.gen @ 787–1037 bp | |
| 587–730 bp | 884–1026 bp | 910–915.gen @ 1134–1278 bp | M146L mutation |
| 731–795 bp | 1027–1092 bp | 925–913.gen @ 413–478 bp | H163R mutation |
| 796–1017 bp | 1093–1314 bp | 849–892.gen @ 336–558 bp | A246E mutation |
| 1018–1116 bp | 1315–1413 bp | 951–952.gen @ 312–412 bp | L286V mutation, variable spl |
| 1117–1204 bp | 1414–1501 bp | 983–1011.gen @ 61–149 bp | |
| 1205–1377 bp | 1502–1674 bp | 874–984.gen @ 452–625 bp | |
| 1378–1497 bp | 1674–1794 bp | 885–1012.gen @ 431–550 bp | C410Y mutation |
| 1498–2760 bp | 1795–3060 bp | 930–919.gen @ ~10 bp–end | last AA, STOP, 3'UTR |

TABLE 7

MUTATIONS AND POLYMORPHISMS IN THE ARMP GENE

| Nucleotide # in ARMP.UPD | Amino acid # in ARMP.PRO | Comment |
|---|---|---|
| A->$C_{684}$ | Met146Leu | Pathogenic, Unique to AD affected. |
| A->$G_{738}$ | His163Arg | Pathogenic, Unique to AD affected. |
| C->$A_{985}$ | Ala246Glu | Pathogenic, Unique to AD affected. |
| C->$T_{1037}$ | Ala260Val | Pathogenic, Unique to AD affected. |
| C->$T_{1102}$ | Ala285Val | Pathogenic, Unique to AD affected. |
| C->$G_{1104}$ | Leu286Val | Pathogenic, Unique to AD affected. |
| C->$G_{1422}$ | Leu392Val | Pathogenic, Unique to AD affected. |

TABLE 7-continued

MUTATIONS AND POLYMORPHISMS IN THE ARMP GENE

| Nucleotide # in ARMP.UPD | Amino acid # in ARMP.PRO | Comment |
|---|---|---|
| G->$A_{1477}$ | Cyc410Tyr | Pathogenic, Unique to AD affected. |
| G->$T_{863}$ | Phe205Leu | Polymorphism in normals |
| C->$A_{1700}$ | non-coding | 3'UTR polymorphism |
| G->$A_{2601}$ | non-coding | " |
| del$C_{2620}$ | non-coding | " |

TABLE 8

```
E5-1   1 MLTFMASDSEFFVCDERTSLMSAESPTPRSC-QEGRQGPEDGE--NTAQWRSQENEED   55
         | | | | |       | |   ||    ||    |||  |||
S182   1 --------------------MT-ELPAPLSYFQNA-QNSEDNHLSNTV--RSQ-N--D   31

E5-1  56 G-E--EDFDRYVCS-GVP-----GRPPGL-----E------EELTLKYGAKHVIMLF   92
         | |   || ||  |       |||     |        ||||||||||||||||
S182  51 NRERQEHNDRR--SLGHFEPLENGRPQGNERQVVEQDEEEDEELTLKYGAKHVIMLF   86

I
                                                           ↓
E5-1  93 VPVTLCMIVVVATIKSVRFYTEKNGQLIYTPFTEDTPSVGQRLLNSVLNTLIMISVI  149
         ||||||| ||||||||| | ||| || ||||||||||||| |||| | || ||||||
S182  87 VPVTLCMVVVVATIKSVSFYTRKDGQLIYTPFTEDTETVGQRALHSILNAAIMISVI  143

E5-1 150 VVMTIFLVVLYKYRCYKFIHGWLIMSSLMLLFLFTYIYLGEVLKTYNVAMDYPTL-L  205
         ||||| |||||||||||| |  | ||| |||| | |||||| |||||||| |  |
S182 144 VVMTILLVVLYKYRCYKVIHAWLIISSLLLLFFFSFIYLGEVFKTYNVAVDYITVAL  200
              ↑                ↑
              L                R

V
                                      ↓
E5-1 206 LTVWNFGAVGMVCIHWEGPLVLQQAYLIMISALMALVFIKYLPEWSAWVILGA-ISV  261
         |  ||||  ||| ||||||||||||||||||||||||||||||||  ||  |  |||
S182 201 LI-WNFGVVGMISIHWEGPLRLQQAYLIMISALMALVFIKYLPEWTAWLIL-AVISV  255
                                                     ↑
                                                     Z

********************************
E5-1 262 TDLVAVLCPKGFLRMLVETAQERNEPIFPALIYSSAMVWTVGMAKLDP------S--  310
         ||||||||||||||||||||||||| | |||||||  || || ||
S182 256 TDLVAVLCPKGFLRMLVETAQERNETLFPALIYSSTMVWLVNMAEGDPEAQRRVSKN  312
             ****************************↑↑****
                                          VV

E5-1 311 SQGAL-------QLFY---DP----EME-EDSYDSP-GEP--SYPE----VYEFPLT  345
         |   |       |  |   ||    | |    || | ||  |||     |  |
S182 301 SKYNAESTERESQDTVAENDDGGFSE-EWEAQRDSHLG-PHRSTPESRAAVQE--LS  365

E5-1 346 GYP--GEELEEEEERGVKLGLGDFIFYSVLVGKAAATGSGDWNTTLACFVAILIGLC  400
         |     ||  |||||||||||||||||||||||| || ||||||||||||||||||
S182 366 SEILAGEDP---EERGVKLGLGDFIFYSVLVGKASATASGDWNTTIACFVAILIGLC  420
                                                      ↑          ↑
                                                      V          Y

E5-1 401 LTLLLLLAVFKKALPALPISITFGLIFYFSTDNLVRPFMDTLASHQLYI*  446
         ||||||| || ||||||||||||||||| || |||||||| | ||||*
S182 421 LTLLLLAIFKKALPALPISITFGLVFYFATDYLVQPFMDQLAFHQFYI*  467
```

TABLE 9

MISSENSE MUTATIONS IN THE PRESENILIN GENES

| Codon | location | mutation | phenotype |
|---|---|---|---|
| PRESENILIN I (S182) | | | |
| 82 | TM1 | Val->Leu | FAD, onset 55 years* |
| 115 | TM1->TM2 loop | Tyr->His | FAD, onset 37 years* |
| 139 | TM2 | Met->Thr | FAD, onset 49 years* |
| 143 | TM2 | Ile->Thr | FAD, onset 35 years† |
| 146 | TM2 | Met->Leu | FAD, onset 45 years |
| 163 | TM3 interface | His->Arg | FAD, onset 50 years* |
| 171 | TM3 | Leu->Pro | FAD, onset 35 years |
| 231 | TM5 | Ala->Thr | FAD, onset 52 years* |
| 246 | TM6 | Ala->Glu | FAD, onset 55 years |
| 260 | TM6 | Ala->Val | FAD, onset 40 years |
| 264 | TM6 | Pro->Leu | FAD, onset 45 years* |
| 285 | TM6->TM7 loop | Ala->Val | FAD, onset 50 years |
| 286 | TM6->TM7 loop | Leu->Val | FAD, onset 50 years |
| 384 | TM6->TM7 loop | Gly->Ala | FAD, onset 35 years† |
| 392 | TM6->TM7 loop | Leu->Val | FAD, onset 25–40 years |
| 410 | TM7 | Cys->Tyr | FAD, onset 48 years |
| PRESENILIN II (E5-1) | | | |
| 141 | TM2 | Asn->Ile | FAD (Volga German), onset 50–65 years |
| 239 | TM5 | Met->Val | FAD (Florence), onset variable |
| 420 | C-terminus | Ile->Thr | FAD (Selkoe) |

*Campion et al., (1995).
†Cruts et al., (1995).

TABLE 10

MURINE LINES CONTAINING MUTANT OR WILD TYPE HUMAN PRESENILIN TRANSGENES

| GENOTYPE (Nickname) | haPrP: haPrP | hPDGF-β: SV40 pA | hβ-Actin: hGH pA | hPGK: PGKpA |
|---|---|---|---|---|
| PSNL1: wild type | transgenic mice | transgenic mice | transgenic mice | newborn mice |
| PSNL1: Tyr115His** (French mutation) | | | transgenic | |
| PSNL1: Met146Leu** (FAD4 mutation) | transgenic mice | transgenic mice | | |
| PSNL1: Met146Leu(tr) | | transgenic mice | transgenic mice | |
| PSNL1: His163Arg (603 mutation) | | | | injected |
| PSNL1: Ala246Glu (FAD1 mutation) | | | | transgenic mice |
| (PSNL1: Ala260Val (JPN1 mutation) | | | | |
| PSNL1: Ala285Val (JPN2 mutation) | | | | |
| PSNL1: Leu286Val (Ger/FAD2 mutation) | transgenic mice | | | |
| PSNL1: Leu392Val** (Borras mutation) | | | transgenic | |
| PSNL1: Cys410Tyr (MHG1/NIH2 mutation) | | transgenic mice | | |
| PSNL2: wild type | prepared | | transgenic | |
| PSNL2: Asn141Ile (Volga mutation) | injected | | transgenic | |
| PSNL2: Met239Val (FLO10 mutation) | prepared | | transgenic | |

**Mutations associated with onset ≦ 45 years of age.

TABLE 11

*C. elgans* transgenes

| GENOTYPE | pPD49.3 hsp 16-41 | pPD49.78 hsp 16-2 |
|---|---|---|
| PSNL1: wild type | transgenic *C. elgans* | injected |
| PSNL1: Leu392Val | transgenic *C. elgans* | injected |
| PSNL1: Met146Leu + Leu392Val; cis double mutation | prepared | prepared |
| PSNL2: wild type | prepared | prepared |
| PSNL2: Asn141Ile | prepared | prepared |

TABLE 12

Platelet derived growth factor promotor (PDGF) (vector pZEOsV)

a) S182

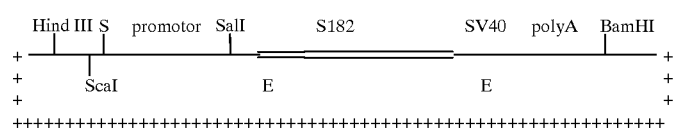

Construct released by HindIII/BamHI digestion b) S182 Truncated (S182t)

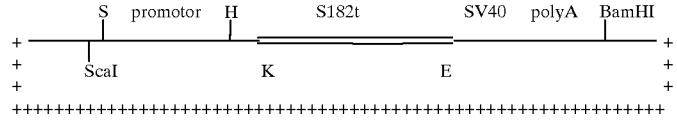

Construct released by ScaI/BamHI digestion c) E5-1

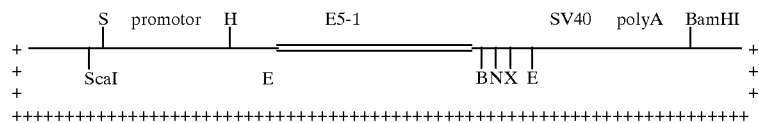

TABLE 12-continued

Construct released by ScaI/BamHI digestion
Legend: S = SpeI; H = HindIII; K = KpnI; E = EcoRI; B = BstXI; N = NotI; X = XhoI
β actin promotor (vector pGem11 Zf*)

a) S182

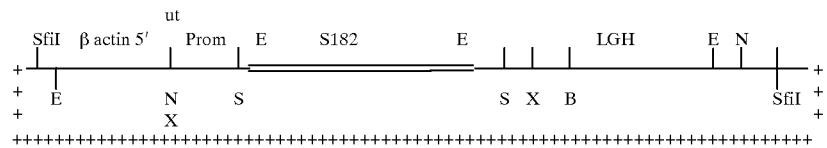

b) S182 Truncated (S182t)

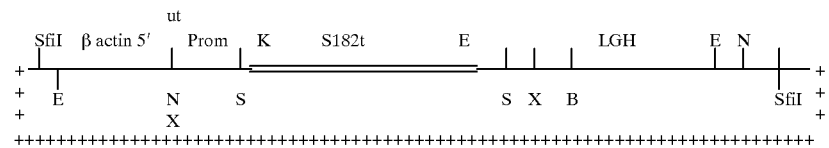

c) E5-1

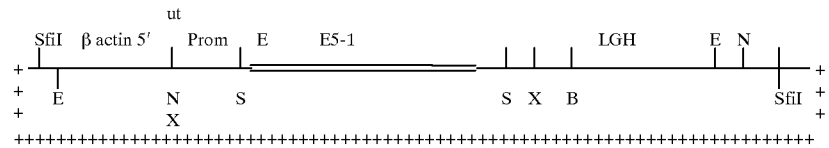

Legend: ut = 5' untranslate; Prom = promotor; E = EcoRI; N = NotI; S = SalI; X = XhoI
B = BamHI; K = KpnI
Constructs released by SfiI digestion
Phosphoglycerate kinase promotor construct (PGK) (vector pPOP)

a) S182

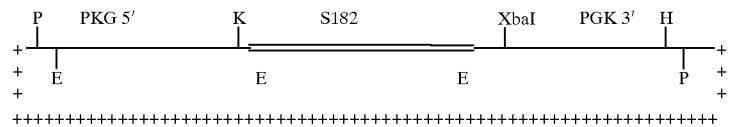

Construct released by PvuII/HindIII digestion
b) S182 Truncated (S182t)

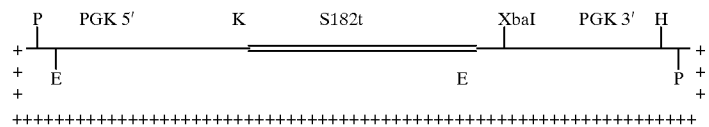

Construct released by PvuII/HindIII digestion
c) 55-1

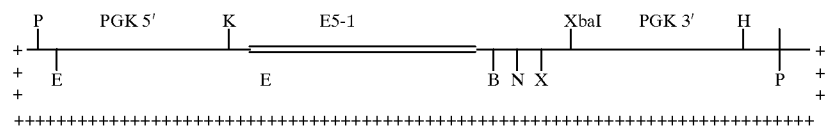

Construct released by PvuII digestion
Legend: P = PvuII; E = EcoRI; K = KpnI; B = BstXI; N = NotI; X = XhoI; H = HindIII

TABLE 13

| Gene name (official) | U of T clone ID | EST in database | Putative gene function |
|---|---|---|---|
| RabII | ps1ly2h-9 | X56740<br>X53143 | Protein/vesicle traffic in ER/Golgi. NB possible relationship to processing of membrane proteins such as βAPP and Notch with resultant overproduction of toxic Aβ peptides (ESP. neurotoxic $A\beta_{1-42(43)}$ isoforms) (Scheuner, et al, 1995). |
| retinoid X receptor-B; nuclear receptor co-regulator; MHCclass I regulatory element | ps1ly2h23b | m8420<br>63522<br>m81766 | Gene involved in inter-cellular signalling - NB possible relationship to intercellular signalling function mediated by C. elegans sell2 (homologue of mammalian presenilins) and C. elegans Notch/lin-12 (transcription activator). |
| unknown gene | ps1ly2h-6<br>ps1ly2y10b<br>ps1ly2h17h2<br>ps1ly2h24<br><br>ps1ly2h25 | F08730<br>T18858<br>H17245<br>T06654<br>T77214<br>h24294<br>M62015<br>T87427<br>G04019 | Weak homology to Cyclic AMP response element binding protein (CREB) involved in transcriptional repsonses to extracellular signals as a second messenger pathway. Strong homology to p120 (NOL) protein also involved in transcription and cell cycle events. Note that these transcriptional event regulatory effects are similar to those postulated for Notch/lin-12 mediated effects on intercellular signalling. Activation of genes (eg βAPP) causing over-expression of βAPP mRNA has been shown in subjects with mutations in the presenilins (Querforth et al, 1995). Modulation of this abberrant transcriptional activation could be used as a therapeutic target to correct abnormalities in the expression of genes (including βAPP and other genes) and thereby prevent/improve the symptoms of AD. |
| unknown gene (cont'd) | ps1ly2h-6<br>ps1ly2y10b<br>ps1ly2h17h2<br>PS1LY2H24<br>ps1ly2h24<br>(cont'd) | F08730<br>T18858<br>H17245<br>ETC<br>(cont'd) | Weak homology to plakophilin a protein involved in stabilization of the cytoskeletal fibrillar proteins Note that more than one member of member of the is gene family was isolated, suggesting a family of genes interacting differently with different preseilins. Note that defects in the cytoskeleton (ie paired helical filaments and neurofibrillary tangles) are a major neuropathologic hallmark of AD. |
| antisecretory factor | ps1ly2h-29<br>ps1ly2h-31 | U24707 | Secretion of fluid in gut, unknown in brain. |
| unknown gene | ps1ly2h-35 | R12984 | homology fown to yeast, function = unknown. |
| cytoplasmic chaperonin | ps1ly2h-27 | U17104<br>X74801 | Chaperonin containing TCP-1 |
| unknown gene | ps1ly2h-41 | T6443<br>F12194 | unknown ESTs. Note: this gene product reacts strongly with both PS-1 and PS-2 which argues for a real effect related to the shared biochemical effects of PS-1 and PS-2 causing AD. |
| unknown gene | ps1y12h-171 | D55326 | expressed repeat sequence |

TABLE 14

```
File1: dros.concensus(1-541) vs File2: PS-1 .s182)(1-468)
   Matching Percentage: 53%   ^ = S182/E5-1 mutations * =
alternative splice: G384->A384 and in frame fusion to E399

1 MAAVNLQASCSSGL-A--SEDDA---N-VGSQIGAAERLERPPRRQQQRNN 50
    |   ||| |    |   |||    | | ||    || |     ||
  1 MTE--LPAPLSYFQNAQMSEDNHLSNTVRSQNDNRERQEHNDRR------ 50
```

TABLE 14-continued

```
File1: dros.concensus(1-541) vs File2: PS-1 .s182)(1-468)
   Matching Percentage: 53%   = S182/E5-1 mutations * =
alternative splice: G384->A384 and in frame fusion to E399

51 YGSSNQDQPDAAILAVPNVVMREPCGS--RPSRLTGGGGSGGPPTN-EM 100
       |     |      | |   | ||      |     |     |
 51 --S----------LGHP-----EPL-SNGRPQ---GN---SRQVVEQDEE 100

101 E-EEQGLKYGAQHVIKLFVPVSLCMLVVVATINSISFYNST--DVYLLYT 150
    | ||  ||||| ||| |||||| ||| |||||||| ||||  |  | ||
101 EDEELTLKYGAKHVIMLFVPVTLCMVVVVATIKSVSFY--TRKDGQLIYT 150

151 PFHEQSPEPSVKFW-SALANSLTMSVVVVMTFLLTVLYKKRCYRI      200
    ||  |           |   |   |  ||||||||| ||||||||
151 PFTEDTETVGQRALHSIL-NAATMISVTVVMTILLVVLYKRCYKV      200

201 IHGWLILSSFMLLFIFTYLYLEELLRAYNIPMDYPT-ALLIMWNFGVVGM 250
    || ||| ||  ||| |      || |   ||   || |||| ||||||||
201 IHAWLTISSLLLLFFFSFIYLGEVFKTYNVAVDYITVALLI-WNFGVVGM 250

251 MSIHWQGPLRLQQGYLIFVAALMALVFIKYLPEWTAWAVLAAISIWDLIA 300
    |||| ||||||||   |||  |||||||||||||||||| || || || |
251 ISTHWGPLRLCQQAYLTMTSALMALVFIKYLPEWTAWLTLAVTSVYDLVA 300
                                              ***

301 VLSPRGPLXTLVETAQERNEQTFPALTYSSTVVYALVNTVT--PQQSQAT 350
    || | |||| ||||||||||| |||||||||||||| |||   |    |
301 VLCPKGPLRMLVETAQERNETLFPALTYSSTMVW-LVNMAEGDPEA-QRR 350
     ***********************  ****

351 ASSSPSSSN--STTTTRATQNSLASPEAAAASGQRTGNSHPRQNQRDDGS 400
       |    | ||   |       |    |    | ||     |||   |
351 VSKN-SKYNAESTE--RESQDTVA--ENDD--G---GFSEEWEAQRD--S 400

*****  **********
401 VLATEGMPLV-TFKSNLRGNAEAAGFTQEWSANLSERVARRQIEVQSTQS 450
       |  |   |   |   |   || ||   ||            |   |
401 HL---G-PHRSTPES--R--A-AV---QE----LS----------S---S 450

451 GNAQRSNEYRTVTAPDQNHPDGQEERGIKLGLGDFIFYSVLVGKAS---S 500
       |       |    |     ||||| ||||||||||||||||    |
451 ILAG---E-------D---P---EERGVKLGLGDFIFYSVLVGKASATAS 500

501 YGDWTTTIACFVAILIGLCLTLLLLAIWRKALPALPISITFGLIFCFATS 550
    |||  ||||||||| ||||||||||||  ||||||| |||||| | |||
501 -GDWNTTIACFVATLIGLCLTLLLLAIFKKALPALPTSITFGLVFYFATD 550

551 AVVKPFMED-LSAK-QVF-I*............................ 600
    | ||| |  |  |   |
551 YLVQPFM-DQL-AFHQ-FYT*............................ 600
```

What is claimed is:

1. A substantially pure presenilin II (PS2) protein having at least 63% identity to human PS2 having an amino acid sequence as depicted in SEQ ID NO:137, wherein said PS2 protein has the ability to process amyloid precursor protein (APP) into Aβ peptide.

2. The protein of claim 1, which is a mammalian PS2 protein.

3. The protein of claim 2, which is a human PS2 protein.

4. The protein of claim 3, comprising the amino acid sequence depicted in SEQ ID NO: 137.

5. A substantially pure mutant presenilin II (PS2) protein, or a splice variant thereof, said mutant comprising SEQ ID NO:137 having amino acid substitutions at positions 141, 239, and/or 420.

6. The mutant PS2 protein of claim 5, having an amino acid substitution at position 141 and/or position 239 of SEQ ID NO: 137.

7. The mutant PS2 protein of claim 6, in which the Asn residue at position 141 is substituted by Ile.

8. The mutant PS2 protein of claim 6, in which the Met residue at position 239 is substituted by Val.

9. The mutant PS2 protein of claim 5 having an amino acid substitution at position 420.

10. The mutant PS2 protein of claim 9, in which the Ile residue at position 420 is substituted by Thr.

11. The mutant PS2 protein of claim 9, which further lacks amino acid residues 263–296 of SEQ ID NO:137.

12. The mutant PS2 protein of claim 9, which further lacks amino acid residue 325 of SEQ ID NO:137.

13. The mutant PS2 protein of claim 9, which is encoded by a polynucleotide having a nucleic acid sequence shown in SEQ ID NO:136, but having a C at a location corresponding to position 1624 thereof.

14. A substantially pure splice variant of presenilin II (PS2) protein which is a splice variant of the amino acid sequence shown in SEQ ID NO:137.

15. The mutant PS2 protein of claim 14, which further lacks amino acid residues 263–296 of SEQ ID NO: 137.

16. The mutant PS2 protein of claim 14, which further lacks amino acid residue 325 of SEQ ID NO: 137.

17. A substantially pure PS2 protein, encoded by the nucleic acid sequence depicted in SEQ ID NO: 136.

18. The protein of claim 17, which is a mammalian PS2 protein.

19. The protein of claim 18, which is a human PS2 protein.

20. A substantially pure mutant presenilin II (PS2) protein which is encoded by the nucleic acid sequence depicted in SEQ ID NO:136, said mutant encoded by a nucleic acid molecule comprising SEQ ID NO:136 having nucleotide substitutions at positions 787, 1080, and/or 1624.

21. The mutant PS2 protein of claim 20, having a substitution at position 787 and/or position 1080 of SEQ ID NO: 136.

22. The mutant PS2 protein of claim 21, in which the A at position 787 is substituted by T.

23. The mutant PS2 protein of claim 21, in which the A at position 1080 is substituted by G.

24. The mutant PS2 protein of claim 20, in which the T at position 1624 is substituted by C.

25. A substantially pure splice variant of presenilin II (PS2) protein, which is encoded by a polynucleotide which is a splice variant of the nucleotide sequence shown in SEQ ID NO:136.

26. The splice variant PS2 protein of claim 25, which is encoded by a polynucleotide lacking the triplet GAA codon at nucleotide positions 1338–1340 of SEQ ID NO:136.

* * * * *

UNITED STATES PATENT AND TRADEMARK OFFICE
CERTIFICATE OF CORRECTION

PATENT NO. : 6,117,978
APPLICATION NO. : 09/124698
DATED : September 12, 2000
INVENTOR(S) : Peter H. St. George-Hyslop et al.

It is certified that error appears in the above-identified patent and that said Letters Patent is hereby corrected as shown below:

In columns 225 and 226, replace Table 8 in its entirety with the attached Table 8.

Signed and Sealed this

Twenty-ninth Day of June, 2010

David J. Kappos
*Director of the United States Patent and Trademark Office*

TABLE 8

```
E5-1    1   MLTFMASDSEEEVCDERTSLMSAESPTPRSC*QEGRQGPEDGE**NTAQWRSQENEED     55
            | ||||| |   |  ||   ||   ||| | |
S182    1   *******************MT*ELPAPLSYFQNA*QMSEDNHLSNTV**RSQ*N**D     31

E5-1   56   G*E**EDPDRYVCS*GVP*****GRPPGL*****E******EELTLKYGAKHVIMLF     92
            | |  |  |||   |        |||          |   ||||||||||||||||
S182   51   NRERQEHNDRR**SLGHPEPLSNGRPQGNSRQVVEQDEEEDEELTLKYGAKHVIMLF     86
                                                                    I
                                                                    ↓
E5-1   93   VPVTLCMIVVVATIKSVRFYTEKNGQLIYTPFTEDTPSVGQRLLNSVLNTLIMISVI    149
            |||||||  ||||||||| ||| | ||||||||||| |||| ||   |  ||||||
S182   87   VPVTLCMVVVVATIKSVSFYTRKDGQLIYTPFTEDTETVGQRALHSILNAAIMISVI    143

E5-1  150   VVMTIFLVVLYKYRCYKFIHGWLIMSSLMLLFLFTYIYLGEVLKTYNVAMDYPTL*L    205
            |||||  |||||||||| |   ||| ||| ||| |   |||| ||||||| || | |
S182  144   VVMTILLVVLYKYRCYKVIHAWLIISSLLLLFFFSFIYLGEVFKTYNVAVDYITVAL    200
                ↑           ↑
                L           R

V
                                     ↓
E5-1  206   LTVWNFGAVGMVCIHWKGPLVLQQAYLIMISALMALVFIKYLPEWSAWVILGA*ISV    261
            |  ||||  ||| ||||||||||||||||||||||||||||||||| || | | |||
S182  201   LI*WNFGVVGMISIHWKGPLRLQQAYLIMISALMALVFIKYLPEWTAWLIL*AVISV    255
                                                         ↑
                                                         E

********************************
E5-1  262   YDLVAVLCPKGPLRMLVETAQERNEPIFPALIYSSAMVWTVGMAKLDP******S**    310
            |||||||||||||||||||||||||  |||||||| | ||  ||  ||         |
S182  256   YDLVAVLCPKGPLRMLVETAQERNETLFPALIYSSTMVWLVNMAEGDPEAQRRVSKN    312
                ****************************↑↑****
                                              VV

E5-1  311   SQGAL****QLPY*DP****EME*EDSYDSF*GEPSYPE**VFEPPLT    345
            |          |      ||    |||  |  | |||  |       |||
S182  301   SKYNAESTERESQDTVAENDDGGFSE*EWEAQRDSHLG*PHRSTPESRAAVQE**LS    365

E5-1  346   GYP**GEELEEEEERGVKLGLGDFIFYSVLVGKAAATGSDWNTTLACFVAILIGLC    400
            ||   ||  ||||||||||||||||| ||||||||  |||||||| ||||||||||
S182  366   SSILAGEDP***EERGVKLGLGDFIFYSVLVGKASATASGDWNTTIACFVAILIGLC    420
                                             ↑              ↑
                                             V              Y

E5-1  401   LTLLLLAVFKKALPALPISITFGLIFYFSTDNLVRPFMDTLASHQLYI* 448  SEQ ID NO: 138
            |||||||  ||||||||||||||| ||| || || |||| | | ||||
S182  421   LTLLLLAIFKKALPALPISITFGLVFYFATDYLVQPFMDQLAFHQFYI* 467  SEQ ID NO: 2
```

TABLE 8

```
E5-1    1  MLTFMASDSEEVCDERTSLMSAESPTPRSC*QEGRQGPEDGE**NTAQWRSQENEED    55
              ||||  |  ||||       ||    ||     |||  |
S182    1  ***************MT*ELPAPLSYFQNA*CSEDNHLSNTV**RSQ*N**D        31
```
(annotations: "FF" above positions near start of E5-1; "All clashes should be stars"; "N" below S182)

```
E5-1   56  G*E**EDDDRYVCS*GVP****GRPPGL*****E******EELTLKYGAKHVIMLF    92
            |  || ||| |||  |||   |||  |       |    ||||||||||||||||
S182   51  NRERQEHNDRR**SLGHEEPISNGRPQGNERQVVEQDEEEDEELTLKYGAKHVIMLF    86
```
(annotations: "F", "E", "E" below S182; "I" above E5-1)

```
E5-1   93  VPVTLCMIVVVATIKSVRFYTEKNGQLIYTPFTEDTPSVGQRLLNSVLNTLIMISVI   149
           ||||||| ||||||||| ||| |||||||||||| ||||| |   |  || ||||||
S182   87  VPVTLCMVVVVATIKSVSFYTRKDGQLIYTPFTEDTETVGQRALHSILNAAIMISVI   143
```

```
E5-1  150  VVMTIFLVVLYKYRCYKFIHGWLIMSSLMLLFLFTYIYLGEVLKTYNVAMDYPTL*L   205
           ||||| |||||||||||||  ||| ||||| ||   |||||| |||||| ||| | |
S182  144  VVMTILLVVLYKYRCYKVIHAWLIISSLLLLFFFSFIYLGEVFKTYNVAVDYITVAL   200
```
(annotations: "L", "R" below S182)

```
E5-1  206  LTVWNFGAVGMVCIHWGGPLVLQQAYLIMISALMALVFIKYLPEWSAWVILGA*ISV   261
           | ||||| ||| | |||||||||||||||||||||||||||||||| | ||  |||
S182  201  LI*WNFGVVGMISIHWGGPLRLQQAYLIMISALMALVFIKYLPEWTAWLIL*AVISV   255
```
(annotations: "E", "V" above E5-1; "E" below S182)

```
E5-1  262  QDLVAVLCPKGQLRMLVETAQERNEPIFPALIYSSAMVWTVGMAKLDP******S**   310
           ||||||||||| |||||||||||| | ||||||| |||||| || ||      |
S182  256  VDLVAVLCPKGQLRMLVETAQERNETLFPALIYSSTMVWLVNMAEGDPEAQRRVSKN   312
```
(annotations: "T", "F" above E5-1; "E" below S182; "VV", "E" between)

```
E5-1  311  SQGAL*****QIDY*DP****EME*EDSYDSEGEPSYPE**VEDPLT    345
           |          |  |   |||   || |  | |    |    |||      ||
S182  301  SKYNAESTERESQDTVAENDDGGFSE*EWEAQRDSHLG*PHRSTPESRAAVQE**LS   365
```
(annotations: "Y", "F" near end)

```
E5-1  346  GYP**GEELEEEEERGVKLGLGDFIFYSVLVGKAAATGSGDWNTTLACFVAILIGLC   400
             |   ||||||||||||||||||| |||||||||||| | | ||||||||||||
S182  366  SSILAGEDP***EERGVKLGLGDFIFYSVLVGKASATGSGDWNTTIACFVAILIGLC   420
```
(annotations: "E" below S182; "V", "Y" between)

```
E5-1  401  LTLLLLAVFKKALPALPISITFGLIFYFSTDNLVRPFMDTLASHQLYI*   448 SEQ ID NO: 138
           ||||||| ||||||||||||||||  |  | ||| ||||  |  ||
S182  421  LTLLLLAIFKKALPALPISITFGLVFYFATDYLVQPFMDQLAFHQFYI*   467 SEQ ID NO: 2
```